US011851484B2

(12) United States Patent
Arenas-Ramirez et al.

(10) Patent No.: US 11,851,484 B2
(45) Date of Patent: *Dec. 26, 2023

(54) IMMUNE-STIMULATING HUMANIZED MONOCLONAL ANTIBODIES AGAINST HUMAN INTERLEUKIN-2, AND FUSION PROTEINS THEREOF

(71) Applicant: Universität Zürich, Zürich (CH)

(72) Inventors: Natalia Arenas-Ramirez, Zürich (CH); Iwan Beuvink, Basel (CH); Onur Boyman, Küsnacht (CH); Barbara Brannetti, Basel (CH); Andreas Katopodis, Basel (CH); Simone Popp, Basel (CH); Catherine Regnier, Basel (CH); Chao Zou, Basel (CH)

(73) Assignee: UNIVERSITÄT ZÜRICH, Zürich (CH)

( * ) Notice: Subject to any disclaimer, the term of this patent is extended or adjusted under 35 U.S.C. 154(b) by 235 days.

This patent is subject to a terminal disclaimer.

(21) Appl. No.: 17/124,930

(22) Filed: Dec. 17, 2020

(65) Prior Publication Data

US 2021/0246200 A1 Aug. 12, 2021

Related U.S. Application Data

(63) Continuation of application No. 16/069,146, filed as application No. PCT/IB2017/050127 on Jan. 11, 2017, now Pat. No. 10,889,643.

(60) Provisional application No. 62/277,113, filed on Jan. 11, 2016.

(51) Int. Cl.
*C07K 16/24* (2006.01)
*C07K 14/55* (2006.01)
*A61K 39/00* (2006.01)
*A61K 38/00* (2006.01)

(52) U.S. Cl.
CPC ............ *C07K 16/246* (2013.01); *C07K 14/55* (2013.01); *A61K 38/00* (2013.01); *A61K 2039/505* (2013.01); *C07K 2317/24* (2013.01); *C07K 2317/34* (2013.01); *C07K 2317/55* (2013.01); *C07K 2317/74* (2013.01); *C07K 2317/92* (2013.01); *C07K 2319/00* (2013.01)

(58) Field of Classification Search
CPC .................................................. C07K 16/246
See application file for complete search history.

(56) References Cited

U.S. PATENT DOCUMENTS

| | | | |
|---|---|---|---|
| 6,111,090 A | 8/2000 | Gorman et al. | |
| 7,025,962 B1 | 4/2006 | Gorman et al. | |
| 2008/0286269 A1 | 11/2008 | Violette et al. | |
| 2013/0142806 A1 | 6/2013 | Lu et al. | |

FOREIGN PATENT DOCUMENTS

| | | |
|---|---|---|
| CA | 1340853 C | 12/1999 |
| EP | 1947183 B1 | 7/2013 |
| WO | 2004060319 A2 | 7/2004 |
| WO | 2006083289 A2 | 8/2006 |
| WO | 2006128690 A1 | 12/2006 |
| WO | 2007095643 A2 | 8/2007 |
| WO | 2009101611 A1 | 8/2009 |
| WO | 2012107417 A1 | 8/2012 |
| WO | 2013157105 A1 | 10/2013 |
| WO | 2014012479 A1 | 1/2014 |
| WO | 2015109212 A1 | 7/2015 |
| WO | 2016005950 A1 | 1/2016 |

OTHER PUBLICATIONS

Al-Lazikani et al., "Standard Conformations for the Canonical Structures of Immunoglobulins", J. Mol. Biol, vol. 273, pp. 927-948 (1997).
Arenas-Ramirez et al., "Improved Cancer Immunotherapy by a CD25-Mimobody Conferring Selectivity to Human Interleukin-2", Sci. Transl. Med., vol. 8, pp. 1-12 (2016).
Bendig, M.M., "Humanization of Rodent Monoclonal Antibodies by CDR Grafting", Methods: A Companion to Methods in Enzymology, vol. 8, pp. 83-93, (1995).
Boyman, et al., "Selective Stimulation Of T Cell Subsets With Antibody-Cytokine Immune Complexes", Science, vol. 311, 2006, pp. 1924-1927.
Budd et al., "Interleukin-2 Monoclonal Antibody Affinity Adsorption", Journal of Immunological Methods, vol. 95, pp. 237-248, (1986).
Casset, F., et al., "A Peptide Mimetic of an Anti-CD4 Monoclonal Antibody by Rational Design", Biochem. Biophys. Res. Comm., vol. 307, pp. 198-205, (2003).
Corrected Version of Kreig, et al.,"Improved IL-2 Immunotherapy By Selective Stimulation Of IL-2 Receptors On Lymphocytes And Endothelial Cells", PNAS, vol. 107, No. 26, May 19, 2010, pp. 11906-11911 (XP002738483).
EP application corresponding to SYO62-26969 8 in corresponding JP Application 62-269698.
European Office Action dated Nov. 14, 2017 and received in European Application No. 15759938.2.
Ide et al., "Neutralizing Monoclonal Antibodies Against Recombinant Human Interleukin-2", Journal of Immunological Methods, vol. 101, pp. 57-62, (1987).
International Preliminary Report on Patentability dated Jan. 10, 2017 and received in PCT/IB2015/055226.
International Search Report and Written Opinion dated Nov. 18, 2015 in PCT/IB2015/055226.
International Search Report dated May 24, 2017.

(Continued)

*Primary Examiner* — Prema M Mertz
(74) *Attorney, Agent, or Firm* — Arrigo, Lee, Guttman & Mouta-Bellum LLP; Carla Mouta-Bellum

(57) ABSTRACT

The present invention relates to antibodies binding to human interleukin-2 (hIL-2). The invention more specifically relates to humanized antibodies specifically binding a particular epitope of hIL-2 and, when bound to this epitope, displaying a unique capability of inhibiting binding of hIL-2 to CD25.

21 Claims, 27 Drawing Sheets
Specification includes a Sequence Listing.

(56) References Cited

OTHER PUBLICATIONS

Jones et al., "Replacing the Complementarity-Determining Regions in a Human Antibody with those from a Mouse", Nature, vol. 321, pp. 522-525 (1986).
Krieg, et al.,"Improved IL-2 Immunotherapy By Selective Stimulation Of IL-2 Receptors On Lymphocytes And Endothelial Cells", PNAS, vol. 107, No. 26, May 19, 2010, pp. 11906-11911 (XP002738483).
Letourneau et al., "IL-2/Anti-IL-2 Antibody Complexes Show Strong Biological Activity by Avoiding Interaction with IL-2 Receptor α Subunit CD25", Proceedings of the National Academy of Sciences, vol. 107, No. 5, pp. 2171-2176, (2010).
Levin et al., "Exploiting a Natural Conformational Switch to Engineer an Interleukin-2 Superkine", Nature, vol. 484 pp. 529-533 (2012).
Maccallum, R.M., et al., "Antibody-Antigen Interactions: Contact Analysis and Binding Site Topography", J. Mol. Biol., vol. 262, pp. 732-745, (1996).
Paul, W.E., "Fundamental Immunology", 3rd Ed., pp. 292-295, (1993).
Phelan, et al.,"Cutting Edge: Mechanism Of Enhancement Of In Vivo Cytokine Effects By Anti-Cytokine Monoclonal Antibodies", The Journal of Immunology, vol. 180, No. 1, 2008, pp. 44-48 (XP002750714).
Queen et al., "A Humanized Antibody that Binds to the Interleukin 2 Receptor", Proc. Natl. Acad. Sci, vol. 86, pp. 10029-10033 (1989).
Rebollo, et al.,"Immunochemical Characterization Of Antigenic Domains On Human IL-2 Spatially Distinct Epitopes Are Associated With Binding To The p55 And p70 Subunits Of IL-2 Receptor", Molecular Immunology, vol. 29, No. 1, 1992, pp. 119-130 (XP023682526).
Rosalia, et al.,"Use Of Enhanced Interleukin-2 Formulations For Improved Immunotherapy Against Cancer", Current Opinion in Chemical Biology, vol. 23, 2014, pp. 39-46.
Rudikoff, S., et al., "Single Amino Acid Substitution Altering Antigen-Binding Specificity", Proc. Natl. Acad. Sci. USA, vol. 79, pp. 1979-1983, (1982).
Schwartzentruber, et al., "In Vitro Predictors of Therapeutic Response in Melanoma Patients Receiving Tumor-Infiltrating Lymphocytes and Interleukin-2", Jul. 1, 1994.
Tomala et al., "Chimera of IL-2 Linked to Light Chain of Anti-IL-2 mAb Mimics IL-2/Anti-IL-2 mAb Complexes Both Structurally and Functionally", ACS Chemical Biology, vol. 8, No. 5, pp. 871-876, (2013).
Tomala et al., "In Vivo Expansion of Activated Naive CD8+ T Cells and NK Cells Driven by Complexes of IL-2 and Anti-IL-2 Monoclonal Antibody as Novel Approach of Cancer Immunotherapy", The Journal of Immunology, vol. 183, No. 8, pp. 4904-4912, (2009).
Vajdos, F.F., et al., "Comprehensive Functional Maps of the Antigen-Binding Site of an Anti-ErbB2 Antibody Obtained with Shotgun Scanning Mutagenesis", J. Mol. Biol., vol. 320, pp. 415-428, (2002).
Wang et al., "Structure of the Quaternary Complex of Interleukin-2 with Its α, β, and γc Receptors", Science, vol. 310, pp. 1159-1163 (2005).
Written Opinion of the International Searching Authority.
Wu, H., et al., "Humanization of a Murine Monoclonal Antibody by Simultaneous Optimization of Framework and CDR Residues", J. Mol. Biol., vol. 294, pp. 151-162, (1999).

SEQUENCE LISTING

<160> NUMBER OF SEQ ID NOS: 423

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Ala Phe Thr Asn Tyr Leu Ile Glu
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Ile Asn Pro Gly Ser Gly Gly Thr Asn Tyr Asn Glu Lys Phe Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Arg Gly Asp Gly Tyr Tyr Ala Tyr Phe Asp Val
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Asn Tyr Leu Ile Glu
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Tyr Ala Phe Thr Asn Tyr
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asn Pro Gly Ser Gly Gly
1               5

<210> SEQ ID NO 7
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Met
            35                  40                  45

Gly Val Ile Asn Pro Gly Ser Gly Gly Thr Asn Tyr Asn Glu Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Arg Gly Asp Gly Tyr Tyr Ala Tyr Phe Asp Val Trp Gly
            100                 105                 110

Gln Gly Thr Thr Val Thr Val Ser Ser
        115                 120

<210> SEQ ID NO 8
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
caagtgcagc tggtgcagtc tggcgctgaa gtgaagaaac ccggctcctc cgtgaaagtg    60
tcctgcaagg cctccggcta cgccttcacc aactacctga tcgagtgggt ccgacaggcc   120
ccaggccagg gcctggagtg gatgggcgtg atcaaccctg ctccggcgg caccaactac   180
aacgagaagt tcaagggcag agtgaccatc accgccgaca gtccacctc caccgcctac   240
atggaactgt cctccctgcg gagcgaggac accgccgtgt actactgtgc ccggtggcgg   300
ggagatggct actacgccta cttcgacgtg tggggccagg gcaccaccgt gaccgtgtcc   360
tct                                                                  363
```

<210> SEQ ID NO 9
<211> LENGTH: 121
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 9

```
Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Lys Gly Leu Glu Trp Val
        35                  40                  45

Ala Val Ile Asn Pro Gly Ser Gly Gly Thr Asn Tyr Asn Glu Lys Phe
    50                  55                  60

Lys Gly Arg Phe Thr Ile Ser Ala Asp Lys Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Arg Gly Asp Gly Tyr Tyr Ala Tyr Phe Asp Val Trp Gly
            100                 105                 110

Gln Gly Thr Thr Val Thr Val Ser Ser
        115                 120
```

<210> SEQ ID NO 10
<211> LENGTH: 363
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 10

```
caggtgcagc tggtggagag cggcggcggc gtggtgcagc ccggccggag cctgcggctg    60
agctgcgccg ccagcggcta cgccttcacc aactacctga tcgagtgggt gcggcaggcc   120
cccggcaagg gcctggagtg ggtggccgtg atcaaccccg cagcggcgg caccaactac   180
aacgagaagt tcaagggccg gttcaccatc agcgccgaca gagcaagag caccgcctac   240
ctgcagatga acagcctgcg ggccgaggac accgccgtgt actactgcgc ccggtggcgg   300
ggcgacggct actacgccta cttcgacgtg tggggccagg gcaccaccgt gaccgtgagc   360
agc                                                                  363
```

<210> SEQ ID NO 11
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Tyr Thr Phe Ser Ser Tyr Leu Ile Glu
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Ile Asn Pro Gly Ser Gly Gly Thr Asn Tyr Ala Asp Ser Val Lys
1               5                   10                  15

Gly

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Tyr Leu Ile Glu
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Tyr Thr Phe Ser Ser Tyr
1               5

<210> SEQ ID NO 15
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Thr Phe Ser Ser Tyr
            20                  25                  30

Leu Ile Glu Trp Val Arg Gln Ala Pro Gly Lys Gly Leu Glu Trp Val
        35                  40                  45

Ala Val Ile Asn Pro Gly Ser Gly Gly Thr Asn Tyr Ala Asp Ser Val
    50                  55                  60

Lys Gly Arg Phe Thr Ile Ser Ala Asp Lys Ser Lys Asn Thr Ala Tyr
```

```
                65                  70                  75                  80
Leu Gln Met Asn Ser Leu Arg Ala Glu Asp Thr Ala Val Tyr Tyr Cys
                    85                  90                  95

Ala Arg Trp Arg Gly Asp Gly Tyr Tyr Ala Tyr Phe Asp Val Trp Gly
            100                 105                 110

Gln Gly Thr Thr Val Thr Val Ser Ser
        115                 120

<210> SEQ ID NO 16
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
caggtgcaat tggtggaaag cggcggaggc gtggtgcagc ctggaagaag cctgagactg      60
agctgtgccg ccagcggcta caccttcagc agctacctga tcgagtgggt gcgccaggcc     120
cctggcaaag gactggaatg ggtggccgtg atcaaccctg gcagcggcgg caccaattac     180
gccgatagcg tgaagggccg gttcaccatc agcgccgaca gagcaagaa caccgcctac     240 ctccagatga acagcctgcg ggccgaggac accgccgtgt actattgtgc tcggtggcgg     300
ggagatggct actacgccta cttcgacgtg tggggccagg gcaccacagt gaccgtcagc     360
tca                                                                   363

<210> SEQ ID NO 17
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Thr Asn Tyr
            20                  25                  30

Leu Ile Glu Trp Val Arg Gln Met Pro Gly Lys Gly Leu Glu Trp Met
        35                  40                  45

Gly Val Ile Asn Pro Gly Ser Gly Gly Thr Asn Tyr Asn Glu Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                    85                  90                  95

Ala Arg Trp Arg Gly Asp Gly Tyr Tyr Ala Tyr Phe Asp Val Trp Gly
            100                 105                 110

Gln Gly Thr Thr Val Thr Val Ser Ser
        115                 120

<210> SEQ ID NO 18
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 18
gaagtgcagc tggtgcagtc tggcgctgaa gtgaagaagc ccggcgagtc cctgaagatc      60
tcctgcaagg gctccggcta cgccttcacc aactacctga tcgagtgggt ccgacagatg     120
cccggcaagg gcctggagtg gatgggcgtg atcaacccg gctccggcgg caccaactac      180
aacgagaagt tcaagggcca agtcacaatc tccgccgaca agtccatctc caccgcctac     240
ctgcagtggt cctccctgaa ggcctccgac accgccatgt actactgcgc cagatggcgg     300
ggagatggct actacgccta cttcgacgtg tggggccagg gcaccaccgt gaccgtgtcc     360
tct                                                                   363

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Ala Ser Gln Ser Val Asp Tyr Asp Gly Asp Ser Tyr Met Asn
1               5                   10                  15

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Ala Ser Asn Leu Glu Ser
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Gln Ser Asn Glu Asp Pro Tyr Thr
1               5

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Gln Ser Val Asp Tyr Asp Gly Asp Ser Tyr
1               5                   10

<210> SEQ ID NO 23
<211> LENGTH: 3
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 23

Ala Ala Ser
1

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Asn Glu Asp Pro Tyr
1               5

<210> SEQ ID NO 25
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Ile Arg Leu Thr Gln Ser Pro Ser Ser Phe Ser Ala Ser Thr Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Ser Glu Asp Phe Ala Thr Tyr Tyr Cys Gln Gln Ser Asn
                85                  90                  95

Glu Asp Pro Tyr Thr Phe Gly Gly Gly Thr Lys Val Glu Ile Lys
            100                 105                 110

<210> SEQ ID NO 26
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
gccatcagac tgacccagag cccctccagc ttctccgcct ccaccggcga cagagtgacc      60
atcacatgca aggcctccca gtccgtggac tacgacggcg actcctacat gaactggtat     120
cagcagaagc ccggcaaggc ccctaagctg ctgatctacg ccgcctccaa cctggaatcc     180
ggcgtgccct ccggttctc cggctctggc tctggcaccg acttcaccct gaccatctcc     240
agcctgcagt ccgaggactt cgccacctac tactgccagc agtccaacga ggacccctac     300
accttcggcg gaggcaccaa agtggaaatc aag                                  333

<210> SEQ ID NO 27

```
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27
```

Asp Ile Val Leu Thr Gln Ser Pro Leu Ser Leu Pro Val Thr Leu Gly
1               5                   10                  15

Gln Pro Ala Ser Ile Ser Cys Lys Ala Ser Gln Ser Val Asp Tyr Asp
            20                  25                  30

Gly Asp Ser Tyr Met Asn Trp Tyr Gln Gln Arg Pro Gly Gln Ser Pro
        35                  40                  45

Arg Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Asn
                85                  90                  95

Glu Asp Pro Tyr Thr Phe Gly Gly Gly Thr Lys Val Glu Ile Lys
            100                 105                 110

```
<210> SEQ ID NO 28
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gacatcgtgc tgacacagag ccctctgtcc ctgcccgtga ccctgggcca gcctgcctcc     60
atctcctgca aggcctccca gtccgtggac tacgacggcg actcctacat gaactggtat    120
cagcagcggc ctggccagtc ccctcggctg ctgatctacg ccgcctccaa cctggaatcc    180
ggcgtgcccg acagattctc cggctccggc tctggcaccg acttcaccct gaagatctcc    240
cgggtggaag ccgaggacgt gggcgtgtac tactgccagc agtccaacga ggaccoctac    300 accttcggcg gaggcaccaa agtggaaatc aag                                 333

<210> SEQ ID NO 29
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29
```

Glu Ile Val Leu Thr Gln Ser Pro Ala Thr Leu Ser Val Ser Pro Gly
1               5                   10                  15

Glu Arg Ala Thr Leu Ser Cys Lys Ala Ser Gln Ser Val Asp Tyr Asp
            20                  25                  30

Gly Asp Ser Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Glu Phe Thr Leu Thr Ile Ser
65                  70                  75                  80

```
Ser Leu Gln Ser Glu Asp Ala Ala Val Tyr Tyr Cys Gln Gln Ser Asn
                85                  90                  95

Glu Asp Pro Tyr Thr Phe Gly Gly Gly Thr Lys Val Glu Ile Lys
            100                 105                 110

<210> SEQ ID NO 30
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gagatcgtgc tgacccagag ccccgccacc ctgagcgtga gccccggcga gcgggccacc       60
ctgagctgca aggccagcca gagcgtggac tacgacggcg acagctacat gaactggtac      120
cagcagaagc ccggccaggc cccccggctg ctgatctacg ccgccagcaa cctggagagc      180
ggcatccccg cccggttcag cggcagcggc agcggcaccg agttcaccct gaccatcagc      240
agcctgcaga gcgaggacgc cgccgtgtac tactgccagc agagcaacga ggacccctac      300
accttcggcg cggcaccaa ggtggagatc aag                                    333

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Ala Ser Gln Ser Val Ser Tyr Asp Gly Asp Ser Tyr Met Asn
1               5                   10                  15

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Ala Ser Asn Leu Ala Ser
1               5

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Gln Ser Val Ser Tyr Asp Gly Asp Ser Tyr
1               5                   10

<210> SEQ ID NO 34
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 34

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Tyr Asp
            20                  25                  30

Gly Asp Ser Tyr Met Asn Trp Tyr Gln Gln Lys Pro Gly Gln Ala Pro
        35                  40                  45

Arg Leu Leu Ile Tyr Ala Ala Ser Asn Leu Ala Ser Gly Ile Pro Ala
    50                  55                  60

Arg Phe Ser Gly Ser Gly Ser Gly Thr Glu Phe Thr Leu Thr Ile Ser
65                  70                  75                  80

Ser Leu Gln Ser Glu Asp Ala Ala Val Tyr Tyr Cys Gln Gln Ser Asn
                85                  90                  95

Glu Asp Pro Tyr Thr Phe Gly Gly Gly Thr Lys Val Glu Ile Lys
            100                 105                 110

<210> SEQ ID NO 35
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
gaaatcgtgc tgacccagag ccctgccacc ctgagtgtgt ctccaggcga gagagccaca      60
ctgagctgta gagccagcca gagcgtgtcc tacgacggcg acagctacat gaactggtat     120
cagcagaagc ccggccaggc ccccagactg ctgatctacg ccgcttccaa tctggccagc     180
ggcatccccg ccagattttc cggctctggc tccggcaccg agttcaccct gacaatcagc     240
agcctccaga gcgaggacgc cgccgtgtac tactgccagc agagcaacga ggaccectac     300 acctttggcg gaggcaccaa ggtggaaatc aag                                   333

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Trp Arg Gly Glu Gly Tyr Tyr Ala Tyr Phe Asp Val
1               5                   10

<210> SEQ ID NO 37
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met

```
                35                  40                  45

Gly Val Ile Asn Pro Gly Ser Gly Gly Thr Asn Tyr Asn Glu Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Arg Gly Glu Gly Tyr Tyr Ala Tyr Phe Asp Val Trp Gly
            100                 105                 110

Gln Gly Thr Thr Val Thr Val Ser Ser
            115                 120
```

<210> SEQ ID NO 38
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38

```
caagtgcagc tggtgcagtc tggcgctgaa gtgaagaaac ccggctcctc cgtgaaagtg     60
tcctgcaagg cctccggcta cgccttcacc aactacctga tcgagtgggt ccgacaggcc    120
ccaggccagg gcctggagtg gatgggcgtg atcaaccctg gctccggcgg caccaactac    180
aacgagaagt tcaagggcag agtgaccatc accgccgaca gtccacctc accgcctac     240 atggaactgt cctccctgcg gagcgaggac accgccgtgt actactgcgc cagatggcgg    300
ggagagggct actacgccta cttcgacgtg tggggccagg gcaccaccgt gaccgtgtcc    360
tct                                                                  363
```

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

```
Trp Arg Gly Asp Ala Tyr Tyr Ala Tyr Phe Asp Val
1               5                   10
```

<210> SEQ ID NO 40
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Lys Phe
    50                  55                  60
```

```
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Arg Gly Asp Ala Tyr Tyr Ala Tyr Phe Asp Val Trp Gly
            100                 105                 110

Gln Gly Thr Thr Val Thr Val Ser Ser
        115                 120

<210> SEQ ID NO 41
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
caagtgcagc tggtgcagtc tggcgctgaa gtgaagaaac ccggctcctc cgtgaaagtg      60
tcctgcaagg cctccggcta cgccttcacc aactacctga tcgagtgggt ccgacaggcc    120
ccaggccagg gcctggagtg gatgggcgtg atcaaccctg gctccggcgg caccaactac    180
aacgagaagt tcaagggcag agtgaccatc accgccgaca gtccacctc caccgcctac     240 atggaactgt cctccctgcg gagcgaggac accgccgtgt actactgtgc ccggtggcgg    300
ggagatgcct actacgccta cttcgacgtg tggggccagg gcaccaccgt gaccgtgtcc    360
tct                                                                  363

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Trp Arg Gly Gln Gly Tyr Tyr Ala Tyr Phe Asp Val
1               5                   10

<210> SEQ ID NO 43
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Lys Phe
    50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95
```

```
Ala Arg Trp Arg Gly Gln Gly Tyr Tyr Ala Tyr Phe Asp Val Trp Gly
            100                 105                 110

Gln Gly Thr Thr Val Thr Val Ser Ser
        115                 120
```

<210> SEQ ID NO 44
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

```
caagtgcagc tggtgcagtc tggcgctgaa gtgaagaaac ccggctcctc cgtgaaagtg    60
tcctgcaagg cctccggcta cgccttcacc aactacctga tcgagtgggt ccgacaggcc   120
ccaggccagg gcctggagtg gatgggcgtg atcaaccctg ctccggcgg caccaactac    180 aacgagaagt tcaagggcag agtgaccatc accgccgaca gtccacctc caccgcctac    240 atggaactgt cctccctgcg gagcgaggac accgccgtgt actactgcgc cagatggcgg   300
ggacagggct actacgccta cttcgacgtg tggggccagg gcaccaccgt gaccgtgtcc   360
tct                                                                 363
```

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Trp Arg Gly Ser Gly Tyr Tyr Ala Tyr Phe Asp Val
1               5                   10
```

<210> SEQ ID NO 46
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Arg Gly Ser Gly Tyr Tyr Ala Tyr Phe Asp Val Trp Gly
            100                 105                 110

Gln Gly Thr Thr Val Thr Val Ser Ser
        115                 120
```

<210> SEQ ID NO 47
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47

```
caagtgcagc tggtgcagtc tggcgctgaa gtgaagaaac ccggctcctc cgtgaaagtg      60
tcctgcaagg cctccggcta cgccttcacc aactacctga tcgagtgggt ccgacaggcc     120
ccaggccagg gcctggagtg gatgggcgtg atcaaccctg gctccggcgg caccaactac     180
aacgagaagt tcaagggcag agtgaccatc accgccgaca gtccacctc caccgcctac     240
atggaactgt cctccctgcg gagcgaggac accgccgtgt actactgcgc cagatggcgg     300
ggatctggct actacgccta cttcgacgtg tggggccagg gcaccaccgt gaccgtgtcc     360
tct                                                                   363
```

<210> SEQ ID NO 48
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

```
Gln Val Gln Leu Val Glu Ser Gly Gly Gly Val Val Gln Pro Gly Arg
1               5                   10                  15
Ser Leu Arg Leu Ser Cys Ala Ala Ser Gly Tyr Ala Phe Thr Asn Tyr
            20                  25                  30
Leu Ile Glu Trp Val Arg Gln Ala Pro Gly Lys Gly Leu Glu Trp Val
        35                  40                  45
Ala Val Ile Asn Pro Gly Ser Gly Gly Thr Asn Tyr Asn Glu Lys Phe
    50                  55                  60
Lys Gly Arg Phe Thr Ile Ser Ala Asp Lys Ser Lys Ser Thr Ala Tyr
65                  70                  75                  80
Leu Gln Met Asn Ser Leu Arg Ala Glu Asp Thr Ala Val Tyr Tyr Cys
                85                  90                  95
Ala Arg Trp Arg Gly Glu Gly Tyr Tyr Ala Tyr Phe Asp Val Trp Gly
            100                 105                 110
Gln Gly Thr Thr Val Thr Val Ser Ser
        115                 120
```

<210> SEQ ID NO 49
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

```
Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ala Phe Thr Asn Tyr
            20                  25                  30
```

Leu Ile Glu Trp Val Arg Gln Met Pro Gly Lys Gly Leu Glu Trp Met
            35                  40                  45

Gly Val Ile Asn Pro Gly Ser Gly Thr Asn Tyr Asn Glu Lys Phe
 50                  55                  60

Lys Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Trp Arg Gly Glu Gly Tyr Tyr Ala Tyr Phe Asp Val Trp Gly
             100                 105                 110

Gln Gly Thr Thr Val Thr Val Ser Ser
             115                 120

<210> SEQ ID NO 50
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
gaagtgcagc tggtgcagtc tggcgctgaa gtgaagaagc ccggcgagtc cctgaagatc      60
tcctgcaagg ctccggcta cgccttcacc aactacctga tcgagtgggt ccgacagatg     120
cccggcaagg gcctggagtg gatgggcgtg atcaaccccg gctccggcgg caccaactac     180
aacgagaagt tcaagggcca agtcacaatc tccgccgaca gtccatctc caccgcctac     240 ctgcagtggt cctccctgaa ggcctccgac accgccatgt actactgcgc cagatggcgg     300
ggagagggct actacgccta cttcgacgtg tggggccagg gcaccaccgt gaccgtgtcc     360
tct                                                                  363

<210> SEQ ID NO 51
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Val Glu Ser Gly Gly Gly Val Val Gln Pro Gly Arg
 1               5                  10                  15

Ser Leu Arg Leu Ser Cys Ala Ala Ser Gly Tyr Ala Phe Thr Asn Tyr
             20                  25                  30

Leu Ile Glu Trp Val Arg Gln Ala Pro Gly Lys Gly Leu Glu Trp Val
             35                  40                  45

Ala Val Ile Asn Pro Gly Ser Gly Gly Thr Asn Tyr Asn Glu Lys Phe
 50                  55                  60

Lys Gly Arg Phe Thr Ile Ser Ala Asp Lys Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Arg Trp Arg Gly Asp Ala Tyr Tyr Ala Tyr Phe Asp Val Trp Gly
             100                 105                 110

Gln Gly Thr Thr Val Thr Val Ser Ser
             115                 120

```
<210> SEQ ID NO 52
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
caggtgcagc tggtggagag cggcggcggc gtggtgcagc ccggccggag cctgcggctg      60
agctgcgccg ccagcggcta cgccttcacc aactacctga tcgagtgggt gcggcaggcc     120
cccggcaagg gcctggagtg ggtggccgtg atcaaccccg gcagcggcgg caccaactac     180
aacgagaagt tcaagggccg gttcaccatc agcgccgaca gagcaagag caccgcctac      240 ctgcagatga acagcctgcg ggccgaggac accgccgtgt actactgcgc ccggtggcgg     300
ggcgacgcct actacgccta cttcgacgtg tggggccagg gcaccaccgt gaccgtgagc     360
agc                                                                   363

<210> SEQ ID NO 53
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Lys Gly Leu Glu Trp Val
        35                  40                  45

Ala Val Ile Asn Pro Gly Ser Gly Gly Thr Asn Tyr Asn Glu Lys Phe
    50                  55                  60

Lys Gly Arg Phe Thr Ile Ser Ala Asp Lys Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Arg Gly Asp Ala Tyr Tyr Ala Tyr Phe Asp Val Trp Gly
            100                 105                 110

Gln Gly Thr Thr Val Thr Val Ser Ser
        115                 120

<210> SEQ ID NO 54
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
caggtgcagc tggtggagag cggcggcggc gtggtgcagc ccggccggag cctgcggctg      60
agctgcgccg ccagcggcta cgccttcacc aactacctga tcgagtgggt gcggcaggcc     120
cccggcaagg gcctggagtg ggtggccgtg atcaaccccg gcagcggcgg caccaactac     180
aacgagaagt tcaagggccg gttcaccatc agcgccgaca gagcaagag caccgcctac      240 ctgcagatga acagcctgcg ggccgaggac accgccgtgt actactgcgc ccggtggcgg     300
```

```
ggccagggct actacgccta cttcgacgtg tggggccagg gcaccaccgt gaccgtgagc      360
agc                                                                    363
```

<210> SEQ ID NO 55
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Lys Gly Leu Glu Trp Val
        35                  40                  45

Ala Val Ile Asn Pro Gly Ser Gly Gly Thr Asn Tyr Asn Glu Lys Phe
    50                  55                  60

Lys Gly Arg Phe Thr Ile Ser Ala Asp Lys Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Arg Gly Ser Gly Tyr Tyr Ala Tyr Phe Asp Val Trp Gly
            100                 105                 110

Gln Gly Thr Thr Val Thr Val Ser Ser
        115                 120
```

<210> SEQ ID NO 56
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
caggtgcagc tggtggagag cggcggcggc gtggtgcagc ccggccggag cctgcggctg      60
agctgcgccg ccagcggcta cgccttcacc aactacctga tcgagtgggt gcggcaggcc     120
cccggcaagg gcctggagtg ggtggccgtg atcaaccccg gcagcggcgg caccaactac     180
aacgagaagt tcaagggccg gttcaccatc agcgccgaca agagcaagag caccgcctac     240
ctgcagatga acagcctgcg ggccgaggac accgccgtgt actactgcgc ccggtggcgg     300
ggcagcggct actacgccta cttcgacgtg tggggccagg gcaccaccgt gaccgtgagc     360
agc                                                                    363
```

<210> SEQ ID NO 57
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Tyr Thr Phe Ser Ser Tyr
            20                  25                  30

Leu Ile Glu Trp Val Arg Gln Ala Pro Gly Lys Gly Leu Glu Trp Val
        35                  40                  45

Ala Val Ile Asn Pro Gly Ser Gly Gly Thr Asn Tyr Ala Asp Ser Val
    50                  55                  60

Lys Gly Arg Phe Thr Ile Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Arg Gly Glu Gly Tyr Tyr Ala Tyr Phe Asp Val Trp Gly
            100                 105                 110

Gln Gly Thr Thr Val Thr Val Ser Ser
            115                 120
```

<210> SEQ ID NO 58
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58

```
caggtgcaat tggtggaaag cggcggaggc gtggtgcagc ctggaagaag cctgagactg      60
agctgtgccg ccagcggcta caccttcagc agctacctga tcgagtgggt gcgccaggcc     120
cctggcaaag gactggaatg ggtggccgtg atcaaccctg gcagcggcgg caccaattac     180
gccgatagcg tgaagggccg gttcaccatc agcgccgaca agagcaagaa caccgcctac     240
ctccagatga acagcctgcg ggccgaggac accgccgtgt actattgtgc tcggtggcgg     300
ggagagggct actacgccta cttcgacgtg tggggccagg caccacagt gaccgtcagc      360 tca                                                                   363
```

<210> SEQ ID NO 59
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

```
Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Thr Phe Ser Ser Tyr
            20                  25                  30

Leu Ile Glu Trp Val Arg Gln Ala Pro Gly Lys Gly Leu Glu Trp Val
        35                  40                  45

Ala Val Ile Asn Pro Gly Ser Gly Gly Thr Asn Tyr Ala Asp Ser Val
    50                  55                  60

Lys Gly Arg Phe Thr Ile Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Arg Gly Asp Ala Tyr Tyr Ala Tyr Phe Asp Val Trp Gly
            100                 105                 110

Gln Gly Thr Thr Val Thr Val Ser Ser
```

<210> SEQ ID NO 60
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
caggtgcaat tggtggaaag cggcggaggc gtggtgcagc ctggaagaag cctgagactg    60
agctgtgccg ccagcggcta ccttcagc agctacctga tcgagtgggt gcgccaggcc    120
cctggcaaag gactggaatg ggtggccgtg atcaaccctg gcagcggcgg caccaattac    180
gccgatagcg tgaagggccg gttcaccatc agcgccgaca agagcaagaa caccgcctac    240
ctccagatga acagcctgcg ggccgaggac accgccgtgt actattgtgc tcggtggcgg    300
ggagatgcct actacgccta cttcgacgtg tggggccagg gcaccacagt gaccgtcagc    360
tca    363

<210> SEQ ID NO 61
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Thr Phe Ser Ser Tyr
            20                  25                  30

Leu Ile Glu Trp Val Arg Gln Ala Pro Gly Lys Gly Leu Glu Trp Val
        35                  40                  45

Ala Val Ile Asn Pro Gly Ser Gly Gly Thr Asn Tyr Ala Asp Ser Val
    50                  55                  60

Lys Gly Arg Phe Thr Ile Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Arg Gly Gln Gly Tyr Tyr Ala Tyr Phe Asp Val Trp Gly
            100                 105                 110

Gln Gly Thr Thr Val Thr Val Ser Ser
        115                 120

<210> SEQ ID NO 62
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
caggtgcaat tggtggaaag cggcggaggc gtggtgcagc ctggaagaag cctgagactg    60
agctgtgccg ccagcggcta ccttcagc agctacctga tcgagtgggt gcgccaggcc    120
cctggcaaag gactggaatg ggtggccgtg atcaaccctg gcagcggcgg caccaattac    180

```
gccgatagcg tgaagggccg gttcaccatc agcgccgaca agagcaagaa caccgcctac    240
ctccagatga acagcctgcg ggccgaggac accgccgtgt actattgtgc tcggtggcgg    300
ggacagggct actacgccta cttcgacgtg tggggccagg gcaccacagt gaccgtcagc    360
tca                                                                 363
```

<210> SEQ ID NO 63
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Thr Phe Ser Ser Tyr
                20                  25                  30

Leu Ile Glu Trp Val Arg Gln Ala Pro Gly Lys Gly Leu Glu Trp Val
            35                  40                  45

Ala Val Ile Asn Pro Gly Ser Gly Gly Thr Asn Tyr Ala Asp Ser Val
        50                  55                  60

Lys Gly Arg Phe Thr Ile Ser Ala Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Arg Gly Ser Gly Tyr Tyr Ala Tyr Phe Asp Val Trp Gly
            100                 105                 110

Gln Gly Thr Thr Val Thr Val Ser Ser
        115                 120
```

<210> SEQ ID NO 64
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

```
caggtgcaat tggtggaaag cggcggaggc gtggtgcagc ctggaagaag cctgagactg    60
agctgtgccg ccagcggcta caccttcagc agctacctga tcgagtgggt gcgccaggcc    120
cctggcaaag gactggaatg ggtggccgtg atcaaccctg gcagcggcgg caccaattac    180
gccgatagcg tgaagggccg gttcaccatc agcgccgaca agagcaagaa caccgcctac    240
ctccagatga acagcctgcg ggccgaggac accgccgtgt actattgtgc tcggtggcgg    300
ggaagcggct actacgccta cttcgacgtg tggggccagg gcaccacagt gaccgtcagc    360
tca                                                                 363
```

<210> SEQ ID NO 65
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Thr Asn Tyr
            20                  25                  30

Leu Ile Glu Trp Val Arg Gln Met Pro Gly Lys Gly Leu Glu Trp Met
            35                  40                  45

Gly Val Ile Asn Pro Gly Ser Gly Gly Thr Asn Tyr Asn Glu Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Arg Gly Asp Ala Tyr Tyr Ala Tyr Phe Asp Val Trp Gly
            100                 105                 110

Gln Gly Thr Thr Val Thr Val Ser Ser
            115                 120

<210> SEQ ID NO 66
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
gaggtgcaat tggtgcagag cggagccgaa gtgaagaagc ccggcgagag cctgaagatc      60
agctgcaagg gcagcggcta cgccttcacc aactacctga tcgagtgggt gcgccagatg     120
cccggcaagg gcctggaatg gatgggcgtg atcaatcctg gcagcggcgg caccaattac     180
aacgagaagt tcaagggcca agtgaccatc agcgccgaca gagcatcag caccgcctac      240 ctccagtggt ccagcctgaa ggccagcgac accgccatgt actactgcgc caggtggcgg     300
ggagatgcct actacgccta cttcgacgtg tggggccagg gcaccacagt gaccgtcagc     360
tca                                                                  363

<210> SEQ ID NO 67
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Thr Asn Tyr
            20                  25                  30

Leu Ile Glu Trp Val Arg Gln Met Pro Gly Lys Gly Leu Glu Trp Met
            35                  40                  45

Gly Val Ile Asn Pro Gly Ser Gly Gly Thr Asn Tyr Asn Glu Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Arg Gly Gln Gly Tyr Tyr Ala Tyr Phe Asp Val Trp Gly

```
                    100                 105                 110
Gln Gly Thr Thr Val Thr Val Ser Ser
        115                 120

<210> SEQ ID NO 68
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
gaggtgcaat tggtgcagag cggagccgaa gtgaagaagc ccggcgagag cctgaagatc      60
agctgcaagg gcagcggcta cgccttcacc aactacctga tcgagtgggt gcgccagatg     120
cccggcaagg gcctggaatg gatgggcgtg atcaatcctg cagcggcgg caccaattac      180 aacgagaagt tcaagggcca agtgaccatc agcgccgaca agagcatcag caccgcctac     240
ctccagtggt ccagcctgaa ggccagcgac accgccatgt actactgcgc caggtggcgg     300
ggacagggct actacgccta cttcgacgtg tggggccagg gcaccacagt gaccgtcagc     360
tca                                                                   363

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Ala Ser Gln Ser Val Asp Tyr Gln Gly Asp Ser Tyr Met Asn
1               5                  10                  15

<210> SEQ ID NO 70
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ala Ile Arg Leu Thr Gln Ser Pro Ser Ser Phe Ser Ala Ser Thr Gly
1               5                  10                  15

Asp Arg Val Thr Ile Thr Cys Lys Ala Ser Gln Ser Val Asp Tyr Gln
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Ser Glu Asp Phe Ala Thr Tyr Tyr Cys Gln Gln Ser Asn
                85                  90                  95

Glu Asp Pro Tyr Thr Phe Gly Gly Gly Thr Lys Val Glu Ile Lys
            100                 105                 110

<210> SEQ ID NO 71
<211> LENGTH: 333
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71

```
gccatcagac tgacccagag cccctccagc ttctccgcct ccaccggcga cagagtgacc    60
atcacatgca aggcctccca gtccgtggac taccagggcg actcctacat gaactggtat   120
cagcagaagc ccggcaaggc ccctaagctg ctgatctacg ccgcctccaa cctggaatcc   180
ggcgtgccct cccggttctc cggctctggc tctggcaccg acttcaccct gaccatctcc   240
agcctgcagt ccgaggactt cgccacctac tactgccagc agtccaacga ggaccctac    300 accttcggcg gaggcaccaa agtggaaatc aag                                333
```

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Lys Ala Ser Gln Ser Val Asp Tyr Asp Ala Asp Ser Tyr Met Asn
1               5                   10                  15

<210> SEQ ID NO 73
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Ala Ile Arg Leu Thr Gln Ser Pro Ser Ser Phe Ser Ala Ser Thr Gly
1               5                   10                  15

Asp Arg Val Thr Ile Thr Cys Lys Ala Ser Gln Ser Val Asp Tyr Asp
            20                  25                  30

Ala Asp Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Ser Glu Asp Phe Ala Thr Tyr Tyr Cys Gln Gln Ser Asn
                85                  90                  95

Glu Asp Pro Tyr Thr Phe Gly Gly Gly Thr Lys Val Glu Ile Lys
            100                 105                 110

<210> SEQ ID NO 74
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
gacatcgtgc tgacacagag ccctctgtcc ctgccgtga ccctgggcca gcctgcctcc    60
```

```
atctcctgca aggcctccca gtccgtggac tacgacgccg actcctacat gaactggtat      120
cagcagcggc ctggccagtc ccctcggctg ctgatctacg ccgcctccaa cctggaatcc      180
ggcgtgcccg acagattctc cggctccggc tctggcaccg acttcaccct gaagatctcc      240
cgggtggaag ccgaggacgt gggcgtgtac tactgccagc agtccaacga ggacccctac      300
accttcggcg gaggcaccaa agtggaaatc aag                                   333
```

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ser Gln Ser Val Asp Tyr Gln Gly Asp Ser Tyr
1               5                   10

<210> SEQ ID NO 76
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Ile Val Leu Thr Gln Ser Pro Ala Thr Leu Ser Val Ser Pro Gly
1               5                   10                  15

Glu Arg Ala Thr Leu Ser Cys Lys Ala Ser Gln Ser Val Asp Tyr Gln
            20                  25                  30

Gly Asp Ser Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Glu Phe Thr Leu Thr Ile Ser
65                  70                  75                  80

Ser Leu Gln Ser Glu Asp Ala Ala Val Tyr Tyr Cys Gln Gln Ser Asn
                85                  90                  95

Glu Asp Pro Tyr Thr Phe Gly Gly Gly Thr Lys Val Glu Ile Lys
            100                 105                 110

<210> SEQ ID NO 77
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

```
gaaatcgtgc tgacccagag ccctgccacc ctgagtgtgt ctccaggcga gagagccaca      60
ctgagctgta aagccagcca gagcgtgtcc taccagggcg acagctacat gaactggtat      120
cagcagaagc ccggccaggc ccccagactg ctgatctacg ccgcttccaa tctggccagc      180
ggcatccccg ccagatttt cggctctggc tccggcaccg agttcaccct gacaatcagc      240
agcctccaga gcgaggacgc cgccgtgtac tactgccagc agagcaacga ggacccctac      300
acctttggcg gaggcaccaa ggtggaaatc aag                                   333
```

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ser Gln Ser Val Asp Tyr Asp Ala Asp Ser Tyr
1               5                   10

<210> SEQ ID NO 79
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Asp Ile Val Leu Thr Gln Ser Pro Leu Ser Leu Pro Val Thr Leu Gly
1               5                   10                  15

Gln Pro Ala Ser Ile Ser Cys Lys Ala Ser Gln Ser Val Asp Tyr Gln
            20                  25                  30

Gly Asp Ser Tyr Met Asn Trp Tyr Gln Gln Arg Pro Gly Gln Ser Pro
        35                  40                  45

Arg Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Asn
                85                  90                  95

Glu Asp Pro Tyr Thr Phe Gly Gly Gly Thr Lys Val Glu Ile Lys
            100                 105                 110

<210> SEQ ID NO 80
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
gagatcgtgc tgacccagag ccccgccacc ctgagcgtga gccccggcga gcgggccacc      60
ctgagctgca aggccagcca gagcgtggac taccagggcg acagctacat gaactggtac     120
cagcagaagc ccggccaggc ccccggctg ctgatctacg ccgccagcaa cctggagagc      180
ggcatccccg cccggttcag cggcagcggc agcggcaccg agttcaccct gaccatcagc     240
agcctgcaga gcgaggacgc cgccgtgtac tactgccagc agagcaacga ggaccccctac   300 accttcggcg gcggcaccaa ggtggagatc aag                                 333

<210> SEQ ID NO 81
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

```
Asp Ile Val Leu Thr Gln Ser Pro Leu Ser Leu Pro Val Thr Leu Gly
1               5                   10                  15

Gln Pro Ala Ser Ile Ser Cys Lys Ala Ser Gln Ser Val Asp Tyr Asp
            20                  25                  30

Ala Asp Ser Tyr Met Asn Trp Tyr Gln Gln Arg Pro Gly Gln Ser Pro
        35                  40                  45

Arg Leu Leu Ile Tyr Ala Ala Ser Asn Leu Glu Ser Gly Val Pro Asp
50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Asn
                85                  90                  95

Glu Asp Pro Tyr Thr Phe Gly Gly Gly Thr Lys Val Glu Ile Lys
            100                 105                 110
```

<210> SEQ ID NO 82
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

```
gagatcgtgc tgacccagag ccccgccacc ctgagcgtga gccccggcga gcgggccacc    60
ctgagctgca aggccagcca gagcgtggac tacgacgccg acagctacat gaactggtac   120
cagcagaagc ccggccaggc ccccggctg ctgatctacg ccgccagcaa cctggagagc    180
ggcatccccg cccggttcag cggcagcggc agcggcaccg agttcaccct gaccatcagc    240
agcctgcaga gcgaggacgc cgccgtgtac tactgccagc agagcaacga ggacccctac    300
accttcggcg gcggcaccaa ggtggagatc aag                                 333
```

<210> SEQ ID NO 83

<400> SEQUENCE: 83

000

<210> SEQ ID NO 84
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

```
Glu Ile Val Leu Thr Gln Ser Pro Ala Thr Leu Ser Val Ser Pro Gly
1               5                   10                  15

Glu Arg Ala Thr Leu Ser Cys Lys Ala Ser Gln Ser Val Asp Tyr Asp
            20                  25                  30

Ala Asp Ser Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
50                  55                  60

Arg Phe Ser Gly Ser Gly Ser Gly Thr Glu Phe Thr Leu Thr Ile Ser
65                  70                  75                  80

Ser Leu Gln Ser Glu Asp Ala Ala Val Tyr Tyr Cys Gln Gln Ser Asn
```

```
                    85                  90                  95

Glu Asp Pro Tyr Thr Phe Gly Gly Gly Thr Lys Val Glu Ile Lys
                100                 105                 110

<210> SEQ ID NO 85
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
gaaatcgtgc tgacccagag ccctgccacc ctgagtgtgt ctccaggcga gagagccaca       60
ctgagctgta gagccagcca gagcgtgtcc tacgacgccg acagctacat gaactggtat      120
cagcagaagc ccggccaggc ccccagactg ctgatctacg ccgcttccaa tctggccagc      180
ggcatccccg ccagattttc cggctctggc tccggcaccg agttcaccct gacaatcagc      240
agcctccaga gcgaggacgc cgccgtgtac tactgccagc agagcaacga gacccctac       300 acctttggcg aggcaccaa ggtggaaatc aag                                    333

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Arg Ala Ser Gln Ser Val Ser Tyr Gln Gly Asp Ser Tyr Met Asn
1               5                  10                  15

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Gln Ser Val Ser Tyr Gln Gly Asp Ser Tyr
1               5                  10

<210> SEQ ID NO 88
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Tyr Gln
            20                  25                  30

Gly Asp Ser Tyr Met Asn Trp Tyr Gln Gln Lys Pro Gly Gln Ala Pro
        35                  40                  45

Arg Leu Leu Ile Tyr Ala Ala Ser Asn Leu Ala Ser Gly Ile Pro Ala
    50                  55                  60
```

```
Arg Phe Ser Gly Ser Gly Ser Gly Thr Glu Phe Thr Leu Thr Ile Ser
 65                  70                  75                  80

Ser Leu Gln Ser Glu Asp Ala Ala Val Tyr Tyr Cys Gln Gln Ser Asn
                 85                  90                  95

Glu Asp Pro Tyr Thr Phe Gly Gly Gly Thr Lys Val Glu Ile Lys
            100                 105                 110
```

```
<210> SEQ ID NO 89
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
gaaatcgtgc tgacccagag ccctgccacc ctgagtgtgt ctccaggcga gagagccaca    60
ctgagctgta gagccagcca gagcgtgtcc taccagggcg acagctacat gaactggtat   120
cagcagaagc ccggccaggc ccccagactg ctgatctacg ccgcttccaa tctggccagc   180
ggcatccccg ccagattttc cggctctggc tccggcaccg agttcaccct gacaatcagc   240
agcctccaga gcgaggacgc cgccgtgtac tactgccagc agagcaacga gggaccctac   300
accttgggcg gaggcaccaa ggtggaaatc aag                                333
```

```
<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Ala Ser Gln Ser Val Ser Tyr Asp Ala Asp Ser Tyr Met Asn
 1               5                  10                  15
```

```
<210> SEQ ID NO 91
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Ile Val Leu Thr Gln Ser Pro Ala Thr Leu Ser Val Ser Pro Gly
 1               5                  10                  15

Glu Arg Ala Thr Leu Ser Cys Arg Ala Ser Gln Ser Val Ser Tyr Asp
                20                  25                  30

Ala Asp Ser Tyr Met Asn Trp Tyr Gln Gln Lys Pro Gly Gln Ala Pro
             35                  40                  45

Arg Leu Leu Ile Tyr Ala Ala Ser Asn Leu Ala Ser Gly Ile Pro Ala
         50                  55                  60

Arg Phe Ser Gly Ser Gly Ser Gly Thr Glu Phe Thr Leu Thr Ile Ser
 65                  70                  75                  80

Ser Leu Gln Ser Glu Asp Ala Ala Val Tyr Tyr Cys Gln Gln Ser Asn
                 85                  90                  95

Glu Asp Pro Tyr Thr Phe Gly Gly Gly Thr Lys Val Glu Ile Lys
            100                 105                 110
```

<210> SEQ ID NO 92
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 92

```
gaaatcgtgc tgacccagag ccctgccacc ctgagtgtgt ctccaggcga gagagccaca      60
ctgagctgta gagccagcca gagcgtgtcc tacgacgccg acagctacat gaactggtat     120
cagcagaagc ccggccaggc ccccagactg ctgatctacg ccgcttccaa tctggccagc     180
ggcatccccg ccagatttc cggctctggc tccggcaccg agttcaccct gacaatcagc     240
agcctccaga gcgaggacgc cgccgtgtac tactgccagc agagcaacga ggacccctac     300
acctttggcg gaggcaccaa ggtggaaatc aag                                  333
```

<210> SEQ ID NO 93
<211> LENGTH: 330
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 93

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr

```
                    245                 250                 255
Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 94
<211> LENGTH: 990
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
gcgtcgacca agggccccag cgtgttcccc ctggccccca gcagcaagag caccagcggc        60
ggcacagccg ccctgggctg cctggtgaag gactacttcc ccgagcccgt gaccgtgtcc       120
tggaacagcg gagccctgac ctccggcgtg cacaccttcc ccgccgtgct gcagagcagc       180
ggcctgtaca gcctgtccag cgtggtgaca gtgcccagca gcagcctggg cacccagacc       240
tacatctgca acgtgaacca caagcccagc aacaccaagg tggacaagag agtggagccc       300
aagagctgcg acaagaccca cacctgcccc cctgcccag ccccagagct gctgggcgga       360 cccctccgtgt tcctgttccc ccccaagccc aaggacaccc tgatgatcag caggaccccc       420
gaggtgacct gcgtggtggt ggacgtgagc cacgaggacc cagaggtgaa gttcaactgg       480
tacgtggacg gcgtggaggt gcacaacgcc aagaccaagc cagagagga gcagtacaac       540 agcacctaca gggtggtgtc cgtgctgacc gtgctgcacc aggactggct gaacggcaag       600
gaatacaagt gcaaggtctc caacaaggcc ctgccagccc ccatcgaaaa gaccatcagc       660
aaggccaagg gccagccacg ggagccccag gtgtacaccc tgccccctc ccgggaggag       720 atgaccaaga accaggtgtc cctgacctgt ctggtgaagg gcttctaccc cagcgacatc       780
gccgtggagt gggagagcaa cggccagccc gagaacaact acaagaccac ccccccagtg       840
ctggacagcg acggcagctt cttcctgtac agcaagctga ccgtggacaa gtccaggtgg       900
cagcagggca acgtgttcag ctgcagcgtg atgcacgagg ccctgcacaa ccactacacc       960
cagaagagcc tgagcctgtc ccccggcaag                                        990

<210> SEQ ID NO 95
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 96
<211> LENGTH: 978
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
gccagcacca agggcccag cgtgttcccc ctggcccct gcagcagaag caccagcgag      60
agcacagccg ccctgggctg cctggtgaag gactacttcc ccgagccagt gaccgtgtcc     120
tggaacagcg gagccctgac cagcggcgtg cacaccttcc ccgccgtgct gcagagcagc    180
ggcctgtaca gcctgtccag cgtggtgacc gtgcccagca gcaacttcgg cacccagacc    240
tacacctgca acgtggacca caagcccagc aacaccaagg tggacaagac cgtggagagg    300
aagtgctgcg tggagtgccc ccctgccca gcccccccag tggccggacc ctccgtgttc    360

-continued

```
ctgttcccc ccaagcccaa ggacaccctg atgatcagca ggaccccga ggtgacctgc    420 gtggtggtgg acgtgagcca cgaggaccca gaggtgcagt tcaactggta cgtggacggc    480
gtggaggtgc acaacgccaa gaccaagccc agagaggaac agtttaacag caccttcagg    540
gtggtgtccg tgctgaccgt ggtgcaccag gactggctga acggcaaaga gtacaagtgc    600
aaggtctcca acaagggcct gccagccccc atcgagaaaa ccatcagcaa gaccaagggc    660
cagccacggg agcccaggt gtacaccctg ccccccagcc gggaggaaat gaccaagaac    720
caggtgtccc tgacctgtct ggtgaagggc ttctacccca gcgacatcgc cgtggagtgg    780
gagagcaacg gccagcccga gaacaactac aagaccaccc ccccatgct ggacagcgac    840 ggcagcttct tcctgtacag caagctgaca gtggacaaga gcaggtggca gcagggcaac    900
gtgttcagct gcagcgtgat gcacgaggcc ctgcacaacc actacaccca gaagagcctg    960
agcctgtccc ccggcaag                                                   978
```

<210> SEQ ID NO 97
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240
```

```
Gln Asp Trp Leu Asn Gly Lys Glu Tyr Lys Cys Lys Val Ser Asn Lys
                245                 250                 255
Ala Leu Pro Ala Pro Ile Glu Lys Thr Ile Ser Lys Thr Lys Gly Gln
        260                 265                 270
Pro Arg Glu Pro Gln Val Tyr Thr Leu Pro Pro Ser Arg Glu Glu Met
    275                 280                 285
Thr Lys Asn Gln Val Ser Leu Thr Cys Leu Val Lys Gly Phe Tyr Pro
290                 295                 300
Ser Asp Ile Ala Val Glu Trp Glu Ser Ser Gly Gln Pro Glu Asn Asn
305                 310                 315                 320
Tyr Asn Thr Thr Pro Pro Met Leu Asp Ser Asp Gly Ser Phe Phe Leu
                325                 330                 335
Tyr Ser Lys Leu Thr Val Asp Lys Ser Arg Trp Gln Gln Gly Asn Ile
            340                 345                 350
Phe Ser Cys Ser Val Met His Glu Ala Leu His Asn Arg Phe Thr Gln
        355                 360                 365
Lys Ser Leu Ser Leu Ser Pro Gly Lys
    370                 375

<210> SEQ ID NO 98
<211> LENGTH: 1131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
gccagcacca agggcccag cgtgttcccc ctggccccct gcagccggag caccagcggc         60
ggcaccgccg ccctgggctg cctggtgaag gactacttcc ccgagcccgt gaccgtgagc       120
tggaacagcg gcgccctgac cagcggcgtg cacaccttcc ccgccgtgct gcagagcagc       180
ggcctgtaca gcctgagcag cgtggtgacc gtgcccagca gcagcctggg cacccagacc       240
tacacctgca acgtgaacca caagcccagc aacaccaagg tggacaagcg ggtggagctg       300
aagacccccc tgggcgacac cacccacacc tgccccccggt gccccgagcc caagagctgc     360
gacaccccc cccctgccc ccggtgcccc gagcccaaga gctgcgacac ccccccccc          420
tgccccccggt gccccgagcc caagagctgc gacaccccccc ccccctgccc ccggtgcccc    480
gcccccgagc tgctgggcgg ccccagcgtg ttcctgttcc cccccaagcc caaggacacc       540
ctgatgatca gccggacccc cgaggtgacc tgcgtggtgg tggacgtgag ccacgaggac       600
cccgaggtgc agttcaagtg gtacgtggac ggcgtggagg tgcacaacgc caagaccaag       660
cccgggagg agcagtacaa cagcaccttc cgggtggtga gcgtgctgac cgtgctgcac       720
caggactggc tgaacggcaa ggagtacaag tgcaaggtga gcaacaaggc cctgcccgcc       780
cccatcgaga gaccatcag caagaccaag ggccagcccc gggagcccca ggtgtacacc       840
ctgccccca gccgggagga gatgaccaag aaccaggtga gcctgacctg cctggtgaag       900
ggcttctacc ccagcgacat cgccgtggag tgggagagca gcggccagcc cgagaacaac       960
tacaacacca cccccccat gctggacagc gacggcagct cttcctgta cagcaagctg        1020
accgtggaca agagccggtg gcagcagggc aacatcttca gctgcagcgt gatgcacgag      1080
gccctgcaca accggttcac ccagaagagc ctgagcctga gccccggcaa g              1131

<210> SEQ ID NO 99
<211> LENGTH: 327
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 100
<211> LENGTH: 981
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

```
gcctctacca agggcccag cgtgttcccc ctggcccct gcagcagaag caccagcgag    60
agcacagccg ccctgggctg cctggtgaag gactacttcc ccgagccagt gaccgtgtcc   120
tggaacagcg gagccctgac cagcggcgtg cacaccttcc ccgccgtgct gcagagcagc   180
ggcctgtaca gcctgtccag cgtggtgacc gtgcccagca gcagcctggg caccaagacc   240
tacacctgca acgtggacca caagcccagc aacaccaagg tggacaagag ggtggagagc   300
aagtacggcc accctgccc ctcttgccca gcccccgagt tcctgggcgg accctccgtg   360
ttcctgttcc cccccaagcc caaggacacc ctgatgatca gcaggacccc cgaggtgacc   420
tgcgtggtgg tggacgtgag ccaggaagat ccagaggtcc agttcaactg gtacgtggac   480
ggcgtggagg tgcacaacgc caagaccaag cccagagagg aacagtttaa cagcacctac   540
agggtggtgt ccgtgctgac cgtgctgcac caggactggc tgaacggcaa agagtacaag   600
tgcaaggtct ccaacaaggg cctgcccagc tccatcgaga aaaccatcag caaggccaag   660
ggccagccac gggagcccca ggtgtacacc ctgccaccct cccaggaaga gatgaccaag   720
aaccaggtgt ccctgacctg tctggtgaag ggcttctacc ccagcgacat cgccgtggag   780
tgggagagca acggccagcc cgagaacaac tacaagacca ccccccagt gctggacagc   840
gacggcagct cttcctgta cagcaggctg accgtggaca gtccaggtg cagaaggc     900
aacgtcttta gctgcagcgt gatgcacgag gccctgcaca accactacac ccagaagagc   960
ctgagcctgt ccctgggcaa g                                            981
```

<210> SEQ ID NO 101
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 101

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

165                 170                 175
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 102
<211> LENGTH: 990
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
gcctccacca agggtccatc ggtcttcccc ctggcaccct cctccaagag cacctctggg      60
ggcacagcgg ccctgggctg cctggtcaag gactacttcc ccgaaccggt gacggtgtcg     120
tggaactcag cgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaagc agcggggga     360 ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gggtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtacaccc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                     990

<210> SEQ ID NO 103

```
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 104
<211> LENGTH: 990
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 104

```
gctagcacca agggcccctc cgtgttccct ctggcccect ccagcaagtc cacctctggc      60
ggcaccgccg ctctgggctg cctggtgaaa gactacttcc ccgagcccgt gaccgtgtcc     120
tggaactctg gcgccctgac ctccggcgtg cacacctttc cagccgtgct gcagtcctcc     180
ggcctgtact ccctgtcctc cgtggtgacc gtgccctcta gctctctggg cacccagacc     240
tacatctgca acgtgaacca caagccctcc aacaccaagg tggacaagcg ggtggaaccc     300
aagtcctgcg acaagaccca cacctgtccc cctgccctg  ccctgaact gctgggcgga     360
ccttccgtgt tcctgttccc cccaaagccc aaggacaccc tgatgatctc ccggaccccc     420
gaagtgacct gcgtggtggt ggacgtgtcc cacgaggacc ctgaagtgaa gttcaattgg     480
tacgtggacg gcgtggaagt gcacaacgcc aagaccaagc cagagagga acagtacgcc     540
tccacctacc gggtggtgtc tgtgctgacc gtgctgcacc aggactggct gaacggcaaa     600
gagtacaagt gcaaggtctc caacaaggcc ctgcctgccc ccatcgaaaa gaccatctcc     660
aaggccaagg gccagccccg cgagccacag gtgtacacac tgcccccag  ccggaagag     720
atgaccaaga accaggtgtc cctgacctgt ctggtcaaag gcttctaccc ctccgatatc     780
gccgtggagt gggagtccaa cggacagccc gagaacaact acaagaccac ccccctgtg     840
ctggactccg acggctcatt cttcctgtac tccaagctga ccgtggacaa gtcccggtgg     900
cagcagggca acgtgttctc ctgctccgtg atgcacgagg ccctgcacaa ccactacacc     960
cagaagtccc tgtccctgag ccccggcaag                                    990
```

<210> SEQ ID NO 105
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175
Glu Gln Tyr Asn Ser Thr Tyr Arg Val Val Ser Val Leu Thr Val Leu
        180                 185                 190
His Gln Asp Trp Leu Asn Gly Lys Glu Tyr Lys Cys Lys Val Ser Asn
    195                 200                 205
Lys Ala Leu Ala Ala Pro Ile Glu Lys Thr Ile Ser Lys Ala Lys Gly
210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

```
<210> SEQ ID NO 106
<211> LENGTH: 990
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
gctagcacca agggcccag cgtgttcccc ctggccccca gcagcaagag caccagcggc     60
ggcacagccg ccctgggctg cctggtgaag gactacttcc ccgagcccgt gaccgtgtcc    120
tggaacagcg gagccctgac ctccggcgtg cacaccttcc ccgccgtgct gcagagcagc    180
ggcctgtaca gcctgtccag cgtggtgaca gtgcccagca gcagcctggg cacccagacc    240
tacatctgca acgtgaacca caagcccagc aacaccaagg tggacaagag agtggagccc    300
aagagctgcg acaagaccca cacctgcccc cctgcccag ccccagagct gctgggcgga    360
ccctccgtgt tcctgttccc ccccaagccc aaggacaccc tgatgatcag caggacccc    420 gaggtgacct gcgtggtggt ggccgtgagc cacgaggacc cagaggtgaa gttcaactgg    480
tacgtggacg gcgtggaggt gcacaacgcc aagaccaagc cagagagga gcagtacaac    540 agcacctaca gggtggtgtc cgtgctgacc gtgctgcacc aggactggct gaacggcaag    600
gaatacaagt gcaaggtctc caacaaggcc ctggcagccc catcgaaaa gaccatcagc    660 aaggccaagg gccagccacg ggagccccag gtgtacaccc tgccccctc ccgggaggag    720 atgaccaaga accaggtgtc cctgacctgt ctggtgaagg gcttctaccc cagcgacatc    780
gccgtggagt gggagagcaa cggccagccc gagaacaact acaagaccac ccccccagtg    840
ctggacagcg acggcagctt cttcctgtac agcaagctga ccgtggacaa gtccaggtgg    900
cagcagggca acgtgttcag ctgcagcgtg atgcacgagg ccctgcacaa ccactacacc    960
cagaagagcc tgagcctgtc ccccggcaag                                     990
```

<210> SEQ ID NO 107
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 107

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 108
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 108
cgtacggtgg ccgctcccag cgtgttcatc ttcccccca gcgacgagca gctgaagagc      60
ggcaccgcca gcgtggtgtg cctgctgaac aacttctacc ccggggaggc caaggtgcag    120
tggaaggtgg acaacgccct gcagagcggc aacagccagg agagcgtcac cgagcaggac    180
agcaaggact ccacctacag cctgagcagc accctgaccc tgagcaaggc cgactacgag    240
aagcataagg tgtacgcctg cgaggtgacc caccagggcc tgtccagccc cgtgaccaag    300
agcttcaaca ggggcgagtg c                                              321

<210> SEQ ID NO 109
<211> LENGTH: 153
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

```
Glu Glu Leu Lys Pro Leu Glu Val Leu Asn Leu Ala Gln Ser Lys
            85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
        130                 135                 140

Cys Gln Ser Ile Ile Ser Thr Leu Thr
145                 150
```

<210> SEQ ID NO 110
<211> LENGTH: 134
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

```
Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ser Gln Ser
        115                 120                 125

Ile Ile Ser Thr Leu Thr
    130
```

<210> SEQ ID NO 111
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 111

```
Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Ser Thr Ala Tyr
65                  70                  75                  80
```

```
Met Gln Leu Ser Ser Leu Thr Ser Asp Asp Ser Ala Val Tyr Phe Cys
                85                  90                  95

Ala Arg Trp Arg Gly Asp Gly Tyr Tyr Ala Tyr Phe Asp Val Trp Gly
            100                 105                 110

Ala Gly Thr Thr Val Thr Val Ser Ser
        115                 120

<210> SEQ ID NO 112
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
caggtccagc tgcagcagtc tggagctgag ctggtaaggc ctgggacttc agtgaaggtg      60
tcctgcaagg cttctggata cgccttcact aattacttga tagagtgggt aaagcagagg     120
cctggacagg gccttgagtg gattggagtg attaatcctg aagtggtgg tactaactac      180 aatgagaagt tcaagggcaa ggcaacactg actgcagaca atcctccag cactgcctac      240 atgcagctca gcagcctgac atctgatgac tctgcggtct atttctgtgc aagatggagg     300
ggggatggtt actacgcgta cttcgatgtc tggggcgcag ggaccacggt caccgtctcc     360
tca                                                                    363

<210> SEQ ID NO 113
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 114
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
gacattgtgc tgacccaatc tccagcttct ttggctgtgt ctctagggca gagggccacc      60
```

```
atctcctgca aggccagcca aagtgttgat tatgatggtg atagttatat gaactggtac    120
caacagaaac caggacagcc acccaaactc ctcatctatg ctgcatccaa tctagaatct    180
gggatcccag ccaggtttag tggcagtggg tctgggacag acttcaccct caacatccat    240
cctgtggagg aggaggatgc tgcaacctat tactgtcagc aaagtaatga ggatccgtac    300
acgttcggag gggggaccaa gctggaaata aaa                                 333
```

<210> SEQ ID NO 115
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 115

```
Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
                20                  25                  30

Leu Ile Glu Trp Val Lys Gln Arg Pro Gly Gln Gly Leu Glu Trp Ile
            35                  40                  45

Gly Val Ile Asn Pro Gly Ser Gly Gly Thr Asn Tyr Asn Glu Lys Phe
        50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Trp Arg Gly Asp Gly Tyr Tyr Ala Tyr Phe Asp Val Trp Gly
            100                 105                 110

Ala Gly Thr Thr Val Thr Val Ser Ser Ala Lys Thr Thr Ala Pro Ser
        115                 120                 125

Val Tyr Pro Leu Ala Pro Val Cys Gly Asp Thr Thr Gly Ser Ser Val
    130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Thr
            180                 185                 190

Ser Ser Thr Trp Pro Ser Gln Ser Ile Thr Cys Asn Val Ala His Pro
        195                 200                 205

Ala Ser Ser Thr Lys Val Asp Lys Lys Ile Glu Pro Arg Gly Pro Thr
    210                 215                 220

Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
                245                 250                 255

Ile Ser Leu Ser Pro Ile Val Thr Cys Val Val Val Asp Val Ser Glu
            260                 265                 270

Asp Asp Pro Asp Val Gln Ile Ser Trp Phe Val Asn Asn Val Glu Val
        275                 280                 285

His Thr Ala Gln Thr Gln Thr His Arg Glu Asp Tyr Asn Ser Thr Leu
    290                 295                 300
```

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
            340                 345                 350

Tyr Val Leu Pro Pro Pro Glu Glu Glu Met Thr Lys Lys Gln Val Thr
        355                 360                 365

Leu Thr Cys Met Val Thr Asp Phe Met Pro Glu Asp Ile Tyr Val Glu
    370                 375                 380

Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val
                405                 410                 415

Glu Lys Lys Asn Trp Val Glu Arg Asn Ser Tyr Ser Cys Ser Val Val
                420                 425                 430

His Glu Gly Leu His Asn His His Thr Thr Lys Ser Phe Ser Arg Thr
            435                 440                 445

Pro Gly Lys
    450

<210> SEQ ID NO 116
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116
caggtccagc tgcagcagtc tggagctgag ctggtaaggc ctgggacttc agtgaaggtg      60
tcctgcaagg cttctggata cgccttcact aattacttga tagagtgggt aaagcagagg     120
cctggacagg gccttgagtg gattggagtg attaatcctg aagtggtgg tactaactac     180 aatgagaagt tcaagggcaa ggcaacactg actgcagaca atcctccag cactgcctac     240 atgcagctca gcagcctgac atctgatgac tctgcggtct atttctgtgc aagatggagg     300
ggggatggtt actacgcgta cttcgatgtc tggggcgcag ggaccacggt caccgtctcc     360
tcagccaaaa caacagcccc atcggtctat ccactggccc ctgtgtgtgg agatacaact     420
ggctcctcgg tgactctagg atgcctggtc aagggttatt tccctgagcc agtgaccttg     480
acctggaact ctggatccct gtccagtggt gtgcacacct tcccagctgt cctgcagtct     540
gacctctaca ccctcagcag ctcagtgact gtaacctcga gcacctggcc cagccagtcc     600
atcacctgca atgtggccca cccggcaagc agcaccaagg tggacaagaa aattgagccc     660
agagggccca caatcaagcc ctgtcctcca tgcaaatgcc cagcacctaa cctcttgggt     720
ggaccatccg tcttcatctt ccctccaaag atcaaggatg tactcatgat ctccctgagc     780
cccatagtca catgtgtggt ggtggatgtg agcgaggatg acccagatgt ccagatcagc     840
tggtttgtga acaacgtgga agtacacaca gctcagacac aaaccatag agaggattac     900 aacagtactc tccgggtggt cagtgccctc cccatccagc accaggactg gatgagtggc     960
aaggagttca atgcaaggt caacaacaaa gacctcccag cgcccatcga gaaccatc     1020 tcaaaaccca agggtcagt aagagctcca caggtatatg tcttgcctcc accagaagaa    1080
gagatgacta agaaacaggt cactctgacc tgcatggtca cagacttcat gcctgaagac    1140

| | |
|---|---|
| atttacgtgg agtggaccaa caacgggaaa acagagctaa actacaagaa cactgaacca | 1200 |
| gtcctggact ctgatggttc ttacttcatg tacagcaagc tgagagtgga aaagaagaac | 1260 |
| tgggtggaaa gaaatagcta ctcctgttca gtggtccacg agggtctgca caatcaccac | 1320 |
| acgactaaga gcttctcccg gactccgggt aaa | 1353 |

<210> SEQ ID NO 117
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 118
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118

| | |
|---|---|
| gacattgtgc tgacccaatc tccagcttct ttggctgtgt ctctagggca gagggccacc | 60 |
| atctcctgca aggccagcca aagtgttgat tatgatggtg atagttatat gaactggtac | 120 |
| caacagaaac caggacagcc acccaaactc ctcatctatg ctgcatccaa tctagaatct | 180 |
| gggatcccag ccaggtttag tggcagtggg tctgggacag acttcaccct caacatccat | 240 |

```
cctgtggagg aggaggatgc tgcaacctat tactgtcagc aaagtaatga ggatccgtac    300
acgttcggag gggggaccaa gctggaaata aaacgggctg atgctgcacc aactgtatcc    360
atcttcccac catccagtga gcagttaaca tctggaggtg cctcagtcgt gtgcttcttg    420
aacaacttct accccaaaga catcaatgtc aagtggaaga ttgatggcag tgaacgacaa    480
aatggcgtcc tgaacagttg gactgatcag gacagcaaag acagcaccta cagcatgagc    540
agcaccctca cgttgaccaa ggacgagtat gaacgacata acagctatac ctgtgaggcc    600
actcacaaga catcaacttc acccattgtc aagagcttca acaggaatga gtgt          654
```

```
<210> SEQ ID NO 119
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (1)..(1)
<223> OTHER INFORMATION: Asn or Ser

<400> SEQUENCE: 119

Xaa Tyr Leu Ile Glu
1               5

<210> SEQ ID NO 120
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (12)..(12)
<223> OTHER INFORMATION: Asn or Ala
<220> FEATURE:
<221> NAME/KEY: VARIANT
<222> LOCATION: (13)..(13)
<223> OTHER INFORMATION: Glu or Asp
<220> FEATURE:
<221> NAME/KEY: VARIANT
<222> LOCATION: (14)..(14)
<223> OTHER INFORMATION: Lys or Ser
<220> FEATURE:
<221> NAME/KEY: VARIANT
<222> LOCATION: (15)..(15)
<223> OTHER INFORMATION: Phe or Val

<400> SEQUENCE: 120

Val Ile Asn Pro Gly Ser Gly Gly Thr Asn Tyr Xaa Xaa Xaa Xaa Lys
1               5                   10                  15

Gly

<210> SEQ ID NO 121
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (4)..(4)
<223> OTHER INFORMATION: Glu, Asp, Ala, Gly or Thr
<220> FEATURE:
<221> NAME/KEY: VARIANT
```

```
<222> LOCATION: (5)..(5)
<223> OTHER INFORMATION: Gly, Ala, Thr or Ser

<400> SEQUENCE: 121

Trp Arg Gly Xaa Xaa Tyr Tyr Ala Tyr Phe Asp Val
1               5                   10

<210> SEQ ID NO 122
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (1)..(1)
<223> OTHER INFORMATION: Arg or Lys
<220> FEATURE:
<221> NAME/KEY: VARIANT
<222> LOCATION: (7)..(7)
<223> OTHER INFORMATION: Ser or Asp
<220> FEATURE:
<221> NAME/KEY: VARIANT
<222> LOCATION: (9)..(9)
<223> OTHER INFORMATION: Asp, Gln, Ala, Gly or Thr
<220> FEATURE:
<221> NAME/KEY: VARIANT
<222> LOCATION: (10)..(10)
<223> OTHER INFORMATION: Gly, Thr or Ser

<400> SEQUENCE: 122

Xaa Ala Ser Gln Ser Val Xaa Tyr Xaa Xaa Asp Ser Tyr Met Asn
1               5                   10                  15

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (6)..(6)
<223> OTHER INFORMATION: Glu or Ala

<400> SEQUENCE: 123

Ala Ala Ser Asn Leu Xaa Ser
1               5

<210> SEQ ID NO 124
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Asp Ile Val Leu Thr Gln Ser Pro Leu Ser Leu Pro Val Thr Leu Gly
1               5                   10                  15

Gln Pro Ala Ser Ile Ser Cys Lys Ala Ser Gln Ser Val Asp Tyr Asp
            20                  25                  30

Gly Asp Ser Tyr Met Asn Trp Tyr Gln Gln Arg Pro Gly Gln Ser Pro
        35                  40                  45

Arg Leu Leu Ile Tyr Ala Ala Ser Asn Leu Glu Ser Gly Val Pro Asp
    50                  55                  60
```

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Asn
                85                  90                  95

Glu Asp Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 125
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
gacatcgtgc tgacacagag ccctctgtcc ctgcccgtga ccctgggcca gcctgcctcc      60
atctcctgca aggcctccca gtccgtggac tacgacggcg actcctacat gaactggtat     120
cagcagcggc ctggccagtc ccctcggctg ctgatctacg ccgcctccaa cctggaatcc     180
ggcgtgcccg acagattctc cggctccggc tctggcaccg acttcaccct gaagatctcc     240
cgggtggaag ccgaggacgt gggcgtgtac tactgccagc agtccaacga ggaccctac      300
accttcggcg aggcaccaa agtggaaatc aagcgtacgg tggccgctcc cagcgtgttc     360
atcttccccc ccagcgacga gcagctgaag agcggcaccg ccagcgtggt gtgcctgctg     420
aacaacttct accccaggga ggccaaggtg cagtggaagg tggacaacgc cctgcagagc     480
ggcaacagcc aggagagcgt caccgagcag gacagcaagg actccaccta cagcctgagc     540
agcaccctga ccctgagcaa ggccgactac gagaagcata aggtgtacgc ctgcgaggtg     600
acccaccagg gcctgtccag ccccgtgacc aagagcttca cagggggcga gtgc            654

<210> SEQ ID NO 126
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Asn Tyr
            20                  25                  30

```
Leu Ile Glu Trp Val Arg Gln Ala Pro Gly Gln Gly Leu Glu Trp Met
         35                  40                  45

Gly Val Ile Asn Pro Gly Ser Gly Gly Thr Asn Tyr Asn Glu Lys Phe
     50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Arg Gly Asp Gly Tyr Tyr Ala Tyr Phe Asp Val Trp Gly
             100                 105                 110

Gln Gly Thr Thr Val Thr Val Ser Ser Ala Ser Thr Lys Gly Pro Ser
         115                 120                 125

Val Phe Pro Leu Ala Pro Ser Ser Lys Ser Thr Ser Gly Gly Thr Ala
     130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                 165                 170                 175

Val Leu Gln Ser Ser Gly Leu Tyr Ser Leu Ser Ser Val Val Thr Val
             180                 185                 190

Pro Ser Ser Ser Leu Gly Thr Gln Thr Tyr Ile Cys Asn Val Asn His
         195                 200                 205

Lys Pro Ser Asn Thr Lys Val Asp Lys Lys Val Glu Pro Lys Ser Cys
     210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                 245                 250                 255

Ile Ser Arg Thr Pro Glu Val Thr Cys Val Val Val Asp Val Ser His
             260                 265                 270

Glu Asp Pro Glu Val Lys Phe Asn Trp Tyr Val Asp Gly Val Glu Val
         275                 280                 285

His Asn Ala Lys Thr Lys Pro Arg Glu Glu Gln Tyr Ala Ser Thr Tyr
     290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                 325                 330                 335

Glu Lys Thr Ile Ser Lys Ala Lys Gly Gln Pro Arg Glu Pro Gln Val
             340                 345                 350

Tyr Thr Leu Pro Pro Ser Arg Glu Glu Met Thr Lys Asn Gln Val Ser
         355                 360                 365

Leu Thr Cys Leu Val Lys Gly Phe Tyr Pro Ser Asp Ile Ala Val Glu
     370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                 405                 410                 415

Asp Lys Ser Arg Trp Gln Gln Gly Asn Val Phe Ser Cys Ser Val Met
             420                 425                 430

His Glu Ala Leu His Asn His Tyr Thr Gln Lys Ser Leu Ser Leu Ser
         435                 440                 445
```

<210> SEQ ID NO 127
<211> LENGTH: 1353
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 127

```
caagtgcagc tggtgcagtc tggcgctgaa gtgaagaaac ccggctcctc cgtgaaagtg     60
tcctgcaagg cctccggcta cgccttcacc aactacctga tcgagtgggt ccgacaggcc    120
ccaggccagg gcctggagtg gatgggcgtg atcaaccctg ctccggcgg caccaactac    180
aacgagaagt tcaagggcag agtgaccatc accgccgaca gtccacctc caccgcctac    240
atggaactgt cctccctgcg gagcgaggac accgccgtgt actactgtgc ccggtggcgg    300
ggagatggct actacgccta cttcgacgtg tggggccagg gcaccaccgt gaccgtgtcc    360
tctgctagca ccaagggccc ctccgtgttc cctctggccc cctccagcaa gtccacctct    420
ggcggcaccg ccgctctggg ctgcctggtg aaagactact cccccgagcc cgtgaccgtg    480
tcctggaact ctggcgccct gacctccggc gtgcacacct tccagccgt gctgcagtcc    540
tccggcctgt actccctgtc ctccgtggtg accgtgccct ctagctctct gggcacccag    600
acctacatct gcaacgtgaa ccacaagccc tccaacacca ggtggacaa gcgggtggaa    660
cccaagtcct gcgacaagac ccacacctgt cccccctgcc ctgcccctga actgctgggc    720
ggaccttccg tgttcctgtt ccccccaaag cccaaggaca ccctgatgat ctcccggacc    780
cccgaagtga cctgcgtggt ggtggacgtg tcccacgagg accctgaagt gaagttcaat    840
tggtacgtgg acggcgtgga agtgcacaac gccaagacca gcccagaga ggaacagtac    900
gcctccacct accgggtggt gtctgtgctg accgtgctgc accaggactg gctgaacggc    960
aaagagtaca agtgcaaggt ctccaacaag gccctgcctg cccccatcga aaagaccatc   1020
tccaaggcca agggccagcc ccgcgagcca caggtgtaca cactgccccc cagccgggaa   1080
gagatgacca agaaccaggt gtccctgacc tgtctggtca aaggcttcta cccctccgat   1140
atcgccgtgg agtgggagtc caacggacag cccgagaaca actacaagac cacccccct   1200
gtgctggact ccgacggctc attcttcctg tactccaagc tgaccgtgga caagtcccgg   1260
tggcagcagg gcaacgtgtt ctcctgctcc gtgatgcacg aggccctgca caaccactac   1320
acccagaagt ccctgtccct gagccccggc aag                                1353
```

<210> SEQ ID NO 128
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 128

```
Ala Ile Arg Leu Thr Gln Ser Pro Ser Ser Phe Ser Ala Ser Thr Gly
 1               5                  10                  15
Asp Arg Val Thr Ile Thr Cys Lys Ala Ser Gln Ser Val Asp Tyr Asp
            20                  25                  30
Gly Asp Ser Tyr Met Asn Trp Tyr Gln Gln Lys Pro Gly Lys Ala Pro
        35                  40                  45
```

Lys Leu Leu Ile Tyr Ala Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Ser Glu Asp Phe Ala Thr Tyr Tyr Cys Gln Gln Ser Asn
                 85                  90                  95

Glu Asp Pro Tyr Thr Phe Gly Gly Thr Lys Val Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 129
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129
gccatcagac tgacccagag cccctccagc ttctccgcct ccaccggcga cagagtgacc      60
atcacatgca aggcctccca gtccgtggac tacgacggcg actcctacat gaactggtat     120
cagcagaagc ccggcaaggc ccctaagctg ctgatctacg ccgcctccaa cctggaatcc     180
ggcgtgccct cccggttctc cggctctggc tctggcaccg acttcaccct gaccatctcc     240
agcctgcagt ccgaggactt cgccacctac tactgccagc agtccaacga gccccctac     300 accttcggcg gaggcaccaa agtggaaatc aagcgtacgg tggccgctcc cagcgtgttc     360
atcttccccc ccagcgacga gcagctgaag agcggcaccg ccagcgtggt gtgcctgctg     420
aacaacttct accccgggga ggccaaggtg cagtggaagg tggacaacgc cctgcagagc     480
ggcaacagcc aggagagcgt caccgagcag gacagcaagg actccaccta cagcctgagc     540
agcaccctga ccctgagcaa ggccgactac gagaagcata aggtgtacgc ctgcgaggtg     600
acccaccagg gcctgtccag ccccgtgacc aagagcttca caggggcga gtgc            654

<210> SEQ ID NO 130
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Val Gln Leu Val Gln Ser Gly Ala Glu Val Lys Lys Pro Gly Glu

```
1               5                   10                  15
Ser Leu Lys Ile Ser Cys Lys Gly Ser Gly Tyr Ala Phe Thr Asn Tyr
                20                  25                  30
Leu Ile Glu Trp Val Arg Gln Met Pro Gly Lys Gly Leu Glu Trp Met
                35                  40                  45
Gly Val Ile Asn Pro Gly Ser Gly Gly Thr Asn Tyr Asn Glu Lys Phe
                50                  55                  60
Lys Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Trp Arg Gly Asp Gly Tyr Tyr Ala Tyr Phe Asp Val Trp Gly
                100                 105                 110
Gln Gly Thr Thr Val Thr Val Ser Ser Ala Ser Thr Lys Gly Pro Ser
                115                 120                 125
Val Phe Pro Leu Ala Pro Ser Ser Lys Ser Thr Ser Gly Gly Thr Ala
                130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Lys Val Glu Pro Lys Ser Cys
210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
                275                 280                 285
His Asn Ala Lys Thr Lys Pro Arg Glu Glu Gln Tyr Ala Ser Thr Tyr
                290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Glu Glu Met Thr Lys Asn Gln Val Ser
                355                 360                 365
Leu Thr Cys Leu Val Lys Gly Phe Tyr Pro Ser Asp Ile Ala Val Glu
                370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
```

His Glu Ala Leu His Asn His Tyr Thr Gln Lys Ser Leu Ser Leu Ser
            435                 440                 445

Pro Gly Lys
    450

<210> SEQ ID NO 131
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131
gaagtgcagc tggtgcagtc tggcgctgaa gtgaagaagc ccggcgagtc cctgaagatc     60
tcctgcaagg gctccggcta cgccttcacc aactacctga tcgagtgggt ccgacagatg    120
cccggcaagg gcctggagtg gatgggcgtg atcaaccccg ctccggcgg caccaactac    180 aacgagaagt tcaagggcca agtcacaatc tccgccgaca gtccatctc caccgcctac    240 ctgcagtggt cctccctgaa ggcctccgac accgccatgt actactgcgc cagatggcgg    300
ggagatggct actacgccta cttcgacgtg tggggccagg caccaccgt gaccgtgtcc    360 tctgctagca ccaagggccc ctccgtgttc cctctggccc cctccagcaa gtccacctct    420
ggcggcaccg ccgctctggg ctgcctggtg aaagactact cccccgagcc cgtgaccgtg    480
tcctggaact ctggcgccct gacctccggc gtgcacacct tccagccgt gctgcagtcc    540 tccggcctgt actccctgtc ctccgtggtg accgtgccct ctagctctct gggcacccag    600
acctacatct gcaacgtgaa ccacaagccc tccaacacca aggtggacaa gcgggtggaa    660
cccaagtcct gcgacaagac ccacacctgt ccccctgcc ctgcccctga actgctgggc    720
ggaccttccg tgttcctgtt ccccccaaag cccaaggaca ccctgatgat ctcccggacc    780
cccgaagtga cctgcgtggt ggtggacgtg tcccacgagg accctgaagt gaagttcaat    840
tggtacgtgg acggcgtgga agtgcacaac gccaagacca gcccagaga ggaacagtac    900 gcctccacct accgggtggt gtctgtgctg accgtgctgc accaggactg gctgaacggc    960
aaagagtaca agtgcaaggt ctccaacaag gccctgcctg cccccatcga aagaccatc   1020 tccaaggcca agggccagcc ccgcgagcca caggtgtaca cactgccccc cagccgggaa   1080
gagatgacca gaaccaggt gtccctgacc tgtctggtca aaggcttcta cccctccgat   1140
atcgccgtgg agtgggagtc caacggacag cccgagaaca actacaagac cacccccct   1200 gtgctggact ccgacggctc attcttcctg tactccaagc tgaccgtgga caagtcccgg   1260
tggcagcagg gcaacgtgtt ctcctgctcc gtgatgcacg aggccctgca caaccactac   1320
acccagaagt ccctgtccct gagccccggc aag                                1353

<210> SEQ ID NO 132
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gly Ile Asn Asn Tyr Lys Asn Pro Lys Leu Thr Arg Met Leu Thr Phe
1               5                   10                  15

Lys Phe Tyr Met Pro Lys Lys Ala Thr Glu Leu Lys His Leu Gln Cys

```
                    20                  25                  30
Leu Glu Glu Glu Leu Lys Pro Leu Glu Glu Val Leu Asn Leu Ala Gln
            35                  40                  45

Ser Lys Asn Phe
    50

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gly Tyr Ala Phe Ser Asn Tyr Leu Ile Glu
1               5                   10

<210> SEQ ID NO 134
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Val Ile Asn Pro Gly Ser Gly Gly Thr Tyr Tyr Asn Glu Lys Phe Lys
1               5                   10                  15

Gly

<210> SEQ ID NO 135
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Trp Arg Gly Glu Gly Tyr Tyr Ala Tyr Tyr Asp Val
1               5                   10

<210> SEQ ID NO 136
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Asn Tyr Leu Ile Glu
1               5

<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Val Ile Asn Pro Gly Ser Gly Gly Thr Tyr Tyr Asn Glu Lys Phe Lys
1               5                   10                  15
```

Gly

<210> SEQ ID NO 138
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Trp Arg Gly Glu Gly Tyr Tyr Ala Tyr Tyr Asp Val
1               5                   10

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Tyr Ala Phe Ser Asn Tyr
1               5

<210> SEQ ID NO 140
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Asn Pro Gly Ser Gly Gly
1               5

<210> SEQ ID NO 141
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Trp Arg Gly Glu Gly Tyr Tyr Ala Tyr Tyr Asp Val
1               5                   10

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Tyr Ala Phe Ser Asn Tyr Leu
1               5

<210> SEQ ID NO 143
<211> LENGTH: 8
<212> TYPE: PRT
<213> ORGANISM: Artificial Sequence
<220> FEATURE:

<223> OTHER INFORMATION: Description of Artificial Sequence: Synthetic
    peptide

<400> SEQUENCE: 143

Ile Asn Pro Gly Ser Gly Gly Thr
1               5

<210> SEQ ID NO 144
<211> LENGTH: 14
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 144

Ala Arg Trp Arg Gly Glu Gly Tyr Tyr Ala Tyr Tyr Asp Val
1               5                   10

<210> SEQ ID NO 145
<211> LENGTH: 121
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 145

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Asn Tyr
            20                  25                  30

Leu Ile Glu Trp Val Arg Gln Met Pro Gly Lys Gly Leu Glu Trp Met
        35                  40                  45

Gly Val Ile Asn Pro Gly Ser Gly Gly Thr Tyr Tyr Asn Glu Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Arg Gly Glu Gly Tyr Tyr Ala Tyr Tyr Asp Val Trp Gly
            100                 105                 110

Gln Gly Thr Thr Val Thr Val Ser Ser
        115                 120

<210> SEQ ID NO 146
<211> LENGTH: 363
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 146
gaggtgcaat tggtgcagag cggagccgaa gtgaagaagc cggcgagag cctgaagatc        60 agctgcaagg gcagcggcta cgccttcagc aactacctga tcgagtgggt gcgccagatg       120
cccggcaagg gcctggaatg gatgggcgtg atcaatcctg gcagcggcgg cacctactac       180
aacgagaagt tcaagggcca agtgaccatc agcgccgaca agagcatcag caccgcctac       240
ctccagtggt ccagcctgaa ggccagcgac accgccatgt actactgcgc caggtggcgg       300
ggagagggct actacgccta ctacgacgtg tggggccagg gcaccacagt gaccgtcagc       360
tca                                                                363

<210> SEQ ID NO 147
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Asn Tyr
            20                  25                  30

Leu Ile Glu Trp Val Arg Gln Met Pro Gly Lys Gly Leu Glu Trp Met
        35                  40                  45

Gly Val Ile Asn Pro Gly Ser Gly Gly Thr Tyr Tyr Asn Glu Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Arg Gly Glu Gly Tyr Tyr Ala Tyr Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

```
Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly Lys
    450

<210> SEQ ID NO 148
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148
```

| | | | | | |
|---|---|---|---|---|---|
| gaggtgcaat | tggtgcagag | cggagccgaa | gtgaagaagc | ccggcgagag | cctgaagatc | 60 |
| agctgcaagg | gcagcggcta | cgccttcagc | aactacctga | tcgagtgggt | gcgccagatg | 120 |
| cccggcaagg | gcctggaatg | gatgggcgtg | atcaatcctg | gcagcggcgg | cacctactac | 180 |
| aacgagaagt | tcaagggcca | agtgaccatc | agcgccgaca | agagcatcag | caccgcctac | 240 |
| ctccagtggt | ccagcctgaa | ggccagcgac | accgccatgt | actactgcgc | caggtggcgg | 300 |
| ggagagggct | actacgccta | ctacgacgtg | tggggccagg | gcaccacagt | gaccgtcagc | 360 |
| tcagctagca | ccaagggccc | cagcgtgttc | cccctggccc | ccagcagcaa | gagcaccagc | 420 |
| ggcggcacag | ccgccctggg | ctgcctggtg | aaggactact | tccccgagcc | cgtgaccgtg | 480 |
| tcctggaaca | gcggagccct | gacctccggc | gtgcacacct | tccccgccgt | gctgcagagc | 540 |
| agcggcctgt | acagcctgtc | cagcgtggtg | acagtgccca | gcagcagcct | gggcacccag | 600 |
| acctacatct | gcaacgtgaa | ccacaagccc | agcaacacca | aggtggacaa | gagagtggag | 660 |
| cccaagagct | gcgacaagac | ccacacctgc | ccccctgcc | cagccccaga | gctgctgggc | 720 |
| ggaccctccg | tgttcctgtt | cccccccaag | cccaaggaca | ccctgatgat | cagcaggacc | 780 |
| cccgaggtga | cctgcgtggt | ggtggacgtg | agccacgagg | acccagaggt | gaagttcaac | 840 |
| tggtacgtgg | acggcgtgga | ggtgcacaac | gccaagacca | agcccagaga | ggagcagtac | 900 |
| gccagcacct | acagggtggt | gtccgtgctg | accgtgctgc | accaggactg | gctgaacggc | 960 |
| aaggaataca | agtgcaaggt | ctccaacaag | gccctgccag | cccccatcga | aaagaccatc | 1020 |
| agcaaggcca | agggccagcc | acgggagccc | caggtgtaca | ccctgccccc | ctcccgggag | 1080 |
| gagatgacca | agaaccaggt | gtccctgacc | tgtctggtga | agggcttcta | ccccagcgac | 1140 |
| atcgccgtgg | agtgggagag | caacggccag | cccgagaaca | actacaagac | cacccccca | 1200 |
| gtgctggaca | gcgacggcag | cttcttcctg | tacagcaagc | tgaccgtgga | caagtccagg | 1260 |
| tggcagcagg | gcaacgtgtt | cagctgcagc | gtgatgcacg | aggccctgca | caaccactac | 1320 |
| acccagaaga | gcctgagcct | gtccccggc | aag | | | 1353 |

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Tyr Ala Phe Thr Asn Tyr Leu Ile Glu
1               5                   10

<210> SEQ ID NO 150
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Val Ile Asn Pro Gly Ser Gly Gly Thr Tyr Tyr Asn Glu Lys Phe Lys
1               5                   10                  15

Gly

<210> SEQ ID NO 151
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Trp Arg Gly Glu Gly Tyr Tyr Ala Tyr Tyr Asp Val
1               5                   10

<210> SEQ ID NO 152
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asn Tyr Leu Ile Glu
1               5

<210> SEQ ID NO 153
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Val Ile Asn Pro Gly Ser Gly Gly Thr Tyr Tyr Asn Glu Lys Phe Lys
1               5                   10                  15

Gly

<210> SEQ ID NO 154
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 154

Trp Arg Gly Glu Gly Tyr Tyr Ala Tyr Tyr Asp Val
1               5                   10

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Tyr Ala Phe Thr Asn Tyr
1               5

<210> SEQ ID NO 156
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Asn Pro Gly Ser Gly Gly
1               5

<210> SEQ ID NO 157
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Trp Arg Gly Glu Gly Tyr Tyr Ala Tyr Tyr Asp Val
1               5                   10

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Tyr Ala Phe Thr Asn Tyr Leu
1               5

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ile Asn Pro Gly Ser Gly Gly Thr
1               5
```

<210> SEQ ID NO 160
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 160

Ala Arg Trp Arg Gly Glu Gly Tyr Tyr Ala Tyr Tyr Asp Val
1               5                   10

<210> SEQ ID NO 161
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 161

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Thr Asn Tyr
            20                  25                  30

Leu Ile Glu Trp Val Arg Gln Met Pro Gly Lys Gly Leu Glu Trp Met
        35                  40                  45

Gly Val Ile Asn Pro Gly Ser Gly Gly Thr Tyr Tyr Asn Glu Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Arg Gly Glu Gly Tyr Tyr Ala Tyr Tyr Asp Val Trp Gly
            100                 105                 110

Gln Gly Thr Thr Val Thr Val Ser Ser
        115                 120

<210> SEQ ID NO 162
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 162
gaggtgcaat tggtgcagag cggagccgaa gtgaagaagc ccggcgagag cctgaagatc      60
agctgcaagg gcagcggcta cgccttcacc aactacctga tcgagtgggt gcgccagatg     120
cccggcaagg gcctggaatg gatgggcgtg atcaatcctg gcagcggcgg cacctactac     180
aacgagaagt tcaagggcca agtgaccatc agcgccgaca agagcatcag caccgcctac     240
ctccagtggt ccagcctgaa ggccagcgac accgccatgt actactgcgc caggtggcgg     300
ggagagggct actacgccta ctacgacgtg tggggccagg gcaccacagt gaccgtcagc     360
tca                                                                  363

<210> SEQ ID NO 163
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 163

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Thr Asn Tyr
            20                  25                  30

Leu Ile Glu Trp Val Arg Gln Met Pro Gly Lys Gly Leu Glu Trp Met
        35                  40                  45

Gly Val Ile Asn Pro Gly Ser Gly Gly Thr Tyr Tyr Asn Glu Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Arg Gly Glu Gly Tyr Tyr Ala Tyr Tyr Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
```

```
                385                 390                 395                 400
Val Leu Asp Ser Asp Gly Ser Phe Phe Leu Tyr Ser Lys Leu Thr Val
                    405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 164
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 164
gaggtgcaat tggtgcagag cggagccgaa gtgaagaagc ccggcgagag cctgaagatc      60
agctgcaagg gcagcggcta cgccttcacc aactacctga tcgagtgggt gcgccagatg     120
cccggcaagg gcctggaatg gatgggcgtg atcaatcctg gcagcggcgg cacctactac     180
aacgagaagt tcaagggcca agtgaccatc agcgccgaca gagcatcag caccgcctac      240 ctccagtggt ccagcctgaa ggccagcgac accgccatgt actactgcgc caggtggcgg     300
ggagagggct actacgccta ctacgacgtg tggggccagg gcaccacagt gaccgtcagc     360
tcagctagca ccaagggccc cagcgtgttc cccctggccc ccagcagcaa gagcaccagc     420
ggcggcacag ccgccctggg ctgcctggtg aaggactact cccccgagcc cgtgaccgtg     480
tcctggaaca gcggagccct gacctccggc gtgcacacct tcccgccgt gctgcagagc      540 agcggcctgt acagcctgtc cagcgtggtg acagtgccca gcagcagcct gggcacccag     600
acctacatct gcaacgtgaa ccacaagccc agcaacacca aggtggacaa gagagtggag     660
cccaagagct gcgacaagac ccacacctgc cccccctgcc cagccccaga gctgctgggc     720
ggaccctccg tgttcctgtt ccccccaag cccaaggaca cctgatgat cagcaggacc       780 cccgaggtga cctgcgtggt ggtggacgtg agccacgagg acccagaggt gaagttcaac     840
tggtacgtgg acggcgtgga ggtgcacaac gccaagacca gcccagaga ggagcagtac      900 gccagcacct acagggtggt gtccgtgctg accgtgctgc accaggactg gctgaacggc     960
aaggaataca agtgcaaggt ctccaacaag gccctgccag cccccatcga aaagaccatc    1020
agcaaggcca agggccagcc acgggagccc caggtgtaca ccctgccccc ctcccgggag    1080
gagatgacca gaaccaggt gtccctgacc tgtctggtga agggcttcta ccccagcgac     1140
atcgccgtgg agtgggagag caacggccag cccgagaaca actacaagac cacccccca      1200 gtgctggaca cgacggcag cttcttcctg tacagcaagc tgaccgtgga caagtccagg     1260
tggcagcagg gcaacgtgtt cagctgcagc gtgatgcacg aggccctgca caaccactac    1320
acccagaaga gcctgagcct gtccccgc aag                                   1353

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 165

Gly Tyr Ala Phe Ser Asn Tyr Leu Ile Glu
1               5                   10

<210> SEQ ID NO 166
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Val Ile Asn Pro Gly Ser Gly Gly Thr Asn Tyr Asn Glu Lys Phe Lys
1               5                   10                  15

Gly

<210> SEQ ID NO 167
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Trp Arg Gly Glu Gly Tyr Tyr Ala Tyr Tyr Asp Val
1               5                   10

<210> SEQ ID NO 168
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Asn Tyr Leu Ile Glu
1               5

<210> SEQ ID NO 169
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Val Ile Asn Pro Gly Ser Gly Gly Thr Asn Tyr Asn Glu Lys Phe Lys
1               5                   10                  15

Gly

<210> SEQ ID NO 170
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Trp Arg Gly Glu Gly Tyr Tyr Ala Tyr Tyr Asp Val
1               5                   10
```

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Tyr Ala Phe Ser Asn Tyr
1               5

<210> SEQ ID NO 172
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Asn Pro Gly Ser Gly Gly
1               5

<210> SEQ ID NO 173
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Trp Arg Gly Glu Gly Tyr Tyr Ala Tyr Tyr Asp Val
1               5                   10

<210> SEQ ID NO 174
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Tyr Ala Phe Ser Asn Tyr Leu
1               5

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ile Asn Pro Gly Ser Gly Gly Thr
1               5

<210> SEQ ID NO 176
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ala Arg Trp Arg Gly Glu Gly Tyr Tyr Ala Tyr Tyr Asp Val
1               5                   10

<210> SEQ ID NO 177
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Asn Tyr
            20                  25                  30

Leu Ile Glu Trp Val Arg Gln Met Pro Gly Lys Gly Leu Glu Trp Met
        35                  40                  45

Gly Val Ile Asn Pro Gly Ser Gly Thr Asn Tyr Asn Glu Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Arg Gly Glu Gly Tyr Tyr Ala Tyr Tyr Asp Val Trp Gly
            100                 105                 110

Gln Gly Thr Thr Val Thr Val Ser Ser
        115                 120

<210> SEQ ID NO 178
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178
gaggtgcaat tggtgcagag cggagccgaa gtgaagaagc ccggcgagag cctgaagatc      60
agctgcaagg gcagcggcta cgccttcagc aactacctga tcgagtgggt gcgccagatg     120
cccggcaagg gcctggaatg gatgggcgtg atcaatcctg gcagcggcgg caccaattac     180
aacgagaagt tcaagggcca agtgaccatc agcgccgaca gagcatcag caccgcctac     240 ctccagtggt ccagcctgaa ggccagcgac accgccatgt actactgcgc caggtggcgg     300
ggagagggct actacgccta ctacgacgtg tggggccagg gcaccacagt gaccgtcagc     360
tca                                                                  363

<210> SEQ ID NO 179
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Glu Val Gln Leu Val Gln Ser Gly Ala Glu Val Lys Lys Pro Gly Glu
1               5                   10                  15

```
Ser Leu Lys Ile Ser Cys Lys Gly Ser Gly Tyr Ala Phe Ser Asn Tyr
            20                  25                  30

Leu Ile Glu Trp Val Arg Gln Met Pro Gly Lys Gly Leu Glu Trp Met
        35                  40                  45

Gly Val Ile Asn Pro Ser Gly Gly Thr Asn Tyr Asn Glu Lys Phe
50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Arg Gly Glu Gly Tyr Tyr Ala Tyr Tyr Asp Val Trp Gly
                100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

His Glu Ala Leu His Asn His Tyr Thr Gln Lys Ser Leu Ser Leu Ser
        435                 440                 445

Pro Gly Lys
    450

<210> SEQ ID NO 180
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180
gaggtgcaat tggtgcagag cggagccgaa gtgaagaagc ccggcgagag cctgaagatc      60
agctgcaagg gcagcggcta cgccttcagc aactacctga tcgagtgggt gcgccagatg     120
cccggcaagg gcctggaatg gatgggcgtg atcaatcctg gcagcggcgg caccaattac     180
aacgagaagt tcaagggcca agtgaccatc agcgccgaca gagcatcag caccgcctac     240 ctccagtggt ccagcctgaa ggccagcgac accgccatgt actactgcgc caggtggcgg     300
ggagagggct actacgccta ctacgacgtg tggggccagg gcaccacagt gaccgtcagc     360
tcagctagca ccaagggccc cagcgtgttc cccctggccc ccagcagcaa gagcaccagc     420
ggcggcacag ccgccctggg ctgcctggtg aaggactact cccccgagcc cgtgaccgtg     480
tcctggaaca gcggagccct gacctccggc gtgcacacct tccccgccgt gctgcagagc     540
agcggcctgt acagcctgtc cagcgtggtg acagtgccca gcagcagcct gggcacccag     600
acctacatct gcaacgtgaa ccacaagccc agcaacacca aggtggacaa gagagtggag     660
cccaagagct gcgacaagac ccacacctgc ccccctgcc cagccccaga gctgctgggc     720
ggaccctccg tgttcctgtt ccccccaag cccaaggaca ccctgatgat cagcaggacc     780
cccgaggtga cctgcgtggt ggtggacgtg agccacgagg acccagaggt gaagttcaac     840
tggtacgtgg acggcgtgga ggtgcacaac gccaagacca gcccagaga ggagcagtac     900 gccagcacct acagggtggt gtccgtgctg accgtgctgc accaggactg gctgaacggc     960
aaggaataca agtgcaaggt ctccaacaag gccctgccag cccccatcga aagaccatc    1020 agcaaggcca agggccagcc acgggagccc caggtgtaca ccctgccccc ctcccgggag    1080
gagatgacca gaaccaggt gtccctgacc tgtctggtga agggcttcta ccccagcgac    1140
atcgccgtgg agtgggagag caacggccag cccgagaaca actacaagac cacccccca    1200 gtgctggaca gcgacggcag cttcttcctg tacagcaagc tgaccgtgga caagtccagg    1260
tggcagcagg gcaacgtgtt cagctgcagc gtgatgcacg aggccctgca caaccactac    1320
acccagaaga gcctgagcct gtccccggc aag                                  1353

<210> SEQ ID NO 181
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gly Tyr Ala Phe Thr Asn Tyr Leu Ile Glu
1               5                   10

<210> SEQ ID NO 182

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Val Ile Asn Pro Gly Ser Gly Gly Thr Asn Tyr Asn Glu Lys Phe Lys
1               5                   10                  15

Gly

<210> SEQ ID NO 183
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Trp Arg Gly Glu Gly Tyr Tyr Ala Tyr Tyr Asp Val
1               5                   10

<210> SEQ ID NO 184
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Asn Tyr Leu Ile Glu
1               5

<210> SEQ ID NO 185
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Val Ile Asn Pro Gly Ser Gly Gly Thr Asn Tyr Asn Glu Lys Phe Lys
1               5                   10                  15

Gly

<210> SEQ ID NO 186
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Trp Arg Gly Glu Gly Tyr Tyr Ala Tyr Tyr Asp Val
1               5                   10

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 187

Gly Tyr Ala Phe Thr Asn Tyr
1               5

<210> SEQ ID NO 188
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Asn Pro Gly Ser Gly Gly
1               5

<210> SEQ ID NO 189
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Trp Arg Gly Glu Gly Tyr Tyr Ala Tyr Tyr Asp Val
1               5                   10

<210> SEQ ID NO 190
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gly Tyr Ala Phe Thr Asn Tyr Leu
1               5

<210> SEQ ID NO 191
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ile Asn Pro Gly Ser Gly Gly Thr
1               5

<210> SEQ ID NO 192
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ala Arg Trp Arg Gly Glu Gly Tyr Tyr Ala Tyr Tyr Asp Val
1               5                   10

<210> SEQ ID NO 193

```
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193
```

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Thr Asn Tyr
            20                  25                  30

Leu Ile Glu Trp Val Arg Gln Met Pro Gly Lys Gly Leu Glu Trp Met
        35                  40                  45

Gly Val Ile Asn Pro Gly Ser Gly Gly Thr Asn Tyr Asn Glu Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Arg Gly Glu Gly Tyr Tyr Ala Tyr Tyr Asp Val Trp Gly
            100                 105                 110

Gln Gly Thr Thr Val Thr Val Ser Ser
        115                 120

```
<210> SEQ ID NO 194
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 194
```
gaggtgcaat tggtgcagag cggagccgaa gtgaagaagc ccggcgagag cctgaagatc      60
agctgcaagg gcagcggcta cgccttcacc aactacctga tcgagtgggt gcgccagatg     120
cccggcaagg gcctggaatg gatgggcgtg atcaatcctg gcagcggcgg caccaattac     180
aacgagaagt tcaagggcca agtgaccatc agcgccgaca agagcatcag caccgcctac     240
ctccagtggt ccagcctgaa ggccagcgac accgccatgt actactgcgc caggtggcgg     300
ggagagggct actacgccta ctacgacgtg tggggccagg gcaccacagt gaccgtcagc     360
tca                                                                  363

```
<210> SEQ ID NO 195
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195
```

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Thr Asn Tyr
            20                  25                  30

Leu Ile Glu Trp Val Arg Gln Met Pro Gly Lys Gly Leu Glu Trp Met
        35                  40                  45

Gly Val Ile Asn Pro Gly Ser Gly Gly Thr Asn Tyr Asn Glu Lys Phe

```
            50                  55                  60
Lys Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                     85                  90                  95

Ala Arg Trp Arg Gly Glu Gly Tyr Tyr Ala Tyr Tyr Asp Val Trp Gly
                100                 105                 110

Gln Gly Thr Thr Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Ala Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
450

<210> SEQ ID NO 196
```

<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 196

```
gaggtgcaat tggtgcagag cggagccgaa gtgaagaagc ccggcgagag cctgaagatc      60
agctgcaagg gcagcggcta cgccttcacc aactacctga tcgagtgggt gcgccagatg     120
cccggcaagg gcctggaatg gatgggcgtg atcaatcctg gcagcggcgg caccaattac     180
aacgagaagt tcaagggcca agtgaccatc agcgccgaca gagcatcag caccgcctac     240
ctccagtggt ccagcctgaa ggccagcgac accgccatgt actactgcgc caggtggcgg     300
ggagagggct actacgccta ctacgacgtg tggggccagg gcaccacagt gaccgtcagc     360
tcagctagca ccaagggccc cagcgtgttc cccctggccc ccagcagcaa gagcaccagc     420
ggcggcacag ccgccctggg ctgcctggtg aaggactact cccccgagcc cgtgaccgtg     480
tcctggaaca gcggagccct gacctccggc gtgcacacct cccgccgt gctgcagagc     540
agcggcctgt acagcctgtc cagcgtggtg acagtgccca gcagcagcct gggcacccag     600
acctacatct gcaacgtgaa ccacaagccc agcaacacca aggtggacaa gagagtggag     660
cccaagagct gcgacaagac ccacacctgc ccccctgcc cagccccaga gctgctgggc     720
ggaccctccg tgttcctgtt cccccccaag cccaaggaca ccctgatgat cagcaggacc     780
cccgaggtga cctgcgtggt ggtggacgtg agccacgagg acccagaggt gaagttcaac     840
tggtacgtgg acggcgtgga ggtgcacaac gccaagacca gcccagaga ggagcagtac     900
gccagcacct acagggtggt gtccgtgctg accgtgctgc accaggactg gctgaacggc     960
aaggaataca agtgcaaggt ctccaacaag gccctgccag cccccatcga aaagaccatc    1020
agcaaggcca agggccagcc acgggagccc caggtgtaca ccctgccccc ctcccgggag    1080
gagatgacca agaaccaggt gtccctgacc tgtctggtga agggcttcta ccccagcgac    1140
atcgccgtgg agtgggagag caacggccag cccgagaaca actacaagac cacccccca    1200
gtgctggaca gcgacggcag cttcttcctg tacagcaagc tgaccgtgga caagtccagg    1260
tggcagcagg gcaacgtgtt cagctgcagc gtgatgcacg aggccctgca caaccactac    1320
acccagaaga gcctgagcct gtcccccggc aag                                 1353
```

<210> SEQ ID NO 197
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gly Tyr Ala Phe Ser Asn Tyr Leu Ile Glu
1               5                   10

<210> SEQ ID NO 198
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

```
Val Ile Asn Pro Gly Ser Gly Gly Thr Tyr Tyr Asn Glu Lys Phe Lys
1               5                   10                  15

Gly

<210> SEQ ID NO 199
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Trp Arg Gly Glu Gly Tyr Tyr Ala Tyr Phe Asp Val
1               5                   10

<210> SEQ ID NO 200
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Asn Tyr Leu Ile Glu
1               5

<210> SEQ ID NO 201
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Val Ile Asn Pro Gly Ser Gly Gly Thr Tyr Tyr Asn Glu Lys Phe Lys
1               5                   10                  15

Gly

<210> SEQ ID NO 202
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Trp Arg Gly Glu Gly Tyr Tyr Ala Tyr Phe Asp Val
1               5                   10

<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Tyr Ala Phe Ser Asn Tyr
1               5
```

```
<210> SEQ ID NO 204
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Asn Pro Gly Ser Gly Gly
1               5

<210> SEQ ID NO 205
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Trp Arg Gly Glu Gly Tyr Tyr Ala Tyr Phe Asp Val
1               5                   10

<210> SEQ ID NO 206
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Tyr Ala Phe Ser Asn Tyr Leu
1               5

<210> SEQ ID NO 207
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ile Asn Pro Gly Ser Gly Gly Thr
1               5

<210> SEQ ID NO 208
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ala Arg Trp Arg Gly Glu Gly Tyr Tyr Ala Tyr Phe Asp Val
1               5                   10

<210> SEQ ID NO 209
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209
```

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Asn Tyr
            20                  25                  30

Leu Ile Glu Trp Val Arg Gln Met Pro Gly Lys Gly Leu Glu Trp Met
        35                  40                  45

Gly Val Ile Asn Pro Gly Ser Gly Gly Thr Tyr Tyr Asn Glu Lys Phe
50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Arg Gly Glu Gly Tyr Tyr Ala Tyr Phe Asp Val Trp Gly
            100                 105                 110

Gln Gly Thr Thr Val Thr Val Ser Ser
        115                 120

<210> SEQ ID NO 210
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 210
gaggtgcaat tggtgcagag cggagccgaa gtgaagaagc ccggcgagag cctgaagatc      60
agctgcaagg gcagcggcta cgccttcagc aactacctga tcgagtgggt gcgccagatg    120
cccggcaagg gcctggaatg gatgggcgtg atcaatcctg gcagcggcgg cacctactac    180
aacgagaagt tcaagggcca agtgaccatc agcgccgaca agagcatcag caccgcctac    240
ctccagtggt ccagcctgaa ggccagcgac accgccatgt actactgcgc caggtggcgg    300
ggagagggct actacgccta cttcgacgtg tggggccagg gcaccacagt gaccgtcagc    360
tca                                                                  363

<210> SEQ ID NO 211
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Asn Tyr
            20                  25                  30

Leu Ile Glu Trp Val Arg Gln Met Pro Gly Lys Gly Leu Glu Trp Met
        35                  40                  45

Gly Val Ile Asn Pro Gly Ser Gly Gly Thr Tyr Tyr Asn Glu Lys Phe
50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Arg Gly Glu Gly Tyr Tyr Ala Tyr Phe Asp Val Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 212
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 212

```
gaggtgcaat tggtgcagag cggagccgaa gtgaagaagc ccggcgagag cctgaagatc        60
agctgcaagg gcagcggcta cgccttcagc aactacctga tcgagtgggt gcgccagatg       120
cccggcaagg gcctggaatg gatgggcgtg atcaatcctg gcagcggcgg cacctactac       180
aacgagaagt tcaagggcca agtgaccatc agcgccgaca gagcatcag caccgcctac        240 ctccagtggt ccagcctgaa ggccagcgac accgccatgt actactgcgc caggtggcgg       300
ggagagggct actacgccta cttcgacgtg tggggccagg gcaccacagt gaccgtcagc       360
tcagctagca ccaagggccc cagcgtgttc cccctggccc ccagcagcaa gagcaccagc       420
ggcggcacag ccgccctggg ctgcctggtg aaggactact ccccgagcc cgtgaccgtg        480 tcctggaaca gcggagccct gacctccggc gtgcacacct ccccgccgt gctgcagagc        540 agcggcctgt acagcctgtc cagcgtggtg acagtgccca gcagcagcct gggcacccag       600
acctacatct gcaacgtgaa ccacaagccc agcaacacca aggtggacaa gagagtggag       660
cccaagagct gcgacaagac ccacacctgc ccccccgcc cagccccaga gctgctgggc        720
ggaccctccg tgttcctgtt ccccccaag cccaaggaca ccctgatgat cagcaggacc       780
cccgaggtga cctgcgtggt ggtggacgtg agccacgagg acccagaggt gaagttcaac       840
tggtacgtgg acggcgtgga ggtgcacaac gccaagacca gcccagaga ggagcagtac        900 gccagcacct acagggtggt gtccgtgctg accgtgctgc accaggactg gctgaacggc       960
aaggaataca agtgcaaggt ctccaacaag gccctgccag ccccatcga aaagaccatc      1020 agcaaggcca agggccagcc acgggagccc caggtgtaca ccctgccccc ctcccgggag      1080
gagatgacca agaaccaggt gtccctgacc tgtctggtga agggcttcta cccagcgac       1140 atcgccgtgg agtgggagag caacggccag cccgagaaca actacaagac caccccccca      1200
gtgctggaca gcgacggcag cttcttcctg tacagcaagc tgaccgtgga caagtccagg      1260
tggcagcagg gcaacgtgtt cagctgcagc gtgatgcacg aggccctgca caaccactac      1320
acccagaaga gcctgagcct gtccccggc aag                                    1353

<210> SEQ ID NO 213
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gly Tyr Ala Phe Thr Asn Tyr Leu Ile Glu
1               5                   10

<210> SEQ ID NO 214
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Val Ile Asn Pro Gly Ser Gly Gly Thr Tyr Tyr Asn Glu Lys Phe Lys
1               5                   10                  15

Gly

<210> SEQ ID NO 215
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Trp Arg Gly Glu Gly Tyr Tyr Ala Tyr Phe Asp Val
1               5                   10

<210> SEQ ID NO 216
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Asn Tyr Leu Ile Glu
1               5

<210> SEQ ID NO 217
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Val Ile Asn Pro Gly Ser Gly Gly Thr Tyr Tyr Asn Glu Lys Phe Lys
1               5                   10                  15

Gly

<210> SEQ ID NO 218
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Trp Arg Gly Glu Gly Tyr Tyr Ala Tyr Phe Asp Val
1               5                   10

<210> SEQ ID NO 219
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Gly Tyr Ala Phe Thr Asn Tyr
1               5

<210> SEQ ID NO 220
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 220

Asn Pro Gly Ser Gly Gly
1               5

<210> SEQ ID NO 221
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Trp Arg Gly Glu Gly Tyr Tyr Ala Tyr Phe Asp Val
1               5                   10

<210> SEQ ID NO 222
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gly Tyr Ala Phe Thr Asn Tyr Leu
1               5

<210> SEQ ID NO 223
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Ile Asn Pro Gly Ser Gly Gly Thr
1               5

<210> SEQ ID NO 224
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ala Arg Trp Arg Gly Glu Gly Tyr Tyr Ala Tyr Phe Asp Val
1               5                   10

<210> SEQ ID NO 225
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Thr Asn Tyr
            20                  25                  30

Leu Ile Glu Trp Val Arg Gln Met Pro Gly Lys Gly Leu Glu Trp Met
```

-continued

```
                35                  40                  45
Gly Val Ile Asn Pro Gly Ser Gly Gly Thr Tyr Tyr Asn Glu Lys Phe
         50                  55                  60
Lys Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Trp Arg Gly Glu Gly Tyr Tyr Ala Tyr Phe Asp Val Trp Gly
            100                 105                 110
Gln Gly Thr Thr Val Thr Val Ser Ser
            115                 120

<210> SEQ ID NO 226
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 226
gaggtgcaat tggtgcagag cggagccgaa gtgaagaagc ccggcgagag cctgaagatc      60
agctgcaagg gcagcggcta cgccttcacc aactacctga tcgagtgggt gcgccagatg     120
cccggcaagg gcctggaatg gatgggcgtg atcaatcctg gcagcggcgg cacctactac     180
aacgagaagt tcaagggcca agtgaccatc agcgccgaca agagcatcag caccgcctac     240
ctccagtggt ccagcctgaa ggccagcgac accgccatgt actactgcgc caggtggcgg     300
ggagagggct actacgccta cttcgacgtg tggggccagg gcaccacagt gaccgtcagc     360
tca                                                                   363

<210> SEQ ID NO 227
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Glu Val Gln Leu Val Gln Ser Gly Ala Glu Val Lys Lys Pro Gly Glu
  1               5                  10                  15
Ser Leu Lys Ile Ser Cys Lys Gly Ser Gly Tyr Ala Phe Thr Asn Tyr
                 20                  25                  30
Leu Ile Glu Trp Val Arg Gln Met Pro Gly Lys Gly Leu Glu Trp Met
             35                  40                  45
Gly Val Ile Asn Pro Gly Ser Gly Gly Thr Tyr Tyr Asn Glu Lys Phe
         50                  55                  60
Lys Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Trp Arg Gly Glu Gly Tyr Tyr Ala Tyr Phe Asp Val Trp Gly
            100                 105                 110
Gln Gly Thr Thr Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
        130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 228
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 228
gaggtgcaat tggtgcagag cggagccgaa gtgaagaagc ccggcgagag cctgaagatc      60
agctgcaagg gcagcggcta cgccttcacc aactacctga tcgagtgggt gcgccagatg     120
cccggcaagg gcctggaatg gatgggcgtg atcaatcctg gcagcggcgg cacctactac     180
aacgagaagt tcaagggcca agtgaccatc agcgccgaca gagcatcag caccgcctac     240
```

-continued

```
ctccagtggt ccagcctgaa ggccagcgac accgccatgt actactgcgc caggtggcgg    300
ggagagggct actacgccta cttcgacgtg tggggccagg gcaccacagt gaccgtcagc    360
tcagctagca ccaagggccc cagcgtgttc cccctggccc ccagcagcaa gagcaccagc    420
ggcggcacag ccgccctggg ctgcctggtg aaggactact ccccgagcc cgtgaccgtg    480 tcctggaaca gcggagccct gacctccggc gtgcacacct tccccgccgt gctgcagagc    540
agcggcctgt acagcctgtc cagcgtggtg acagtgccca gcagcagcct gggcacccag    600
acctacatct gcaacgtgaa ccacaagccc agcaacacca aggtggacaa gagagtggag    660
cccaagagct gcgacaagac ccacacctgc ccccctgcc cagcccagaa gctgctgggc    720
ggaccctccg tgttcctgtt ccccccaag cccaaggaca ccctgatgat cagcaggacc    780
cccgaggtga cctgcgtggt ggtggacgtg agccacgagg acccagaggt gaagttcaac    840
tggtacgtgg acggcgtgga ggtgcacaac gccaagacca gcccagaga ggagcagtac    900 gccagcacct acagggtggt gtccgtgctg accgtgctgc accaggactg gctgaacggc    960
aaggaataca agtgcaaggt ctccaacaag gccctgccag cccccatcga aagaccatc    1020 agcaaggcca agggccagcc acgggagccc caggtgtaca ccctgccccc ctcccgggag    1080
gagatgacca agaaccaggt gtccctgacc tgtctggtga agggcttcta ccccagcgac    1140
atcgccgtgg agtgggagag caacggccag cccgagaaca actacaagac cacccccca    1200 gtgctggaca gcgacggcag cttcttcctg tacagcaagc tgaccgtgga caagtccagg    1260
tggcagcagg gcaacgtgtt cagctgcagc gtgatgcacg aggccctgca caaccactac    1320
acccagaaga gcctgagcct gtcccccggc aag                                1353
```

<210> SEQ ID NO 229
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Thr Asn Tyr
                20                  25                  30

Leu Ile Glu Trp Val Arg Gln Met Pro Gly Lys Gly Leu Glu Trp Met
            35                  40                  45

Gly Val Ile Asn Pro Gly Ser Gly Thr Asn Tyr Asn Glu Lys Phe
        50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Arg Gly Glu Gly Tyr Tyr Ala Tyr Phe Asp Val Trp Gly
                100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160
```

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 230
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 230
gaggtgcaat tggtgcagag cggagccgaa gtgaagaagc ccggcgagag cctgaagatc        60
agctgcaagg gcagcggcta cgccttcacc aactacctga tcgagtgggt gcgccagatg       120
cccggcaagg gcctggaatg gatgggcgtg atcaatcctg gcagcggcgg caccaattac       180
aacgagaagt tcaagggcca agtgaccatc agcgccgaca gagcatcag caccgcctac       240 ctccagtggt ccagcctgaa ggccagcgac accgccatgt actactgcgc caggtggcgg       300

```
ggagagggct actacgccta cttcgacgtg tggggccagg gcaccacagt gaccgtcagc    360
tcagctagca ccaagggccc cagcgtgttc cccctggccc ccagcagcaa gagcaccagc    420
ggcggcacag ccgccctggg ctgcctggtg aaggactact tccccgagcc cgtgaccgtg    480
tcctggaaca gcggagccct gacctccggc gtgcacacct tccccgccgt gctgcagagc    540
agcggcctgt acagcctgtc cagcgtggtg acagtgccca gcagcagcct gggcacccag    600
acctacatct gcaacgtgaa ccacaagccc agcaacacca aggtggacaa gagagtggag    660
cccaagagct gcgacaagac ccacacctgc ccccctgcc cagccccaga gctgctgggc     720
ggaccctccg tgttcctgtt ccccccaag cccaaggaca ccctgatgat cagcaggacc      780
cccgaggtga cctgcgtggt ggtggacgtg agccacgagg acccagaggt gaagttcaac    840
tggtacgtgg acggcgtgga ggtgcacaac gccaagacca gcccagaga ggagcagtac     900 gccagcacct acagggtggt gtccgtgctg accgtgctgc accaggactg gctgaacggc    960
aaggaataca agtgcaaggt ctccaacaag gccctgccag cccccatcga aaagaccatc   1020
agcaaggcca agggccagcc acgggagccc caggtgtaca ccctgccccc ctcccgggag   1080
gagatgacca gaaccaggt gtccctgacc tgtctggtga agggcttcta ccccagcgac     1140
atcgccgtgg agtgggagag caacggccag cccgagaaca actacaagac caccccccca   1200
gtgctggaca gcgacggcag cttcttcctg tacagcaagc tgaccgtgga caagtccagg   1260
tggcagcagg gcaacgtgtt cagctgcagc gtgatgcacg aggccctgca caaccactac   1320
acccagaaga gcctgagcct gtcccccggc aag                                 1353
```

<210> SEQ ID NO 231
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Lys Ala Ser Gln Ser Val Asp Tyr Gln Gly Asp Ser Tyr Met Asn
1               5                   10                  15

<210> SEQ ID NO 232
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Ser Ala Ser Asn Leu Glu Ser
1               5

<210> SEQ ID NO 233
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Gln Gln Ser Asn Glu Asp Pro Tyr Thr
1               5

```
<210> SEQ ID NO 234
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Lys Ala Ser Gln Ser Val Asp Tyr Gln Gly Asp Ser Tyr Met Asn
1               5                   10                  15

<210> SEQ ID NO 235
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ser Ala Ser Asn Leu Glu Ser
1               5

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gln Gln Ser Asn Glu Asp Pro Tyr Thr
1               5

<210> SEQ ID NO 237
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ser Gln Ser Val Asp Tyr Gln Gly Asp Ser Tyr
1               5                   10

<210> SEQ ID NO 238
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ser Ala Ser
1

<210> SEQ ID NO 239
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239
```

```
Ser Asn Glu Asp Pro Tyr
1               5
```

<210> SEQ ID NO 240
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

```
Gln Ser Val Asp Tyr Gln Gly Asp Ser Tyr
1               5                   10
```

<210> SEQ ID NO 241
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

```
Ser Ala Ser
1
```

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

```
Gln Gln Ser Asn Glu Asp Pro Tyr Thr
1               5
```

<210> SEQ ID NO 243
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

```
Ala Ile Arg Leu Thr Gln Ser Pro Ser Ser Phe Ser Ala Ser Thr Gly
1               5                   10                  15

Asp Arg Val Thr Ile Thr Cys Lys Ala Ser Gln Ser Val Asp Tyr Gln
            20                  25                  30

Gly Asp Ser Tyr Met Asn Trp Tyr Gln Gln Lys Pro Gly Lys Ala Pro
        35                  40                  45

Lys Leu Leu Ile Tyr Ser Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Ser Glu Asp Phe Ala Thr Tyr Tyr Cys Gln Gln Ser Asn
                85                  90                  95

Glu Asp Pro Tyr Thr Phe Gly Gly Gly Thr Lys Val Glu Ile Lys
            100                 105                 110
```

<210> SEQ ID NO 244
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 244

```
gccatcagac tgacccagag ccccagcagc tttagcgcca gcaccggcga cagagtgacc      60
atcacatgca aggccagcca gagcgtggac taccagggcg acagctacat gaactggtat     120
cagcagaagc ccggcaaggc ccccaagctg ctgatctact ccgccagcaa tctggaaagc     180
ggcgtgccca gcagattcag cggctctggc agcggcaccg acttcaccct gacaatcagc     240
agcctccagt ccgaggactt cgccacctac tactgccagc agagcaacga ggacccctac     300
acctttggcg gaggcaccaa ggtggaaatc aag                                  333
```

<210> SEQ ID NO 245
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

```
Ala Ile Arg Leu Thr Gln Ser Pro Ser Ser Phe Ser Ala Ser Thr Gly
1               5                   10                  15
Asp Arg Val Thr Ile Thr Cys Lys Ala Ser Gln Ser Val Asp Tyr Gln
            20                  25                  30
Gly Asp Ser Tyr Met Asn Trp Tyr Gln Gln Lys Pro Gly Lys Ala Pro
        35                  40                  45
Lys Leu Leu Ile Tyr Ser Ala Ser Asn Leu Glu Ser Gly Val Pro Ser
    50                  55                  60
Arg Phe Ser Gly Ser Gly Ser Gly Thr Asp Phe Thr Leu Thr Ile Ser
65                  70                  75                  80
Ser Leu Gln Ser Glu Asp Phe Ala Thr Tyr Tyr Cys Gln Gln Ser Asn
                85                  90                  95
Glu Asp Pro Tyr Thr Phe Gly Gly Gly Thr Lys Val Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

<210> SEQ ID NO 246
<211> LENGTH: 654
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 246
gccatcagac tgacccagag ccccagcagc tttagcgcca gcaccggcga cagagtgacc      60
atcacatgca aggccagcca gagcgtggac taccagggcg acagctacat gaactggtat     120
cagcagaagc ccggcaaggc ccccaagctg ctgatctact ccgccagcaa tctggaaagc     180
ggcgtgccca gcagattcag cggctctggc agcggcaccg acttcaccct gacaatcagc     240
agcctccagt ccgaggactt cgccacctac tactgccagc agagcaacga gacccctac      300 acctttggcg aggcaccaa ggtggaaatc aagcgtacgg tggccgctcc cagcgtgttc      360
atcttccccc ccagcgacga gcagctgaag agcggcaccg ccagcgtggt gtgcctgctg     420
aacaacttct accccgggga ggccaaggtg cagtggaagg tggacaacgc cctgcagagc     480
ggcaacagcc aggagagcgt caccgagcag gacagcaagg actccaccta cagcctgagc     540
agcaccctga ccctgagcaa ggccgactac gagaagcata aggtgtacgc ctgcgaggtg     600
acccaccagg gcctgtccag ccccgtgacc aagagcttca caggggcga gtgc            654

<210> SEQ ID NO 247
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Lys Ala Ser Gln Ser Val Asp Tyr Gln Gly Asp Ser Tyr Met Asn
1               5                   10                  15

<210> SEQ ID NO 248
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Thr Ala Ser Asn Leu Glu Ser
1               5

<210> SEQ ID NO 249
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gln Gln Ser Asn Glu Asp Pro Tyr Thr
1               5

<210> SEQ ID NO 250
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 250

Lys Ala Ser Gln Ser Val Asp Tyr Gln Gly Asp Ser Tyr Met Asn
1               5                   10                  15

<210> SEQ ID NO 251
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Thr Ala Ser Asn Leu Glu Ser
1               5

<210> SEQ ID NO 252
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gln Gln Ser Asn Glu Asp Pro Tyr Thr
1               5

<210> SEQ ID NO 253
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Ser Gln Ser Val Asp Tyr Gln Gly Asp Ser Tyr
1               5                   10

<210> SEQ ID NO 254
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Thr Ala Ser
1

<210> SEQ ID NO 255
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ser Asn Glu Asp Pro Tyr
1               5

<210> SEQ ID NO 256
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Gln Ser Val Asp Tyr Gln Gly Asp Ser Tyr
1               5                   10

<210> SEQ ID NO 257
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Thr Ala Ser
1

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Gln Gln Ser Asn Glu Asp Pro Tyr Thr
1               5

<210> SEQ ID NO 259
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Ala Ile Arg Leu Thr Gln Ser Pro Ser Ser Phe Ser Ala Ser Thr Gly
1               5                   10                  15

Asp Arg Val Thr Ile Thr Cys Lys Ala Ser Gln Ser Val Asp Tyr Gln
            20                  25                  30

Gly Asp Ser Tyr Met Asn Trp Tyr Gln Gln Lys Pro Gly Lys Ala Pro
        35                  40                  45

Lys Leu Leu Ile Tyr Thr Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Ser Glu Asp Phe Ala Thr Tyr Tyr Cys Gln Gln Ser Asn
                85                  90                  95

Glu Asp Pro Tyr Thr Phe Gly Gly Gly Thr Lys Val Glu Ile Lys
            100                 105                 110

<210> SEQ ID NO 260
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 260

```
gccatcagac tgacccagag ccccagcagc tttagcgcca gcaccggcga cagagtgacc      60
atcacatgca aggccagcca gagcgtggac taccagggcg acagctacat gaactggtat     120
cagcagaagc ccggcaaggc ccccaagctg ctgatctaca ccgccagcaa tctggaaagc     180
ggcgtgccca gcagattcag cggctctggc agcggcaccg acttcaccct gacaatcagc     240
agcctccagt ccgaggactt cgccacctac tactgccagc agagcaacga ggacccctac     300
acctttggcg gaggcaccaa ggtggaaatc aag                                  333
```

<210> SEQ ID NO 261
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

```
Ala Ile Arg Leu Thr Gln Ser Pro Ser Ser Phe Ser Ala Ser Thr Gly
1               5                   10                  15

Asp Arg Val Thr Ile Thr Cys Lys Ala Ser Gln Ser Val Asp Tyr Gln
                20                  25                  30

Gly Asp Ser Tyr Met Asn Trp Tyr Gln Gln Lys Pro Gly Lys Ala Pro
            35                  40                  45

Lys Leu Leu Ile Tyr Thr Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Ser Glu Asp Phe Ala Thr Tyr Tyr Cys Gln Gln Ser Asn
                85                  90                  95

Glu Asp Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 262
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 262

```
gccatcagac tgacccagag ccccagcagc tttagcgcca gcaccggcga cagagtgacc    60
atcacatgca aggccagcca gagcgtggac taccagggcg acagctacat gaactggtat   120
cagcagaagc ccggcaaggc ccccaagctg ctgatctaca ccgccagcaa tctggaaagc   180
ggcgtgccca gcagattcag cggctctggc agcggcaccg acttcaccct gacaatcagc   240
agcctccagt ccgaggactt cgccacctac tactgccagc agagcaacga ggacccctac   300
acctttggcg gaggcaccaa ggtggaaatc aagcgtacgg tggccgctcc cagcgtgttc   360
atcttccccc ccagcgacga gcagctgaag agcggcaccg ccagcgtggt gtgcctgctg   420
aacaacttct accccgggga ggccaaggtg cagtggaagg tggacaacgc cctgcagagc   480
ggcaacagcc aggagagcgt caccgagcag gacagcaagg actccaccta cagcctgagc   540
agcaccctga ccctgagcaa ggccgactac gagaagcata aggtgtacgc ctgcgaggtg   600
acccaccagg gcctgtccag ccccgtgacc aagagcttca caggggcga gtgc         654
```

```
<210> SEQ ID NO 263
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Lys Ala Ser Gln Ser Val Asp Tyr Gln Gly Asp Ser Tyr Leu Asn
1               5                   10                  15

<210> SEQ ID NO 264
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Ser Ala Ser Asn Leu Glu Ser
1               5

<210> SEQ ID NO 265
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Gln Gln Ser Asn Glu Asp Pro Tyr Thr
1               5

<210> SEQ ID NO 266
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Lys Ala Ser Gln Ser Val Asp Tyr Gln Gly Asp Ser Tyr Leu Asn
1               5                   10                  15
```

```
<210> SEQ ID NO 267
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ser Ala Ser Asn Leu Glu Ser
1               5

<210> SEQ ID NO 268
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Gln Gln Ser Asn Glu Asp Pro Tyr Thr
1               5

<210> SEQ ID NO 269
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Ser Gln Ser Val Asp Tyr Gln Gly Asp Ser Tyr
1               5                   10

<210> SEQ ID NO 270
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Ser Ala Ser
1

<210> SEQ ID NO 271
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Ser Asn Glu Asp Pro Tyr
1               5

<210> SEQ ID NO 272
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272
```

Gln Ser Val Asp Tyr Gln Gly Asp Ser Tyr
1               5                   10

<210> SEQ ID NO 273
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Ser Ala Ser
1

<210> SEQ ID NO 274
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Gln Gln Ser Asn Glu Asp Pro Tyr Thr
1               5

<210> SEQ ID NO 275
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Ala Ile Arg Leu Thr Gln Ser Pro Ser Ser Phe Ser Ala Ser Thr Gly
1               5                   10                  15

Asp Arg Val Thr Ile Thr Cys Lys Ala Ser Gln Ser Val Asp Tyr Gln
            20                  25                  30

Gly Asp Ser Tyr Leu Asn Trp Tyr Gln Gln Lys Pro Gly Lys Ala Pro
        35                  40                  45

Lys Leu Leu Ile Tyr Ser Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Ser Glu Asp Phe Ala Thr Tyr Tyr Cys Gln Gln Ser Asn
                85                  90                  95

Glu Asp Pro Tyr Thr Phe Gly Gly Gly Thr Lys Val Glu Ile Lys
            100                 105                 110

<210> SEQ ID NO 276
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 276
gccatcagac tgacccagag ccccagcagc tttagcgcca gcaccggcga cagagtgacc      60
atcacatgca aggccagcca gagcgtggac taccagggcg acagctacct gaactggtat     120

```
cagcagaagc ccggcaaggc ccccaagctg ctgatctact ccgccagcaa tctggaaagc      180
ggcgtgccca gcagattcag cggctctggc agcggcaccg acttcaccct gacaatcagc      240
agcctccagt ccgaggactt cgccacctac tactgccagc agagcaacga ggaccectac      300 acctttggcg gaggcaccaa ggtggaaatc aag                                   333
```

```
<210> SEQ ID NO 277
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277
```

```
Ala Ile Arg Leu Thr Gln Ser Pro Ser Ser Phe Ser Ala Ser Thr Gly
  1               5                  10                  15

Asp Arg Val Thr Ile Thr Cys Lys Ala Ser Gln Ser Val Asp Tyr Gln
             20                  25                  30

Gly Asp Ser Tyr Leu Asn Trp Tyr Gln Gln Lys Pro Gly Lys Ala Pro
         35                  40                  45

Lys Leu Leu Ile Tyr Ser Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Ser Glu Asp Phe Ala Thr Tyr Tyr Cys Gln Gln Ser Asn
                 85                  90                  95

Glu Asp Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

```
<210> SEQ ID NO 278
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 278
```

```
gccatcagac tgacccagag ccccagcagc tttagcgcca gcaccggcga cagagtgacc      60
atcacatgca aggccagcca gagcgtggac taccagggcg acagctacct gaactggtat     120
cagcagaagc ccggcaaggc ccccaagctg ctgatctact ccgccagcaa tctggaaagc     180
ggcgtgccca gcagattcag cggctctggc agcggcaccg acttcaccct gacaatcagc     240
```

```
agcctccagt ccgaggactt cgccacctac tactgccagc agagcaacga ggacccctac    300
acctttggcg gaggcaccaa ggtggaaatc aagcgtacgg tggccgctcc cagcgtgttc    360
atcttccccc ccagcgacga gcagctgaag agcggcaccg ccagcgtggt gtgcctgctg    420
aacaacttct accccgggga ggccaaggtg cagtggaagg tggacaacgc cctgcagagc    480
ggcaacagcc aggagagcgt caccgagcag gacagcaagg actccaccta cagcctgagc    540
agcaccctga ccctgagcaa ggccgactac gagaagcata aggtgtacgc ctgcgaggtg    600
acccaccagg gcctgtccag ccccgtgacc aagagcttca caggggcga gtgc           654
```

<210> SEQ ID NO 279
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Lys Ala Ser Gln Ser Val Asp Tyr Gln Gly Asp Ser Tyr Leu Asn
1               5                   10                  15

<210> SEQ ID NO 280
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Ala Ala Ser Asn Leu Glu Ser
1               5

<210> SEQ ID NO 281
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Gln Gln Ser Asn Glu Asp Pro Tyr Thr
1               5

<210> SEQ ID NO 282
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Lys Ala Ser Gln Ser Val Asp Tyr Gln Gly Asp Ser Tyr Leu Asn
1               5                   10                  15

<210> SEQ ID NO 283
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 283

Ala Ala Ser Asn Leu Glu Ser
1               5

<210> SEQ ID NO 284
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Gln Gln Ser Asn Glu Asp Pro Tyr Thr
1               5

<210> SEQ ID NO 285
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Ser Gln Ser Val Asp Tyr Gln Gly Asp Ser Tyr
1               5                   10

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292
```

```
<400> SEQUENCE: 292
000

<210> SEQ ID NO 293
<400> SEQUENCE: 293
000

<210> SEQ ID NO 294
<400> SEQUENCE: 294
000

<210> SEQ ID NO 295
<400> SEQUENCE: 295
000

<210> SEQ ID NO 296
<400> SEQUENCE: 296
000

<210> SEQ ID NO 297
<400> SEQUENCE: 297
000

<210> SEQ ID NO 298
<400> SEQUENCE: 298
000

<210> SEQ ID NO 299
<400> SEQUENCE: 299
000

<210> SEQ ID NO 300
<400> SEQUENCE: 300
000

<210> SEQ ID NO 301
<400> SEQUENCE: 301
000

<210> SEQ ID NO 302
<400> SEQUENCE: 302
000

<210> SEQ ID NO 303
<400> SEQUENCE: 303
```

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

```
<210> SEQ ID NO 315
<400> SEQUENCE: 315
000

<210> SEQ ID NO 316
<400> SEQUENCE: 316
000

<210> SEQ ID NO 317
<400> SEQUENCE: 317
000

<210> SEQ ID NO 318
<400> SEQUENCE: 318
000

<210> SEQ ID NO 319
<400> SEQUENCE: 319
000

<210> SEQ ID NO 320
<400> SEQUENCE: 320
000

<210> SEQ ID NO 321
<400> SEQUENCE: 321
000

<210> SEQ ID NO 322
<400> SEQUENCE: 322
000

<210> SEQ ID NO 323
<400> SEQUENCE: 323
000

<210> SEQ ID NO 324
<400> SEQUENCE: 324
000

<210> SEQ ID NO 325
<400> SEQUENCE: 325
000

<210> SEQ ID NO 326
```

```
<400> SEQUENCE: 326
000

<210> SEQ ID NO 327
<400> SEQUENCE: 327
000

<210> SEQ ID NO 328
<400> SEQUENCE: 328
000

<210> SEQ ID NO 329
<400> SEQUENCE: 329
000

<210> SEQ ID NO 330
<400> SEQUENCE: 330
000

<210> SEQ ID NO 331
<400> SEQUENCE: 331
000

<210> SEQ ID NO 332
<400> SEQUENCE: 332
000

<210> SEQ ID NO 333
<400> SEQUENCE: 333
000

<210> SEQ ID NO 334
<400> SEQUENCE: 334
000

<210> SEQ ID NO 335
<400> SEQUENCE: 335
000

<210> SEQ ID NO 336
<400> SEQUENCE: 336
000

<210> SEQ ID NO 337
<400> SEQUENCE: 337
```

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359

<400> SEQUENCE: 359

000

```
<210> SEQ ID NO 360
<400> SEQUENCE: 360
000

<210> SEQ ID NO 361
<400> SEQUENCE: 361
000

<210> SEQ ID NO 362
<400> SEQUENCE: 362
000

<210> SEQ ID NO 363
<400> SEQUENCE: 363
000

<210> SEQ ID NO 364
<400> SEQUENCE: 364
000

<210> SEQ ID NO 365
<400> SEQUENCE: 365
000

<210> SEQ ID NO 366
<400> SEQUENCE: 366
000

<210> SEQ ID NO 367
<400> SEQUENCE: 367
000

<210> SEQ ID NO 368
<400> SEQUENCE: 368
000

<210> SEQ ID NO 369
<400> SEQUENCE: 369
000

<210> SEQ ID NO 370
<400> SEQUENCE: 370
000

<210> SEQ ID NO 371
```

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

```
000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Ala Ala Ser
1

<210> SEQ ID NO 387
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Ser Asn Glu Asp Pro Tyr
1               5

<210> SEQ ID NO 388
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Gln Ser Val Asp Tyr Gln Gly Asp Ser Tyr
1               5                   10

<210> SEQ ID NO 389
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Ala Ala Ser
1
```

<210> SEQ ID NO 390
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Gln Gln Ser Asn Glu Asp Pro Tyr Thr
1               5

<210> SEQ ID NO 391
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 391

Ala Ile Arg Leu Thr Gln Ser Pro Ser Ser Phe Ser Ala Ser Thr Gly
1               5                   10                  15

Asp Arg Val Thr Ile Thr Cys Lys Ala Ser Gln Ser Val Asp Tyr Gln
            20                  25                  30

Gly Asp Ser Tyr Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Ser Glu Asp Phe Ala Thr Tyr Tyr Cys Gln Gln Ser Asn
                85                  90                  95

Glu Asp Pro Tyr Thr Phe Gly Gly Gly Thr Lys Val Glu Ile Lys
            100                 105                 110

<210> SEQ ID NO 392
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 392
gccatcagac tgacccagag ccccagcagc tttagcgcca gcaccggcga cagagtgacc        60
atcacatgca aggccagcca gagcgtggac taccagggcg acagctacct gaactggtat       120
cagcagaagc ccggcaaggc ccccaagctg ctgatctacg ccgccagcaa tctggaaagc       180
ggcgtgccca gcagattcag cggctctggc agcggcaccg acttcaccct gacaatcagc       240
agcctccagt ccgaggactt cgccacctac tactgccagc agagcaacga gaccccctac       300
acctttggcg gaggcaccaa ggtggaaatc aag                                    333

<210> SEQ ID NO 393
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 393

```
Ala Ile Arg Leu Thr Gln Ser Pro Ser Ser Phe Ser Ala Ser Thr Gly
1               5                   10                  15

Asp Arg Val Thr Ile Thr Cys Lys Ala Ser Gln Ser Val Asp Tyr Gln
            20                  25                  30

Gly Asp Ser Tyr Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Ser Glu Asp Phe Ala Thr Tyr Tyr Cys Gln Gln Ser Asn
                85                  90                  95

Glu Asp Pro Tyr Thr Phe Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 394
<211> LENGTH: 654
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 394

```
gccatcagac tgacccagag ccccagcagc tttagcgcca gcaccggcga cagagtgacc      60
atcacatgca aggccagcca gagcgtggac taccagggcg acagctacct gaactggtat     120
cagcagaagc ccggcaaggc ccccaagctg ctgatctacg ccgccagcaa tctggaaagc     180
ggcgtgccca gcagattcag cggctctggc agcggcaccg acttcaccct gacaatcagc     240
agcctccagt ccgaggactt cgccacctac tactgccagc agagcaacga ggaccoctac     300
acctttggcg gaggcaccaa ggtggaaatc aagcgtacgg tggccgctcc cagcgtgttc     360
atcttccccc ccagcgacga gcagctgaag agcggcaccg ccagcgtggt gtgcctgctg     420
aacaacttct accccccggga ggccaaggtg cagtggaagg tggacaacgc cctgcagagc     480
ggcaacagcc aggagagcgt caccgagcag gacagcaagg actccaccta cagcctgagc     540
agcaccctga ccctgagcaa ggccgactac gagaagcata aggtgtacgc ctgcgaggtg     600
acccaccagg gcctgtccag ccccgtgacc aagagcttca caggggcga gtgc           654
```

<210> SEQ ID NO 395
<211> LENGTH: 218

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 395

```
Ala Ile Arg Leu Thr Gln Ser Pro Ser Ser Phe Ser Ala Ser Thr Gly
1               5                  10                  15

Asp Arg Val Thr Ile Thr Cys Lys Ala Ser Gln Ser Val Asp Tyr Gln
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Ser Glu Asp Phe Ala Thr Tyr Tyr Cys Gln Gln Ser Asn
                85                  90                  95

Glu Asp Pro Tyr Thr Phe Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 396
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 396

```
gccatcagac tgacccagag ccccagcagc tttagcgcca gcaccggcga cagagtgacc      60
atcacatgca aggccagcca gagcgtggac taccagggcg acagctacat gaactggtat     120
cagcagaagc ccggcaaggc ccccaagctg ctgatctacg ccgccagcaa tctggaaagc     180
ggcgtgccca gcagattcag cggctctggc agcggcaccg acttcaccct gacaatcagc     240
agcctccagt ccgaggactt cgccacctac tactgccagc agagcaacga ggacccctac     300
acctttggcg gaggcaccaa ggtggaaatc aagcgtacgg tggccgctcc cagcgtgttc     360
atcttccccc ccagcgacga gcagctgaag agcggcaccg ccagcgtggt gtgcctgctg     420
aacaacttct accccgggga ggccaaggtg cagtggaagg tggacaacgc cctgcagagc     480
ggcaacagcc aggagagcgt caccgagcag gacagcaagg actccaccta cagcctgagc     540
```

```
agcaccctga ccctgagcaa ggccgactac gagaagcata aggtgtacgc ctgcgaggtg     600
acccaccagg gcctgtccag ccccgtgacc aagagcttca acaggggcga gtgc           654
```

<210> SEQ ID NO 397
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Gly Gly Gly Gly Ser Gly Gly Gly Gly Ser Gly Gly Gly Gly Ser
1               5                   10                  15

<210> SEQ ID NO 398
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Gly Gly Gly Gly Ser Gly Gly Gly Gly Ser Gly Gly Gly Gly Ser Gly
1               5                   10                  15

Gly Gly Gly Ser
            20

<210> SEQ ID NO 399
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 400
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 400

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 401
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 401

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser
        35

<210> SEQ ID NO 402
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 402

Gly Gly Gly Gly Ser Gly Gly Gly Ser Gly Gly Gly Ser Gly
1               5                   10                  15

Gly Gly Gly Ser Gly Gly Gly Gly Ser Gly Gly Gly Ser Gly Gly
                20                  25                  30

Gly Gly Ser Gly Gly Gly Gly Ser
        35                  40

<210> SEQ ID NO 403
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 403

Gly Gly Gly Gly Ser Gly Gly Gly Ser Gly Gly Gly Ser Gly
1               5                   10                  15

Gly Gly Gly Ser Gly Gly Gly Gly Ser Gly Gly Gly Ser Gly Gly
                20                  25                  30

Gly Gly Ser Gly Gly Gly Gly Ser Gly Gly Gly Gly Ser
        35                  40                  45

<210> SEQ ID NO 404
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Gly Gly Gly Ser Gly Gly Gly Ser Gly Gly Ser Gly Gly Gly Ser
1               5                   10                  15

<210> SEQ ID NO 405
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Gly Gly Gly Ser Gly Gly Gly Ser Gly Gly Gly Ser Gly Gly Gly Ser
1               5                   10                  15

Gly Gly Gly Ser

```
                        20

<210> SEQ ID NO 406
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Gly Gly Gly Ser Gly Gly Gly Ser Gly Gly Gly Ser Gly Gly Gly Ser
1               5                   10                  15

Gly Gly Gly Ser Gly Gly Gly Ser
            20

<210> SEQ ID NO 407
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser
            20                  25

<210> SEQ ID NO 408
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 408

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

<210> SEQ ID NO 409
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 409

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser
        35

<210> SEQ ID NO 410
<211> LENGTH: 40
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 410

Gly Gly Gly Ser Gly Gly Gly Ser Gly Gly Gly Ser Gly Gly Gly Ser
1               5                   10                  15
Gly Gly Gly Ser Gly Gly Gly Ser Gly Gly Gly Ser Gly Gly Gly Ser
            20                  25                  30
Gly Gly Gly Ser Gly Gly Gly Ser
        35                  40

<210> SEQ ID NO 411
<211> LENGTH: 44
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 411

Gly Gly Gly Ser Gly Gly Gly Ser Gly Gly Gly Ser Gly Gly Gly Ser
1               5                   10                  15
Gly Gly Gly Ser Gly Gly Gly Ser Gly Gly Gly Ser Gly Gly Gly Ser
            20                  25                  30
Gly Gly Gly Ser Gly Gly Gly Ser Gly Gly Gly Ser
        35                  40

<210> SEQ ID NO 412
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 412

Gly Gly Gly Gly
1

<210> SEQ ID NO 413
<211> LENGTH: 1077
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 413
atgtacagga tgcaactcct gtcttgcatt gcactaagtc ttgcacttgt cacaaacagt      60
gcacctactt caagttctac aaagaaaaca cagctacaac tggagcattt acttctggat     120
ttacagatga ttttgaatgg aattaataat acaagaatc ccaaactcac caggatgctc     180
acatttaagt tttacatgcc caagaaggcc acagaactga acatcttca gtgtctagaa     240 gaagaactca aacctctgga ggaagtgcta aatttagctc aaagcaaaaa ctttcactta     300
agacccaggg acttaatcag caatatcaac gtaatagttc tggaactaaa gggatctgaa     360
acaacattca tgtgtgaata tgctgatgag acagcaacca ttgtagaatt ctgaacaga     420 tggattacct tttgtcaaag catcatctca acactgactg gcggggagg ttctggcggt     480 gggggatcgg gcggtggagg gagcgacatt gtgctgaccc aatctccagc ttcttttggct     540 gtgtctctag ggcagagggc caccatctcc tgcaaggcca gccaaagtgt tgattatgat     600

```
ggtgatagtt atatgaactg gtaccaacag aaaccaggac agccacccaa actcctcatc      660
tatgctgcat ccaatctaga atctgggatc ccagccaggt ttagtggcag tgggtctggg      720
acagacttca ccctcaacat ccatcctgtg gaggaggagg atgctgcaac ctattactgt      780
cagcaaagta atgaggatcc gtacacgttc ggaggggggga ccaagctgga aataaaacgg      840
gctgatgctg caccaactgt atccatcttc ccaccatcca gtgagcagtt aacatctgga      900
ggtgcctcag tcgtgtgctt cttgaacaac ttctacccca aagacatcaa tgtcaagtgg      960
aagattgatg gcagtgaacg acaaaatggc gtcctgaaca gttggactga tcaggacagc     1020
aaagacagca cctacagcat gagcagcacc ctcacgttga ccaaggacga gtatgaa       1077
```

<210> SEQ ID NO 414
<211> LENGTH: 1173
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 414

```
atgtacagga tgcaactcct gtcttgcatt gcactaagtc ttgcacttgt cacaaacagt       60
gcacctactt caagttctac aaagaaaaca cagctacaac tggagcattt acttctggat      120
ttacagatga ttttgaatgg aattaataat tacaagaatc ccaaactcac caggatgctc      180
acatttaagt tttacatgcc caagaaggcc acagaactga acatcttca gtgtctagaa       240 gaagaactca aacctctgga ggaagtgcta aatttagctc aaagcaaaaa ctttcactta      300
agacccaggg acttaatcag caatatcaac gtaatagttc tggaactaaa gggatctgaa      360
acaacattca tgtgtgaata tgctgatgag acagcaacca ttgtagaatt tctgaacaga      420
tggattaccc tttgtcaaag catcatctca acactgactg gcggtggggg atcagggggc      480
ggaggttctg gaggtggcgg gtcggggggga ggtgggagcg acattgtgct gacccaatct      540
ccagcttctt tggctgtgtc tctagggcag agggccacca tctcctgcaa ggccagccaa      600
agtgttgatt atgatggtga tagttatatg aactggtacc aacagaaacc aggacagcca      660
cccaaactcc tcatctatgc tgcatccaat ctagaatctg ggatcccagc caggtttagt      720
ggcagtgggt ctgggacaga cttcacctc aacatccatc ctgtggagga ggaggatgct       780
gcaacctatt actgtcagca aagtaatgag gatccgtaca cgttcggagg ggggaccaag      840
ctggaaataa aacgggctga tgctgcacca actgtatcca tcttcccacc atccagtgag      900
cagttaacat ctggaggtgc ctcagtcgtg tgcttcttga caacttcta ccccaaagac       960 atcaatgtca gtggaagat tgatggcagt gaacgacaaa atggcgtcct gaacagttgg      1020
actgatcagg acagcaaaga cagcacctac agcatgagca gcaccctcac gttgaccaag     1080
gacgagtatg aacgacataa cagctatacc tgtgaggcca ctcacaagac atcaacttca     1140
cccattgtca agagcttcaa caggaatgag tgt                                   1173
```

<210> SEQ ID NO 415
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 415

```
atgtacagga tgcaactcct gtcttgcatt gcactaagtc ttgcacttgt cacaaacagt       60
```

-continued

```
gcacctactt caagttctac aaagaaaaca cagctacaac tggagcattt acttctggat    120
ttacagatga ttttgaatgg aattaataat tacaagaatc ccaaactcac caggatgctc    180
acatttaagt tttacatgcc caagaaggcc acagaactga acatcttca gtgtctagaa     240 gaagaactca aacctctgga ggaagtgcta aatttagctc aaagcaaaaa ctttcactta    300
agacccaggg acttaatcag caatatcaac gtaatagttc tggaactaaa gggatctgaa    360
acaacattca tgtgtgaata tgctgatgag acagcaacca ttgtagaatt tctgaacaga    420
tggattacct tttgtcaaag catcatctca acactgactg gcggtggggg atcagggggc    480
ggaggttctg gaggtggcgg gtcggggggga ggtgggagcg gtggcggggg atcagacatt   540
gtgctgaccc aatctccagc ttctttggct gtgtctctag gcagagggc accatctcc     600 tgcaaggcca gccaaagtgt tgattatgat ggtgatagtt atatgaactg gtaccaacag    660
aaaccaggac agccacccaa actcctcatc tatgctgcat ccaatctaga atctgggatc    720
ccagccaggt ttagtggcag tgggtctggg acagacttca ccctcaacat ccatcctgtg    780
gaggaggagg atgctgcaac ctattactgt cagcaaagta tgaggatcc gtacacgttc     840 ggagggggga ccaagctgga aataaaacgg gctgatgctg caccaactgt atccatcttc    900
ccaccatcca gtgagcagtt aacatctgga ggtgcctcag tcgtgtgctt cttgaacaac    960
ttctacccca aagacatcaa tgtcaagtgg aagattgatg gcagtgaacg acaaaatggc   1020
gtcctgaaca gttggactga tcaggacagc aaagacagca cctacagcat gagcagcacc   1080
ctcacgttga ccaaggacga gtatgaacga cataacagct atacctgtga ggccactcac   1140
aagacatcaa cttcacccat tgtcaagagc ttcaacagga atgagtgt               1188
```

<210> SEQ ID NO 416
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 416

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Gly Ser Gly
        130                 135                 140

Gly Gly Gly Ser Asp Ile Val Leu Thr Gln Ser Pro Ala Ser Leu Ala
145                 150                 155                 160
```

```
Val Ser Leu Gly Gln Arg Ala Thr Ile Ser Cys Lys Ala Ser Gln Ser
            165                 170                 175

Val Asp Tyr Asp Gly Asp Ser Tyr Met Asn Trp Tyr Gln Gln Lys Pro
        180                 185                 190

Gly Gln Pro Pro Lys Leu Leu Ile Tyr Ala Ala Ser Asn Leu Glu Ser
            195                 200                 205

Gly Ile Pro Ala Arg Phe Ser Gly Ser Gly Ser Gly Thr Asp Phe Thr
    210                 215                 220

Leu Asn Ile His Pro Val Glu Glu Glu Asp Ala Ala Thr Tyr Tyr Cys
225                 230                 235                 240

Gln Gln Ser Asn Glu Asp Pro Tyr Thr Phe Gly Gly Gly Thr Lys Leu
                245                 250                 255

Glu Ile Lys Arg Ala Asp Ala Ala Pro Thr Val Ser Ile Phe Pro Pro
                260                 265                 270

Ser Ser Glu Gln Leu Thr Ser Gly Gly Ala Ser Val Val Cys Phe Leu
            275                 280                 285

Asn Asn Phe Tyr Pro Lys Asp Ile Asn Val Lys Trp Lys Ile Asp Gly
        290                 295                 300

Ser Glu Arg Gln Asn Gly Val Leu Asn Ser Trp Thr Asp Gln Asp Ser
305                 310                 315                 320

Lys Asp Ser Thr Tyr Ser Met Ser Ser Thr Leu Thr Leu Thr Lys Asp
                325                 330                 335

Glu Tyr Glu Arg His Asn Ser Tyr Thr Cys Glu Ala Thr His Lys Thr
                340                 345                 350

Ser Thr Ser Pro Ile Val Lys Ser Phe Asn Arg Asn Glu Cys
            355                 360                 365

<210> SEQ ID NO 417
<211> LENGTH: 371
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 417

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Gly Ser Gly Gly Gly Gly Ser Gly
    130                 135                 140

Gly Gly Gly Ser Gly Gly Gly Gly Ser Asp Ile Val Leu Thr Gln Ser
```

```
                145                 150                 155                 160
Pro Ala Ser Leu Ala Val Ser Leu Gly Gln Arg Ala Thr Ile Ser Cys
            165                 170                 175

Lys Ala Ser Gln Ser Val Asp Tyr Asp Gly Asp Ser Tyr Met Asn Trp
        180                 185                 190

Tyr Gln Gln Lys Pro Gly Gln Pro Lys Leu Leu Ile Tyr Ala Ala
        195                 200                 205

Ser Asn Leu Glu Ser Gly Ile Pro Ala Arg Phe Ser Gly Ser Gly Ser
    210                 215                 220

Gly Thr Asp Phe Thr Leu Asn Ile His Pro Val Glu Glu Asp Ala
225                 230                 235                 240

Ala Thr Tyr Tyr Cys Gln Gln Ser Asn Glu Asp Pro Tyr Thr Phe Gly
            245                 250                 255

Gly Gly Thr Lys Leu Glu Ile Lys Arg Ala Asp Ala Ala Pro Thr Val
        260                 265                 270

Ser Ile Phe Pro Pro Ser Ser Glu Gln Leu Thr Ser Gly Gly Ala Ser
        275                 280                 285

Val Val Cys Phe Leu Asn Asn Phe Tyr Pro Lys Asp Ile Asn Val Lys
    290                 295                 300

Trp Lys Ile Asp Gly Ser Glu Arg Gln Asn Gly Val Leu Asn Ser Trp
305                 310                 315                 320

Thr Asp Gln Asp Ser Lys Asp Ser Thr Tyr Ser Met Ser Ser Thr Leu
            325                 330                 335

Thr Leu Thr Lys Asp Glu Tyr Glu Arg His Asn Ser Tyr Thr Cys Glu
        340                 345                 350

Ala Thr His Lys Thr Ser Thr Ser Pro Ile Val Lys Ser Phe Asn Arg
        355                 360                 365

Asn Glu Cys
    370

<210> SEQ ID NO 418
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 418

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
        100                 105                 110

Thr Ile Val Glu Phe Leu Asn Arg Trp Ile Thr Phe Cys Gln Ser Ile
    115                 120                 125
```

```
Ile Ser Thr Leu Thr Gly Gly Gly Ser Gly Gly Gly Ser Gly
    130                 135                 140

Gly Gly Gly Ser Gly Gly Gly Ser Gly Gly Gly Ser Asp Ile
145                 150                 155                 160

Val Leu Thr Gln Ser Pro Ala Ser Leu Ala Val Ser Leu Gly Gln Arg
                165                 170                 175

Ala Thr Ile Ser Cys Lys Ala Ser Gln Ser Val Asp Tyr Asp Gly Asp
            180                 185                 190

Ser Tyr Met Asn Trp Tyr Gln Gln Lys Pro Gly Gln Pro Pro Lys Leu
        195                 200                 205

Leu Ile Tyr Ala Ala Ser Asn Leu Glu Ser Gly Ile Pro Ala Arg Phe
    210                 215                 220

Ser Gly Ser Gly Ser Gly Thr Asp Phe Thr Leu Asn Ile His Pro Val
225                 230                 235                 240

Glu Glu Glu Asp Ala Ala Thr Tyr Tyr Cys Gln Gln Ser Asn Glu Asp
                245                 250                 255

Pro Tyr Thr Phe Gly Gly Gly Thr Lys Leu Glu Ile Lys Arg Ala Asp
            260                 265                 270

Ala Ala Pro Thr Val Ser Ile Phe Pro Pro Ser Ser Glu Gln Leu Thr
        275                 280                 285

Ser Gly Gly Ala Ser Val Val Cys Phe Leu Asn Asn Phe Tyr Pro Lys
    290                 295                 300

Asp Ile Asn Val Lys Trp Lys Ile Asp Gly Ser Glu Arg Gln Asn Gly
305                 310                 315                 320

Val Leu Asn Ser Trp Thr Asp Gln Asp Ser Lys Asp Ser Thr Tyr Ser
                325                 330                 335

Met Ser Ser Thr Leu Thr Leu Thr Lys Asp Glu Tyr Glu Arg His Asn
            340                 345                 350

Ser Tyr Thr Cys Glu Ala Thr His Lys Thr Ser Thr Ser Pro Ile Val
        355                 360                 365

Lys Ser Phe Asn Arg Asn Glu Cys
    370                 375

<210> SEQ ID NO 419
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 419
caggtgcagc tggtggagag cggcggcggc gtggtgcagc ccggccggag cctgcggctg      60
agctgcgccg ccagcggcta cgccttcacc aactacctga tcgagtgggt gcggcaggcc     120
cccggcaagg gcctggagtg ggtggccgtg atcaaccccg gcagcggcgg caccaactac     180
aacgagaagt tcaagggccg gttcaccatc agcgccgaca agagcaagag caccgcctac     240
ctgcagatga acagcctgcg ggccgaggac accgccgtgt actactgcgc ccggtggcgg     300
ggcgagggct actacgccta cttcgacgtg tggggccagg gcaccaccgt gaccgtgagc     360
agc                                                                   363

<210> SEQ ID NO 420
<211> LENGTH: 11
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 420

Ser Gln Ser Val Ser Tyr Asp Ala Asp Ser Tyr
1               5                   10

<210> SEQ ID NO 421
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 421

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Thr Asn Tyr
                20                  25                  30

Leu Ile Glu Trp Val Arg Gln Met Pro Gly Lys Gly Leu Glu Trp Met
            35                  40                  45

Gly Val Ile Asn Pro Gly Ser Gly Gly Thr Asn Tyr Asn Glu Lys Phe
        50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Arg Gly Ser Gly Tyr Tyr Ala Tyr Phe Asp Val Trp Gly
            100                 105                 110

Gln Gly Thr Thr Val Thr Val Ser Ser
        115                 120

<210> SEQ ID NO 422
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 422
gaggtgcaat tggtgcagag cggagccgaa gtgaagaagc ccggcgagag cctgaagatc      60
agctgcaagg gcagcggcta cgccttcacc aactacctga tcgagtgggt gcgccagatg     120
cccggcaagg gcctggaatg gatgggcgtg atcaatcctg gcagcggcgg caccaattac     180
aacgagaagt tcaagggcca agtgaccatc agcgccgaca agagcatcag caccgcctac     240
ctccagtggt ccagcctgaa ggccagcgac accgccatgt actactgcgc caggtggcgg     300
ggaagcggct actacgccta cttcgacgtg tggggccagg gcaccacagt gaccgtcagc     360
tca                                                                    363

<210> SEQ ID NO 423
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)

```
<223> OTHER INFORMATION: This sequence may encompass 1-10 Gly residues
      wherein some positions may be absent

<400> SEQUENCE: 423

Gly Gly Gly Gly Gly Gly Gly Gly Gly Gly
1               5                   10
```

IMMUNE-STIMULATING HUMANIZED MONOCLONAL ANTIBODIES AGAINST HUMAN INTERLEUKIN-2, AND FUSION PROTEINS THEREOF

CROSS-REFERENCE TO RELATED APPLICATIONS

This application is a Continuation of Ser. No. 16/069,146 filed on Jul. 10, 2018, which is a § 371 National Stage Application of PCT/IB2017/050127 filed on Jan. 11, 2017, which claims priority to U.S. 62/277,113 filed on Jan. 11, 2016, all of which are hereby incorporated by reference in their entirety.

REFERENCE TO A SEQUENCE LISTING SUBMITTED ELECTRONICALLY

This application contains a Sequence Listing in computer readable form. The computer readable form is incorporated herein by reference. Said ASCII copy, created on Jul. 14, 2023, is named NOV_02_US-C1_SL.TXT and is 263,830 bytes in size.

TECHNICAL FIELD

The present invention relates to antibodies binding to human interleukin-2 (hIL-2). The invention more specifically relates to humanized antibodies specifically binding a particular epitope of hIL-2 and, when bound to this epitope, displaying a unique capability of inhibiting binding of hIL-2 to CD25, and fusions between said antibodies and hIL-2. Furthermore, the invention relates to in vitro and in vivo therapeutic applications of the antibodies in combination with hIL-2, and in vitro and in vivo therapeutic applications of the fusions.

BACKGROUND

Interleukin-2 (IL-2) is a cytokine able to potently stimulate cytotoxic lymphocytes against metastatic tumors. However, IL-2 is also able to stimulate so-called $CD25^+$ $CD4^+$ regulatory T cells (Treg cells) that are crucial for prevention of autoimmune disease. Importantly, Treg cells can significantly dampen anti-tumor responses by cytotoxic lymphocytes, thus somewhat antagonizing the beneficial anti-tumor effects of IL-2. Moreover, at doses required to achieve a clinical anti-tumor response, IL-2 can exert toxic adverse effects.

Immunotherapy using IL-2 has been used since the early 1980's for the immunotherapy of metastatic melanoma and metastatic renal cell carcinoma, leading to the approval by the FDA for these indications in 1996 and 1992, respectively. While IL-2 given at high doses has shown objective response rates in about 17% and complete regression in about 6-9% of patients suffering from these deadly metastatic cancers, IL-2 given at these doses frequently led to toxic adverse effects, such as hypotension, pulmonary edema, liver cell damage, gastrointestinal toxicity, vascular leakage syndrome (VLS) and general edema. Moreover, as mentioned above, IL-2 is able to stimulate immunosuppressive Treg cells, which in turn are able to dampen the activity of anti-tumor $CD8^+$ T cells and NK cells.

Several variants of human IL-2 exist, and different strategies have been employed to find IL-2 based compounds with improved in vivo properties, such as described in Rosalia et al. Current Opinion in Chemical Biology 2014, 23:39-46.

However, no successful therapy based on this principle has yet been made available for use in patients due to the lack of appropriate anti-human IL-2 antibodies.

SUMMARY OF THE INVENTION

The present disclosure relates generally to antibodies or fragments thereof that bind to a specific epitope of human IL-2, methods for their preparation and use, including methods for treating disorders.

The anti-IL-2 antibodies or fragments thereof disclosed herein can be used (alone or in combination with other agents or therapeutic modalities) to treat, prevent and/or diagnose disorders, such as cancerous disorders (for example solid and soft-tissue tumors, and hematological tumors), as well as infectious diseases (for example chronic infectious disorders). Thus, compositions comprising the anti-IL-2 antibodies or fragments thereof, as well as methods for treating various disorders including cancer and/or infectious diseases, using the anti-IL-2 antibodies or fragments thereof, or compositions comprising the anti-IL-2 antibodies or fragments thereof, are disclosed herein.

In a first aspect, the present disclosure provides an isolated antibody, or antigen-binding portion thereof, which binds human IL-2 according to SEQ ID NO: 109, wherein said antibody or antigen-binding portion thereof comprises a light chain variable region comprising LCDR1, a LCDR2 and a LCDR3 and a heavy chain variable region comprising a HCDR1, a HCDR2 and a HCDR3 and wherein the LCDR1 comprises SEQ ID NO: 122; wherein LCDR2 comprises SEQ ID NO: 123; wherein LCDR3 comprises SEQ ID NO: 21; wherein HCDR1 comprises SEQ ID NO: 119; wherein HCDR2 comprises SEQ ID NO: 120; and wherein HCDR3 comprises SEQ ID NO: 121.

In an embodiment, the isolated antibody or antigen-binding portion thereof according to the first aspect, wherein said antibody or antigen-binding portion thereof comprises a light variable region comprising a: LCDR1 selected from the group consisting of SEQ ID NO: 19, SEQ ID NO: 31, SEQ ID NO: 69, SEQ ID NO: 72, SEQ ID NO: 86 and SEQ ID NO: 90; LCDR2 selected from the group consisting of SEQ ID NO: 20 and SEQ ID NO: 32; LCDR3 as set forth in SEQ ID NO: 21, and a heavy variable region comprising a: HCDR1 selected from the group consisting of SEQ ID NO: 4, and SEQ ID NO: 13; HCDR2 selected from the group consisting of SEQ ID NO: 2, and SEQ ID NO: 12; and HCDR3 selected from the group consisting of SEQ ID NO: 3, SEQ ID NO: 36, SEQ ID NO: 39, SEQ ID NO: 42, and SEQ ID NO: 45.

In a further embodiment, the isolated antibody or antigen-binding portion thereof according to the first aspect, wherein the LCDR1, LCDR2 and LCDR3 are SEQ ID NO: 19, 20 and 21, respectively and the HCDR1, HCDR2 and HCDR3 are SEQ ID NO: 4, 2 and 3, respectively; or LCDR1, LCDR2 and LCDR3 are SEQ ID NO: 31, 32 and 21, respectively and the HCDR1, HCDR2 and HCDR3 are SEQ ID NO: 4, 2 and 3, respectively; or LCDR1, LCDR2 and LCDR3 are SEQ ID NO: 19, 20 and 21 and the HCDR1, HCDR2 and HCDR3 are SEQ ID NO: 13, 12 and 3; or LCDR1, LCDR2 and LCDR3 are SEQ ID NO: 31, 32 and 21 and the HCDR1, HCDR2 and HCDR3 are SEQ ID NO: 13, 12 and 3; or LCDR1, LCDR2 and LCDR3 are SEQ ID NO: 69, 20 and 21 and the HCDR1, HCDR2 and HCDR3 are SEQ ID NO: 4, 2, and 3, respectively; or LCDR1, LCDR2 and LCDR3 are SEQ ID NO: 31, 32 and 21, respectively and the HCDR1, HCDR2 and HCDR3 are SEQ ID NO: 4, 2, and 3, respectively; or LCDR1, LCDR2 and LCDR3 are SEQ ID NO: 69, 20, and 21, respectively and the HCDR1, HCDR2 and HCDR3 are SEQ ID NO: 4, 2, and 3, respectively; or LCDR1, LCDR2 and LCDR3 are SEQ ID NO: 19, 20, and 21, respectively, and the HCDR1, HCDR2 and HCDR3 are 4, 2, and 36, respectively; or the LCDR1, LCDR2 and LCDR3 are SEQ ID NO: 69, 20, and 21, respectively, and the HCDR1, HCDR2 and HCDR3 are 4, 2, and 36, respectively; or the LCDR1, LCDR2 and LCDR3 are SEQ ID NO: 19, 20, 21, respectively, and the HCDR1, HCDR2 and HCDR3 are 4, 2, and 36, respectively; and the LCDR1, LCDR2 and LCDR3 are SEQ ID NO: 69, 20, 21, respectively, and the HCDR1, HCDR2 and HCDR3 are 4, 2, and 36, respectively.

In another embodiment, the isolated antibody or antigen-binding portion thereof according to the first aspect, comprises the heavy chain variable (VH) and light chain variable (VL) regions have at least 95%, such as 95%, 96%, 97%, 98%, or 99% identity to the amino acid sequences: VL, SEQ ID NO: 25; VH, SEQ ID NO: 7, or VL, SEQ ID NO: 27; VH, SEQ ID NO: 7, or VL, SEQ ID NO: 34; VH, SEQ ID NO: 7, or VL, SEQ ID NO: 25; VH, SEQ ID NO: 15, or VL, SEQ ID NO: 27; VH, SEQ ID NO: 15, or VL, SEQ ID NO: 34; VH, SEQ ID NO: 15, or VL, SEQ ID NO: 25; VH, SEQ ID NO: 17, or VL, SEQ ID NO: 27; VH, SEQ ID NO: 17, or VL, SEQ ID NO: 34; VH, SEQ ID NO: 17, or VL, SEQ ID NO: 70; VH, SEQ ID NO: 7, or VL, SEQ ID NO: 25; VH, SEQ ID NO: 37, or VL, SEQ ID NO: 70; VH, SEQ ID NO: 37, VL, SEQ ID NO: 79; VH, SEQ ID NO: 7, or VL, SEQ ID NO: 27; VH, SEQ ID NO: 37, or VL, SEQ ID NO: 79; VH, SEQ ID NO: 37, or VL, SEQ ID NO: 70; VH, SEQ ID NO: 17, or VL, SEQ ID NO: 25; VH, SEQ ID NO: 49, or VL, SEQ ID NO: 70; VH, SEQ ID NO: 49, or VL, SEQ ID NO: 79; VH, SEQ ID NO: 17, or VL, SEQ ID NO: 27; VH, SEQ ID NO: 49, or VL, SEQ ID NO: 79; VH, SEQ ID NO: 49.

In one embodiment, the isolated antibody or antigen-binding portion thereof according to the first aspect has the heavy chain variable (VH) and light chain variable (VL) regions have the amino acid sequences: VL, SEQ ID NO: 25; VH, SEQ ID NO: 7, or VL, SEQ ID NO: 27; VH, SEQ ID NO: 7, or VL, SEQ ID NO: 34; VH, SEQ ID NO: 7, or VL, SEQ ID NO: 25; VH, SEQ ID NO: 15, or VL, SEQ ID NO: 27; VH, SEQ ID NO: 15, or VL, SEQ ID NO: 34; VH, SEQ ID NO: 15, or VL, SEQ ID NO: 25; VH, SEQ ID NO: 17, or VL, SEQ ID NO: 27; VH, SEQ ID NO: 17, or VL, SEQ ID NO: 34; VH, SEQ ID NO: 17, or VL, SEQ ID NO: 70; VH, SEQ ID NO: 7, or VL, SEQ ID NO: 25; VH, SEQ ID NO: 37, or VL, SEQ ID NO: 70; VH, SEQ ID NO: 37, VL, SEQ ID NO: 79; VH, SEQ ID NO: 7, or VL, SEQ ID NO: 27; VH, SEQ ID NO: 37, or VL, SEQ ID NO: 79; VH, SEQ ID NO: 37, or VL, SEQ ID NO: 70; VH, SEQ ID NO: 17, or VL, SEQ ID NO: 25; VH, SEQ ID NO: 49, or VL, SEQ ID NO: 70; VH, SEQ ID NO: 49, or VL, SEQ ID NO: 79; VH, SEQ ID NO: 17, or VL, SEQ ID NO: 27; VH, SEQ ID NO: 49, or VL, SEQ ID NO: 79; VH, SEQ ID NO: 49.

The isolated antibody according to previous embodiments may comprise an Fc domain selected from the group consisting of SEQ ID NO: 93, SEQ ID NO: 95, SEQ ID NO: 97, SEQ ID NO: 99, SEQ ID NO: 101, SEQ ID NO: 103 and SEQ ID NO: 105. In a preferred embodiment, the isolated antibody comprises the Fc domain according to SEQ ID NO: 93, SEQ ID NO: 101, SEQ ID NO: 103 or SEQ ID NO: 105.

In a specific embodiment, the isolated antibody comprises the light chain according to SEQ ID NO: 124 and the heavy chain according to SEQ ID NO: 126, or the light chain according to SEQ ID NO: 128 and the heavy chain according to SEQ ID NO: 130.

According to a second aspect of the invention, an isolated antibody or antigen-binding fragment thereof is provided, which binds to a human interleukin-2 (hIL-2) epitope which comprises the amino acids K52, P54, K55, T57, R58, T61, F62, K63, Q94, and K96.

In an embodiment, the isolated antibody or antigen-binding fragment thereof according to the second aspect, binds specifically to the amino acids K52, P54, K55, T57, R58, T61, F62, K63, Q94, and K96.

The isolated antibody or antigen-binding fragment thereof according to the second aspect, may bind to a human interleukin-2 (hIL-2) epitope which, in addition to the amino acids K52, P54, K55, T57, R58, T61, F62, K63, Q94, and K96, further comprises any one or more of the amino acids N50, N53, N91, L92, A93, and N97.

In one embodiment, the antibody or antigen-binding fragment thereof according to the second aspect binds specifically to the amino acids N50, K52, N53, P54, K55, T57, R58, T61, F62, K63, N91, L92, A93, Q94, K96, and N97.

In one embodiment, the antibody or antigen-binding fragment thereof comprises a light chain variable region comprising, in sequence a LCDR1, a LCDR2 and a LCDR3, and a heavy chain variable region comprising, in sequence a HCDR1, a HCDR2 and a HCDR3, wherein the LCDR1, LCDR2 and LCDR3 are SEQ ID NO: 231, 232 and 233, respectively and the HCDR1, HCDR2 and HCDR3 are SEQ ID NO: 181, 182 and 183, respectively; or the LCDR1, LCDR2 and LCDR3 are SEQ ID NO: 279, 280 and 281, respectively and the HCDR1, HCDR2 and HCDR3 are SEQ ID NO: 213, 214 and 215, respectively; or the LCDR1, LCDR2 and LCDR3 are SEQ ID NO: 231, 232 and 233, respectively and the HCDR1, HCDR2 and HCDR3 are SEQ ID NO: 213, 214 and 215, respectively; or the LCDR1, LCDR2 and LCDR3 are SEQ ID NO: 263, 264 and 265, respectively and the HCDR1, HCDR2 and HCDR3 are SEQ ID NO: 213, 214 and 215, respectively; or the LCDR1, LCDR2 and LCDR3 are SEQ ID NO: 263, 264 and 265, respectively and the HCDR1, HCDR2 and HCDR3 are SEQ ID NO: 149, 150 and 151, respectively; or the LCDR1, LCDR2 and LCDR3 are SEQ ID NO: 69, 20 and 21, respectively and the HCDR1, HCDR2 and HCDR3 are SEQ ID NO: 197, 198, and 199, respectively; or the LCDR1, LCDR2 and LCDR3 are SEQ ID NO: 231, 232 and 233, respectively and the HCDR1, HCDR2 and HCDR3 are SEQ ID NO: 197, 198, and 199, respectively.

In one embodiment, the antibody or antigen-binding fragment thereof comprises the heavy chain variable (VH) and light chain variable (VL) regions have at least 95% identity, such as 100% identity, to the amino acid sequences VL, SEQ ID NO: 243; VH, SEQ ID NO: 193, or VL, SEQ ID NO: 391; VH, SEQ ID NO: 225, or VL, SEQ ID NO: 243; VH, SEQ ID NO: 225, or VL, SEQ ID NO: 275; VH, SEQ ID NO: 225, or VL, SEQ ID NO: 275; VH, SEQ ID NO: 161, or VL, SEQ ID NO: 70; VH, SEQ ID NO: 209, or VL, SEQ ID NO: 243; VH, SEQ ID NO: 209.

In a specific embodiment, the isolated antibody comprises wherein the heavy chain and light chain regions have the amino acid sequences; heavy chain according to SEQ ID NO: 195 and light chain according to SEQ ID NO: 245, or heavy chain according to SEQ ID NO: 227 and light chain according to SEQ ID NO: 393, or heavy chain according to SEQ ID NO: 227 and light chain according to SEQ ID NO: 245, or heavy chain according to SEQ ID NO: 227 and light chain according to SEQ ID NO: 277, or heavy chain according to SEQ ID NO: 163 and light chain according to SEQ ID NO: 277, or heavy chain according to SEQ ID NO: 211 and light chain according to SEQ ID NO: 261, or heavy chain according to SEQ ID NO: 211 and light chain according to SEQ ID NO: 277.

According to a third aspect of the invention, a composition comprising the antibody according to the first or the second aspect of the invention, and optionally but preferably, human IL-2, is provided.

In an embodiment, the composition according to the third aspect comprises the human IL-2 selected from the group consisting of human IL-2 according to SEQ ID NO: 109 or aldesleukin according to SEQ ID NO: 110, preferably aldesleukin according to SEQ ID NO: 110.

According to a fourth aspect of the invention, a fusion protein is provided, comprising an antibody according to the first or second aspect of the invention, and human IL-2.

In one embodiment, the antibody and the human IL-2 is joined by a linker sequence selected from the group consisting of SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, SEQ ID NO: 406, SEQ ID NO: 407, SEQ ID NO: 408, SEQ ID NO: 409, SEQ ID NO: 410, and SEQ ID NO: 411, preferably SEQ ID NO: 405 or SEQ ID NO: 407.

In one embodiment the fusion protein comprises an antibody according to the first or second aspect of the invention, wherein the LCDR1 of the antibody comprises a residue Y27 and a residue D30 according to the Kabat definition, and wherein the residue Y27 is joined to residue N97 of human IL-2 with a GG linker, and wherein residue D30 is joined to residue K96 residue of human IL-2 with a linker according to SEQ ID NO: 412.

According to a fifth aspect of the invention, an antibody or antigen-binding fragment thereof according to the first or second aspect of the invention, or a composition according to the third aspect of the invention, or the fusion protein according to the fourth aspect of the invention, for use as a medicament is provided.

According to a sixth aspect of the invention, an antibody or antigen-binding fragment thereof according to the first or second aspect of the invention, or a composition according to the third aspect of the invention, or the fusion protein according to the fourth aspect of the invention, for use in the manufacture of a medicament is provided.

According to a seventh aspect of the invention, an antibody or antigen-binding fragment thereof according to the first or second aspect of the invention, or a composition according to the third aspect of the invention, or the fusion protein according to the fourth aspect of the invention, for use in treatment of cancer is provided.

According to an eight aspect of the invention, a method of treating cancer by administering an antibody or antigen-binding fragment thereof according to the first or second aspect of the invention, or a composition according to the third aspect of the invention, or the fusion protein according to the fourth aspect of the invention.

According to a ninth aspect of the invention, a vector is provided, comprising the nucleic acid molecule capable of encoding an antibody, or fragment thereof, according to the first or second aspects of the invention, or the fusion protein according to the fourth aspect of the invention.

According to a tenth aspect of the invention, a cell is provided, comprising the vector according to the eight aspect of the invention.

According to an eleventh aspect of the invention, a cell, able to produce a human interleukin-2 (hIL-2) specific monoclonal antibody, or antigen-binding fragment thereof, according to the first or second aspect, is provided.

According to a twelfth aspect of the invention, a monoclonal antibody-producing hybridoma cell line is provided, characterized in that said produced antibodies are those the first or second aspect of the invention, or the fusion protein according to the fourth aspect of the invention.

The antibodies according to aspects of the invention are advantageous, e.g. because they possess one or more of the following properties. Upon binding of antibody to hIL-2, the resulting mAb*hIL-2 complex cannot efficiently bind human IL-2 receptor alpha (also known as CD25) anymore, effectively reducing the binding of human CD25 to mAb*hIL-2 to background levels as compared to the binding of human CD25 to free (non-complexed) hIL-2 when measured by surface plasmon resonance. Furthermore, the antibodies may display no measurable cross-reactivity to murine IL-2.

BRIEF DESCRIPTION OF THE DRAWINGS

FIG. 11 discloses $(G)_4$ as SEQ ID NO: 412.

BRIEF DESCRIPTION OF THE TABLES

Figure 1:
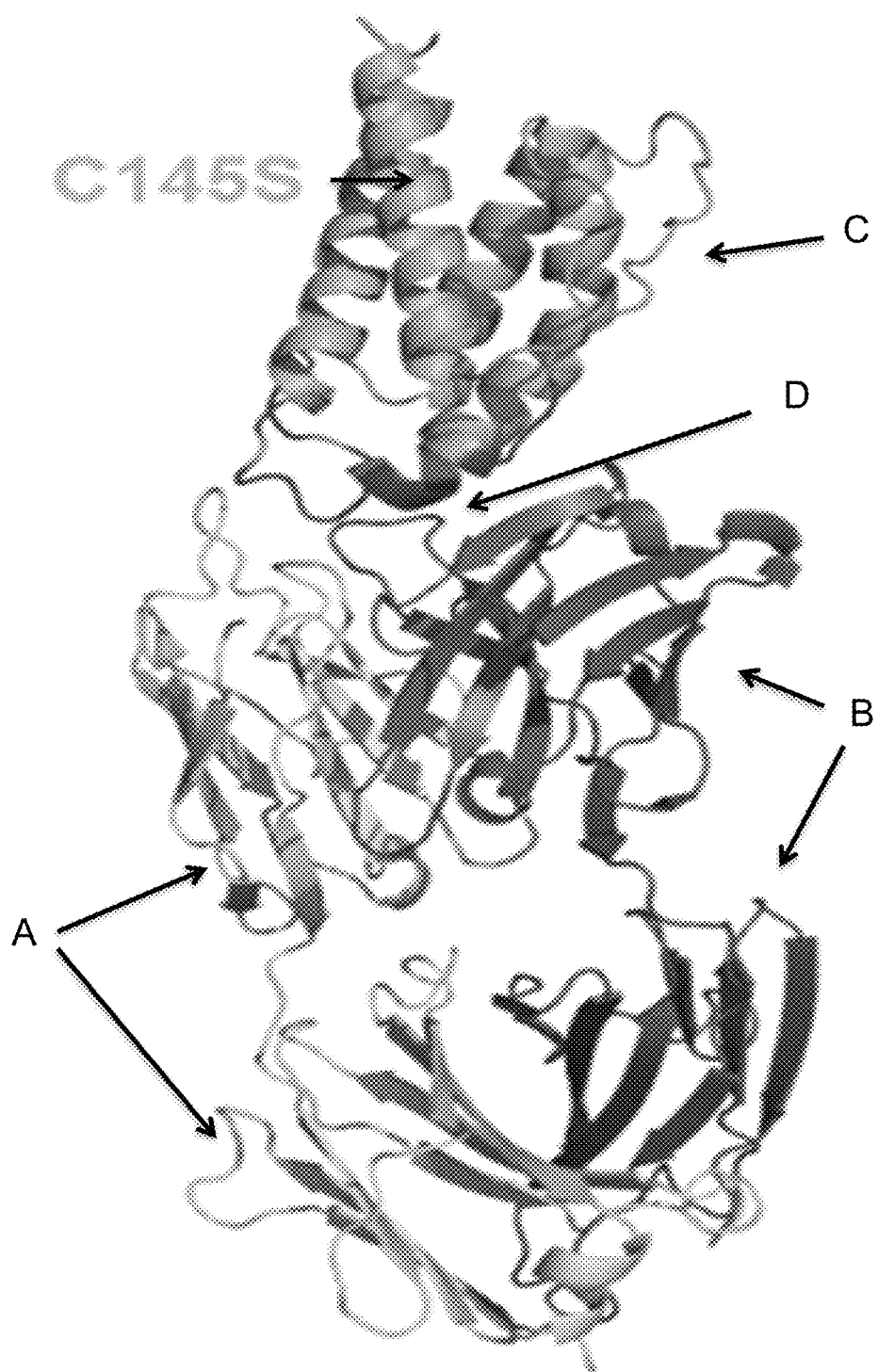
FIG. 1 provides the overview of the three-dimensional structure of Proleukin®/Fab-NARA1 complex as obtained in Example 2.

Table 1 is an overview of anti-IL-2 antibodies according to embodiments of the invention.

Table 2 is an overview of IL-2 muteins according to embodiments of the invention.

Table 3 represents structure statistics for a Proleukin®/NARA1-Fab complex.

Table 4 is an overview of epitope and paratope according to embodiments of the invention.

Table 5 is an overview of variable heavy regions according to embodiments of the invention.

Table 6 is an overview of variable light regions according to embodiments of the invention.

Table 7 comprises pI data of antibodies according to some embodiments.

Table 8 comprises comparison variable regions and variable germline regions.

Table 9 comprises structure-refined variable regions according to embodiments of the invention.

Table 10 comprises information about variable light chains and variable heavy chains according to embodiments of the invention.

Table 11 comprises light chain CDRs according to embodiments of the invention.

Table 12 comprises heavy chain CDRs according to embodiments of the invention.

Table 13 comprises optimized variable light chains and variable heavy chains according to embodiments of the invention.

Table 14 is an overview of VH mutation sequences.

Table 15 is an overview of VK mutation sequences.

Table 16 is an overview of plasmid sequences.

Table 17 is an overview of affinity-matured antibodies according to embodiments of the invention.

Table 18 is a sequence overview of first set of antibodies

Table 19 is an overview of ELISA values according to an example.

Table 20 is an overview of EC50 values according to an example.

Table 21 is a subset of affinity matured antibodies according to embodiments of the invention.

Table 22 is a sequence overview of the subset of antibodies according to Table 21.

Table 23 represents binding affinity data.

Table 24 represents CD8⁺ T cell proliferation data.

Table 25 represents CD8⁺ T and NK cell proliferation data.

Table 26 and Table 27 represent cell count data.

Table 28 is an overview of linker sequences according to embodiments of the invention.

Table 29 is an overview of fusion proteins according to embodiments of the invention.

Table 30 represents CD8⁺ T and NK cell proliferation data.

Table 31 represents CD8⁺ T, NK and Treg cell count data.

Table 32 and Table 33 represent cell count data.

Table 34 represents ratios of cell count data.

Table 35 and Table 36 represent light region sequences of fusion proteins.

Table 37 is an overview of fusion proteins.

Table 38 represents cell count data.

Table 39 and Table 40 represent EC50 values according to an example.

Table 41 is a sequence listing comprising sequences useful for practicing the invention.

DETAILED DESCRIPTION

The present disclosure relates to antibodies and fragments thereof that bind to human IL-2, and affect the in vivo function of this cytokine.

By "human interleukin-2" or "hIL-2" as used herein is meant human IL-2 (wildtype or wt) with UniProt ID number P60568, reproduced herein as SEQ ID NO: 109. In various embodiments of the invention, variants, isoforms, and species homologs of human wildtype IL-2 are also included. Accordingly, antibodies of this disclosure may, in certain cases, cross-react with IL-2 from species other than human. In certain embodiments, the antibodies may be completely specific for one or more human IL-2 proteins and may not exhibit species or other types of non-human cross-reactivity.

The term "mutein" means a polypeptide wherein specific substitutions to the interleukin-2 protein have been made. As used in reference to administrative modalities and treatments, the term "IL-2 mutein" means 1, 2, 3, 4, or 5 or more IL-2 muteins. For example, treatment using an IL-2 mutein may refer to treatment with a single IL-2 mutein, or a combination of multiple IL-2 muteins. An example of human IL-2 is the IL-2 mutein disclosed in WO2012/107417A1, having 3 mutations compared to wt hIL-2.

Proleukin® (aldesleukin) is another example of a variant of human wt IL-2, well known to a person skilled in the art, and represented herein by SEQ ID NO: 110.

The term "antibody" or "antibody to IL-2" and the like as used herein refers to whole antibodies that interact with (e.g., by binding, steric hindrance, stabilizing/destabilizing, spatial distribution) an IL-2 epitope and interfere with IL-2's binding to IL-2 receptor alpha (also termed CD25). A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FRs). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. The term "antibody" includes for example, monoclonal antibodies, human antibodies, humanized antibodies, camelid antibodies, or chimeric antibodies. The antibodies can be of any isotype (e.g., IgG, IgE, IgM, IgD, IgA and IgY), class (e.g., IgG1, IgG2, IgG3, IgG4, IgA1 and IgA2) or subclass.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminus is a variable region and at the C-terminus is a constant region; the CH3 and CL domains actually comprise the carboxy-terminus of the heavy and light chain, respectively. In particular, the term "antibody" specifically includes an IgG-scFv format.

The term "antigen-binding portion" of an antibody (or simply "antigen portion"), as used herein, refers to full length or one or more fragments of an antibody, such as a protein, that retain the ability to specifically bind to an antigen or epitope (e.g., a portion of IL-2).

The "Complementarity Determining Regions" ("CDRs") are amino acid sequences with boundaries determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme) and ImMunoGenTics (IMGT) numbering (Lefranc, M.-P., The Immunologist, 7, 132-136 (1999); Lefranc, M.-P. et al., Dev. Comp. Immunol., 27, 55-77 (2003) ("IMGT" numbering scheme). For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL. Under IMGT the CDR amino acid residues in the VH are numbered approximately 26-35 (CDR1), 51-57 (CDR2) and 93-102 (CDR3), and the CDR amino acid residues in the VL are numbered approximately 27-32 (CDR1), 50-52 (CDR2), and 89-97 (CDR3) (numbering according to "Kabat"). Under IMGT, the CDR regions of an antibody can be determined using the program IMGT/DomainGap Align.

The term "epitope binding domain" or "EBD" refers to portions of the antigen-binding portion (e.g., an antibody or epitope-binding fragment or derivative thereof), that specifically interacts with (e.g., by binding, steric hindrance, stabilizing/destabilizing, spatial distribution) a binding site on a target epitope. EBD also refers to one or more fragments of an antibody that retain the ability to specifically interact with (e.g., by binding, steric hindrance, stabilizing/destabilizing, spatial distribution) an IL-2 epitope and interferes with IL-2's binding to IL-2 receptor alpha (CD25). Examples of antibody fragments include, but are not limited to, an scFv, a Fab fragment, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature 341:544-546), which consists of a VH domain; and an isolated complementarity determining region (CDR).

The term "epitope" as used herein refers to any determinant capable of binding with high affinity to an immunoglobulin. An epitope is a region of an antigen that is bound by an antibody that specifically targets that antigen, and when the antigen is a protein, includes specific amino acids that directly contact the antibody. Most often, epitopes reside on proteins, but in some instances, may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. 85:5879-5883).

Such single chain antibodies are also intended to be encompassed within the terms "fragment", "epitope-binding fragment" or "antibody fragment". These fragments are obtained using conventional techniques known to those of skill in the art, and the fragments are screened for utility in the same manner as are intact antibodies.

Antibody fragments can be incorporated into single chain molecules comprising a pair of tandem Fv segments (VH—CH1-VH—CH1) which, together with complementary light chain polypeptides, form a pair of antigen-binding regions (Zapata et al., (1995) Protein Eng. 8:1057-1062; and U.S. Pat. No. 5,641,870), and also include Fab fragments, F(ab') fragments, F(ab')$_2$ fragments, and anti-idiotypic (anti-Id)

antibodies (including, e.g., anti-Id antibodies to antibodies of the invention), and epitope-binding fragments of any of the above.

EBDs also include single domain antibodies, maxibodies, unibodies, minibodies, triabodies, tetrabodies, v-NAR and bis-scFv, as is known in the art (see, e.g., Hollinger and Hudson, (2005) Nature Biotechnology 23: 1126-1136), bispecific single chain diabodies, or single chain diabodies designed to bind two distinct epitopes. EBDs also include antibody-like molecules or antibody mimetics, which include, but not limited to minibodies, maxybodies, Fn3 based protein scaffolds, Ankrin repeats (also known as DARpins), VASP polypeptides, Avian pancreatic polypeptide (aPP), Tetranectin, Affililin, Knottins, SH3 domains, PDZ domains, Tendamistat, Neocarzinostatin, Protein A domains, Lipocalins, Transferrin, and Kunitz domains that specifically bind epitopes, which are within the scope of the invention. Antibody fragments can be grafted into scaffolds based on polypeptides such as Fibronectin type III (Fn3) (see U.S. Pat. No. 6,703,199, which describes fibronectin polypeptide monobodies).

The phrase "isolated antibody", as used herein, refers to antibody that is substantially free of other antibodies having different antigenic specificities (e.g., an isolated antibody that specifically binds IL-2 is substantially free of antibodies that specifically bind antigens other than IL-2). An isolated antibody that specifically binds IL-2 may, however, have cross-reactivity to other antigens, such as IL-2 molecules from other species. Moreover, an isolated antibody may be substantially free of other cellular material and/or chemicals.

The term "monovalent antibody" as used herein, refers to an antibody that binds to a single epitope on a target molecule such as IL-2.

The term "bivalent antibody" as used herein, refers to an antibody that binds to two epitopes on at least two identical IL-2 target molecules. The bivalent antibody may also crosslink the target IL-2 molecules to one another. A "bivalent antibody" also refers to an antibody that binds to two different epitopes on at least two identical IL-2 target molecules.

The term "multivalent antibody" refers to a single binding molecule with more than one valency, where "valency" is described as the number of antigen-binding moieties present per molecule of an antibody construct. As such, the single binding molecule can bind to more than one binding site on a target molecule. Examples of multivalent antibodies include, but are not limited to bivalent antibodies, trivalent antibodies, tetravalent antibodies, pentavalent antibodies, and the like, as well as bispecific antibodies and biparatopic antibodies. For example, for the IL-2, the mutivalent antibody (e.g., an IL-2 biparatopic antibody) has a binding moiety for two domains of IL-2, respectively.

The multivalent antibody mediates biological effect or which modulates a disease or disorder in a subject (e.g., by mediating or promoting cell killing, or by modulating the amount of a substance which is bioavailable.

The term "multivalent antibody" also refers to a single binding molecule that has more than one antigen-binding moieties for two separate IL-2 target molecules. For example, an antibody that binds to both an IL-2 target molecule and a second target molecule that is not IL-2. In one embodiment, a multivalent antibody is a tetravalent antibody that has four epitope binding domains. A tetravalent molecule may be bispecific and bivalent for each binding site on that target molecule.

The term "biparatopic antibody" as used herein, refers to an antibody that binds to two different epitopes on a single IL-2 target. The term also includes an antibody, which binds to two domains of at least two IL-2 targets, e.g., a tetravalent biparatopic antibody.

The term "bispecific antibody" as used herein, refers to an antibody that binds to two or more different epitopes on at least two different targets (e.g., an IL-2 and a target that is not IL-2).

The phrases "monoclonal antibody" or "monoclonal antibody composition" as used herein refers to polypeptides, including antibodies, bispecific antibodies, etc. that have substantially identical to amino acid sequence or are derived from the same genetic source. This term also includes preparations of antibody molecules of single molecular composition. A monoclonal antibody composition displays a single binding specificity and affinity for a particular epitope.

The term "humanized antibody" or "humanized anti-IL-2 antibody" as used herein includes antibodies in which CDR sequences derived from the germline of another mammalian species, such as a mouse, have been grafted onto human framework sequences. Additional framework region modifications may be made within the human framework sequences as well as within the CDR sequences derived from the germline of another mammalian species.

The humanized antibodies of the invention may include amino acid residues not encoded by human sequences (e.g., mutations introduced by random or site-specific mutagenesis in vitro or by somatic mutation in vivo, or a conservative substitution to promote stability or manufacturing).

The phrase "recombinant humanized antibody" as used herein, includes all human antibodies that are prepared, expressed, created or isolated by recombinant means, such as antibodies isolated from a host cell transformed to express the humanized antibody, e.g., from a transfectoma, and antibodies prepared, expressed, created or isolated by any other means that involve splicing of all or a portion of a human immunoglobulin gene, sequences to other DNA sequences.

The term "Fc region" as used herein refers to a polypeptide comprising the CH3, CH2 and at least a portion of the hinge region of a constant domain of an antibody. Optionally, an Fc region may include a CH4 domain, present in some antibody classes. An Fc region, may comprise the entire hinge region of a constant domain of an antibody. In one embodiment, the invention comprises an Fc region and a CH1 region of an antibody. In one embodiment, the invention comprises an Fc region CH3 region of an antibody. In another embodiment, the invention comprises an Fc region, a CH1 region and a Ckappa/lambda region from the constant domain of an antibody. In one embodiment, a binding molecule of the invention comprises a constant region, e.g., a heavy chain constant region. In one embodiment, such a constant region is modified compared to a wild-type constant region. That is, the polypeptides of the invention disclosed herein may comprise alterations or modifications to one or more of the three heavy chain constant domains (CH1, CH2 or CH3) and/or to the light chain constant region domain (CL). Example modifications include additions, deletions or substitutions of one or more amino acids in one or more domains. Such changes may be included to optimize effector function, half-life, etc.

The term "binding site" as used herein comprises an area on an IL-2 target molecule to which an antibody or antigen-binding fragment selectively binds.

The term "fusion protein" is a fusion of two separate proteins, with or without an additional linker sequence.

The term "linker sequence" is an amino acid sequence used to link or join two proteins.

Generally, antibodies specific for a particular target antigen will bind to an epitope on the target antigen in a complex mixture of proteins and/or macromolecules.

As used herein, the term "Affinity" refers to the strength of interaction between antibody and antigen at single antigenic sites. Within each antigenic site, the variable region of the antibody "arm" interacts through weak non-covalent forces with the antigen at numerous sites; the more interactions, the stronger the affinity. As used herein, the term "high affinity" for an IgG antibody or fragment thereof (e.g., a Fab fragment) refers to an antibody having a KD of $10^{-8}$ M or less, $10^{-9}$ M or less, or $10^{-10}$ M, or $10^{-11}$ M or less, or $10^{-12}$ M or less, or $10^{-13}$ M or less for a target antigen. However, high affinity binding can vary for other antibody isotypes. For example, high affinity binding for an IgM isotype refers to an antibody having a KD of $10^{-7}$ M or less, or $10^{-8}$ M or less.

As used herein, the term "Avidity" refers to an informative measure of the overall stability or strength of the antibody-antigen complex. It is controlled by three major factors: antibody epitope affinity; the valence of both the antigen and antibody; and the structural arrangement of the interacting parts. Ultimately these factors define the specificity of the antibody, that is, the likelihood that the particular antibody is binding to a precise antigen epitope.

Regions of a given polypeptide that include an epitope can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., (1984) Proc. Natl. Acad. Sci. USA 8:3998-4002; Geysen et al., (1985) Proc. Natl. Acad. Sci. USA 82:78-182; Geysen et al., (1986) Mol. Immunol. 23:709-715. Similarly, conformational epitopes are readily identified by determining spatial conformation of amino acids such as by, e.g., x-ray crystallography and two-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., (1981) Proc. Natl. Acad. Sci USA 78:3824-3828; for determining antigenicity profiles, and the Kyte-Doolittle technique, Kyte et al., (1982) J. Mol. Biol. 157:105-132; for hydropathy plots.

As used in the specification and claims, the singular form "a", "an" and "the" include plural references unless the context clearly dictates otherwise. For example, the term "a cell" includes a plurality of cells, including mixtures thereof.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about." It also is to be understood, although not always explicitly stated, that the reagents described herein are merely examples and that equivalents of such are known in the art.

As used herein the term "amino acid" refers to either natural and/or unnatural or synthetic amino acids, and both the D and L optical isomers, amino acid analogs, and peptidomimetics. A peptide of three or more amino acids is commonly called an oligopeptide if the peptide chain is short. If the peptide chain is long, the peptide is commonly called a polypeptide or a protein. The terms "biomarker" or "marker" are used interchangeably herein. A biomarker is a nucleic acid or polypeptide and the presence or absence of a mutation or differential expression of the polypeptide is used to determine sensitivity to any treatment comprising an anti-IL-2 antibody according to the invention. For example, a protein is a biomarker for a cancer cell when it is deficient, mutated, deleted, or decreased in post-translational modification, production, expression, level, stability and/or activity, as compared to the same protein in a normal (non-cancerous) cell or control cell.

The term "cDNA" refers to complementary DNA, i.e. mRNA molecules present in a cell or organism made into cDNA with an enzyme such as reverse transcriptase. A "cDNA library" is a collection of all of the mRNA molecules present in a cell or organism, all turned into cDNA molecules with the enzyme reverse transcriptase, then inserted into "vectors" (other DNA molecules that can continue to replicate after addition of foreign DNA). Example vectors for libraries include bacteriophage (also known as "phage"), viruses that infect bacteria, for example, lambda phage. The library can then be probed for the specific cDNA (and thus mRNA) of interest.

The term "cell proliferative disorders" shall include dysregulation of normal physiological function characterized by abnormal cell growth and/or division or loss of function. Examples of "cell proliferative disorders" include, but are not limited to, hyperplasia, neoplasia, metaplasia, and various autoimmune disorders, e.g., those characterized by the dysregulation of T cell apoptosis.

"Combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of the present invention and a combination partner, are both administered to a patient simultaneously in the form of a single entity or dosage. The term "non-fixed combination" means that the active ingredients, e.g. a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

A "gene" refers to a polynucleotide containing at least one open reading frame (ORF) that is capable of encoding a particular polypeptide or protein after being transcribed and translated. A polynucleotide sequence can be used to identify larger fragments or full-length coding sequences of the gene with which they are associated. Methods of isolating larger fragment sequences are known to those of skill in the art.

"Gene expression" or alternatively a "gene product" refers to the nucleic acids or amino acids (e.g., peptide or polypeptide) generated when a gene is transcribed and translated.

As used herein, "expression" refers to the process by which DNA is transcribed into mRNA and/or the process by which the transcribed mRNA is subsequently translated into peptides, polypeptides or proteins. If the polynucleotide is derived from genomic DNA, expression may include splicing of the mRNA in a eukaryotic cell.

"Differentially expressed" as applied to a gene, refers to the differential production of the mRNA transcribed and/or translated from the gene or the protein product encoded by the gene. A differentially expressed gene may be overexpressed or under expressed as compared to the expression level of a normal or control cell. However, as used herein, overexpression is an increase in gene expression and generally is at least 1.25 fold or, alternatively, at least 1.5 fold or, alternatively, at least 2 fold, or alternatively, at least 3 fold or alternatively, at least 4 fold expression over that detected in a normal or control counterpart cell or tissue. As used herein, under expression, is a reduction of gene expression and generally is at least 1.25 fold, or alternatively, at least 1.5 fold, or alternatively, at least 2 fold or alternatively, at least 3 fold or alternatively, at least 4 fold expression under that detected in a normal or control counterpart cell or tissue. The term "differentially expressed" also refers to where expression in a cancer cell or cancerous tissue is detected but expression in a control cell or normal tissue (e.g. non-cancerous cell or tissue) is undetectable.

A high expression level of the gene can occur because of over expression of the gene or an increase in gene copy number. The gene can also be translated into increased protein levels because of deregulation or absence of a negative regulator. Lastly, high expression of the gene can occur due to increased stabilization or reduced degradation of the protein, resulting in accumulation of the protein.

As used herein, the term "inhibit", "inhibiting", or "inhibit the growth" or "inhibiting the proliferation" of a cancer cell refers to slowing, interrupting, arresting or stopping the growth of the cancer cell, and does not necessarily indicate a total elimination of the cancer cell growth. The terms "inhibit" and "inhibiting", or the like, denote quantitative differences between two states; refer to at least statistically significant differences between the two states. For example, "an amount effective to inhibit growth of cancer cells" means that the rate of growth of the cells will be at least statistically significantly different from the untreated cells. Such terms are applied herein to, for example, rates of cell proliferation.

The term "isolated" means separated from constituents, cellular and otherwise, in which the polynucleotide, peptide, polypeptide, protein, antibody or fragment(s) thereof, are normally associated with in nature. For example, an isolated polynucleotide is separated from the 3' and 5' contiguous nucleotides with which it is normally associated within its native or natural environment, e.g., on the chromosome. As is apparent to those of skill in the art, a non-naturally occurring polynucleotide, peptide, polypeptide, protein, antibody, or fragment(s) thereof, does not require "isolation" to distinguish it from its naturally occurring counterpart. In addition, a "concentrated," "separated" or "diluted" polynucleotide, peptide, polypeptide, protein, antibody or fragment(s) thereof, is distinguishable from its naturally occurring counterpart in that the concentration or number of molecules per volume is greater in a "concentrated" version or less than in a "separated" version than that of its naturally occurring counterpart.

As used herein, the terms "neoplastic cells," "neoplastic disease," "neoplasia," "tumor," "tumor cells," "cancer," and "cancer cells," (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign. A "metastatic cell or tissue" means that the cell can invade and destroy neighboring body structures.

The terms "nucleic acid" and "polynucleotide" are used interchangeably and refer to a polymeric form of nucleotides of any length, either deoxyribonucleotides or ribonucleotides or analogs thereof. Polynucleotides can have any three-dimensional structure and can perform any function. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, siRNAs, shRNAs, RNAi agents, and primers. A polynucleotide can be modified or substituted at one or more base, sugar and/or phosphate, with any of various modifications or substitutions described herein or known in the art. A polynucleotide can comprise modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

The term "polypeptide" is used interchangeably with the term "protein" and in its broadest sense refers to a compound of two or more subunit amino acids, amino acid analogs, or peptidomimetics. The subunits can be linked by peptide bonds. In another embodiment, the subunit may be linked by other bonds, e.g., ester, ether, etc.

A polynucleotide or polynucleotide region (or a polypeptide or polypeptide region) has a certain percentage (for example, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Current Protocols in Molecular Biology, Ausubel et al., eds., (1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cut-off=60; expect=10; Matrix=BLOSUM62; Descriptions=50 sequences; sort by=HIGH SCORE; Databases=non-redundant.

"Suppressing" or "suppression" of tumor growth indicates a reduction in tumor cell growth when contacted with an Anti-IL-2 antibody according to the invention compared to tumor growth without contact with an Anti-IL-2 antibody according to the invention compound. Tumor cell growth can be assessed by any means known in the art, including, but not limited to, measuring tumor size, determining whether tumor cells are proliferating using a 3H-thymidine incorporation assay, measuring glucose uptake by FDG-PET (fluorodeoxyglucose positron emission tomography) imaging, or counting tumor cells. "Suppressing" tumor cell growth means any or all of the following states: slowing, delaying and stopping tumor growth, as well as tumor shrinkage. A "subject," "individual" or "patient" is used interchangeably herein, which refers to a vertebrate, preferably a mammal, more preferably a human. Mammals include, but are not limited to, mice, simians, humans, farm animals, sport animals, and pets.

Anti-IL-2 Antibodies

In a first aspect the present invention provides an isolated antibody, or antigen-binding portion thereof, which binds human IL-2, wherein said antibody or antigen-binding portion thereof comprises a light chain variable region comprising LCDR1, a LCDR2 and a LCDR3 according to Table 11 and a heavy chain variable region comprising a HCDR1, a HCDR2 and a HCDR3 according to Table 12.

In some embodiments the isolated antibody or antigen-binding portion thereof, comprises a light variable region according to Table 6 or Table 10 and a heavy variable region comprising a heavy variable region according to Table 5 or Table 10.

In some embodiments the isolated antibody, comprises variable light chains and variable heavy chains as set out in Table 10 or Table 13.

In another aspect the present invention provides variants of an antibody or fragment thereof that binds to human IL-2. Thus the present invention provides antibodies or fragments thereof that have an amino acid sequence of the non-CDR regions of the heavy and/or light chain variable region sequence which is at least 80% identical (having at least 80% amino acid sequence identity) to the amino acid sequence of the non-CDR regions of the heavy and/or light chain variable region sequence of the parent antibody of either the heavy or the light chain e.g. of either the heavy and light variable region sequences as Table 5 and Table 6, respectively. As well antibodies or fragments thereof that have an amino acid sequence of the non-extended CDR regions of the heavy and/or light chain variable region sequence which is at least 80% identical to the amino acid sequence of the non-extended CDR regions of the heavy and/or light chain variable region sequence of the parent antibody of either the heavy or the light chain are provided by the present invention. Preferably the amino acid sequence identity of the non-CDR regions or of the non-extended CDR regions of the heavy and/or light chain variable region sequence is at least 85%, more preferably at least 90%, and most preferably at least 95%, in particular 96%, more particular 97%, even more particular 98%, most particular 99%, including for example, 80%, 81%, 82%, 83%, 84%, 85%, 86%, 87%, 88%, 89%, 90%, 91%, 92%, 93%, 94%, 95%, 96%, 97%, 98%, 99%, and 100%.

The present disclosure also provides an antibody or fragment thereof that binds to human IL-2 which further comprises a heavy and/or light constant region in particular a human heavy and/or a human light constant region. Human heavy constant regions may be selected from the group of human immunoglobulins consisting of IgG 1 (IGHG 1), IgG2 (IGHG2), IgG3 (IGHG3), IgG4 (IGHG4), IgA1 (IGHA1), IgA2 (IGHA2), IgM (IGHM), IgD (IGHD), or IgE (IGHE), whereas the human heavy constant region IgG, in particular IgG 1 (IGHG 1) is preferred. Human light constant region may be selected from the group of human immunoglobulins consisting of kappa or lambda constant regions, whereas human kappa constant region is preferred. In a preferred embodiment the antibody or fragment thereof that binds to human IL-2 comprises a human IgG 1 (IGHG 1) heavy constant domain and a human light kappa constant domain.

In addition or alternative to modifications made within the framework regions or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity.

Furthermore, an antibody of the invention may be chemically modified (e.g., one or more Chemical moieties can be attached to the antibody) or be modified to alter its glycosylation.

The present invention provides for antibodies that specifically bind to human IL-2 which resulting in altered half-life in vivo.

Many factors may affect a protein's half-life in vivo. For examples, kidney filtration, metabolism in the liver, degradation by proteolytic enzymes (proteases), and immunogenic responses (e.g., protein neutralization by antibodies and uptake by macrophages and dentritic cells). A variety of strategies can be used to extend the half-life of the antibodies and antigen-binding fragments thereof of the present invention. For example, by chemical linkage to polyethyleneglycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanobodies, Fabs, DARPins, avimers, affibodies, and anticalins; by genetic fusion to rPEG, albumin, domain of albumin, albumin-binding proteins, and Fc; or by incorporation into nancarriers, slow release formulations, or medical devices.

To prolong the serum circulation of antibodies in vivo, inert polymer molecules such as high molecular weight PEG can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, antigen-binding fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10)alkoxy- or aryloxy-polyethylene glycol or polyethylene glycol-maleimide. In one embodiment, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies and antigen-binding fragments thereof of the invention. See for example, EP 0 154 316 by Nishimura et al. and EP 0 401 384 by Ishikawa et al., each of which is incorporated by reference.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in E. coli, yeast, and mammalian cells. The tRNA incorporates a normative amino acid any place an amber codon is positioned, converting the amber from a stop codon to one that signals incorporation of the chemically specified amino acid.

Recombinant pegylation technology (rPEG) can also be used for serum halflife extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum halflife of the protein is greatly increased. In contrast to traditional PEGylation, which requires chemical conjugation and repurification, the manufacturing process is greatly simplified and the product is homogeneous.

Polysialylation is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology include the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

Antibodies having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375, each of which is incorporated by reference.

Further, antibodies can be conjugated to albumin in order to make the antibody or antibody fragment more stable in vivo or have a longer half-life in vivo. The techniques are well-known in the art, see, e.g., International Publication Nos. WO 93/15199, WO 93/15200, and WO 01/77137; and European Patent No. EP 413,622, each of which is incorporated by reference.

The strategies for increasing half-life is especially useful in nanobodies, fibronectin-based binders, and other antibodies or proteins for which increased in vivo half-life is desired.

In another embodiment, the antibody is modified to increase its biological half-life. Various approaches are possible. For example, one or more of the following mutations can be introduced: T252L, T254S, T256F, as described in U.S. Pat. No. 6,277,375 to Ward, which is incorporated by reference. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al, which is incorporated by reference.

In one embodiment, antibodies according to the invention comprises light and heavy chains according to Table 1.

TABLE 1

Heavy and light chain SEQ ID Nos for antibodies according to an embodiment.

| Antibody | Light chain SEQ ID | Heavy chain SEQ ID |
|---|---|---|
| 104343 | SEQ ID NO: 124 | SEQ ID NO: 126 |
| 104348 | SEQ ID NO: 128 | SEQ ID NO: 130 |

1. Nucleic Acids, Vectors and Host Cells

The present invention is also directed to cell lines that express an anti-IL-2 antibody of the invention or portion thereof. Creation and isolation of cell lines producing a antibody of the invention can be accomplished using standard techniques known in the art. The CHO cell line is preferred (available from public repositories such as ATCC, American Type Culture Collection, Manassas, Va.).

A wide variety of host expression systems can be used to express an antibody of the present invention including prokaryotic and eukaryotic expression systems (such as yeast, baculovirus, plant, mammalian and other animal cells, transgenic animals, and hybridoma cells), as well as phage display expression systems. One example of a suitable bacterial expression vector is pUC119 and a suitable eukaryotic expression vector is a modified pcDNA3.1 vector with a weakened dhfr selection system. Other antibody expression systems are also known in the art.

An antibody of the invention can be prepared by recombinant expression of immunoglobulin light and heavy chain genes in a host cell, as is well known to a person skilled in the art. To express an antibody recombinantly, a host cell is transformed, transduced, infected or the like with one or more recombinant expression vectors carrying DNA fragments encoding the immunoglobulin light and/or heavy chains of the antibody such that the light and/or heavy chains are expressed in the host cell. The heavy chain and light chain may be expressed in the same or different host cells. Preferably, the recombinant antibodies are secreted into the medium in which the host cells are cultured, from which the antibodies can be recovered or purified.

Standard recombinant DNA methodologies are used to obtain antibody heavy and light chain genes, incorporate these genes into recombinant expression vectors, and introduce the vectors into host cells. Such standard recombinant DNA technologies are described, for example, in Green and Sambrook (Eds.), Molecular Cloning; A Laboratory Manual, Fourth Edition, Cold Spring Harbor, N.Y., 2012.

In one embodiment, the invention provides a vector, preferably (but not limited to) a plasmid, a recombinant expression vector, a yeast expression vector, or a retroviral expression vector comprising a polynucleotide encoding an anti-IL-2 antibody of the invention. The coding region(s) in the vector may be separated by a linker sequence of any size or content, preferably such linker, when present, is a polynucleotide encoding an internal ribosome entry site.

To express an antibody of the invention, a DNA encoding a partial amino acid chain, as described in Table 41, are inserted into an expression vector such that the gene is operably linked to transcriptional and translational control sequences. The expression vector and expression control sequences are chosen to be compatible with the expression host cell used. Additionally, the recombinant expression vector can encode a signal peptide that facilitates secretion of the anti-IL-2 antibody light and/or heavy chain from a host cell. The anti-IL-2 antibody light and/or heavy chain gene can be cloned into the vector such that the signal peptide is operably linked in-frame to the amino terminus of the antibody chain gene. The signal peptide can be an immunoglobulin signal peptide or a heterologous signal peptide.

For expression of the light and/or heavy chains, the expression vector(s) encoding the heavy and/or light chains is introduced into a host cell by standard techniques e.g., electroporation, calcium phosphate precipitation, DEAE-dextran transfection, transduction, infection and the like. Although it is theoretically possible to express the antibodies of the invention in either prokaryotic or eukaryotic host cells, eukaryotic cells are preferred and most preferably mammalian host cells, because such cells are more likely to assemble and secrete a properly folded and immunologically active antibody.

Preferred mammalian host cells for expressing the recombinant antibodies of the invention include Chinese Hamster Ovary (CHO cells), e.g. as described in Urlaub and Chasin, Proc. Natl. Acad. Sci. USA 77:4216-20, 1980. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown under appropriate conditions known in the art. Antibodies can be recovered from the host cell and/or the culture medium using standard purification methods.

IL-2 Variants

In certain embodiments of the invention, human IL-2 of wildtype (wt) is used. It has UniProt ID number P60568 and is reproduced as SEQ ID NO: 109. Another example of human IL-2 is the IL-2 mutein disclosed in WO2012/107417A1, having 3 mutations compared to wt hIL-2. Aldesleukin (trade name Proleukin) is another example of a variant of human IL-2, well known to a person skilled in the art, and represented herein by SEQ ID NO: 110. Other examples of IL-2 variants are no-alpha mutein and IL-2 superkine, as shown in Table 2.

TABLE 2

| | IL-2 muteins | | |
|---|---|---|---|
| | Mutein | substitution at position x relative to full length wt IL-2 | substitution at position x relative to mature wt IL-2 |
| 1 | Proleukin ® (Aldesleukin) | C145S | C125S |
| 2 | no-alpha mutein | R58A, F62A, Y65A, E82A | R38A, F42A, Y45A, E62A |
| 3 | WO2012/107417A1 | F62A, Y65A, L92G | F42A, Y45A, L72G |
| 4 | IL-2 superkine | L100F, R101D, L105V, I106V, I112F | L80F, R81D, L85V, I86V, I92F |

IL-2/Anti-IL-2 Antibody Combinations

In an embodiment, the antibodies, or antigen-binding portion thereof, as described above, are combined with human IL-2 or IL-2 mutants as described above.

The combination can be a pre-made mixture with 1:1, 2:1 or other proportion of IL-2:antibody binding site.

In one embodiment, the anti-IL-2 antibody and IL-2 are administered in sequence with a first injection of antibody, and a subsequent injection of anti-IL-2 antibody/IL-2 combination.

In another embodiment, the anti-IL-2 antibody and IL-2 are administered in sequence with a first injection of anti-IL-2 antibody/IL-2 combination, and a subsequent injection of IL-2.

Pharmaceutical Compositions

Pharmaceutical compositions of the disclosure also can be administered in combination therapy, i.e., combined with other agents. For example, the combination therapy can include an anti-IL-2 antibody or fragment thereof according to the present disclosure combined with at least one other anti-inflammatory or another chemotherapeutic agent. Examples of therapeutic agents that can be used in combination therapy are described in greater detail below in the section on combination therapies.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). In one embodiment, the carrier should be suitable for subcutaneous route. Depending on the route of administration, the active compound, i.e., antibody, immunoconjugate, or bispecific molecule, may be coated in a material to protect the compound from the action of acids and other natural conditions that may inactivate the compound.

The pharmaceutical compositions of the disclosure may include one or more pharmaceutically acceptable salts. A "pharmaceutically acceptable salt" refers to a salt that retains the desired biological activity of the parent compound and does not impart any undesired toxicological effects (see e.g., Berge, S. M., et al. 1977, J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as, aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, one can include isotonic agents, for example, sugars, polyalcohols such as mannitol, sorbitol, or sodium chloride in the composition. Prolonged absorption of the injectable compositions can be brought about by including in the composition an agent that delays absorption for example, monostearate salts and gelatin.

Reviews on the development of stable protein (e.g. antibody) formulations may be found in Cleland et al. 1993, Crit. Reviews. Ther. Drug Carrier Systems 10(4):307-377 and Wei Wang 1999, Int. J. Pharmaceutcs 185:129-88. Additional formulation discussions for antibodies may be found, e.g., in Daugherty and Mrsny 2006, Advanced Drug Delivery Reviews 58: 686-706; U.S. Pat. Nos. 6,171,586, 4,618,486, US Publication No. 20060286103, PCT Publication WO 06/044908, WO 07/095337, WO 04/016286, Colandene et al. 2007, J. Pharm. Sci 96: 1598-1608; Schulman 2001, Am. J. Respir. Crit. Care Med. 164:S6-S11 and other known references, each of which is incorporated by reference.

Solutions or suspensions used for intradermal or subcutaneous application typically include one or more of the following components: a sterile diluent such as water for injection, saline solution, fixed oils, polyethylene glycols, glycerine, propylene glycol or other synthetic solvents, antibacterial agents such as benzyl alcohol or methyl parabens, antioxidants such as ascorbic acid or sodium bisulfite, chelating agents such ethylenediaminetetraacetic acid, buffers such as acetates, citrates or phosphates, and agents for the adjustment of tonicity such as sodium chloride or dextrose. The pH can be adjusted with acids or bases, such as hydrochloric acid or sodium hydroxide. Such preparations may be enclosed in ampoules, disposables syringes or multiple dose vials made of glass or plastic.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the antibodies or proteins of the disclosure into a sterile vehicle that contains a basic dispersion medium and the required other ingredients from those enumerated above. In the case of sterile powders for the preparation of sterile injectable solutions, the methods of preparation are vacuum drying and freeze-drying (lyophilization) that yield a powder of the active ingredient plus any additional desired ingredient from a previously sterile-filtered solution thereof.

In one specific embodiment, the antibodies according to the disclosure were administered as a liquid formulation in a vial. The amount of drug per vial was 150 mg. The liquid contained 150 mg/mL antibody, 4.8 mM L-Histidine, 15.2 mM L-Histidine-HCl 220 mM Sucrose and 0.04% Polysorbate 20, at pH 6.0±0.5. A 20% overfill was added to permit complete removal of the intended dose.

Therapeutic and Other Uses

The antibodies of the present invention have numerous in vitro and in vivo diagnostic and therapeutic utilities involving the diagnosis and treatment of disorders with IL-2-dependent pathophysiology. For example, these molecules can be administered to cells in culture, in vitro or ex vivo, or to human subjects, e.g., in vivo, to treat, prevent and to diagnose a variety disorders with IL-2-dependent pathophysiology.

Accordingly, in one embodiment, the invention provides a method of inhibiting growth of tumor cells in a subject, comprising administering to the subject a therapeutically effective amount of an anti-IL-2 antibody as disclosed herein. In one embodiment, the methods are suitable for the treatment of cancer in vivo. In one embodiment, the antibodies to IL-2 are administered together with IL-2, such as in combination with IL-2.

When antibodies to IL-2 are administered in combination with one or more agents, the combination can be administered in either order or simultaneously.

In another aspect, a method of treating a subject, e.g., reducing or ameliorating, a proliferative condition or disorder (e.g., a cancer), e.g., solid tumor, a soft tissue tumor, or a metastatic lesion, in a subject is provided.

The term cancer is meant to include all types of cancerous growths or oncogenic processes, metastatic tissues or malignantly transformed cells, tissues, or organs, irrespective of histopathologic type or stage of invasiveness. Examples of cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. In one embodiment, the cancer is a melanoma, e.g., an advanced stage melanoma. Metastatic lesions of the aforementioned cancers can also be treated or prevented using the methods and compositions of the invention.

Exemplary cancers whose growth can be inhibited using the antibodies molecules disclosed herein include cancers typically responsive to immunotherapy. Non-limiting examples of preferred cancers for treatment include melanoma (e.g., metastatic malignant melanoma), renal cancer (e.g., clear cell carcinoma), prostate cancer (e.g., hormone refractory prostate adenocarcinoma), breast cancer, colon cancer and lung cancer (e.g., non-small cell lung cancer). Additionally, refractory or recurrent malignancies can be treated using the antibody molecules described herein.

Examples of other cancers that can be treated include bone cancer, pancreatic cancer, skin cancer, cancer of the head or neck, cutaneous or intraocular malignant melanoma, uterine cancer, ovarian cancer, rectal cancer, anal cancer, gastro-esophageal, stomach cancer, testicular cancer, uterine cancer, carcinoma of the fallopian tubes, carcinoma of the endometrium, carcinoma of the cervix, carcinoma of the vagina, carcinoma of the vulva, Hodgkin Disease, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

In other embodiments, the cancer is a hematological malignancy or cancer including but is not limited to a leukemia or a lymphoma. For example, the anti-IL-2 therapy can be used to treat cancers and malignancies including, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell-oralargecell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. In some embodiments, the lymphoma (e.g., an anaplastic large-cell lymphoma or non-Hodgkin lymphoma) has, or is identified as having, an ALK translocation, e.g., an EML4-ALK fusion.

In one embodiment, the cancer is chosen from a lung cancer (e.g., a non-small cell lung cancer (NSCLC) (e.g., a NSCLC with squamous and/or non-squamous histology)), a melanoma (e.g., an advanced melanoma), a renal cancer (e.g., a renal cell carcinoma, e.g., clear cell renal cell carcinoma), a liver cancer, a myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), a colorectal cancer, a pancreatic cancer, a head and neck cancer (e.g., head and neck squamous cell carcinoma (HNSCC), anal cancer, gastro-esophageal cancer, thyroid cancer, cervical cancer, a lymphoproliferative disease (e.g., a post-transplant lymphoproliferative disease) or a hematological cancer, T-cell lymphoma, a non-Hodgkin's lymphoma, or a leukemia (e.g., a myeloid leukemia).

In another embodiment, the cancer is chosen form a carcinoma (e.g., advanced or metastatic carcinoma), melanoma or a lung carcinoma, e.g., a non-small cell lung carcinoma.

In one embodiment, the cancer is a lung cancer, e.g., a non-small cell lung cancer (NSCLC). In certain embodiments, the lung cancer, e.g., the non-small cell lung cancer, has, or is identified as having, an ALK rearrangement or translocation, e.g., an ALK fusion, e.g., an EML4-ALK fusion.

In another embodiment, the cancer is an inflammatory myofibroblastic tumor (IMT). In certain embodiments, the inflammatory myofibroblastic tumor has, or is identified as having, an ALK rearrangement or translocation, e.g., an ALK fusion, e.g., an EML4-ALK fusion.

In other embodiments, the cancer is NSCLC wherein the NSCLC is characterized by one or more of: aberrant activation, amplification, or a mutation of epidermal growth factor receptor (EGFR). In certain embodiments the cancer is NSCLC wherein the NSCLC is characterized by harbouring an EGFR exon 20 insertion, an EGFR exon 19 deletion, EGFR L858R mutation, EGFR T790M, or any combination thereof. In some embodiments, the NSCLC is characterized by harboring L858R and T790M mutations of EGFR. In some embodiments, the NSCLC is characterized by harboring an EGFR exon insertion and T790M mutations of EGFR. In some embodiments, the NSCLC is characterized by harboring an EGFR exon 19 deletion and T790M mutations of EGFR. In some embodiments, the NSCLC is characterized by harboring EGFR mutation selected from the group consisting of an exon 20 insertion, an exon 19 deletion, L858R mutation, T790M mutation, and any combination thereof.

In yet another embodiment, the cancer is a neuroblastoma.

In certain embodiments, the neuroblastoma has, or is identified as having, an ALK rearrangement or translocation, e.g., an ALK fusion, e.g., an EML4-ALK fusion. Methods and compositions disclosed herein are useful for treating metastatic lesions associated with the aforementioned cancers.

In another embodiment, the cancer is a hepatocarcinoma, e.g., an advanced hepatocarcinoma, with or without a viral infection, e.g., a chronic viral hepatitis.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC or clear cell renal cell carcinoma).

In one embodiment, the cancer is a melanoma, e.g., an advanced melanoma. In one embodiment, the cancer is an advanced or unresectable melanoma that does not respond to other therapies. In other embodiments, the cancer is a melanoma with a BRAF mutation (e.g., a BRAF V600 mutation).

In another embodiment, the cancer is an inflammatory myofibroblastic tumor (IMT). In certain embodiments, the inflammatory myofibroblastic tumor has, or is identified as having, an ALK rearrangement or translocation, e.g., an ALK fusion, e.g., an EML4-ALK fusion.

In yet another embodiment, the cancer is a neuroblastoma. In certain embodiments, the neuroblastoma has, or is identified as having, an ALK rearrangement or translocation, e.g., an ALK fusion, e.g., an EML4-ALK fusion. Methods and compositions disclosed herein are useful for treating metastatic lesions associated with the aforementioned cancers.

Combination Therapies

The antibodies, or antigen-binding portion thereof of the disclosure may be administered as the sole active ingredient or in conjunction with, e.g. as an adjuvant to or in combination to, other drugs e.g. immunomodulating agents or cytotoxic or anti-cancer agents, e.g. for the treatment or prevention of diseases mentioned above.

1. Exemplary STING Agonists

In an embodiment, the combination includes a STING agonist. In some embodiments, the combination is used to treat a cancer, e.g., a cancer described herein e.g., a solid tumor (e.g., a breast cancer, a squamous cell carcinoma, a melanoma, an ovarian cancer, a fallopian tube carcinoma, a peritoneal carcinoma, a soft tissue sarcoma, a melanoma, a breast cancer, an esophageal cancer, a head and neck cancer, an endometrial cancer, a cervical cancer, or a basal cell carcinoma), e.g., a hematologic malignancy (e.g., a leukemia (e.g., a chronic lymphocytic leukemia (CLL), or a lymphoma (e.g., a marginal zone B-cell lymphoma, a small lymphocytic lymphoma, a follicular lymphoma, Hodgkin lymphoma, non-Hodgkin lymphoma)).

In some embodiments, the STING agonist is cyclic dinucleotide, e.g., a cyclic dinucleotide comprising purine or pyrimidine nucleobases (e.g., adenosine, guanine, uracil, thymine, or cytosine nucleobases). In some embodiments, the nucleobases of the cyclic dinucleotide comprise the same nucleobase or different nucleobases.

In some embodiments, the STING agonist comprises an adenosine or a guanosine nucleobase. In some embodiments, the STING agonist comprises one adenosine nucleobase and one guanosine nucleobase. In some embodiments, the STING agonist comprises two adenosine nucleobases or two guanosine nucleobases.

In some embodiments, the STING agonist comprises a modified cyclic dinucleotide, e.g., comprising a modified nucleobase, a modified ribose, or a modified phosphate linkage. In some embodiments, the modified cyclic dinucleotide comprises a modified phosphate linkage, e.g., a thiophosphate.

In some embodiments, the STING agonist comprises a cyclic dinucleotide (e.g., a modified cyclic dinucleotide) with 2',5' or 3',5' phosphate linkages. In some embodiments, the STING agonist comprises a cyclic dinucleotide (e.g., a modified cyclic dinucleotide) with Rp or Sp stereochemistry around the phosphate linkages.

In some embodiments, the STING agonist is Rp,Rp dithio 2',3' c-di-AMP (e.g., Rp,Rp-dithio c-[A(2',5')pA(3',5')p]), or a cyclic dinucleotide analog thereof. In some embodiments, the STING agonist is a compound depicted in U.S. Patent Publication No. US2015/0056224 (e.g., a compound in FIG. 2c, e.g., compound 21 or compound 22). In some embodiments, the STING agonist is c-[G(2',5')pG(3',5')p], a dithio ribose O-substituted derivative thereof, or a compound depicted in FIG. 4 of PCT Publication Nos. WO 2014/189805 and WO 2014/189806, each of which is incorporated by reference. In some embodiments, the STING agonist is c-[A(2',5')pA(3',5')p] or a dithio ribose O-substituted derivative thereof, or is a compound depicted in FIG. 5 of PCT Publication Nos. WO 2014/189805 and WO 2014/189806. In some embodiments, the STING agonist is 2'-O-propargyl-cyclic-[A(2',5')pA(3',5')p] (2'-O-propargyl-ML-CDA) or a compound depicted in FIG. 7 of PCT Publication No. WO 2014/189806, which is incorporated by reference.

Other exemplary STING agonists are disclosed, e.g., in PCT Publication Nos. WO 2014/189805 and WO 2014/189806, and U.S. Publication No. 2015/0056225, each of which is incorporated by reference.

2. Exemplary PD-1 Inhibitors

In an embodiment, the combination includes an anti-PD-1, or anti-PD-1 ligand (PD-L1) antibody molecule. In some embodiments, the combination is used to treat a cancer, e.g., a cancer described herein e.g., a solid tumor (e.g., a breast cancer, a squamous cell carcinoma, a melanoma, an ovarian cancer, a fallopian tube carcinoma, a peritoneal carcinoma, a soft tissue sarcoma, a melanoma, a breast cancer, an esophageal cancer, a head and neck cancer, an endometrial cancer, a cervical cancer, or a basal cell carcinoma), e.g., a hematologic malignancy (e.g., a leukemia (e.g., a chronic lymphocytic leukemia (CLL), or a lymphoma (e.g., a marginal zone B-cell lymphoma, a small lymphocytic lymphoma, a follicular lymphoma, Hodgkin lymphoma, non-Hodgkin lymphoma)).

Exemplary non-limiting combinations and uses of the anti-PD-1 antibody molecules are disclosed in US 2015/0210769, published on Jul. 30, 2015, entitled "Antibody Molecules to PD-1 and Uses Thereof," incorporated by reference in its entirety.

In one embodiment, the anti-PD-1 antibody molecule includes at least one or two heavy chain variable domain (optionally including a constant region), at least one or two light chain variable domain (optionally including a constant region), or both, comprising the amino acid sequence of BAP49-Clone-A, BAP49-Clone-B, BAP49-Clone-C, BAP49-Clone-D, or BAP49-Clone-E; or as described in Table 1 of US 2015/0210769, or encoded by the nucleotide sequence in Table 1 of US 2015/0210769; or a sequence substantially identical (e.g., at least 80%, 85%, 90%, 92%, 95%, 97%, 98%, 99% or higher identical) to any of the aforesaid sequences. The anti-PD-1 antibody molecule, optionally, comprises a leader sequence from a heavy chain, a light chain, or both, as shown in Table 4 of US 2015/0210769; or a sequence substantially identical thereto.

In yet another embodiment, the anti-PD-1 antibody molecule includes at least one, two, or three complementarity determining regions (CDRs) from a heavy chain variable region and/or a light chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1 of US 2015/0210769, or encoded by the nucleotide sequence in Table 1 of US 2015/0210769; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule includes at least one, two, or three CDRs (or collectively all of the CDRs) from a heavy chain variable region comprising an amino acid sequence shown in Table 1 of US 2015/0210769, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1 of US 2015/0210769, or encoded by a nucleotide sequence shown in Table 1.

In yet another embodiment, the anti-PD-1 antibody molecule includes at least one, two, or three CDRs (or collectively all of the CDRs) from a light chain variable region comprising an amino acid sequence shown in Table 1 of US 2015/0210769, or encoded by a nucleotide sequence shown in Table 1 of US 2015/0210769. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1 of US 2015/0210769. In certain embodiments, the anti-PD-1 antibody molecule includes a substitution in a light chain CDR, e.g., one or more substitutions in a CDR1, CDR2 and/or CDR3 of the light chain.

In one embodiment, the anti-PD-1 antibody molecule includes a substitution in the light chain CDR3 at position 102 of the light variable region, e.g., a substitution of a cysteine to tyrosine, or a cysteine to serine residue, at position 102 of the light variable region according to Table 1 of US 2015/0210769 (e.g., SEQ ID NO: 16 or 24 for murine or chimeric, unmodified; or any of SEQ ID NOs: 34, 42, 46, 54, 58, 62, 66, 70, 74, or 78 for a modified sequence).

In another embodiment, the anti-PD-1 antibody molecule includes at least one, two, three, four, five or six CDRs (or collectively all of the CDRs) from a heavy and light chain variable region comprising an amino acid sequence shown in Table 1 of US 2015/0210769, or encoded by a nucleotide sequence shown in Table 1 of US 2015/0210769. In one embodiment, one or more of the CDRs (or collectively all of the CDRs) have one, two, three, four, five, six or more changes, e.g., amino acid substitutions or deletions, relative to the amino acid sequence shown in Table 1 of US 2015/0210769, or encoded by a nucleotide sequence shown in Table 1 of US 2015/0210769.

In one embodiment, the anti-PD-1 antibody molecule includes:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33, each disclosed in Table 1 of US 2015/0210769;

(b) a VH comprising a VHCDR1 amino acid sequence chosen from SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32, each disclosed in Table 1 of US 2015/0210769;

(c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33, each disclosed in Table 1 of US 2015/0210769; or (d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32, each disclosed in Table 1 of US 2015/0210769.

In the combinations herein below, in another embodiment, the anti-PD-1 antibody molecule comprises (i) a heavy chain variable region (VH) comprising a VHCDR1 amino acid sequence chosen from SEQ ID NO: 1, SEQ ID NO: 4, or SEQ ID NO: 224; a VHCDR2 amino acid sequence of SEQ ID NO: 2 or SEQ ID NO: 5; and a VHCDR3 amino acid sequence of SEQ ID NO: 3; and (ii) a light chain variable region (VL) comprising a VLCDR1 amino acid sequence of SEQ ID NO: 10 or SEQ ID NO: 13, a VLCDR2 amino acid sequence of SEQ ID NO: 11 or SEQ ID NO: 14, and a VLCDR3 amino acid sequence of SEQ ID NO: 32 or SEQ ID NO: 33, each disclosed in Table 1 of US 2015/0210769.

In other embodiments, the PD-1 inhibitor is an anti-PD-1 antibody chosen from Nivolumab, Pembrolizumab or Pidilizumab.

In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168. In one embodiment, the inhibitor of PD-1 is Nivolumab, and having a sequence disclosed herein (or a sequence substantially identical or similar thereto, e.g., a sequence at least 85%, 90%, 95% identical or higher to the sequence specified).

In some embodiments, the anti-PD-1 antibody is Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) New England Journal of Medicine 369 (2): 134-44, U.S. Pat. No. 8,354,509 and WO2009/114335.

In one embodiment, the inhibitor of PD-1 is Pembrolizumab disclosed in, e.g., U.S. Pat. No. 8,354,509 and WO 2009/114335, and having a sequence disclosed herein (or a sequence substantially identical or similar thereto, e.g., a sequence at least 85%, 90%, 95% identical or higher to the sequence specified).

In some embodiments, the anti-PD-1 antibody is Pidilizumab. Pidilizumab (CT-011; Cure Tech) is a humanized IgG1k monoclonal antibody that binds to PD1. Pidilizumab and other humanized anti-PD-1 monoclonal antibodies are disclosed in WO2009/101611.

Other anti-PD1 antibodies include AMP 514 (Amplimmune), among others, e.g., anti-PD1 antibodies disclosed in U.S. Pat. No. 8,609,089, US 2010028330, and/or US 20120114649.

In some embodiments, the PD-1 inhibitor is an immunoadhesin (e.g., an immunoadhesin comprising an extracellular or PD-1 binding portion of PD-LI or PD-L2 fused to a constant region (e.g., an Fc region of an immunoglobulin sequence). In some embodiments, the PD-1 inhibitor is AMP-224 (B7-DCIg; Amplimmune; e.g., disclosed in WO2010/027827 and WO2011/066342), is a PD-L2 Fc fusion soluble receptor that blocks the interaction between PD-1 and B7-H1.

3. Exemplary TIM-3 Inhibitors

In an embodiment, the combination includes a TIM-3 inhibitor. In some embodiments, the combination is used to treat a cancer, e.g., a cancer described herein e.g., a solid tumor (e.g., a breast cancer, a squamous cell carcinoma, a melanoma, an ovarian cancer, a fallopian tube carcinoma, a peritoneal carcinoma, a soft tissue sarcoma, a melanoma, a breast cancer, an esophageal cancer, a head and neck cancer, an endometrial cancer, a cervical cancer, or a basal cell carcinoma), e.g., a hematologic malignancy (e.g., a leukemia (e.g., a chronic lymphocytic leukemia (CLL), or a lymphoma (e.g., a marginal zone B-cell lymphoma, a small lymphocytic lymphoma, a follicular lymphoma, Hodgkin lymphoma, non-Hodgkin lymphoma)).

In one embodiment, a combination described herein includes a TIM-3 inhibitor. In some embodiments, the combination is used to treat a cancer, e.g., a cancer described herein, e.g., a solid tumor or a hematologic malignancy.

Exemplary non-limiting combinations and uses of the anti-TIM-3 antibody molecules are disclosed in US 2015/0218274, published on Aug. 6, 2015, entitled "Antibody Molecules to TIM-3 and Uses Thereof," incorporated by reference in its entirety.

In one embodiment, the anti-TIM-3 antibody molecule includes at least one or two heavy chain variable domain (optionally including a constant region), at least one or two light chain variable domain (optionally including a constant region), or both, comprising the amino acid sequence of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4 of US 2015/0218274; or a sequence substantially identical (e.g., at least 80%, 85%, 90%, 92%, 95%, 97%, 98%, 99% or higher identical) to any of the aforesaid sequences. The anti-TIM-3 antibody molecule, optionally, comprises a leader sequence from a heavy chain, a light chain, or both, as shown in US 2015/0218274; or a sequence substantially identical thereto.

In yet another embodiment, the anti-TIM-3 antibody molecule includes at least one, two, or three complementarity determining regions (CDRs) from a heavy chain variable region and/or a light chain variable region of an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4 of US 2015/0218274; or a sequence substantially identical (e.g., at least 80%, 85%, 90%, 92%, 95%, 97%, 98%, 99% or higher identical) to any of the aforesaid sequences.

In yet another embodiment, the anti-TIM-3 antibody molecule includes at least one, two, or three CDRs (or collectively all of the CDRs) from a heavy chain variable region comprising an amino acid sequence shown in Tables 1-4 of US 2015/0218274, or encoded by a nucleotide sequence shown in Tables 1-4 of US 2015/0218274. In one embodiment, one or more of the CDRs (or collectively all of the CDRs) have one, two, three, four, five, six or more changes, e.g., amino acid substitutions or deletions, relative to the amino acid sequence shown in Tables 1-4 of US 2015/0218274, or encoded by a nucleotide sequence shown in Table 1-4 of US 2015/0218274.

In yet another embodiment, the anti-TIM-3 antibody molecule includes at least one, two, or three CDRs (or collectively all of the CDRs) from a light chain variable region comprising an amino acid sequence shown in Tables 1-4 of US 2015/0218274, or encoded by a nucleotide sequence shown in Tables 1-4 of US 2015/0218274. In one embodiment, one or more of the CDRs (or collectively all of the CDRs) have one, two, three, four, five, six or more changes, e.g., amino acid substitutions or deletions, relative to the amino acid sequence shown in Tables 1-4 of US 2015/0218274, or encoded by a nucleotide sequence shown in Tables 1-4 of US 2015/0218274. In certain embodiments, the anti-TIM-3 antibody molecule includes a substitution in a light chain CDR, e.g., one or more substitutions in a CDR1, CDR2 and/or CDR3 of the light chain.

In another embodiment, the anti-TIM-3 antibody molecule includes at least one, two, three, four, five or six CDRs (or collectively all of the CDRs) from a heavy and light chain variable region comprising an amino acid sequence shown in Tables 1-4 of US 2015/0218274, or encoded by a nucleotide sequence shown in Tables 1-4 of US 2015/0218274. In one embodiment, one or more of the CDRs (or collectively all of the CDRs) have one, two, three, four, five, six or more changes, e.g., amino acid substitutions or deletions, relative to the amino acid sequence shown in Tables 1-4 of US 2015/0218274, or encoded by a nucleotide sequence shown in Tables 1-4 of US 2015/0218274.

In one embodiment, the anti-TIM-3 antibody molecule includes:

(a) a heavy chain variable region (VH) comprising a VHCDR1 amino acid sequence chosen from SEQ ID NO: 9; a VHCDR2 amino acid sequence of SEQ ID NO: 10; and a VHCDR3 amino acid sequence of SEQ ID NO: 5; and a light chain variable region (VL) comprising a VLCDR1 amino acid sequence of SEQ ID NO: 12, a VLCDR2 amino acid sequence of SEQ ID NO: 13, and a VLCDR3 amino acid sequence of SEQ ID NO: 14, each disclosed in Tables 1-4 of US 2015/0218274;

(b) a VH comprising a VHCDR1 amino acid sequence chosen from SEQ ID NO: 3; a VHCDR2 amino acid sequence of SEQ ID NO: 4; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each disclosed in Tables 1-4 of US 2015/0218274;

(c) a VH comprising a VHCDR1 amino acid sequence chosen from SEQ ID NO: 9; a VHCDR2 amino acid sequence of SEQ ID NO: 25; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14, each disclosed in Tables 1-4 of US 2015/0218274;

(d) a VH comprising a VHCDR1 amino acid sequence chosen from SEQ ID NO: 3; a VHCDR2 amino acid sequence of SEQ ID NO: 24; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each disclosed in Tables 1-4 of US 2015/0218274;

(e) a VH comprising a VHCDR1 amino acid sequence chosen from SEQ ID NO: 9; a VHCDR2 amino acid sequence of SEQ ID NO: 31; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14, each disclosed in Tables 1-4 of US 2015/0218274; or (f) a VH comprising a VHCDR1 amino acid sequence chosen from SEQ ID NO: 3; a VHCDR2 amino acid sequence of SEQ ID NO: 30; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each disclosed in Tables 1-4 of US 2015/0218274.

Exemplary anti-TIM-3 antibodies are disclosed in U.S. Pat. No. 8,552,156, WO 2011/155607, EP 2581113 and U.S Publication No.: 2014/044728.

4. Exemplary LAG-3 Inhibitors

In an embodiment, the combination includes a LAG-3 inhibitor. In some embodiments, the combination is used to treat a cancer, e.g., a cancer described herein e.g., a solid tumor (e.g., a breast cancer, a squamous cell carcinoma, a melanoma, an ovarian cancer, a fallopian tube carcinoma, a peritoneal carcinoma, a soft tissue sarcoma, a melanoma, a breast cancer, an esophageal cancer, a head and neck cancer, an endometrial cancer, a cervical cancer, or a basal cell carcinoma), e.g., a hematologic malignancy (e.g., a leukemia (e.g., a chronic lymphocytic leukemia (CLL), or a lymphoma (e.g., a marginal zone B-cell lymphoma, a small lymphocytic lymphoma, a follicular lymphoma, Hodgkin lymphoma, non-Hodgkin lymphoma)).

In one embodiment, a combination described herein includes a LAG-3 inhibitor. In some embodiments, the combination is used to treat a cancer, e.g., a cancer described herein, e.g., a solid tumor or a hematologic malignancy.

Exemplary non-limiting combinations and uses of the anti-LAG-3 antibody molecules are disclosed in US 2015/0259420 published on Sep. 17, 2015, entitled "Antibody Molecules to LAG-3 and Uses Thereof," incorporated by reference in its entirety.

In one embodiment, the anti-LAG-3antibody molecule includes at least one or two heavy chain variable domain (optionally including a constant region), at least one or two light chain variable domain (optionally including a constant region), or both, comprising the amino acid sequence of any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum0l-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-1, or BAP050-Clone-J; or as described in Table 1 of US 2015/0259420, or encoded by the nucleotide sequence in Table 1 of US 2015/0259420; or a sequence substantially identical (e.g., at least 80%, 85%, 90%, 92%, 95%, 97%, 98%, 99% or higher identical) to any of the aforesaid sequences.

In yet another embodiment, the anti-LAG-3 antibody molecule includes at least one, two, or three complementarity determining regions (CDRs) from a heavy chain variable region and/or a light chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum0l-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-1, or BAP050-Clone-J; or as described in Table 1 of US 2015/0259420, or encoded by the nucleotide sequence in Table 1 of US 2015/0259420; or a sequence substantially identical (e.g., at least 80%, 85%, 90%, 92%, 95%, 97%, 98%, 99% or higher identical) to any of the aforesaid sequences.

In yet another embodiment, the anti-LAG-3 antibody molecule includes at least one, two, or three CDRs (or collectively all of the CDRs) from a heavy chain variable region comprising an amino acid sequence shown in Table 1 of US 2015/0259420, or encoded by a nucleotide sequence shown in Table 1 of US 2015/0259420. In one embodiment, one or more of the CDRs (or collectively all of the CDRs) have one, two, three, four, five, six or more changes, e.g., amino acid substitutions or deletions, relative to the amino acid sequence shown in Table 1 of US 2015/0259420, or encoded by a nucleotide sequence shown in Table 1 of US 2015/0259420.

In yet another embodiment, the anti-LAG-3 antibody molecule includes at least one, two, or three CDRs (or collectively all of the CDRs) from a light chain variable region comprising an amino acid sequence shown in Table 1 of US 2015/0259420, or encoded by a nucleotide sequence shown in Table 1 of US 2015/0259420. In one embodiment, one or more of the CDRs (or collectively all of the CDRs) have one, two, three, four, five, six or more changes, e.g., amino acid substitutions or deletions, relative to the amino acid sequence shown in Table 1 of US 2015/0259420, or encoded by a nucleotide sequence shown in Table 1 of US 2015/0259420. In certain embodiments, the anti-PD-L1 antibody molecule includes a substitution in a light chain CDR, e.g., one or more substitutions in a CDR1, CDR2 and/or CDR3 of the light chain.

In another embodiment, the anti-LAG-3 antibody molecule includes at least one, two, three, four, five or six CDRs (or collectively all of the CDRs) from a heavy and light chain variable region comprising an amino acid sequence shown in Table 1 of US 2015/0259420, or encoded by a nucleotide sequence shown in Table 1 of US 2015/0259420. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1 of US 2015/0259420.

In one embodiment, the anti-LAG-3 antibody molecule includes:

(i) a heavy chain variable region (VH) including a VHCDR1 amino acid sequence chosen from SEQ ID NO: 1, SEQ ID NO: 4 or SEQ ID NO: 286; a VHCDR2 amino acid sequence of SEQ ID NO: 2; and a VHCDR3 amino acid sequence of SEQ ID NO: 3, each disclosed in Table 1 of US 2015/0259420; and (ii) a light chain variable region (VL) including a VLCDR1 amino acid sequence of SEQ ID NO: 10, a VLCDR2 amino acid sequence of SEQ ID NO: 11, and a VLCDR3 amino acid sequence of SEQ ID NO: 12, each disclosed in Table 1 of US 2015/0259420.

In another embodiment, the anti-LAG-3 antibody molecule includes:

(i) a heavy chain variable region (VH) including a VHCDR1 amino acid sequence chosen from SEQ ID NO: 1, SEQ ID NO: 4 or SEQ ID NO: 286; a VHCDR2 amino acid sequence of SEQ ID NO: 5, and a VHCDR3 amino acid sequence of SEQ ID NO: 3, each disclosed in Table 1 of US 2015/0259420; and (ii) a light chain variable region (VL) including a VLCDR1 amino acid sequence of SEQ ID NO: 13, a VLCDR2 amino acid sequence of SEQ ID NO: 14, and a VLCDR3 amino acid sequence of SEQ ID NO: 15, each disclosed in Table 1 of US 2015/0259420.

In one embodiment, the anti-LAG-3 antibody molecule comprises the VHCDR1 amino acid sequence of SEQ ID NO: 1. In another embodiment, the anti-LAG-3 antibody molecule comprises the VHCDR1 amino acid sequence of SEQ ID NO: 4. In yet another embodiment, the anti-LAG-3 antibody molecule comprises the VHCDR1 amino acid sequence of SEQ ID NO: 286, each disclosed in Table 1 of US 2015/0259420.

In some embodiments, the anti-LAG-3 antibody is BMS-986016. BMS-986016 (also referred to as BMS986016; Bristol-Myers Squibb) is a monoclonal antibody that binds to LAG-3. BMS-986016 and other humanized anti-LAG-3 antibodies are disclosed in US 2011/0150892, WO2010/019570, and WO2014/008218.

5. Exemplary CTLA-4 Inhibitors

In an embodiment, the combination includes a CTLA-4 inhibitor. In some embodiments, the combination is used to treat a cancer, e.g., a cancer described herein e.g., a solid tumor (e.g., a breast cancer, a squamous cell carcinoma, a melanoma, an ovarian cancer, a fallopian tube carcinoma, a peritoneal carcinoma, a soft tissue sarcoma, a melanoma, a breast cancer, an esophageal cancer, a head and neck cancer, an endometrial cancer, a cervical cancer, or a basal cell carcinoma), e.g., a hematologic malignancy (e.g., a leukemia (e.g., a chronic lymphocytic leukemia (CLL), or a lymphoma (e.g., a marginal zone B-cell lymphoma, a small lymphocytic lymphoma, a follicular lymphoma, Hodgkin lymphoma, non-Hodgkin lymphoma)).

In one embodiment, a combination described herein includes a CTLA-4 inhibitor. In some embodiments, the combination is used to treat a cancer, e.g., a cancer described herein, e.g., a solid tumor or a hematologic malignancy.

Exemplary anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9).

In one embodiment, the combination includes an anti-PD-1 antibody molecule, e.g., as described herein, and an anti-CTLA-4 antibody, e.g., ipilimumab. Exemplary doses that can be use include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

Other exemplary anti-CTLA-4 antibodies are disclosed, e.g., in U.S. Pat. No. 5,811,097, which is incorporated by reference.

6. Exemplary GITR Modulator

In an embodiment, the combination includes a GITR modulator, such as an agonist or antagonist. In an embodiment, the GITR modulator is an antagonist. In some embodiments, the combination is used to treat a cancer, e.g., a cancer described herein e.g., a solid tumor (e.g., a breast cancer, a squamous cell carcinoma, a melanoma, an ovarian cancer, a fallopian tube carcinoma, a peritoneal carcinoma, a soft tissue sarcoma, a melanoma, a breast cancer, an esophageal cancer, a head and neck cancer, an endometrial cancer, a cervical cancer, or a basal cell carcinoma), e.g., a hematologic malignancy (e.g., a leukemia (e.g., a chronic lymphocytic leukemia (CLL), or a lymphoma (e.g., a marginal zone B-cell lymphoma, a small lymphocytic lymphoma, a follicular lymphoma, Hodgkin lymphoma, non-Hodgkin lymphoma)).

Exemplary GITR modulators include, e.g., GITR fusion proteins and anti-GITR antibodies (e.g., bivalent anti-GITR antibodies), such as, a GITR fusion protein described in U.S. Pat. No. 6,111,090, European Patent No.: 0920505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, U.S. Pat. No. 8,709,424, PCT Publication No.: WO 2013/039954, International Publication No.: WO2013/039954, U.S. Publication No.: US2014/0072566, International Publication NO.: WO2015/026684, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, U.S. Pat. No. 6,689,607, PCT Publication No.: WO2006/083289, PCT Publication No.: WO 2005/115451, U.S. Pat. No. 7,618,632, PCT Publication No.: WO 2011/051726, International Publication No.: WO2004060319, and International Publication No.: WO2014012479, each of which is incorporated by reference.

EXAMPLES

Example 1: Generation and Screening of Mouse Anti-Human IL-2 Antibody NARA1

A reference antibody, designated NARA1, was derived, isolated and structurally characterized according to methods well known to a person skilled in the art.

Balb/c mice were immunized with human (h) IL-2 (34-8029, eBioscience) in Freund's adjuvant (F-5881, Sigma) on days 0, 14 (subcutaneously) and 28 (intravenously). Serum was collected before the first immunization and 9-11 days after every immunization in order to check for anti-hIL-2 antibody titers. On day 35, mice were euthanized and spleen cells were collected following standard procedures. Splenocytes were mixed with myeloma cells at a 5:1 ratio with polyethylene glycol 1500 (10783641001, Roche). A feeder layer obtained from peritoneal lavage of Balb/c mice was used to grow clones in IMDM selective media (21980, Life Technologies) supplemented with 10% ultra-low IgG FBS (16250, Life Technologies), 50 μM mercaptoethanol (313050, Life technologies), 1:100 Insulin-Transferrin-Selenium (41400-045, Life Technologies), 2% IL-6-conditioned media, penicillin-streptomycin (15240, Life Technologies), gentamycin (15750, Life Technologies), and hypoxanthine-aminopterin-thymidine (HAT, H037, Sigma-Aldrich) for several days. Polyclonals were then screened for hIL-2 binding using a direct binding ELISA and for specificity using a competition ELISA, and diluted to obtain monoclonal clones. For expansion of monoclonals, HAT media was replaced by hypoxanthine-thymidine media (HT, 41065, Life Technologies). Monoclonals were then concentrated using 100 kDa centrifugal filter units according to supplier's recommendations (UFC9100, Merck Millipore). Concentrate was further tested for specificity in a dose-dependent manner using a competition ELISA and in vivo using 4 daily intraperitoneally injections of 200 μl concentrate complexed with 1.5 μg hIL-2, followed by assessment by flow cytometry of T cell subsets and natural killer (NK) cells. NARA1 was purified using Protein G agarose (20398, ThermoFisher Scientific) according to supplier's recommendations.

The full length heavy chain of NARA1 is SEQ ID NO: 115 and the full length light chain amino acid sequence of NARA1 is SEQ ID NO: 117.

The corresponding variable regions, VH and VL amino acid sequences of NARA1 are SEQ ID NO: 111 (variable heavy) and SEQ ID NO: 113 (variable light).

Full length light and heavy chain nucleotide coding sequences of NARA1 are SEQ ID NO: 116 (heavy chain coding sequence, including leader sequence) and SEQ ID NO: 118 (light chain coding sequence, including leader sequence).

Variable light and heavy chains nucleotide coding sequences of NARA1 are SEQ ID NO: 112 (variable heavy coding sequence) and SEQ ID NO: 114 (variable light coding sequence).

The CDR regions of NARA1 are delineated using the Kabat system (Kabat, E. A., et al. 1991, Sequences of Proteins of Immunological Interest, Fifth Edition, U.S. Department of Health and Human Services, NIH Publication No. 91-3242, see also Zhao&Lu 2009, Molecular Immunology 47:694-700). For the ease of reading, when CDR regions are delineated according to Kabat definition, they are called hereafter HCDR1, HCDR2, HCDR3, LCDR1, LCDR2, LCDR3 respectively. The CDR regions of NARA1 are: HCDR1 according to SEQ ID NO: 4, HCDR2 according to SEQ ID NO: 2, HCDR3 according to SEQ ID NO: 3, LCDR1 according to SEQ ID NO: 19, LCDR2 according to SEQ ID NO: 20, LCDR3 according to SEQ ID NO: 21.

Example 2: Crystal Structure of NARA1

(1) Material and Methods

The complex structure of a human Interleukin 2 mutant (SEQ ID NO: 110), generally known to a person skilled in the art as Proleukin® (aldesleukin), bound to the Fab fragment of antibody NARA 1 was determined. The resulting numbering of residues on Proleukin® is given according to the numbering of wt IL-2.

As will be discussed in detail below, the differences in sequence between Proleukin® and wt hIL-2 are irrelevant and Proleukin® is a valid model for structural analysis of hIL-2.

To define the epitope, X-ray crystallography was used to solve the atomic-resolution structure of the complex mentioned above. X-ray crystallography is a technology that has become routinely and widely used to generate structural data for biomolecules including antibodies and their complexes with antigens (Adams et al, (2013) Annual Review Biophysics 42:265-287; Garman, (2014) Science 343:1102-1108; Joachimiak, (2009) Current Opinion Structural Biology 19:573-584.)

The antigen, Proleukin®, is commercially available as lyophilized powder together with excipients (every 1 mg Proleukin® is mixed with approximately 50 mg mannitol, 0.18 mg sodium dodecyl sulfate, 0.173 mg sodium dihydrogen phosphate, and 0.89 mg disodium hydrogen phosphate). Before used for complex formation, Proleukin® was purified by reverse-phase HPLC to remove the excipients.

The Fab fragment of NARA1 (NARA1-Fab) was generated by papain cleavage of the full-length antibody followed by Protein A chromatography. Briefly, 6.5 ml full-length NARA1 (9 mg/ml in 50 mM citrate buffer with 90 mM sodium chloride at pH 7.0) was mixed with 5 mM DTT and 590 ug Papain (Roche). The cleavage reaction was kept at room temperature for 16 h and stopped by addition of 15 ul 56 mM E64 solution (Roche). The cleavage solution was then diluted 10 times with 25 mM Tris, 25 mM NaCl, pH 8.0 and loaded onto a 5 ml Protein A column (GE Healthcare) equilibrate with 5 column volume of 25 mM Tris, 25 mM NaCl, pH 8.0 and Fab fragment was in the loading-through fraction and Fc fragment was bound to the Protein A column.

To form complex, Proleukin® powder after HPLC was dissolved in $H_2O$ at the concentration of 5.5 mg/ml. 6.6 mg Proleukin®, in excess, was added to 11.5 mg NARA1 Fab fragment solution drop by drop. Centrifugation was used to remove the excess Proleukin® that was precipitated under current condition. The complex was then purified by gel filtration with Superdex 200 10×300 (GE Healthcare) with running buffer of 25 mM Tris, 25 mM NaCl, pH 7.4.

Proleukin®/NARA1-Fab complex after gel filtration was concentrated to 14 mg/ml and was screened by vapor diffusion method as sitting drops. The protein solution was mixed 1:1 with reservoir buffer to a total size of 0.4 ul. The experiments were set up with Phoenix robotic system (Art Robbins Instruments), stored in a Rocklmager hotel (Formulatrix) at 19° C., and imaged automatically. Crystals were harvested 4 days after screening under condition of 20% w/v polyethylene Glycol 3350 and 0.2M sodium nitrate. Crystals were cryo-protected with reservoir buffer containing 10% glycerol and flashed frozen in liquid nitrogen prior to data collection. Diffraction data were collected at the Swiss Light Source (Villigen, Switzerland) at beam-line PX-II with a Pilatus pixel detector using x-ray radiation wavelength of 0.99998 Å.

The dataset was processed with XDS and XSCALE (version Dec. 6, 2010) and the structure was resolved with molecular replacement method with the program PHASER by using Protein Data Bank entry "3lNK" as search model for IL-2 and Protein Data Bank entry "3TTI" as search model for Fab fragment. Iterative model building and refinement were performed with the programs Coot (Crystallographic Object-Oriented Toolkit) and AUTOBUSTER (Bricogne et al., 2011). All figures were generated with the program PyMOL (Molecular Graphics System; DeLano Scientific: Palo Alto, Calif.; http://www.pymol.org).

Epitope residues are defined as those residues from Proleukin® that are within 4 Å distance from any atom in Fab fragment of NARA1 and are further confirmed by CCP4 program CONTACT and AREAIMOL (Collaborative Computational Project, Number 4, version 6.4.0). Similarly paratope residues are defined as those residues from NARA1-Fab that are within 4 Å distance from any atom in Proleukin®.

(2) Results

The Proleukin®/NARA1-Fab complex was solved to 1.95 Å in space group C 1 2 1 with unit cell dimension a=201.8 Å, b=36.2 Å, c=88.7 Å, alpha=90°, beta=102.9°, gamma=90°. Please refer to Table 3 for detailed structure statistics. In each asymmetric unit, there is one complex molecule.

TABLE 3

Structure statistics for Proleukin ®/NARA1-Fab complex

| Data collection | |
| --- | --- |
| Space group | C1 2 1 |
| Cell dimensions | |
| a, b, c (Å) | 201.757, 36.233, 88.707 |
| a, b, g (°) | 90, 102.93, 90 |
| Resolution (Å) | 58.74-1.95 |
| $R_{merge}$ | 0.066 (0.472) |
| I/σI | 14.18 (2.59) |

TABLE 3-continued

Structure statistics for Proleukin ®/NARA1-Fab complex

| Completeness (%) | 84.8 (96) |
| --- | --- |
| Redundancy | 3.19 |
| Refinement | |
| Resolution (Å) | 58.74-1.95 |
| No. reflections | 34750 |
| $R_{work}/R_{free}$ | 0.2052/0.2872 |
| Ramachandran plot | |
| Outliners | 0.0162 |
| Allowed | 0.0378 |
| Favored | 0.9459 |
| R.m.s. deviations | |
| Bond lengths (Å) | 0.01 |
| Bond angles (°) | 1.7 |

(3) Epitope and Paratope Analysis

FIG. 1 provides the overview of the three-dimension structure of Proleukin®/Fab-NARA1 complex as obtained in Example 1. Light chain of Fab fragment of NARA1 is designated A, heavy chain of Fab fragment of NARA1 is shown as B, epitope residues recognized by NARA1-Fab are designated D, and Proleukin® is designated C and the mutation, C145S, is highlighted.

Figure 2:
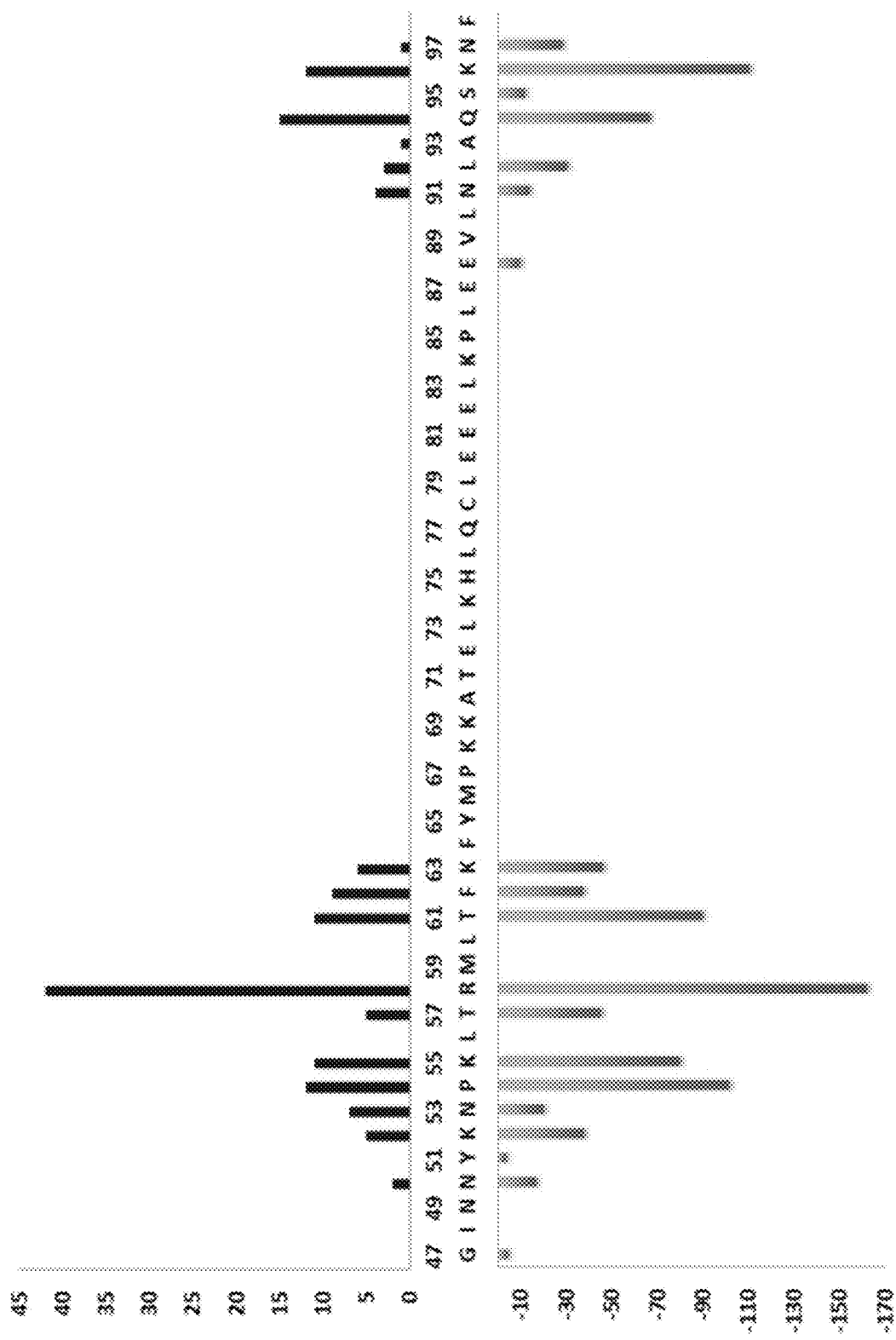
FIG. 2 provides further analysis of epitope residues. The X-axis lists the amino acid sequence and numbering according to SEQ ID NO: 110. The upper side of Y-axis shows the total number of atoms of NARA1-Fab that are within 4 Å from corresponding residue from Proleukin® and the lower side of Y-axis shows the reduced solvent-accessible area (Å$^2$) of corresponding residue from Proleukin® as a consequence of binding to NARA1-Fab, according to SEQ ID NO: 132.

FIG. 2 provides further analysis of epitope residues. The X-axis lists the amino acid sequence and numbering according to SEQ ID No 110. The upper side of Y-axis demonstrates the total number of atoms of NARA1-Fab that are within 4 Å from corresponding residue from Proleukin® and the lower side of Y-axis demonstrates the reduced solvent-accessible area ($Å^2$) after binding to NARA1-Fab.

Proleukin® used in Example 1 contains mutation of C145S. As shown in FIG. 1, C145S is far away from the epitope region. In addition the superposition of Cα atoms between Proleukin® in Example 1 with Ca atoms from wt hIL-2 in complex with CD25, CD122, and CD132 (PDB: 2B5I) shows r.m.s.d of 0.447 Å, which indicates that the mutation does not disturb the over-all structure. Hence Proleukin® with C145S mutation is a valid model for structural analysis for wt hIL-2.

hIL-2 is 4-helix bundle protein and the 4 helices are named from N-terminus to C-terminus as A, B, C, and D, respectively. The epitope recognized by NARA1-Fab as shown in FIG. 1 is a conformational epitope and spans two regions as shown in FIG. 2: one region (N50-K63) comprises a loop and a short helix and connects helix A and B, and the other region (N91-N97) comprises a loop and connects helix B and C.

Figure 3:
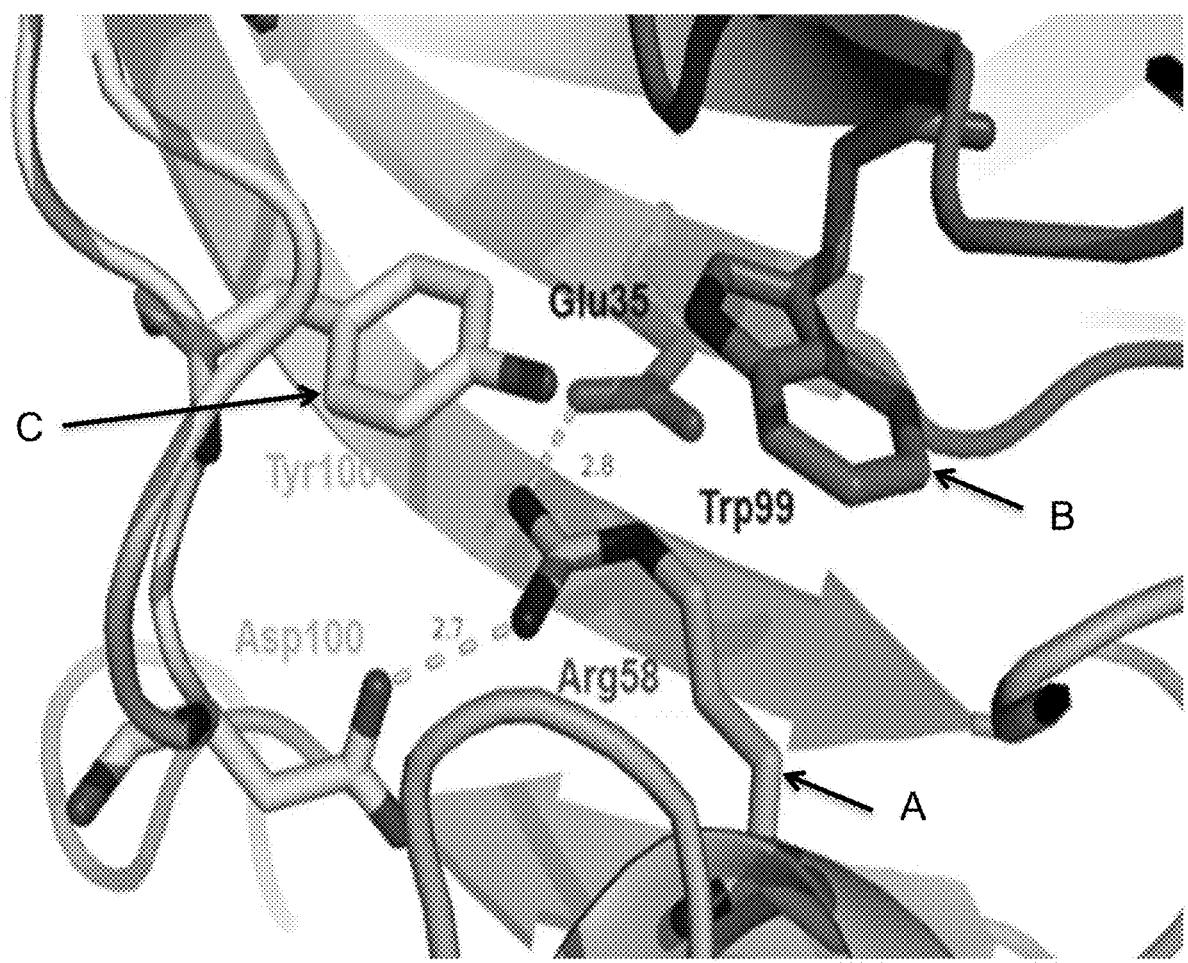
FIG. 3 illustrates the most critical epitope residue recognized by the NARA1-Fab.

The epitope residues together with interacting paratope residues from NARA1-Fab are summarized in Table 4. Among all the epitope residues, Arg58 as shown in FIG. 2 is the most critical epitope residue for binding with NARA1-Fab, as this residue alone has 42 interacting atoms from NARA1-Fab and accounts for 17.7% of total reduced solvent-accessible surface area as a consequence of binding to NARA1-Fab. Furthermore Arg58, as shown in FIG. 3, forms two strong salt-bridges with Glu35 in HCDR1 and with Asp100 from LCDR3, respectively. Arg58 also makes π-action interaction with the aromatic ring of Tyr100 from LCDR3. Residues K52, P54, K55, T57, T61, F62, K63, Q94, and K96 are also considered important for the binding to NARA1-Fab, since they all show equal to/more than 5 interacting atoms from NARA1-Fab and larger than 30 Å² reduced solvent-accessible area as shown in FIG. 2.

TABLE 4

Epitope and paratope summary

| Light chain residue | Epitope residue | Heavy chain residue |
|---|---|---|
| Y31 | N50 | |
| Y31 | K52 | |
| Y31 | N53 | |
| Y31, Y36, S95, N96 | P54 | |
| | K55 | W99, G101, G103, Y105 |
| D98 | T57 | |
| D98, Y100 | R58 | L33, E35, W47, W99 |
| | T61 | N52, S55, N59 |
| | F62 | L33, N52 |
| | K63 | S55 |
| | N91 | G101, D102, G103 |
| | L92 | W99, G101 |
| | A93 | G101 |
| | Q94 | D102, G103, Y104 |
| D32, D34 | K96 | Y104 |
| D32 | N97 | |

FIG. 3 illustrates Arg58 as the most critical epitope residue recognized the NARA1-Fab. A represents Proleukin®, B represents heavy chain, and C represents light chain. The involved residues are shown as sticks.

(4) NARA1-Fab Binding Properties

Figure 4:
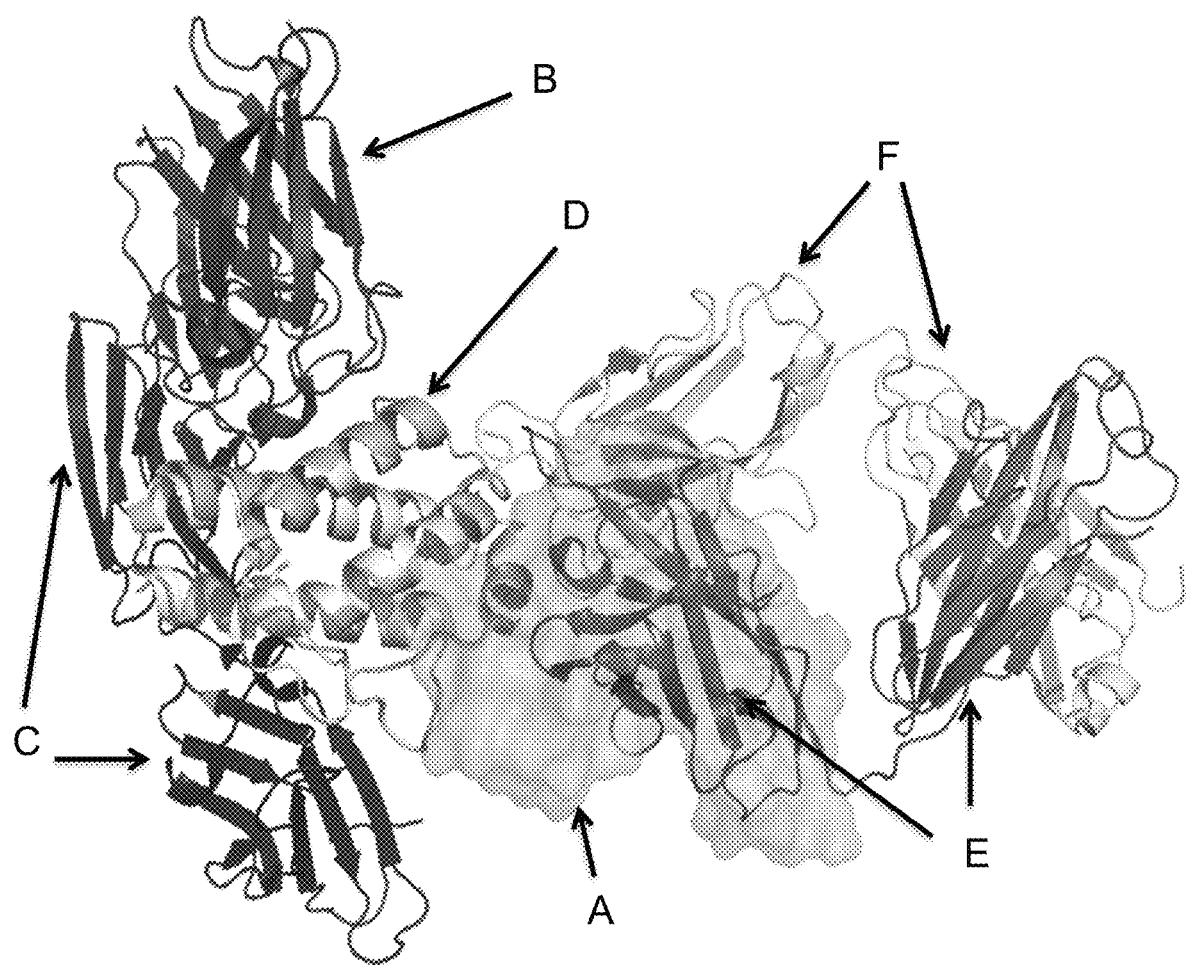
FIG. 4 shows the overlay of Proleukin®/NARA1-Fab complex with IL-2/CD25/CD122/CD132 quaternary complex.

FIG. 4 shows the overlay of Proleukin®/NARA1-Fab complex with IL-2/CD25/CD122/CD132 quaternary complex. The quaternary complex structure comes from PDB entry "2B5I" with cartoon D in pale cyan representing wt hIL-2, cartoon B in red representing CD122, cartoon C in blue representing CD132, and surface A in green representing CD25. In the Proleukin®/NARA1-Fab complex structure, cyan cartoon D overlayed with wt hIL-2 represents Proleukin, cartoon E in magenta represents heavy chain, and cartoon F in yellow represents the light chain.

The structure overlay of the two complexes as shown in FIG. 4 clearly shows that NARA1-Fab forms direct competition against CD25 but not against CD122/CD132, which is consistent with the observation that IL-2/NARA1 complex demonstrates mainly pro-Teffector cell activity rather than pro-Treg activity.

Figure 5:
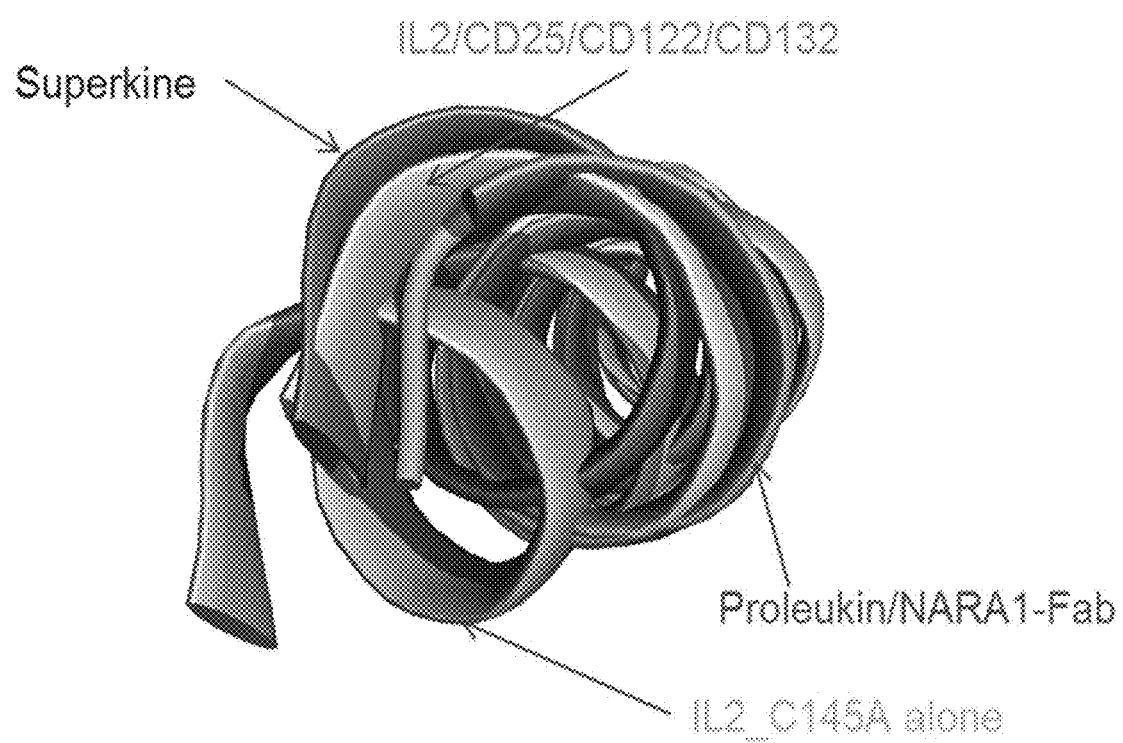
FIG. 5 displays the overlay of C helices from IL-2_C145A (PDB: 3INK), the D10 IL-2-mutein ("Superkine": PDB: 3QB1), IL-2/CD25/CD122/CD132 (PDB: 2B5I), and Proleukin®/NARA1-Fab.

(5) C Helix of Proleukin® in Complex with NARA1-Fab Adopts Conformation that is Similar to that in Quaternary Complex FIG. 5 displays the overlay of C helices from IL-2_C145A (PDB: 3INK), Superkine (PDB: 3QB1), IL-2/CD25/CD122/CD132 (PDB: 2B5I), and Proleukin®/NARA1-Fab.

The polar interface between helix C in IL-2 and CD122 plays an important role in binding between the two parts (Wang et al (2005) Science 310:1159-1163). In 2012 Levin, et al have demonstrated that superkine, an IL-2 mutant, alone has a Helix C adopting confirmation similar to that in the quaternary complex and superkine showed ~215 times higher binding affinity towards CD122 than wtIL-2 (Levin et al, (2012) Nature 484:529-533). It was observed that such a conformational change in helix C is associated with conformational stabilization, which then reduces the energetic penalties for binding to CD122. As shown in FIG. 5, The conformation of helix C from Proleukin® in complex with NARA1-Fab is also similar to that observed in superkine as well as in IL-2/CD25/CD122/CD132 quaternary complex, therefore it is possible that Proleukin®/NARA1-Fab complex may demonstrate higher binding affinity towards CD122 than wt hIL-2 does.

Example 3: Humanization of Mouse Monoclonal Antibody NARA1

Humanizing the anti-human IL-2 mouse antibody NARA1 including selection of human acceptor frameworks, back mutations, and mutations that substantially retain and/or improve the binding properties of human CDR-grafted acceptor frameworks is described herein.

The process of humanization is well described in the art (Jones, et al 1986, Queen, et al 1989, Riechmann, et al 1988, Verhoeyen, Milstein and Winter 1988). The term humanization describes as the transfer of the antigen-binding site of a non-human antibody, e.g. a murine derived antibody, to a human acceptor framework, e.g. a human germline sequence (Retter, et al 2005). Main rationale of humanizing an antibody is seen in minimizing the risk of developing an immunogenic response to the antibody in human (Rebello, et al 1999).

The antigen-binding site comprises the complementary determining regions (CDRs) (Chothia and Lesk 1987, Kabat, et al 1991) and positions outside the CDR, i.e. in the framework region of the variable domains (VL and VH) that directly or indirectly affect binding. Framework residues that may directly affect binding can, for example, be found in the so called "outer" loop region located between CDR2 and CDR3. Residues that indirectly affect binding are for example found at so called Vernier Zones (Foote and Winter 1992). They are thought to support CDR conformation. Those positions outside the CDRs are taken into account when choosing a suitable acceptor framework to minimize the number of deviations of the final humanized antibody to the human germline acceptor sequence in the framework regions.

1. Sequence Optimization Affinity Maturation

Certain amino acid sequence motifs are known to undergo post-translational modification (PTM) such as glycosylation (i.e. N×S/T, x any but P), oxidation of free cysteines, deamidation (e.g. NG) or isomerization (e.g. DG). If present in the CDR regions, those motifs are ideally removed by site-directed mutagenesis in order to increase product homogeneity.

The process of affinity maturation is well described in the art. Among many display systems, phage display (Smith 1985) and display on eukaryotic cells such as yeast (Boder E. and Wittrup K. (1997). Yeast surface display for screening combinatorial polypeptide libraries. Nat Biotechnol, 15(6), pp. 553-7), seem to be the most commonly applied systems to select for antibody-antigen interaction. Advantages of those display systems are that they are suitable for a wide range of antigens and that the selection stringency can be easily adjusted. In phage display, scFv or Fab fragments can be displayed and in yeast display full-length IgG in addition. Those commonly applied methods allow selection of a desired antibody variant from larger libraries with diversities of more than 107. Libraries with smaller diversity, e.g. 103, may be screen by micro-expression and ELISA.

Non-targeted or random antibody variant libraries can be generated for example by error-prone PCR (Cadwell and Joyce 1994) and provide a very simple, but sometimes limited approach. Another strategy is the CDR directed diversification of an antibody candidate. One or more positions in one or more CDRs can be targeted specifically using for example degenerated oligos (Thompson, et al 1996), trinucloetide mutagenesis (TRIM) (Kayushin, et al 1996) or any other approach known to the art.

2. Generation of Expression Plasmids

DNA sequences coding for humanized VL and VH domains were ordered at GeneArt (Life Technologies Inc. Regensburg, Germany) including codon optimization for *Homo sapiens*. Sequences coding for VL and VH domains were subcloned by cut and paste from the GeneArt derived vectors into expression vectors suitable for secretion in mammalian cells. The heavy and light chains were cloned into individual expression vectors to allow co-transfection. Elements of the expression vector include a promoter (Cytomegalovirus (CMV) enhancer-promoter), a signal sequence to facilitate secretion, a polyadenylation signal and transcription terminator (Bovine Growth Hormone (BGH) gene), an element allowing episomal replication and replication in prokaryotes (e.g. SV40 origin and ColE1 or others known in the art) and elements to allow selection (ampicillin resistance gene and zeocin marker).

3. Expression and Purification of Humanized Antibody Candidates

Human Embryonic Kidney cells constitutively expressing the SV40 large T antigen (HEK293-T ATCC11268) are one of the preferred host cell lines for transient expression of humanized and/or optimized IgG proteins. Transfection is performed using PEI (Polyethylenimine, MW 25.000 linear, Polysciences, USA Cat. No. 23966) as transfection reagent. The PEI stock solution is prepared by carefully dissolving 1 g of PEI in 900 ml cell culture grade water at room temperature (RT). To facilitate dissolution of PEI, the solution is acidified by addition of HCl to pH 3-5, followed by neutralization with NaOH to a final pH of 7.05. Finally, the volume is adjusted to 1 L and the solution is filtered through a 0.22 µm filter, aliquotted and frozen at −80° C. until further use. Once thawed, an aliquot can be re-frozen up to 3 times at −20° C. but should not be stored long term at −20° C. HEK 293T cells are cultivated using a Novartis proprietary serum-free culture medium for transfection and propagation of the cells, and ExCell VPRO serum-free culture medium (SAFC Biosciences, USA, Cat. No. 24561C) as production/feed medium. Cells prepared for transient transfections are cultivated in suspension culture. For small scale (<5 L) transfections, cells are grown in Corning shake flasks (Corning, Tewksbury, MA) on an orbital shaker (100-120 rpm) in a humidified incubator at 5% $CO_2$ (seed flasks). Cells in the seed cultures should be maintained in the exponential growth phase (cell densities between $5 \times 10^5$ and $3 \times 10^6$/mL) and display a viability of >90% for transfection. Cell densities outside of this range will result in either a lag phase after dilution or reduced transfection efficiency. For small scale (<5 L) transfection an aliquot of cells is taken out of the seed cultures and adjusted to $1.4 \times 10^6$ cells/mL in 36% of the final volume with Novartis serum-free culture medium. The DNA solution (Solution 1:0.5 mg of heavy chain and 0.5 mg of light chain expression plasmid for a 1 L transfection) is prepared by diluting the DNA to 1 mg/L (final volume) in 7% of the final culture volume followed by gentle mixing. To prevent bacterial contamination, this solution is filtered using a 0.22 µm filter (e.g. Millipore Stericup). Then 3 mg/L (final volume) of PEI solution is also diluted in 7% of final culture volume and mixed gently (Solution 2). Both solutions are incubated for 5-10 min at room temperature (RT). Thereafter solution 2 is added to solution 1 with gentle mixing and incubated for another 5-15 minutes at room temperature. The transfection mix is then added to the cells and the cultivation of cells is continued for 4 to 6 hours. Finally, the remaining 50% of total production volume are achieved by addition of ExCell® VPRO serum-free culture medium. The cell cultivation is continued for eleven days post transfection. The culture is harvested by centrifugation at 4500 rpm for 20 minutes at 4° C. (Heraeus®, Multifuge 3 S-R, Thermo Scientific, Rockford, Ill.). The cell supernatant recovered is sterile filtered through a stericup filter (0.22 µm) and stored at 4° C. until further processing.

Purification was performed on an "AKTA 100 explorer Air" chromatography system at 4° C. in a cooling cabinet, using a freshly sanitized (0.25 M NaOH) HiTrap ProtA MabSelect®SuRe, 5 ml column. The column was equilibrated with 5 CV of PBS (Gibco, Life Technologies, Carlsbad, Calif.), and then the sterile filtered supernatant (2 L) was loaded at 4.0 ml/min. The column was washed with 8 CV of PBS to elute the unbound sample and again washed with 5 CV of PBS. Antibody was eluted with 5 CV of 50 mM citrate, 70 mM NaCl pH 3.2. The eluate was collected in 3 ml fractions; fractions were pooled and adjusted at pH 7 with 1 M Tris HCl pH10. The pools were pooled and sterile filtered (Millipore Steriflip, 0.22 um), the OD 280 nm was measured in a Spectrophotometer ND-1000 (NanoDrop), and the protein concentration was calculated based on the sequence data. The eluate was tested for aggregation (SEC-MALS) and purity (SDS-PAGE, LAL and MS). For the second purification step, if needed, pools from the first purification were loaded into a freshly sanitised (0.5 M NaOH) SPX (Hi Load 16/60 Superdex 200 grade 120 mL (GE-Helthcare). The column was equilibrated with PBS and the run was done with PBS buffer at 1 ml/min, the eluate was collected in 1.2 ml fractions and analyzed as described for the first purification step.

Accordingly, three humanized variable heavy regions; VH1, VH3 and VH5 were generated, as highlighted in Table 5.

TABLE 5

Variable heavy regions

| Variable heavy region | Sequence listing |
|---|---|
| VH1 | SEQ ID NO: 7 |
| VH3 | SEQ ID NO: 9 |
| VH5 | SEQ ID NO: 17 |

Also, three humanized variable light (kappa) regions; VK1, VK2 and VK3, were generated as highlighted in Table 6.

TABLE 6

Variable light regions

| Variable light region | Sequence listing |
|---|---|
| VK1 | SEQ ID NO: 25 |
| VK2 | SEQ ID NO: 27 |
| VK3 | SEQ ID NO: 29 |

Example 4: Structure-Revised Humanization

Using the crystal structure NARA1/hIL-2 results of Example 2, the humanization design was refined.

Identity was calculated between initial humanized sequences of Example 3 and closest germline. Separately, the isoelectric point (pI) was calculated for heavy and light chains. The results are shown in the Table 7 and below.

TABLE 7 pI data

| Variable region | pI Heavy | pI Heavy refined version | pI Light | pI Light refined version |
|---|---|---|---|---|
| VH1 | 9.3 | 9.4 | | |
| VH3 | 9.4 | 9.4 | | |
| VH5 | 9.3 | 9.4 | | |
| VK1 | | | 5.3 | 6.6 |
| VK2 | | | 4.7 | 4.6 |
| VK3 | | | 4.7 | 5.0 |

TABLE 8

Comparison variable regions and variable germline regions

| Variable region | % ID (% sim) VH/VL germline | % ID (% sim) VH/VL germline refined |
|---|---|---|
| VH1 | 85% (89%) | 89% (90%) |
| VH3 | 77% (84%) | 85% (88%) |
| VH5 | 86% (91%) | 89% (91%) |
| VK1 | 85% (90%) | 89% (91%) |
| VK2 | 82% (93%) | 84% (93%) |
| VK3 | 83% (87%) | 86% (89%) |

Based on this data, it was decided to refine the structures VH3 and VK3, leading to the sequences in were generated as highlighted in Table 9. VH3 was chosen because the germline refined sequence by using structure information helped to increase the % of identity with the human template till 85% from 77%.

VK3 was chosen because of the increase in pI from 4.7 to 5.0. (VK1 is already 5.3 and VK2 we are not going to increase the pI by using the structure information so we decided for VK3.)

TABLE 9

Structure-refined variable regions

| | Sequence listing |
|---|---|
| Variable light region | |
| VK3s | SEQ ID NO: 34 |
| Variable heavy region | |
| VH3s | SEQ ID NO: 15 |

Based on these six variable heavy and light regions, nine antibodies were generated using a human IgG1 Fc domain with the N297A point mutation, as represented by SEQ ID NO: 103, according to the overview in Table 10.

TABLE 10

Antibodies

| Antibody | Variable Light region | Variable Light SEQ ID | Variable Heavy region | Variable Heavy SEQ ID |
|---|---|---|---|---|
| 104341 | VK1 | SEQ ID NO: 25 | VH1 | SEQ ID NO: 7 |
| 104343 | VK2 | SEQ ID NO: 27 | VH1 | SEQ ID NO: 7 |
| 104344 | VK3s | SEQ ID NO: 34 | VH1 | SEQ ID NO: 7 |
| 104345 | VK1 | SEQ ID NO: 25 | VH3s | SEQ ID NO: 15 |
| 104346 | VK2 | SEQ ID NO: 27 | VH3s | SEQ ID NO: 15 |
| 104347 | VK3s | SEQ ID NO: 34 | VH3s | SEQ ID NO: 15 |
| 104348 | VK1 | SEQ ID NO: 25 | VH5 | SEQ ID NO: 17 |
| 104349 | VK2 | SEQ ID NO: 27 | VH5 | SEQ ID NO: 17 |
| 104350 | VK3s | SEQ ID NO: 34 | VH5 | SEQ ID NO: 17 |

Any Fc domain can be used to generate further antibodies, as known to a person skilled in the art. Particularly contemplated Fc domains are non Fc modified human IgG1 according to SEQ ID NO: 93, human IgG2 according to SEQ ID NO: 95, human IgG3 according to SEQ ID NO: 97, human IgG4 according to SEQ ID NO: 99, human IgG1 Fc modified with LALA mutation according to SEQ ID NO: 101, human IgG1 Fc modified with N297A mutation according to SEQ ID NO: 103, human IgG1 Fc modified with DAPA mutation according to SEQ ID NO: 105.

According to a preferred embodiment, the Fc domain is a human IgG1 according to SEQ ID NO: 93, and according to an even more preferred embodiment, the Fc domain is a human IgG1 Fc modified with N297A mutation according to SEQ ID NO: 103.

According to a specific embodiment, the full light chain sequence of antibody 104343 is according to SEQ ID NO: 124 and full the heavy chain sequence is according to SEQ ID NO: 126. According to another specific embodiment the full light chain sequence of antibody 104348 is according to SEQ ID NO: 128 and the full heavy chain sequence is according to SEQ ID NO: 130.

Example 5: Structural Optimization

Using the crystal structure NARA1/hIL-2 results of Example 2, certain amino acid residues in the CDRs were identified for further structure optimization. Particularly, a so called DG site was identified in LCDR1, and another DG site in HCDR3. Surprisingly, some mutations in these sites dramatically reduce the affinity for human IL-2, whereas other mutations have little to no impact on affinity.

The structure of the complex was analyzed by using modeling software like PyMOL or MOE and residues on the CDR loops that are not in close contact with the antigen (i.e. more than 4 Angstrom from the antigen) have been chosen for further humanization in order to increase the % of identity between the humanized sequence and the human template.

The resulting light chain (kappa) CDRs according to the Kabat definition are found in Table 11.

TABLE 11

| Light chain CDRs | | | |
|---|---|---|---|
| VL | LCDR1 | LCDR2 | LCDR3 |
| VK1 | SEQ ID NO: 19 | SEQ ID NO: 20 | SEQ ID NO: 21 |
| VK2 | SEQ ID NO: 19 | SEQ ID NO: 20 | SEQ ID NO: 21 |
| VK3 | SEQ ID NO: 19 | SEQ ID NO: 20 | SEQ ID NO: 21 |
| VK3s | SEQ ID NO: 31 | SEQ ID NO: 32 | SEQ ID NO: 21 |
| VK1_D28Q | SEQ ID NO: 69 | SEQ ID NO: 20 | SEQ ID NO: 21 |
| VK1_G29A | SEQ ID NO: 72 | SEQ ID NO: 20 | SEQ ID NO: 21 |
| VK2_D28Q | SEQ ID NO: 69 | SEQ ID NO: 20 | SEQ ID NO: 21 |
| VK2_G29A | SEQ ID NO: 72 | SEQ ID NO: 20 | SEQ ID NO: 21 |
| VK3_D28Q | SEQ ID NO: 69 | SEQ ID NO: 20 | SEQ ID NO: 21 |
| VK3_G29A | SEQ ID NO: 72 | SEQ ID NO: 20 | SEQ ID NO: 21 |
| VK3s_D28Q | SEQ ID NO: 86 | SEQ ID NO: 32 | SEQ ID NO: 21 |

TABLE 11-continued

Light chain CDRs

| VL | LCDR1 | LCDR2 | LCDR3 |
|---|---|---|---|
| VK3s_G29A | SEQ ID NO: 90 | SEQ ID NO: 32 | SEQ ID NO: 21 |
| Consensus | SEQ ID NO: 122 | SEQ ID NO: 123 | SEQ ID NO: 21 |

The resulting heavy chain CDRs according to the Kabat definition are found in Table 12.

TABLE 12

Heavy chain CDRs

| VH | HCDR1 | HCDR2 | HCDR3 |
|---|---|---|---|
| VH1 | SEQ ID NO: 4 | SEQ ID NO: 2 | SEQ ID NO: 3 |
| VH3 | SEQ ID NO: 4 | SEQ ID NO: 2 | SEQ ID NO: 3 |
| VH3s | SEQ ID NO: 13 | SEQ ID NO: 12 | SEQ ID NO: 3 |
| VH5 | SEQ ID NO: 4 | SEQ ID NO: 2 | SEQ ID NO: 3 |
| VH1_D98E | SEQ ID NO: 4 | SEQ ID NO: 2 | SEQ ID NO: 36 |
| VH1_G99A | SEQ ID NO: 4 | SEQ ID NO: 2 | SEQ ID NO: 39 |
| VH1_D98Q | SEQ ID NO: 4 | SEQ ID NO: 2 | SEQ ID NO: 42 |
| VH1_D98S | SEQ ID NO: 4 | SEQ ID NO: 2 | SEQ ID NO: 45 |
| VH3_D98E | SEQ ID NO: 4 | SEQ ID NO: 2 | SEQ ID NO: 36 |
| VH3_G99A | SEQ ID NO: 4 | SEQ ID NO: 2 | SEQ ID NO: 39 |
| VH3_D98Q | SEQ ID NO: 4 | SEQ ID NO: 2 | SEQ ID NO: 42 |
| VH3_D98S | SEQ ID NO: 4 | SEQ ID NO: 2 | SEQ ID NO: 45 |
| VH3s_D98E | SEQ ID NO: 13 | SEQ ID NO: 12 | SEQ ID NO: 36 |
| VH3s_G99A | SEQ ID NO: 13 | SEQ ID NO: 12 | SEQ ID NO: 39 |
| VH3s_D98Q | SEQ ID NO: 13 | SEQ ID NO: 12 | SEQ ID NO: 42 |
| VH3s_D98S | SEQ ID NO: 13 | SEQ ID NO: 12 | SEQ ID NO: 45 |
| VH5_D98E | SEQ ID NO: 4 | SEQ ID NO: 2 | SEQ ID NO: 36 |
| VH5_G99A | SEQ ID NO: 4 | SEQ ID NO: 2 | SEQ ID NO: 39 |
| VH5_D98Q | SEQ ID NO: 4 | SEQ ID NO: 2 | SEQ ID NO: 42 |
| VH5_D98S | SEQ ID NO: 4 | SEQ ID NO: 2 | SEQ ID NO: 45 |
| Consensus | SEQ ID NO: 119 | SEQ ID NO: 120 | SEQ ID NO: 121 |

The VH5 mutation D98E was tolerated while D98S and D98Q were surprisingly not tolerated. The mutation G99A was also tolerated. For VK1, the mutation D28Q was tolerated, while surprisingly the mutation G29A was not tolerated.

According to a non-binding theory of the inventors, substituting the VH D98 amino acid, and/or the VL D28 amino acid, with amino acids A, G or T could also be tolerated. Also, substituting the VH G99 amino acid, or the VL G29 amino acid, with amino acids T or S, could also be tolerated.

Based on these optimized variable heavy and light regions, twelve optimized antibodies were generated using a human IgG1 Fc domain with the N297A point mutation, and variable light and heavy regions according to the overview in Table 13.

TABLE 13

Optimized antibodies

| Antibody | Variable Light region | Variable Light SEQ ID | Variable Heavy region | Variable Heavy SEQ ID |
|---|---|---|---|---|
| 104341_VH1_VK1D28Q | VK1_D28Q | SEQ ID NO: 70 | VH1 | SEQ ID NO: 7 |
| 104341_VH1D98E_VK1 | VK1 | SEQ ID NO: 25 | VH1_D98E | SEQ ID NO: 37 |
| 104341_VH1D98E_VK1D28Q | VK1_D28Q | SEQ ID NO: 70 | VH1_D98E | SEQ ID NO: 37 |
| 104343_VH1_VK2D28Q | VK2_D28Q | SEQ ID NO: 79 | VH1 | SEQ ID NO: 7 |
| 104343_VH1D98E_VK2 | VK2 | SEQ ID NO: 27 | VH1_D98E | SEQ ID NO: 37 |
| 104343_VH1D98E_VK2D28Q | VK2_D28Q | SEQ ID NO: 79 | VH1_D98E | SEQ ID NO: 37 |
| 104348_VH5_VK1D28Q | VK1_D28Q | SEQ ID NO: 70 | VH5 | SEQ ID NO: 17 |
| 104348_VH5D98E_VK1 | VK1 | SEQ ID NO: 25 | VH5_D98E | SEQ ID NO: 49 |
| 104348_VH5D98E_VK1D28Q | VK1_D28Q | SEQ ID NO: 70 | VH5_D98E | SEQ ID NO: 49 |
| 104349_VH5_VK2D28Q | VK2_D28Q | SEQ ID NO: 79 | VH5 | SEQ ID NO: 17 |
| 104349_VH5D98E_VK2 | VK2 | SEQ ID NO: 27 | VH5_D98E | SEQ ID NO: 49 |
| 104349_VH5D98E_VK2D28Q | VK2_D28Q | SEQ ID NO: 79 | VH5_D98E | SEQ ID NO: 49 |

Any Fc domain can be used to generate further antibodies, as known to a person skilled in the art. Particularly contemplated Fc domains are non Fc modified human IgG1 according to SEQ ID NO: 93, human IgG2 according to SEQ ID NO: 95, human IgG3 according to SEQ ID NO: 97, human IgG4 according to SEQ ID NO: 99, human IgG1 Fc modified with LALA mutation according to SEQ ID NO: 101, human IgG1 Fc modified with N297A mutation according to SEQ ID NO: 103, human IgG1 Fc modified with DAPA mutation according to SEQ ID NO: 105.

According to a preferred embodiment, the Fc domain is a human IgG1 according to SEQ ID NO: 93, and according to an even more preferred embodiment, the Fc domain is a human IgG1 Fc modified with N297A mutation according to SEQ ID NO: 103.

According to one specific embodiment, the full heavy chain sequence of antibody 104348_VH5D98E_VK1D28Q is according to SEQ ID NO: 229 and the full light chain sequence of is according to SEQ ID NO: 395

Example 6: Affinity Maturation

A humanized NARA1 (104348_VH5D98E_VK1D28Q) was used as a starting point for an affinity maturation process based on multiple steps starting with the cloning and expression of the parental VH (SEQ ID NO: 49) and VK (SEQ ID NO: 70) as Fab on the surface of yeast and the determination of the optimal and sub-optimal binding concentrations of biotinylated Proleukin®.

In brief, parental or wildtype (WT) VH (SEQ ID NO: 49) and VK (SEQ ID NO: 70) sequences were cloned as Fab in a yeast display vector containing the aga2 sequence in-frame with the carboxyl-terminus of VH and a 6 amino acid tag derived from beta-amyloid (APP-tag) in-frame with the carboxyl-terminus of the light chain. Detection of this tag allows for the visualization of the expression level of the Fab on the surface, which is well known to a person skilled in the art. After electroporation of the vector in yeast (Benatuil L. et al. (2010). An improved yeast transformation method for the generation of very large human antibody libraries. *Protein Eng Des Sel.*, 23(4), pp. 155-9), the cells were grown in CM Glucose Broth minus Uracil. At time of induction, 7.8E+4 yeast cells growing in their exponential phase were washed with 7 ml induction-medium (CM Galactose Broth minus Ura/0.05% Glucose) and pelleted by spinning the cells 10 minutes at 4000 rpm. The pellet was re-suspended in induction-medium (1E+7 cells/ml) and grown for 16 Hours (HR) at 22° C. in a shaker. Induced yeast cells (4E+7) were collected by centrifugation at 13000 rpm for 1 minute in a 4° C. pre-cooled centrifuge. Cells were washed by re-suspending the pellet in 1 ml FACS buffer (PBS+0.5% BSA) followed by 1 minute centrifugation at 13000 rpm in a 4° C. pre-cooled centrifuge. The yeast pellet was re-suspended in 1 ml FACS buffer and 50 µl was transferred to 12 tubes containing various concentration of biotinylated Proleukin® diluted in FACS buffer (0 nm/0.02 nM/0.05 nM/0.15 nM/0.45 nM/1.3 nM/4 nM/12 nM/36 nM/100 nM/333 nM/1 µM). Yeast was incubated for 1 hour at room temperature (RT) on a rotator, washed two times with 1 ml FACS buffer as described above and pellets re-suspended in 200 µl FACS buffer containing anti-APP mouse monoclonal antibody. After 30 minutes incubation at RT on a rotator, yeast was washed twice with 1 ml FACS buffer and pellets re-suspended in 200 µl labelling buffer (Allophycocyanin (APC)-conjugated Streptavidin/Phycoerythrin (PE)-labelled anti-mouse antibody/FACS buffer). After 30 minutes incubation at RT on a rotor the cells were washed twice with 1 ml FACS buffer and re-suspended in 500 µl cold FACS buffer and filtered through the cap of the FACS tube. Samples were kept in the dark until FACS analysis. The gating-strategy of the FACS analysis was chosen in such a way that PE signals (level of Fab expression on the surface of the yeast) and APC signals (binding of biotinylated Proleukin®) were measured of single yeast cells (singlets). Binding of biotinylated Proleukin® to the Fab on the surface of the yeast could be visualized as events in the FACS-plots that were positive in both PE-signal and APC-signal (data not shown). As expected, incubation of yeast with high amounts of biotinylated Proleukin® (1 µM-12 nM) resulted in the detection of large number of events positive for both PE and APC. This concentration range was considered as the optimal concentration range. Incubation of yeast with 4 nM and 1.3 nM biotinylated Proleukin® resulted in similar levels of PE signal but a dramatic drop in APC signal indicating that less biotinylated Proleukin® was bound to the Fab on the surface of the yeast. This concentration range was considered as the sub-optimal concentration. Yeast incubated with biotinylated Proleukin® concentrations below 1.3 nM (0.45 nM/0.15 nM/0.05 nM/0.02 nM) displayed background levels of APC signal indicating that no biotinylated Proleukin® was bound to the Fab.

In the next step, VH (SEQ ID NO: 49) and VK (SEQ ID NO: 70) were individually random mutagenized by error-prone PCR (Cadwell R. and Joyce G. (1994). Mutagenic PCR. *PCR Methods Appl.*, 3(6), pp. 136-40) using the GeneMorph II Random Mutagenesis Kit (Agilent, Catalog #200550). From this, two yeast libraries were generated (Benatuil et al. 2010) expressing either Fabs consisting of the mutagenized VH (VHep) paired with the parental VK (VKp) (SEQ ID NO: 70) or Fabs consisting of the mutagenized VK (VKep) paired with the parental VH (VHp) (SEQ ID NO: 49). In the first round of selection, both yeast libraries (VHep/VKp and VHp/VKep) as well as the parental (VHp/VKp) expressing yeast were induced and FACS stained (1E+9 VHep/VKp and VHp/VKep: 1E+7 VHp/VKp) with an optimal concentration (10 nM) biotinylated Proleukin® using the protocol described above. At least 80 000 yeast cells positive for both PE and APC were FACS sorted in a 15 ml Falcon tube containing 1 ml CM Glucose Broth minus Uracil. This selection allows for the enrichment of yeast expressing a functional Fab on their surface.

After expansion of the FACS sorted yeast from the first round, a second round of selection was applied. Yeast (1E+7) expressing VHp/VKp, VHep/VKp and VHp/VKep were incubated without biotinylated Proleukin®, 10 nM biotinylated Proleukin® (optimal concentration) or 2 nM biotinylated Proleukin® (sub-optimal concentration) and FACS stained as described above. As observed previously, incubation of yeast expressing VHp/VKp with 10 nM Proleukin® resulted in the detection of significant number of events positive for both PE and APC. A similar result was obtained for the Yeast expressing the VHp/VKep library. Interestingly, at this concentration, the APC signal was much stronger in the VHep/VKp library whereas the PE signals were comparable to those observed in yeast expressing VHp/VKp and VHp/VKep suggesting that more biotinylated Proleukin® was bound on the Fabs expressed on the surface of the yeast. This trend became even more pronounced when yeast was incubated with sub-optimal concentrations of biotinylated Proleukin®. Under these conditions, both the VHp/VKp and the VHp/VKep expressing yeast displayed a low number of events that were positive for both PE and APC whereas yeast expressing VHep/VKp displayed similar levels of PE but much higher levels of APC. Based on these findings, all yeast expressing the VHep/VKp library incubated with 2 nM biotinylated Proleukin®, positive for both PE and APC was FACS sorted as described previously. The same was done for the yeast library expressing VHp/VKep incubated with 10 nM biotinylated Proleukin®.

After expansion of the two libraries, plasmids were extracted from the yeast by pre-incubation of the yeast-pellet with Zymolase (Zymoresearch, Catalog #E1004) followed by plasmid recovery using mini-prep spin columns (Qiagen, Catalog #27106). Recovered plasmids were electroporated into bacteria and grown on selection plates. Single colonies were picked and grown overnight in 96-well plates followed by plasmid isolation using the Nucleospin 96 Plasmid Core Kit according to the manufacturers protocol (Macherey-Nagel, Catalog #740616.24). Plasmids were sequenced and analyzed. The VH mutations are summarized in Table 14

The observed mutations were cloned in various combinations (Table 14 for VH SEQ ID Nos and Table 15 for VK SEQ ID NOs) into the parental IgG mammalian expression vector (Table 16).

TABLE 14

| Designation | VH |
| --- | --- |
| VHp/WT (VH5_D98E) | SEQ ID NO: 49 |
| VH-F100dY/N58Y/T30S | SEQ ID NO: 145 |
| VH-F100dY/N58Y | SEQ ID NO: 161 |
| VH-F100dY/T30S | SEQ ID NO: 177 |
| VH-F100dY | SEQ ID NO: 193 |
| VH-N58Y/T30S | SEQ ID NO: 209 |
| VH-N58Y | SEQ ID NO: 225 |

TABLE 15

VK mutations

| Designation | VL |
| --- | --- |
| VKp/WT(VK1_D28Q) | SEQ ID NO: 70 |
| VK-A50S | SEQ ID NO: 243 |
| VK-A50T | SEQ ID NO: 259 |
| VK-M33L/A50S | SEQ ID NO: 275 |
| VK-M33L | SEQ ID NO: 391 |

TABLE 16

Plasmids

| Plasmid ID | Mutation/s | VH |
| --- | --- | --- |
| SP#2764 | WT | SEQ ID NO: 49 |
| SP#3563 | F100d_Y | SEQ ID NO: 193 |
| SP#3564 | N58Y | SEQ ID NO: 225 |
| SP#3569 | F100d_Y + N58Y | SEQ ID NO: 161 |
| SP#3566 | F100d_Y + T30S | SEQ ID NO: 177 |
| SP#3567 | N58Y + T30S | SEQ ID NO: 209 |
| SP#3587 | F100d_Y + N58Y + T30S | SEQ ID NO: 145 |

| Plasmid ID | Mutation/s | VL |
| --- | --- | --- |
| SP#2445 | WT | SEQ ID NO: 70 |
| SP#3568 | M33L | SEQ ID NO: 391 |
| SP#3569 | A50S | SEQ ID NO: 243 |
| SP#3570 | A50T | SEQ ID NO: 259 |
| SP#3571 | M33L + A50S | SEQ ID NO: 275 |

Subsequently, a transfection matrix was designed of plasmids encoding either wild type or mutated versions of VH and VK generating 35 unique antibodies, as seen in Table 17. The plasmids were transfected into HEK293F cells grown in 6-well plates using Fugene® HD (Promega, Catalog #E2311) according to the manufacturers' protocol. Supernatants were harvested three days post transfection and the antibody titer (internal process control, IPC) in the supernatant was determined using proteinA/HPLC (Holenstein F. et al. (2015) Automated harvesting and 2-step purification of unclarified mammalian cell-culture broths containing antibodies. *J Chromatogr A.*, 1418, pp. 103-9).

TABLE 17

First set of antibodies

| Antibody No: | VH-plasmid ID | VH-mutations | VK-plasmid ID | VK-mutations |
| --- | --- | --- | --- | --- |
| 1 | SP#2764 | WT | SP#2445 | WT |
| 2 | | | SP#3568 | M33L |
| 3 | | | SP#3569 | A50S |
| 4 | | | SP#3570 | A50T |
| 5 | | | SP#3571 | M33L + A50S |
| 6 | SP#3563 | F100d_Y | SP#2445 | WT |
| 7 | | | SP#3568 | M33L |
| 8 | | | SP#3569 | A50S |
| 9 | | | SP#3570 | A50T |
| 10 | | | SP#3571 | M33L + A50S |
| 11 | SP#3564 | N58Y | SP#2445 | WT |
| 12 | | | SP#3568 | M33L |
| 13 | | | SP#3569 | A50S |
| 14 | | | SP#3570 | A50T |
| 15 | | | SP#3571 | M33L + A50S |
| 16 | SP#3569 | F100d_Y + N58Y | SP#2445 | WT |
| 17 | | | SP#3568 | M33L |
| 18 | | | SP#3569 | A50S |
| 19 | | | SP#3570 | A50T |
| 20 | | | SP#3571 | M33L + A50S |
| 21 | SP#3566 | F100d_Y + T30S | SP#2445 | WT |
| 22 | | | SP#3568 | M33L |
| 23 | | | SP#3569 | A50S |
| 24 | | | SP#3570 | A50T |
| 25 | | | SP#3571 | M33L + A50S |
| 26 | SP#3567 | N58Y + T30S | SP#2445 | WT |
| 27 | | | SP#3568 | M33L |
| 28 | | | SP#3569 | A50S |
| 29 | | | SP#3570 | A50T |
| 30 | | | SP#3571 | M33L + A50S |
| 31 | SP#3587 | F100d_Y + N58Y + T30S | SP#2445 | WT |
| 32 | | | SP#3568 | M33L |
| 33 | | | SP#3569 | A50S |
| 34 | | | SP#3570 | A50T |
| 35 | | | SP#3571 | M33L + A50S |

The sequences of the antibodies are set forth in Table 41, and summarized in Table 18 below.

TABLE 18

Sequence overview of first set of antibodies

| Antibody | VH | VL | Full length heavy chain | Full length light chain |
| --- | --- | --- | --- | --- |
| 1 | SEQ ID NO: 49 | SEQ ID NO: 70 | SEQ ID NO: 229 | SEQ ID NO: 395 |
| 2 | SEQ ID NO: 49 | SEQ ID NO: 391 | SEQ ID NO: 229 | SEQ ID NO: 393 |
| 3 | SEQ ID NO: 49 | SEQ ID NO: 243 | SEQ ID NO: 229 | SEQ ID NO: 245 |
| 4 | SEQ ID NO: 49 | SEQ ID NO: 259 | SEQ ID NO: 229 | SEQ ID NO: 261 |
| 5 | SEQ ID NO: 49 | SEQ ID NO: 275 | SEQ ID NO: 229 | SEQ ID NO: 277 |
| 6 | SEQ ID NO: 193 | SEQ ID NO: 70 | SEQ ID NO: 195 | SEQ ID NO: 395 |
| 7 | SEQ ID NO: 193 | SEQ ID NO: 391 | SEQ ID NO: 195 | SEQ ID NO: 393 |
| 8 | SEQ ID NO: 193 | SEQ ID NO: 243 | SEQ ID NO: 195 | SEQ ID NO: 245 |
| 9 | SEQ ID NO: 193 | SEQ ID NO: 259 | SEQ ID NO: 195 | SEQ ID NO: 261 |
| 10 | SEQ ID NO: 193 | SEQ ID NO: 275 | SEQ ID NO: 195 | SEQ ID NO: 277 |
| 11 | SEQ ID NO: 225 | SEQ ID NO: 70 | SEQ ID NO: 227 | SEQ ID NO: 395 |
| 12 | SEQ ID NO: 225 | SEQ ID NO: 391 | SEQ ID NO: 227 | SEQ ID NO: 393 |
| 13 | SEQ ID NO: 225 | SEQ ID NO: 243 | SEQ ID NO: 227 | SEQ ID NO: 245 |
| 14 | SEQ ID NO: 225 | SEQ ID NO: 259 | SEQ ID NO: 227 | SEQ ID NO: 261 |
| 15 | SEQ ID NO: 225 | SEQ ID NO: 275 | SEQ ID NO: 227 | SEQ ID NO: 277 |
| 16 | SEQ ID NO: 161 | SEQ ID NO: 70 | SEQ ID NO: 163 | SEQ ID NO: 395 |
| 17 | SEQ ID NO: 161 | SEQ ID NO: 391 | SEQ ID NO: 163 | SEQ ID NO: 393 |
| 18 | SEQ ID NO: 161 | SEQ ID NO: 243 | SEQ ID NO: 163 | SEQ ID NO: 245 |
| 19 | SEQ ID NO: 161 | SEQ ID NO: 259 | SEQ ID NO: 163 | SEQ ID NO: 261 |
| 20 | SEQ ID NO: 161 | SEQ ID NO: 275 | SEQ ID NO: 163 | SEQ ID NO: 277 |
| 21 | SEQ ID NO: 177 | SEQ ID NO: 70 | SEQ ID NO: 179 | SEQ ID NO: 395 |
| 22 | SEQ ID NO: 177 | SEQ ID NO: 391 | SEQ ID NO: 179 | SEQ ID NO: 393 |

TABLE 18-continued

Sequence overview of first set of antibodies

| Antibody | VH | VL | Full length heavy chain | Full length light chain |
|---|---|---|---|---|
| 23 | SEQ ID NO: 177 | SEQ ID NO: 243 | SEQ ID NO: 179 | SEQ ID NO: 245 |
| 24 | SEQ ID NO: 177 | SEQ ID NO: 259 | SEQ ID NO: 179 | SEQ ID NO: 261 |
| 25 | SEQ ID NO: 177 | SEQ ID NO: 275 | SEQ ID NO: 179 | SEQ ID NO: 277 |
| 26 | SEQ ID NO: 209 | SEQ ID NO: 70 | SEQ ID NO: 211 | SEQ ID NO: 395 |
| 27 | SEQ ID NO: 209 | SEQ ID NO: 391 | SEQ ID NO: 211 | SEQ ID NO: 393 |
| 28 | SEQ ID NO: 209 | SEQ ID NO: 243 | SEQ ID NO: 211 | SEQ ID NO: 245 |
| 29 | SEQ ID NO: 209 | SEQ ID NO: 259 | SEQ ID NO: 211 | SEQ ID NO: 261 |
| 30 | SEQ ID NO: 209 | SEQ ID NO: 275 | SEQ ID NO: 211 | SEQ ID NO: 277 |
| 31 | SEQ ID NO: 145 | SEQ ID NO: 70 | SEQ ID NO: 147 | SEQ ID NO: 395 |
| 32 | SEQ ID NO: 145 | SEQ ID NO: 391 | SEQ ID NO: 147 | SEQ ID NO: 393 |
| 33 | SEQ ID NO: 145 | SEQ ID NO: 243 | SEQ ID NO: 147 | SEQ ID NO: 245 |
| 34 | SEQ ID NO: 145 | SEQ ID NO: 259 | SEQ ID NO: 147 | SEQ ID NO: 261 |
| 35 | SEQ ID NO: 145 | SEQ ID NO: 275 | SEQ ID NO: 147 | SEQ ID NO: 277 |

Subsequently, hIL-2 binding efficiency of the antibodies present in the supernatants was determined using ELISA. In brief, ELISA plates (Maxisorp 96-well black microtiter plate) were coated overnight at 4° C. with 100p/well of Proleukin® (5 µg/ml PBS). ELISA plates were washed once with TBST (1×TBS/0.05% Tween 20) using a plate-washer (BioTek). Plates were blocked by adding 350 µl/well blocking buffer (TBS/1× casein (Vector laboratories 10× solution #SP-5020), filtered 0.22 µm) and incubated for 2 hours at RT under gentle agitation. After removal of the blocking buffer, plates were washed once with TBST using the plate washer. Supernatants were diluted 1:2 in blocking buffer and 50 µl transferred to the designated well of the ELISA plate. Each sample was present on three ELISA plates. The three plates were incubated at RT under gentle agitation. After 2 hours incubation one of the plates was washed three times with TBST before 1001/well detection antibody (TBST/goat polyclonal HRP-conjugated anti-human Fab2; Dianova/Jackson ImmunResearch, Catalog #109-036-006) was added. The other two plates were washed either every hour three times with TBST for 4 hours or washed every hour three times for 12 hours before adding the detection antibody. After 1 hour incubation at RT under gentle agitation, the wells were washed three times with washing buffer and the plates tapped dry on a stack of paper towels before adding 100 µl/well BM ChemiLuminesence ELISA Substrate (POD) (Roche Diagnostics #11582950001). Luminescence signal was measured after 5 minutes incubation in the dark. The ELISA values for the 35 antibodies are seen in Table 19. All ELISA values are mean values based on two measurements.

TABLE 19

ELISA values

| Antibody No: | IPC (mg/L) | Normal ELISA | wash 3x every hour for 4 HRS | wash 3x every hour for 12 HRS |
|---|---|---|---|---|
| 1 | 3.89 | 1182 | 1063 | 717 |
| 2 | 3.34 | 1355 | 1231 | 518 |
| 3 | 4.75 | 4496 | 4580 | 1313 |
| 4 | 4 | 2175 | 1987 | 705 |
| 5 | 4.17 | 4974 | 4490 | 873 |
| 6 | 2.77 | 5849 | 5115 | 1732 |
| 7 | 2.7 | 7638 | 6360 | 1553 |
| 8 | 2.75 | 9373 | 7314 | 2533 |
| 9 | 2.1 | 1944 | 1427 | 686 |
| 10 | 2.3 | 6047 | 4433 | 1630 |
| 11 | 3.78 | 12391 | 10500 | 3498 |

TABLE 19-continued

ELISA values

| Antibody No: | IPC (mg/L) | Normal ELISA | wash 3x every hour for 4 HRS | wash 3x every hour for 12 HRS |
|---|---|---|---|---|
| 12 | 4.15 | 20047 | 17398 | 5960 |
| 13 | 3.17 | 14541 | 14591 | 4524 |
| 14 | 2.86 | 7181 | 7203 | 2538 |
| 15 | 2.71 | 11086 | 10494 | 3796 |
| 16 | 2.14 | 10215 | 9814 | 2277 |
| 17 | 1.85 | 3048 | 2815 | 1141 |
| 18 | 1.91 | 8060 | 7319 | 3656 |
| 19 | 1.89 | 5402 | 4875 | 2208 |
| 20 | 1.93 | 11719 | 11055 | 5200 |
| 21 | 2.15 | 2195 | 1839 | 892 |
| 22 | 2.27 | 3972 | 3188 | 1204 |
| 23 | 2.39 | 6168 | 4635 | 1248 |
| 24 | 2.06 | 2772 | 1877 | 674 |
| 25 | 2.16 | 3574 | 3050 | 1084 |
| 26 | 2.74 | 4029 | 4212 | 1800 |
| 27 | 3.01 | 7755 | 6997 | 2770 |
| 28 | 3.27 | 18459 | 18060 | 5872 |
| 29 | 2.65 | 6954 | 6848 | 2724 |
| 30 | 2.8 | 14920 | 14375 | 2803 |
| 31 | 2.06 | 11389 | 10263 | 3403 |
| 32 | 1.9 | 7187 | 6211 | 3332 |
| 33 | 1.82 | 3988 | 3566 | 1823 |
| 34 | 1.84 | 3857 | 3077 | 1362 |
| 35 | 1.82 | 4914 | 4045 | 1789 |

Most of the introduced mutations (e.g. Antibody No: 8/11/12/13/15/16/20/28/30/31) displayed similar or lower titers when compared to the parental antibody (Antibody No: 1) but dramatically improved the binding efficiency. Even after 12 hours excessive washing, some of the mutants still displayed high level of binding (e.g. Antibody No: 12/13/15/20/28). In order to rank the various antibodies, the supernatants were serial diluted and binding affinities determined by ELISA.

EC50 values were calculated using the titers determined by proteinA/HPLC, according to standard methods well known to a person skilled in the art. The results are summarized in Table 20.

TABLE 20

EC50 values

| Antibody No: | VH-mutations | VK-mutations | Cell Sups EC50 (nM) |
|---|---|---|---|
| 1 | WT | WT | 1.04 |
| 2 | | M33L | 0.79 |
| 3 | | A50S | 0.51 |
| 4 | | A50T | 0.73 |
| 5 | | M33L + A50S | 0.50 |
| 6 | F100d_Y | WT | 0.34 |
| 7 | | M33L | 0.31 |
| 8 | | A50S | 0.24 |
| 9 | | A50T | 0.50 |
| 10 | | M33L + A50S | 0.35 |
| 11 | N58Y | WT | 0.34 |

TABLE 20-continued

EC50 values

| Antibody No: | VH-mutations | VK-mutations | Cell Sups EC50 (nM) |
|---|---|---|---|
| 12 | | M33L | 0.25 |
| 13 | | A50S | 0.19 |
| 14 | | A50T | 0.36 |
| 15 | | M33L + A50S | 0.28 |
| 16 | F100d_Y + N58Y | WT | 0.38 |
| 17 | | M33L | 1.39 |
| 18 | | A50S | 0.54 |
| 19 | | A50T | 0.50 |
| 20 | | M33L + A50S | 0.27 |
| 21 | F100d_Y + T30S | WT | 0.65 |
| 22 | | M33L | 0.43 |
| 23 | | A50S | 0.26 |
| 24 | | A50T | 0.59 |
| 25 | | M33L + A50S | 0.42 |
| 26 | N58Y + T30S | WT | 0.49 |
| 27 | | M33L | 0.39 |
| 28 | | A50S | 0.16 |
| 29 | | A50T | 0.24 |
| 30 | | M33L + A50S | 0.22 |
| 31 | F100d_Y + N58Y + T30S | WT | 0.39 |
| 32 | | M33L | 0.65 |
| 33 | | A50S | 0.67 |
| 34 | | A50T | 0.65 |
| 35 | | M33L + A50S | 0.72 |

Based on binding efficiency and representation of the mutation, a panel of 7 antibodies (Table 21) were selected, expressed and purified (Holenstein et al. 2015) and further characterized.

TABLE 21

Selected antibodies

| Antibody No: | VH-mutations | VK-mutations | Designation |
|---|---|---|---|
| 8 | F100d_Y | A50S | 108923 |
| 12 | N58Y | M33L | 108924 |
| 13 | N58Y | A50S | 108925 |
| 15 | N58Y | M33L + A50S | 108926 |
| 20 | F100d_Y + N58Y | M33L + A50S | 108928 |
| 26 | N58Y + T30S | WT | 108929 |
| 28 | N58Y + T30S | A50S | 108930 |

The sequences of the selected antibodies are set forth in Table 41, and summarized in Table 22 below.

TABLE 22

Sequence overview of selected of antibodies

| Antibody | VH | VL | Full length heavy chain | Full length light chain |
|---|---|---|---|---|
| 108923 | SEQ ID NO: 193 | SEQ ID NO: 243 | SEQ ID NO: 195 | SEQ ID NO: 245 |
| 108924 | SEQ ID NO: 225 | SEQ ID NO: 391 | SEQ ID NO: 227 | SEQ ID NO: 393 |
| 108925 | SEQ ID NO: 225 | SEQ ID NO: 243 | SEQ ID NO: 227 | SEQ ID NO: 245 |
| 108926 | SEQ ID NO: 225 | SEQ ID NO: 275 | SEQ ID NO: 227 | SEQ ID NO: 277 |
| 108928 | SEQ ID NO: 161 | SEQ ID NO: 275 | SEQ ID NO: 163 | SEQ ID NO: 277 |
| 108929 | SEQ ID NO: 209 | SEQ ID NO: 259 | SEQ ID NO: 211 | SEQ ID NO: 261 |
| 108930 | SEQ ID NO: 209 | SEQ ID NO: 275 | SEQ ID NO: 211 | SEQ ID NO: 277 |

Example 7: Binding Affinity

1. Enzyme-Linked Immunosorbent Assay (ELISA)

ELISA, well known to a person skilled in the art, was used to screen the candidates.

ELISA plates (Corning) were coated with human IL-2 (Proleukin) at 10 µg/mL in PBS overnight at 4° C. The plates were washed 6 times with PBST, then blocked in 1% BSA/PBST for 2 hours. After blocking and washing, the anti-human IL-2 antibodies were added on the plate in an 11-point dilution series in 1% BSA/PBST and incubated for 2 hours. Afterwards the plates were washed again, followed by the incubation with the detection antibodies, either anti-mouse IgG-biotinylated (NARA1) or anti-human IgG-biotinylated (humanized antibodies) in an 1:10'000 dilution in 1% BSA/PBST for 2 hours. The plates were then washed again and incubated with Streptavidin-Horseradish Peroxidase in 1% BSA/PBS for 45 minutes. After washing, the substrate (R&D Systems) was added into the plates and the enzymatic reaction was stopped after 3 minutes by adding Stop Solution. The plates were read by a microplate reader at 450 nm with a wavelength correction set to 540 nm.

The whole process was performed at room temperature.

The mean of 3 independent ELISA experiments are found in Table 23.

2. Solution Equilibration Titration (SET) Assays

A SET assay, well known to a person skilled in the art, was conducted to determine and compare the affinity ($K_D$) of five humanized anti-IL-2 antibodies and the anti-IL-2 (NARA1)-mouse IgG2a to IL-2 protein.

The solution equilibration titration (SET) assay allows the determination of antibody-antigen interaction affinities ($K_D$) for tight binders. This technique does not require immobilization or labelling of either interaction partner and is suitable for strong interactions ($K_D$=pM to low nM range).

Mixtures of a constant concentration of antibody (concentrations at or below the expected $K_D$) are co-incubated with antigen within a suitable concentration range (well below and well above the $K_D$) until equilibrium is reached. The amount of free antibody binding sites is determined by transferring the mixtures on antigen-coated plates and a brief incubation. The free antibody consequently bind to the plate and is detected with a detection antibody. The resulting signal is plotted versus the antigen concentration. The $K_D$ is accurately determined by non-linear curve fitting.

(1) Materials and Methods

The following antibodies were used:
anti-IL-2 (NARA1)-mIgG2a: 8.7 mg/ml, 150 kDa, 58.00 µM
anti-IL-2-hsIgG1 104340 (chimeric NARA1 antibody): 4.25 mg/ml, 150 kDa, 28.33 µM
anti-IL-2-hsIgG1 104343: 3.69 mg/ml, 150 kDa, 24.60 µM
anti-IL-2-hsIgG1 104347: 4.03 mg/ml, 150 kDa, 26.87 µM
anti-IL-2-hsIgG1 104348: 2.71 mg/ml, 150 kDa, 18.07 µM
anti-IL-2-hsIgG1 104349: 3.29 mg/ml, 150 kDa, 21.93 µM Antigens
IL-2 (Proleukin®): 1.00 mg/ml, 15.33 kDa, 65.24 µM
IL-2 (WT): 0.15 mg/ml, 15.55 kDa, 9.65 µM Detection Antibodies
MSD Sulfo-tag-labeled goat anti-human antibody, Meso Scale Discovery, Cat #R32AJ-5
MSD Sulfo-tag-labeled goat anti-mouse antibody, Jackson I R, Cat #115-005-071

Instrument and Software
MSD SECTOR Imager 6000 controlled by Discovery Workbench software
Data processing with XLfit, a MS Excel add-in software Assay Plates
Standard 384-well plate for SECTOR Imager 6000, Meso Scale Discovery Cat #L21XA
Polypropylene 384-well plate, Greiner Cat #781280

Reagents
Bovine serum albumin (BSA), VWR Cat #422351S
Phosphate-buffered saline (PBS) 10×, Teknova Cat #P0195
MSD Read Buffer T 4×, Meso Scale Discovery Cat #R92TC-1
Tris-buffered saline (TBS) 20×, Teknova Cat #T1680
Tween-20, VWR Cat #437082Q Buffers
Blocking buffer: 1×PBS+5% (w/v) BSA
Coating buffer: 1×PBS
Sample buffer: 1×PBS+0.5% (w/v) BSA+0.02% (v/v) Tween-20
Wash buffer: 1×TBS+0.05% (v/v) Tween-20
Read buffer: 1×MSD Read Buffer A 22 serial 2n dilution of the antigen was prepared in sample buffer. A constant concentration of the antibody was added. The antigen and antibody concentrations are listed below. A volume of 60 µl of each antigen:antibody mix was distributed in duplicates to a 384-well polypropylene microtiter plate (PP MTP). Sample buffer served as negative control and a sample containing no antigen as positive control ($B_{max}$). The plate was sealed and incubated overnight (o/n) at room temperature (RT). A 384-well standard MSD array plate was coated o/n with 2 µg/ml of IL-2. After three times washing with washing buffer, the plate was blocked with 50 µl/well blocking buffer for 1 hour at RT. After washing, a volume of 30 µl/well of the antigen: antibody mix was transferred from the PP MTP to the coated MSD plate and incubated for 20 min at RT. After an additional wash step, 30 µl of detection antibody (diluted 1:2000) in sample buffer was added to each well and incubated for 30 min at RT. The MSD plate was washed and 35 µl/well of read buffer was added and incubated for 5 min. ECL signals were measured with the MSD SECTOR Imager 6000.

(2) Results

The results of the SET are found in Table 23. All tested anti-IL-2 antibodies showed similar affinities to IL-2 proteins in the low pM range (IL-2 wt not shown).

TABLE 23

Binding affinity data

| Antibody | EC50 from IL-2 ELISA (nM) | Kd from SET assay (nM) |
|---|---|---|
| NARA1 | 0.3 | 0.078 |
| 104341 | 0.4 | |
| 104343 | 0.3 | 0.075 |
| 104344 | 0.7 | |
| 104345 | 2.9 | |
| 104346 | 1.7 | |
| 104347 | 39 | 10 |
| 104348 | 0.3 | 0.105 |
| 104349 | 0.3 | 0.082 |
| 104350 | 0.8 | |
| 104343_VH1_VK2D28Q | 0.59 | 0.069 |
| 104343_VH1D98E_VK2 | 0.57 | 0.098 |
| 104343_VH1D98E_VK2D28Q | 0.75 | 0.111 |
| 104348_VH5_VK1D28Q | 0.97 | 0.155 |
| 104348_VH5D98E_VK1 | 0.77 | 0.206 |
| 104348_VH5D98E_VK1D28Q | 1.18 | 0.272 |
| 104349_VH5_VK2D28Q | 0.43 | 0.069 |
| 104349_VH5D98E_VK2 | 0.56 | 0.178 |
| 104349_VH5D98E_VK2D28Q | 0.66 | 0.188 |
| 108923 | 0.05 | |
| 108924 | 0.11 | |
| 108925 | 0.06 | |
| 108926 | 0.05 | |
| 108928 | 0.71 | |
| 108929 | 0.15 | |
| 108930 | 0.06 | |

As can be seen in Table 23, most of the humanized antibodies have similar binding affinity to human IL-2 as NARA1. However, surprisingly, some humanized antibodies have lower binding affinity, which is the case of 104347.

Example 8: Evaluation of IL-2/Anti-IL-2 mAb Complex In Vitro

The activity of the humanized anti-IL-2 antibodies was compared to NARA1 in a PBMC derived-CD8 T cell proliferation assay.

Human CD8 T cells isolated by negative magnetic separation after Ficoll from Buffy-coat were plated at 100000 cells/well in complete RPMI medium supplemented with 5% human serum. Cells were stimulated for 48 hours at 37° C. with the anti-IL-2 antibody alone (0.5 µg/ml) or with IL-2 (Proleukin®; 0.1 µg/ml) plus anti-IL-2 antibodies (0.5 µg/ml) at a 2:1 molar ratio. Cells were pulsed for the last 16 hours with 3H-Thymidine, harvested and proliferation was measured with p-counter. The experiment was run in triplicates and the counts of the antibody alone were equivalent to the background signal level of unstimulated cells.

TABLE 24

CD8 T cell proliferation data

| Antibody | [H3] Thymidine Incorporation (cpm) Antibody (0.5 μg/ml) | [H3] Thymidine Incorporation (cpm) Proleukin ® (0.1 μg/ml) + Antibody (0.5 μg/ml) 2:1 molar ratio |
|---|---|---|
| NARA1 | 453 | 2766 |
| 104340 | 491 | 3363 |
| 104341 | 671 | 3463 |
| 104343 | 639 | 3457 |
| 104344 | 532 | 3799 |
| 104345 | 577 | 4874 |
| 104346 | 626 | 4607 |
| 104347 | 645 | 4636 |
| 104348 | 543 | 3360 |
| 104349 | 560 | 3348 |
| 104350 | 653 | 3974 |

As seen in Table 24 most of the humanized antibodies have a similar ability to NARA1 for induction of human CD8 T cell proliferation in vitro.

In an alternative method, the activity of some humanized anti-IL-2 antibodies was evaluated in 7-day proliferation assay in human PBMC derived-CD8 T and NK cells.

Human PBMCs purified from buffy coats by Ficoll density gradient centrifugation were subjected to magnetic bead negative selection to isolate CD8+ T and NK cells. Cells were labelled with the CellTrace Violet Proliferation Kit and plated in 96 U-bottom plate at 50000 cells/well in RPMI 1640 Medium supplemented 10% fetal calf serum. Cells were then stimulated with hIL-2 or hIL-2/anti-IL-2 mAb complex (at a 2:1 molar ratio, 10-fold serial dilutions) and incubated for 7 days at 37° C. Proliferation was assessed by CellTrace Violet incorporation measured by FACS. The experiment was run in triplicates and average EC50 values were calculated from 2 independent experiments.

TABLE 25

CD8 T and NK cell proliferation data

| IL-2/anti-IL-2 complex | hCD8 T Cell Proliferation EC50 (nM) | hNK Cell Proliferation EC50 (nM) |
|---|---|---|
| Proleukin ® alone | 3.5 | 0.3 |
| Proleukin ®/104343_VH1D98E_VK2D28Q | 8.1 | 0.5 |
| Proleukin ®/104348_VH5D98E_VK1D28Q | 9.2 | 0.5 |
| Proleukin ®/104349_VH5D98E_VK2D28Q | 6.9 | 0.4 |
| Proleukin ®/108923 | 19.1 | 1.6 |
| Proleukin ®/108924 | 18.5 | 1.6 |
| Proleukin ®/108925 | 12.1 | 1.1 |
| Proleukin ®/108926 | 14.8 | 1.1 |
| Proleukin ®/108929 | 11.9 | 0.8 |
| Proleukin ®/108930 | 12.1 | 1.0 |

Example 9: Evaluation of IL-2/Anti-IL-2 mAb Complex In Vivo

Counts of CD8+ T cells, CD4+ T cells, and NK cells were determined in WT C57BL/6 mice receiving IL-2/anti-IL-2 mAb complex as described below. In parallel, the proliferation levels of CD8+ T cells and NK cells were evaluated using bromodeoxyuridine (BrdU).

(1) Materials and Methods

The following antibodies were used: 104340 (chimeric NARA1 antibody), 104343, 104347, 104348, 104349, 104341.

Proleukin® IL-2 was used.

This experiment was performed in duplicate; the first time the humanized 104341 was not included.

Mice received 4 consecutive injections of hIL-2 at 1.5 g (low dose; LD) or 20 g (high dose; HD), or hIL-2/monoclonal antibody (1.5 g and 15 g, respectively, corresponding to a 1:1 molar ratio). The day of the last injection 5-bromo-2'-deoxyuridine (BrdU) was given in the drinking water at 0.8 mg/ml for 24 hours. The following day, mice were sacrificed and spleens and lymph nodes (LNs) were analyzed by flow cytometry. To do so, single cell suspensions of LNs and spleens were prepared according to standard protocols and 2*10⁶ cells were stained for flow cytometry analysis using PBS with 2% fetal calf serum (FCS), 2 mM EDTA and fluorochrome-conjugated antibodies (see below).

Two different stains were performed: The first staining was done in order to identify and quantify CD4+ CD25+ forkhead box P3 (FoxP3)+ T regulatory cells. To this end, single cell suspensions were stained using the FoxP3 staining buffer and following the supplier's recommendations (eBiosciences, 00-5523-00) and using fluorochrome-conjugated antibodies to the following markers: CD25, CD8a, CD4, CD3, FoxP3.

A second staining was performed in order to identify and quantify cell proliferation of particular cell subsets whereby a fluorochrome-conjugated anti-BrdU antibody was used to stain cells that had proliferated. The BrdU stain was performed using the FITC BrdU kit and following the supplier's recommendations (BD Pharmingen, 51-2354 AK) and using fluorochrome-conjugated antibodies to the following markers: CD44, CD8a, CD4, NK1.1, CD3, CD122, Brdu.

Data was collected using a Becton Dickinson LSR Fortessa flow cytometer, well known to a person skilled in the art.

(2) Results

The results of the cell count data is shown in Table 26 and Table 27.

TABLE 26

Cell count data
Cell counts (×10^6)

| | CD3+CD8+ | | CD3+CD4+ | | CD3−NK1.1+ | |
|---|---|---|---|---|---|---|
| IL-2 LD | 13.41994 | 11.89759 | 19.95176 | 16.30791 | 2.042918 | 1.484522 |
| IL-2/104340 | 23.41843 | 25.82988 | 11.81956 | 11.59474 | 5.065738 | 5.448658 |
| IL-2/104343 | 14.45484 | 20.53916 | 18.5848 | 15.89161 | 5.286026 | 7.333515 |

TABLE 26-continued

| | Cell count data Cell counts (×10^6) | | | | | |
|---|---|---|---|---|---|---|
| | CD3+CD8+ | | CD3+CD4+ | | CD3−NK1.1+ | |
| IL-2/104347 | 13.79718 | 14.83423 | 18.27195 | 21.03542 | 2.442164 | 2.597084 |
| IL-2/104348 | 23.68391 | 28.30016 | 14.75169 | 19.55284 | 7.37502 | 10.09379 |
| IL-2/104349 | 21.18129 | 24.34502 | 16.2933 | 14.88262 | 5.719003 | 11.14665 |
| IL-2/104341 | 27.68841 | 25.55466 | 19.12686 | 18.45614 | 13.83036 | 9.069159 |
| IL-2 HD | 21.4074 | 15.66434 | 27.66495 | 19.26853 | 5.97563 | 3.492621 |
| PBS | 8.776036 | 11.32218 | 12.99657 | 14.99693 | 0.730655 | 1.437321 |

TABLE 27

| | Cell count data Cell counts (×10^6) | | | |
|---|---|---|---|---|
| | CD3+CD8+CD44+ | | CD3+CD4+CD25+FoxP3+ | |
| IL-2 LD | 1.599656 | 1.169533 | 1.701715 | 1.612555 |
| IL-2/104340 | 14.98077 | 17.97501 | 3.949957 | 3.390384 |
| IL-2/104343 | 3.928826 | 7.53171 | 2.086871 | 3.359948 |
| IL-2/104347 | 2.127526 | 1.809776 | 2.563509 | 2.514805 |
| IL-2/104348 | 12.50984 | 12.61338 | 4.282856 | 4.927512 |
| IL-2/104349 | 7.286364 | 3.648101 | 3.578653 | 3.063865 |
| IL-2/104341 | 12.83635 | 11.69892 | 5.273673 | 4.708051 |
| IL-2 HD | 4.964377 | 3.648225 | 7.348498 | 4.172373 |
| PBS | 0.581851 | 1.25563 | 0.802762 | 1.019274 |

As can be seen in the Table 26 and Table 27, the antibodies 104343, 104347, 104348, 104349 and 104341 in complex with IL-2 can stimulate CD8 and NK cells in vivo.

Figure 6:
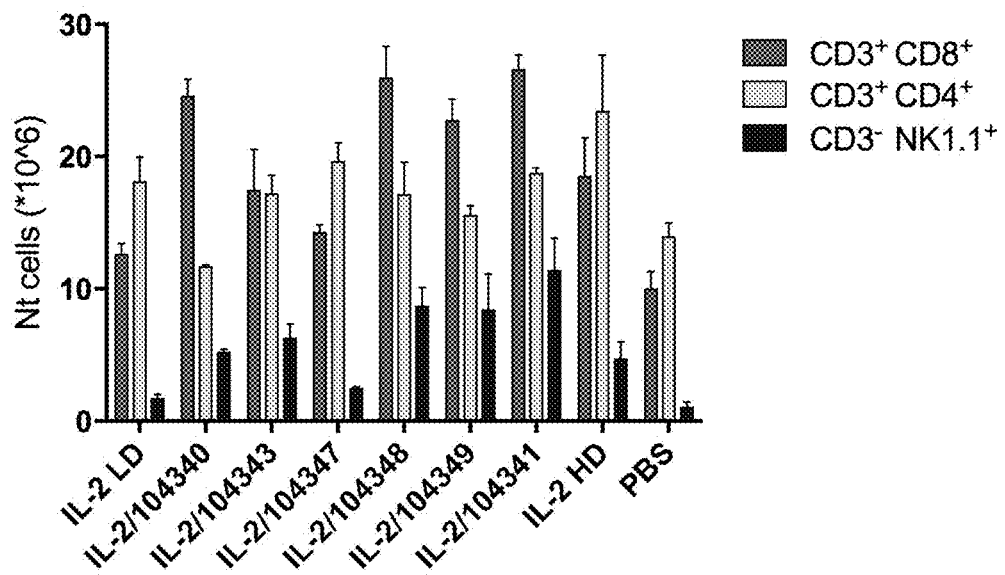
FIG. 6 shows the counts of immune cells from spleens of mice receiving phosphate-buffered saline (PBS), low dose human IL-2 (IL-2 LD), high dose human IL-2 (IL-2 HD), or IL-2/antibody complexes made by using the indicated monoclonal antibodies. The values are shown in tables 14 and 15.
Figure 6:
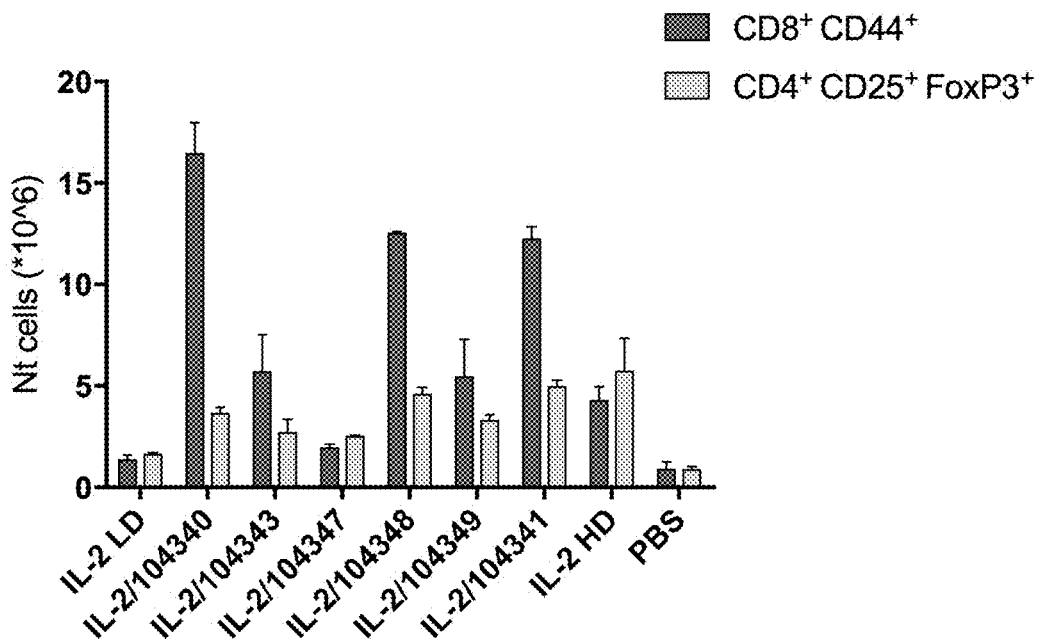
Figure 7:
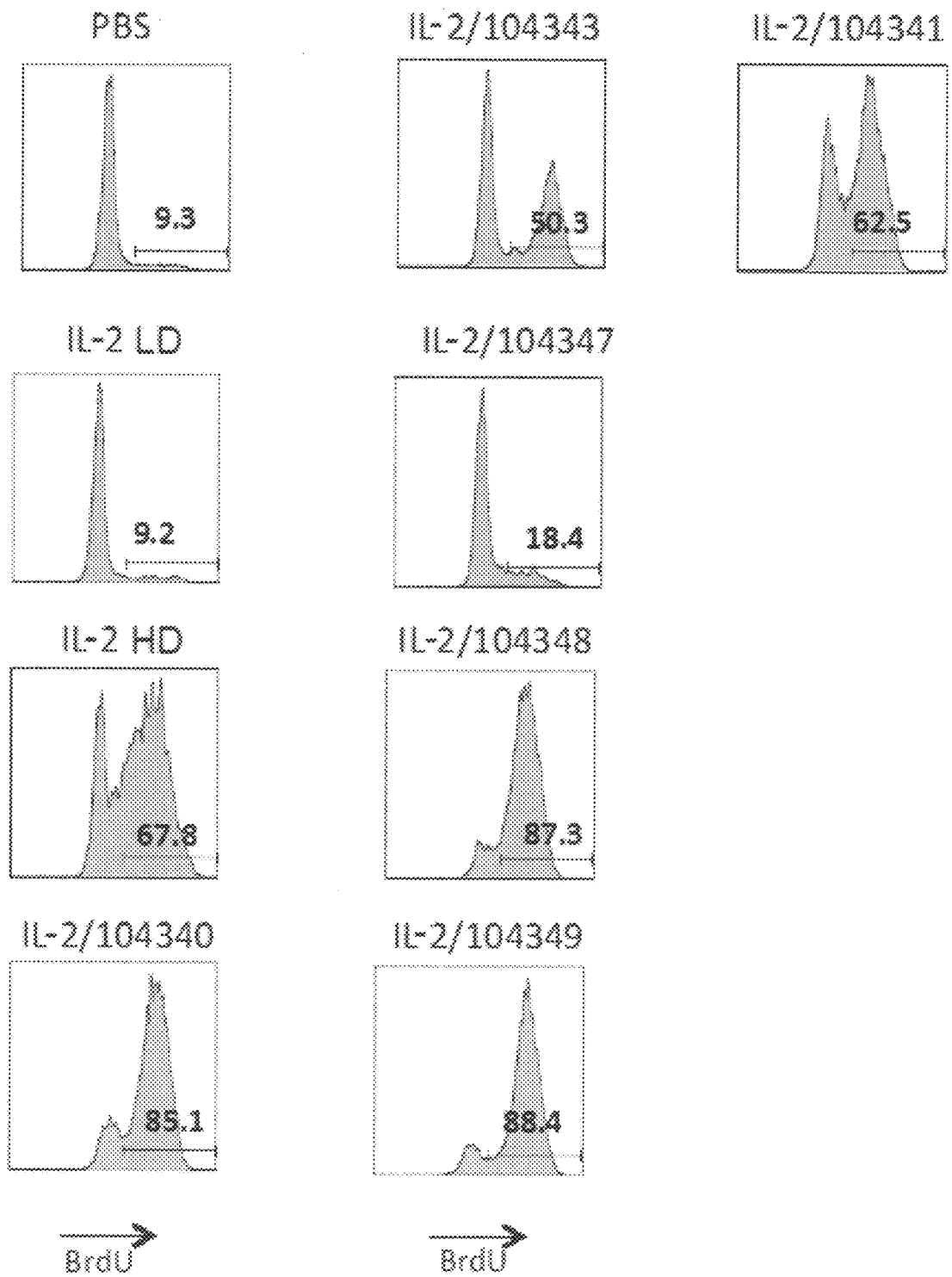
FIG. 7 shows representative bromodeoxyuridine (BrdU) profiles of $CD8^+CD44^+CD122^+$ T cells from the spleens of mice treated as in FIG. 6.
Figure 8:
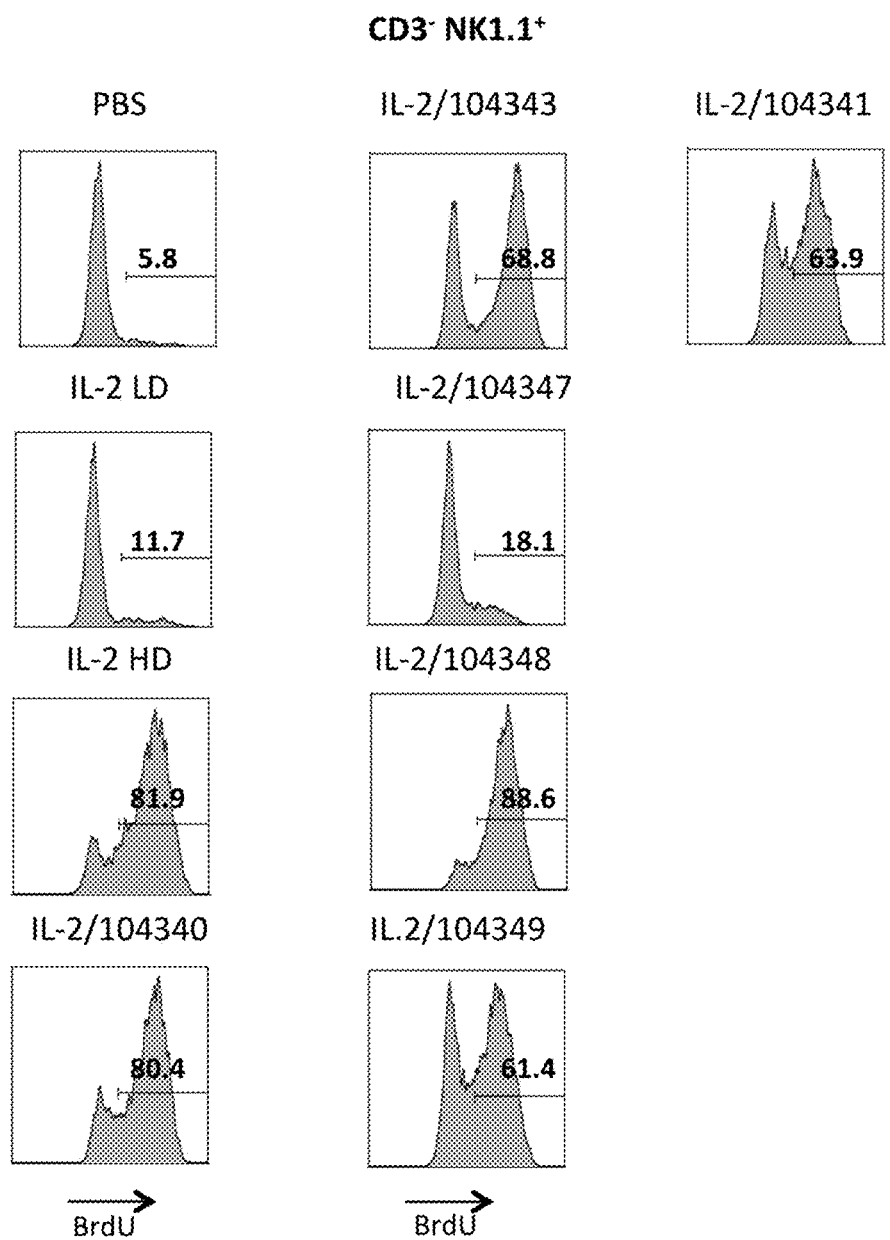
FIG. 8 shows representative BrdU profiles of $CD3^-NK1.1^+$ NK cells from spleens of mice treated as in FIG. 6.

Also, FIG. 6 shows the number of immune cells obtained in the spleen of mice. Plotted values are seen in Table 23 and Table 24. FIG. 7 shows representative BrdU profiles of CD8+CD44+CD122+ T cells in the spleen of mice. FIG. 8 shows representative BrdU profiles of CD3−NK1.1+ NK cells in the spleen of mice.

From these results we can conclude that the humanized antibodies 104343, 104348, 104349 and 104341 like the chimeric NARA1 antibody 104340 in combination with IL-2 are able to preferentially stimulate CD8+ T cells and NK cells. This is not the case for the humanized 104347 antibody.

Example 10: Generation of IL-2/Anti-IL-2 mAb Fusion Protein Using a Linker

Using the crystal structure NARA1/hIL-2 results of Example 2, ways have been identified for connecting NARA1 heavy and light chain N-terminal regions to hIL-2.

The structure of the complex was analyzed by using modeling software like PyMOL or MOE and it has been observed that the C-terminal end of hIL-2 is on opposite side of the antibody's antigen-binding site, thus linkers are needed for the connection. The resulting fusion protein is composed of IL-2 followed by a linker region followed by an antibody heavy chain region. The linker region has to cover a distance that is of least 60 Angstroms (Å), thus different linker's length and also composition may be designed and tested for optimal connection.

The fusion molecule can also be IL-2 followed by the linker followed by the light chain of an antibody. In this type of fusion, the linker region has to cover a distance of at least 50 Angstroms (Å), thus also here several linker's length and composition may be designed and tested for finding the optimal candidates.

The sequence of the antibody heavy or light chain can be any of the antibodies that were generated using a human IgG1 Fc domain, as represented by SEQ ID NO: 93, and the variable domains as reported in Table 10.

The IL-2 sequence can be wt IL-2, represented by SEQ ID NO: 109 or aldesleukin, represented by SEQ ID NO: 110.

The linker sequences that can be used to connect the C-terminal end of IL-2 and the N-terminal residue of the antibody heavy or light chains are reported in Table 28.

TABLE 28

| Example of Linker's length and composition | |
|---|---|
| Linker | Sequence ID |
| (G4S)3 | SEQ ID NO: 397 |
| (G4S)4 | SEQ ID NO: 398 |
| (G4S)5 | SEQ ID NO: 399 |
| (G4S)6 | SEQ ID NO: 400 |
| (G4S)7 | SEQ ID NO: 401 |
| (G4S)8 | SEQ ID NO: 402 |
| (G4S)9 | SEQ ID NO: 403 |
| (G3S)4 | SEQ ID NO: 404 |
| (G3S)5 | SEQ ID NO: 405 |
| (G3S)6 | SEQ ID NO: 406 |
| (G3S)7 | SEQ ID NO: 407 |
| (G3S)8 | SEQ ID NO: 408 |
| (G3S)9 | SEQ ID NO: 409 |
| (G3S)10 | SEQ ID NO: 410 |
| (G3S)11 | SEQ ID NO: 411 |

Two specific fusion proteins were generated, according to Table 29.

TABLE 1

| Fusion proteins | | | |
|---|---|---|---|
| Designation | IL-2 | Linker | mAb |
| 107348 | Aldesleukin | (G4S)5, 25 aa (SEQ ID NO: 399) | VH5_D98E_VK1_D28Q-hIgG1 |
| 107350 | Aldesleukin | (G4S)7, 35 aa (SEQ ID NO: 401) | VH5_D98E_VK1_D28Q-hIgG1 |

Example 11: Generation of IL-2/Anti-IL-2 mAb Fusion Protein

Figure 9:
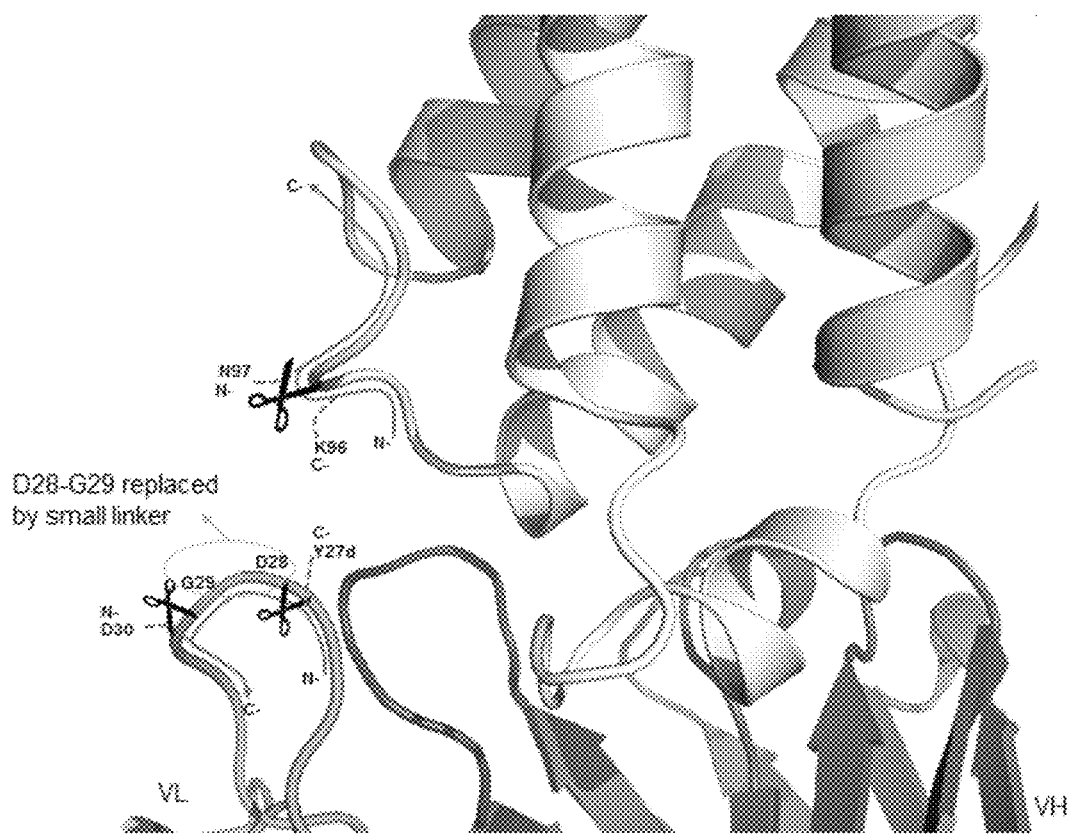
FIG. 9 and FIG. 10 is a schematic illustrating a fusion protein according to an embodiment.

The structure of the complex NARA1/hIL-2 has been used to guide the embedding of IL-2 into the heavy or light chain of NARA1 antibody. The LCDR1 of the antibody and the region connecting hIL-2 helix B and helix C between residue K96 and N97, can be identified as regions to be used for further engineering. The LCDR1 was opened between Y27d and D28 and between G29 and D30, numbering according to Kabat definition. hIL-2 was opened between K96 and N97. See FIG. 9.

Figure 10:
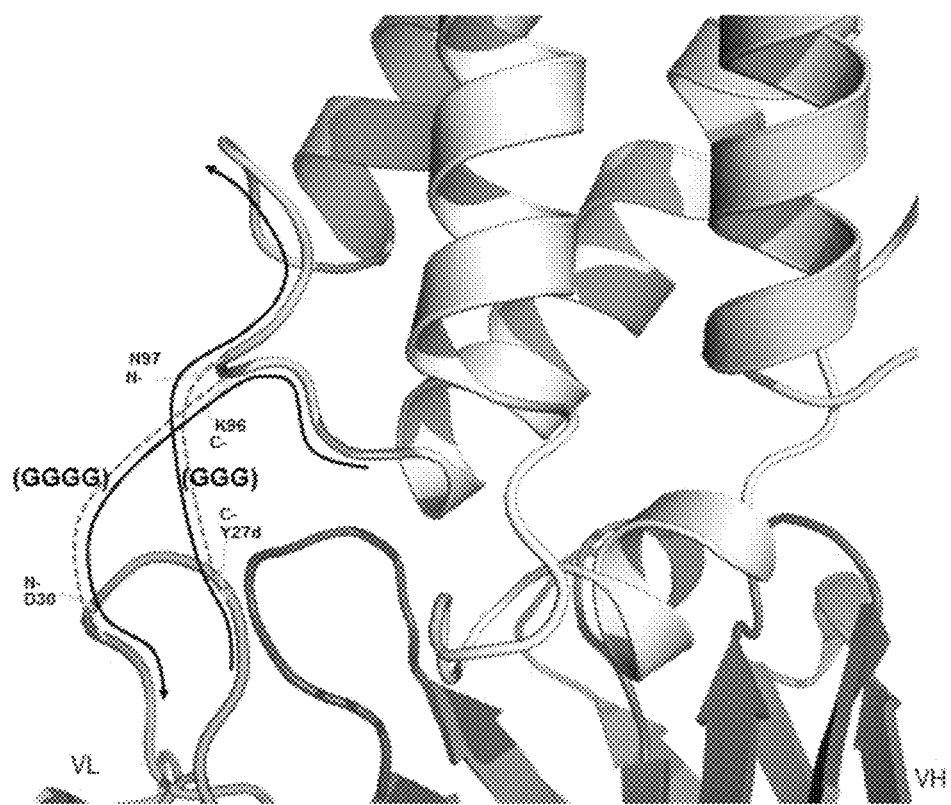
Figure 11:
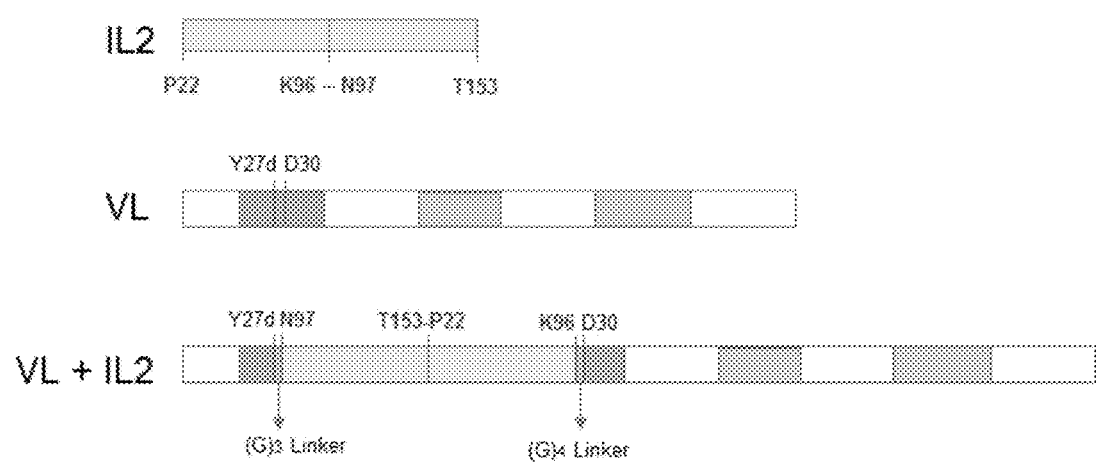
FIG. 11 illustrates alignment of a fusion protein according to an embodiment.
Figure 12:
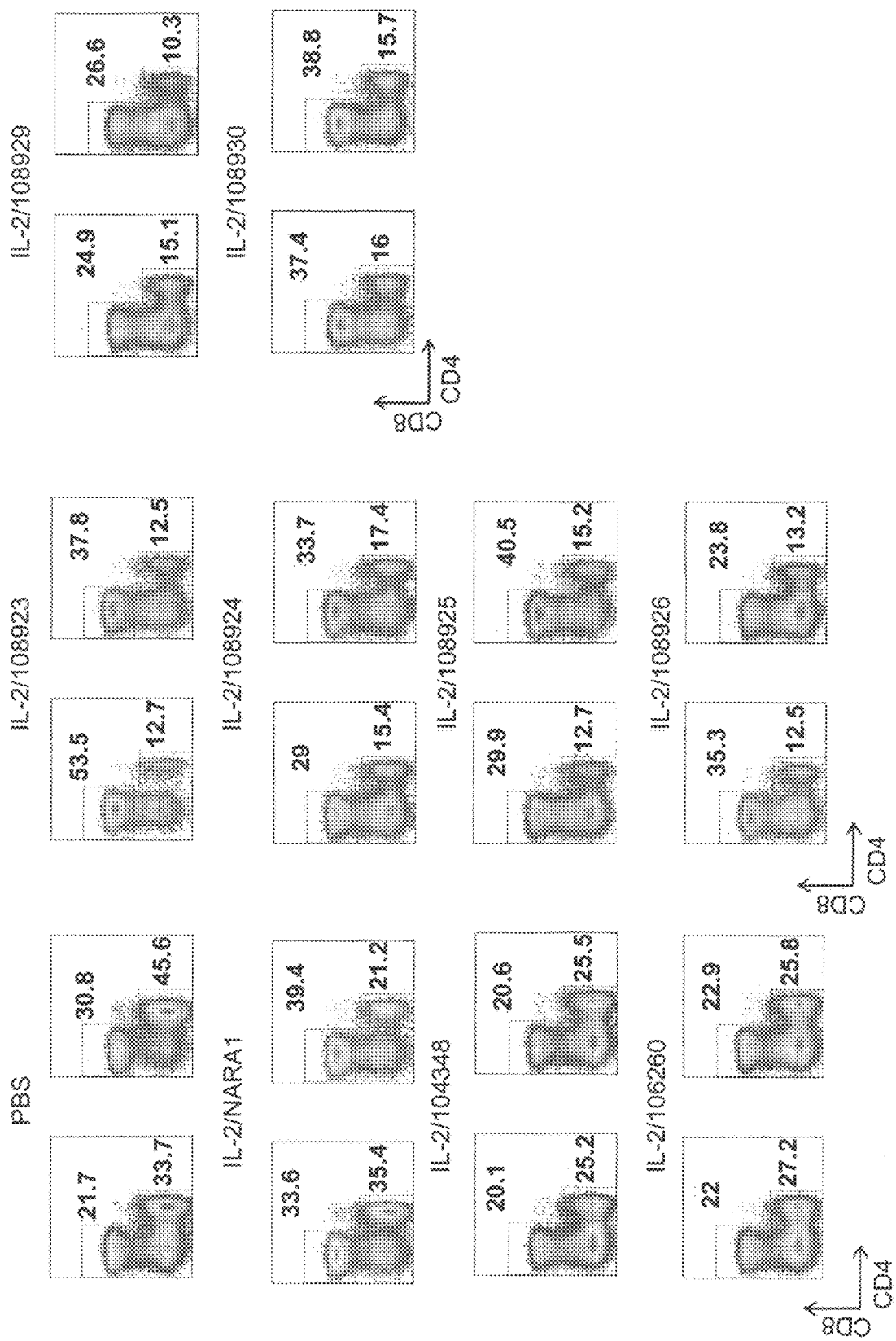
FIGS. 12 to 15 show phenotypic characterization of endogenous $CD8^+$ T cells, $CD8^+$ $CD44^+$ $CD122^+$ T cells, $CD4^+$ T cells, $CD4^+CD25^{high}Foxp3^+$ Treg cells and $CD3^-NK1.1^+$ NK cells from spleens of mice treated as in FIG. 6, according to an example.
Figure 13:
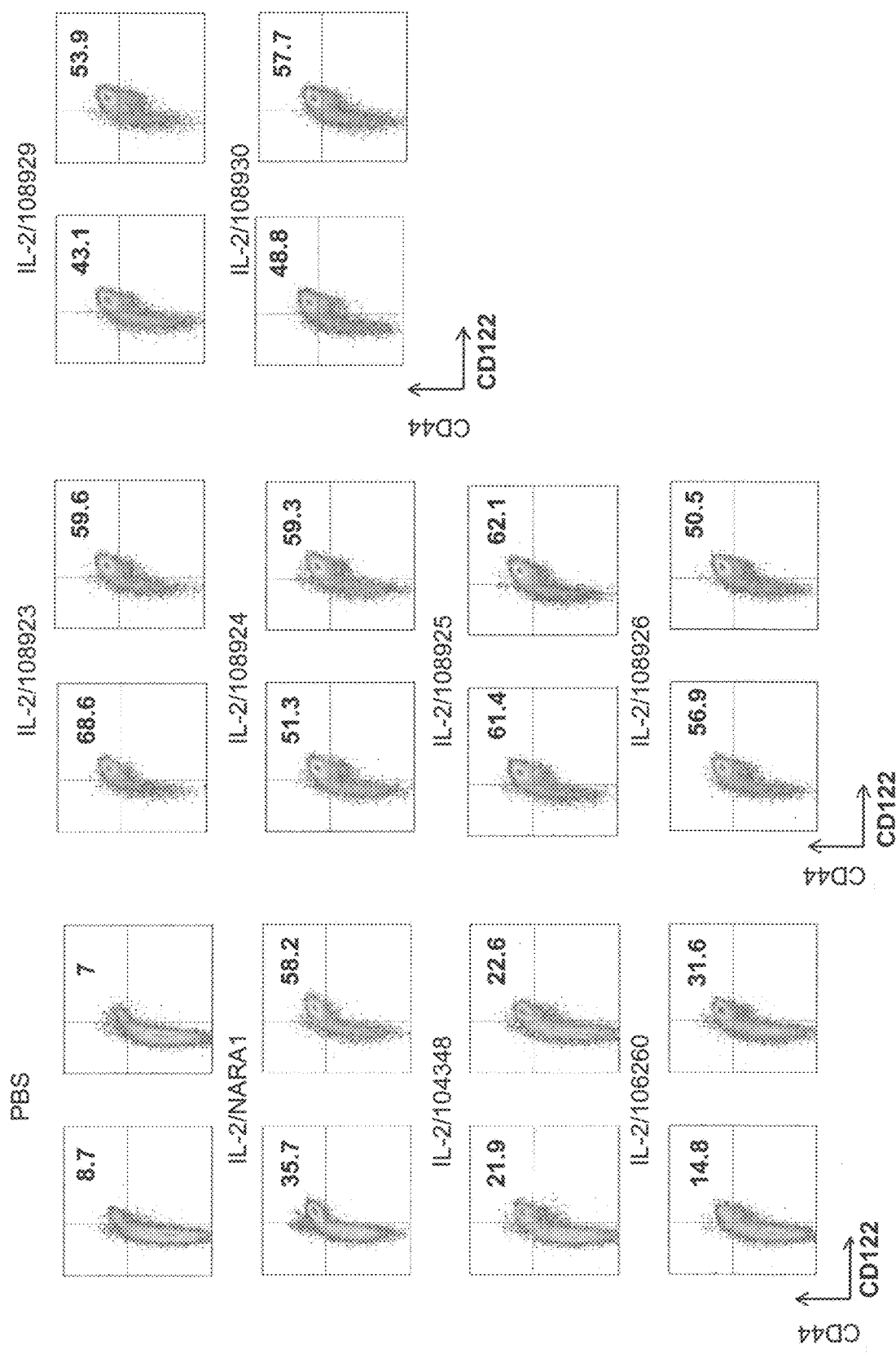
Figure 14:
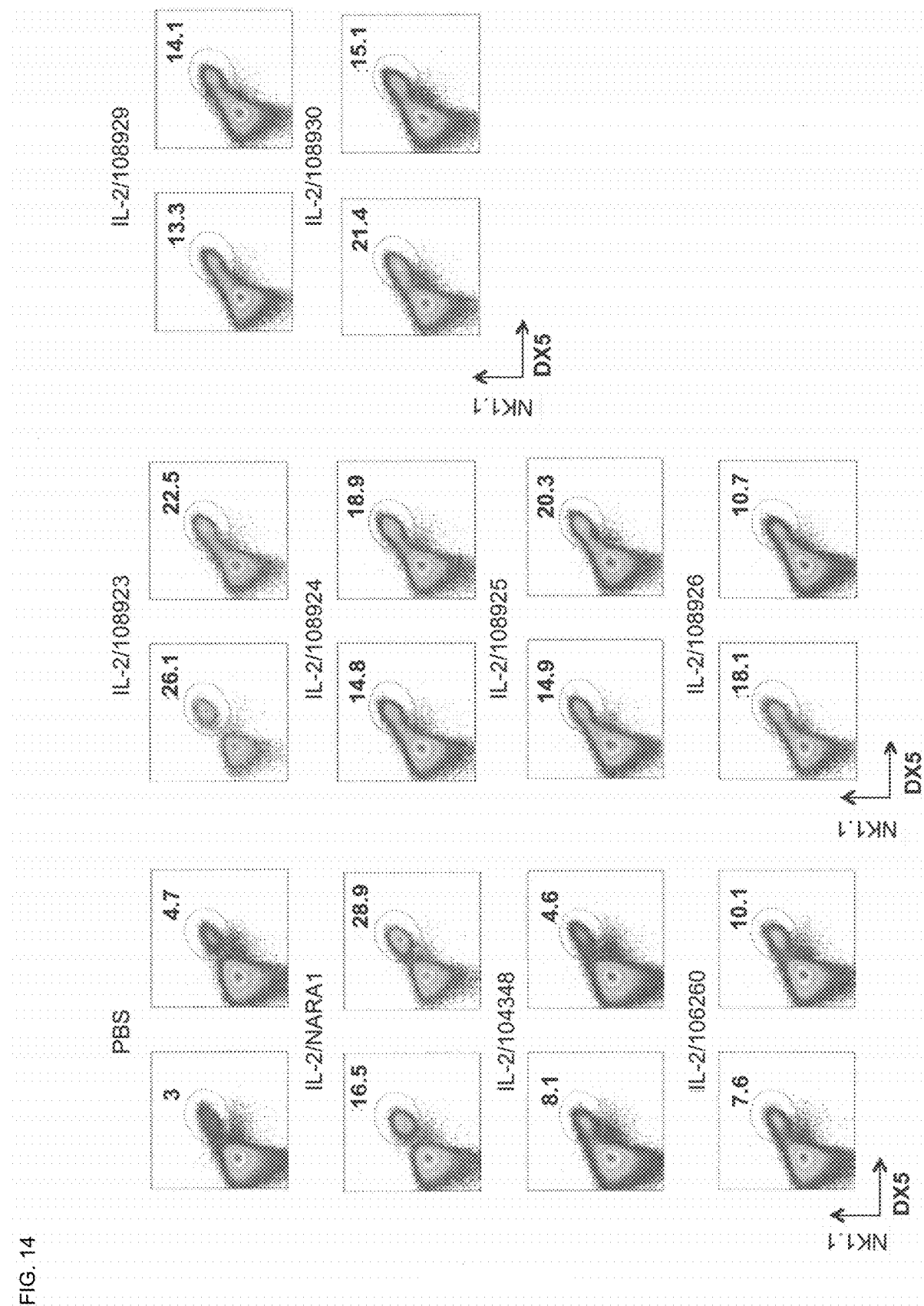
Figure 15:
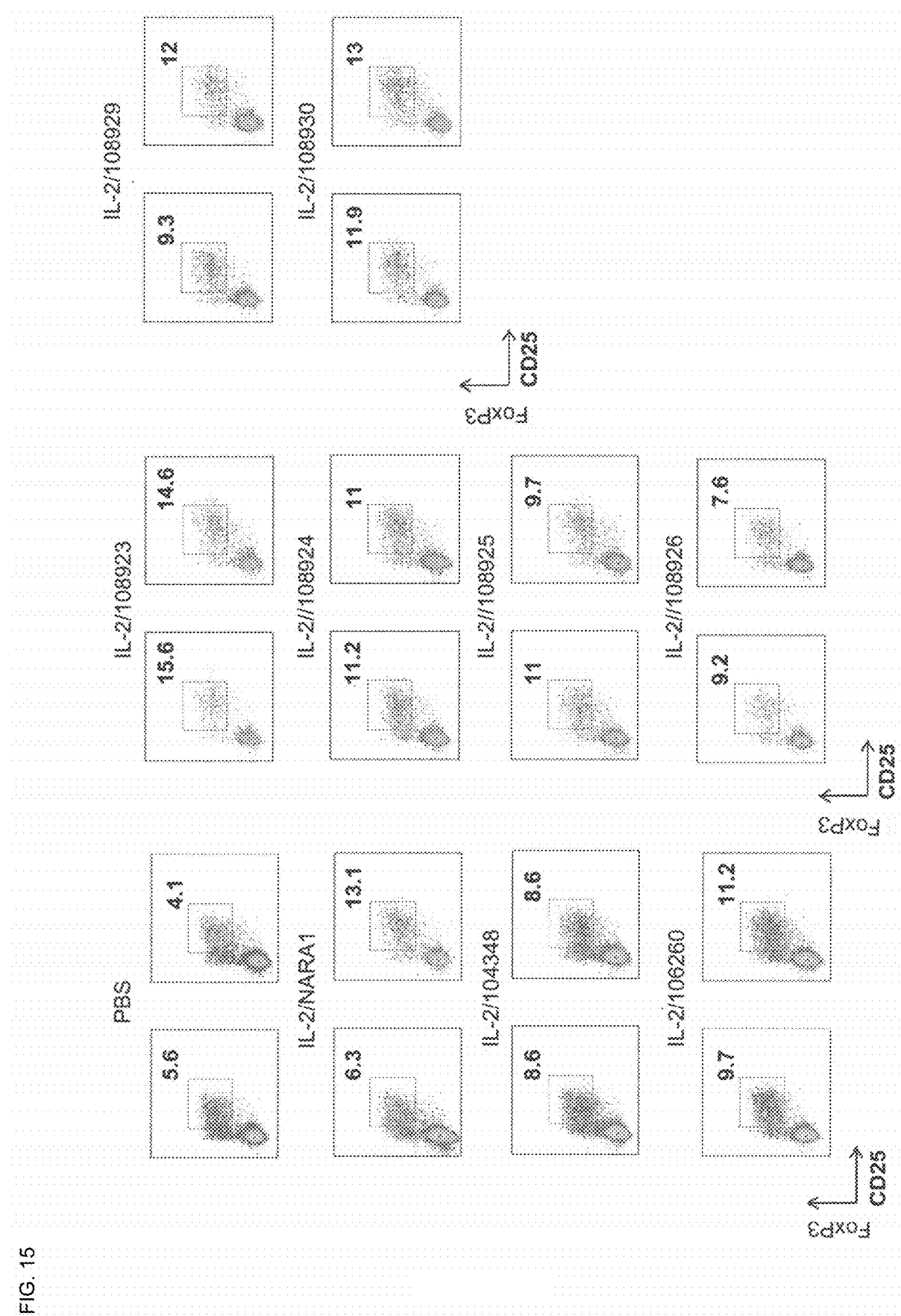

Residues D28G29 of LCDR1 of the antibody were replaced by Gs. hIL-2 new N-terminal end N97 is connected via a GGG linker to the new C-terminal end of LCDR1 Y27d. hIL-2 C-terminal end K96 is connected via a GGGG linker (SEQ ID NO: 412) to LCDR1 N-terminal D30. See FIG. 10. The two original N- and C-terminal ends of hIL-2 are connected together, i.e. IL-2-T153 C-terminal residue is directly fused to IL-2 N-terminal residue P22. FIG. 11 is a schematic overview of how the IL-2 and antibody VL sequences are fused together.

The resulting fusion protein was designated 107351.

This engineering procedure allowed hIL-2 to be completely embedded into the light chain of the NARA1 antibody. This embedding can be done by using any of the humanized sequences as reported in Table 10. The linker's sequence and length used to embed hIL-2 into the light chain may be a repetition of 1 to 10 of Glycine (G) (SEQ ID NO: 423), a fusion may be tested also in which LCDR1 Y27d and hIL-2 N97, LCDR1 D30 and hIL-2 K96 are directly connected without any linker sequence in between. The numbering of hIL-2 refers to the full length sequence as reported in SEQ ID: 109. The corresponding residues in aldesleukin, represented by SEQ ID NO: 110, can also be used for the embedding procedure.

Example 12: Activity of IL-2/Anti-IL-2 mAb Fusion Protein

The activity of some IL-2/anti-IL-2 mAb fusion proteins was evaluated in 7-day proliferation assay in human PBMC derived-CD8 T and NK cells.

Human PBMCs purified from buffy coats by Ficoll density gradient centrifugation were subjected to magnetic bead negative selection to isolate CD8+ T and NK cells. Cells were labelled with the CellTrace Violet Proliferation Kit and plated in 96 U-bottom plate at 50000 cells/well in RPMI 1640 Medium supplemented 10% fetal calf serum. Cells were then stimulated with hIL-2 or hIL-2/anti-IL-2 mAb complex (at a 2:1 molar ratio, 10-fold serial dilutions) and incubated for 7 days at 37° C. Proliferation was assessed by CellTrace Violet incorporation measured by FACS. The experiment was run in triplicates and average EC50 values were calculated from 3 independent experiments, and are shown in Table 30.

TABLE 2

CD8 T and NK cell proliferation data

| IL-2/anti-IL-2 mAb fusion protein | hCD8 T Cell Proliferation EC50 AVE (nM) | hNK Cell Proliferation EC50 AVE (nM) |
| --- | --- | --- |
| Proleukin® alone | 3.24 | 0.34 |
| 107348 [L25 = (G4S)5] (SEQ ID NO: 399) | >100 | 8.72 |
| 107350 [L35 = (G4S)7] (SEQ ID NO: 401) | >100 | 2.21 |
| 107351 [LCDR1 graft] | 3.79 | 0.15 |

The IL-2/anti-IL-2 mAb fusion proteins using linker sequences of 25 or 35 residues have limited to no activity on NK cell proliferation and CD8 T cell proliferation, respectively. In contrast, the IL-2/anti-IL-2 mAb fusion protein grafted to the light chain of a humanized NARA1 antibody is as potent as IL-2 alone to activate CD8 T cell proliferation and more potent than IL-2 to stimulate NK cell proliferation.

This latter fusion protein was subsequently evaluated in vivo. Mice received one single dose of 107351 (360 µg/kg, 720 µg/kg or 1440 µg/kg) or PBS and were sacrificed 96 h post-injection. Splenocytes were analyzed by flow cytometry following standard protocols, and the results are summarized in Table 31.

TABLE 31

CD8 T, NK and Treg cell counts

| Reagent | CD8+CD44+ T cell count AVE ($10^6$) | CD3−NK1.1+ NK cell count AVE ($10^6$) | CD4+CD25+FoxP3+ Treg cell count AVE ($10^6$) |
| --- | --- | --- | --- |
| PBS | 1.5 | 1.3 | 0.5 |
| 107351 (360 µg/kg) | 41.5 | 17.3 | 1.1 |
| 107351 (720 µg/kg) | 57.2 | 24.8 | 1.5 |
| 107351 (1440 µg/kg) | 65.5 | 26.3 | 2.6 |

The fusion protein 107351 can induce in a dose-dependent manner a robust expansion of CD8+ and NK cells with very limited activation of regulatory T cells in vivo.

Example 13: Evaluation of IL-2/Anti-IL-2 mAb Complex In Vivo (Humanized and Affinity-Matured Humanized Anti-hIL-2 Antibodies)

In order to evaluate the effect of IL-2/antiII-IL-2 mAb Complex in vivo two experimental approaches were performed. In the first one, counts of CD8+ T cells, CD4+ T cells, and NK cells were determined in WT C57BL/6 mice receiving two injections of IL-2/anti-IL-2 mAb complex as described below. In the second experiment the proliferation levels of CD8+ T cells, CD4+ T cells and NK cells were evaluated using BrdU after one single injection of IL-2/antiI-IL-2 mAb complexes.

(1) Materials and Methods

The following antibodies were used: NARA1, 104348, 106260, 108923, 108924, 108925, 108926, 108929, and 108930.

Proleukin® IL-2 was used.

In the first experiment mice received 2 injections at days 1 and 3 of hIL-2 at 1.5 g and hIL-2/monoclonal antibody (15 g, corresponding to a 1:1 molar ratio). At day 5 mice were sacrificed and spleens and lymph nodes (LNs) were analyzed by flow cytometry. To do so, single cell suspensions of LNs and spleens were prepared according to standard protocols and 2-3*10⁶ cells were stained for flow cytometry analysis using PBS with 2% fetal calf serum (FCS), 2 mM EDTA and fluorochrome-conjugated antibodies. The stain was done in order to identify and quantify CD4⁺ CD25⁺ forkhead box P3 (FoxP3)⁺ T regulatory cells (Tregs). To this end, single cell suspensions were stained using the FoxP3 staining buffer and following the supplier's recommendations (eBiosciences, 00-5523-00) and using fluorochrome-conjugated antibodies to the following markers: CD25, CD8a, CD44, CD122, NK1.1, DX5, CD4, CD3, FoxP3.

In the second experiment, mice received one single injection of hIL-2 at 1.5 g and hIL-2/monoclonal antibody (15 μg, corresponding to a 1:1 molar ratio). In parallel, BrdU was given in the drinking water at 0.8 mg/ml The following day (24 hours after injection and BrdU), stain was performed in order to identify and quantify cell proliferation of particular cell immune subsets whereby a fluorochrome-conjugated anti-BrdU antibody was used to stain cells that had proliferated. The BrdU stain was performed using the FITC BrdU kit and following the supplier's recommendations (BD Pharmingen, 51-2354 AK) and using fluorochrome-conjugated antibodies to the following markers: CD44, CD8a, CD4, NK1.1, CD3, CD122, Brdu, CD4.

Data was collected using a Becton Dickinson LSR Fortessa flow cytometer, well known to a person skilled in the art.

(2) Results

The results of the cell count data is shown in Table 32 and Table 33.

TABLE 34

Ratios of Cell count data

| | Ratio cell counts | |
|---|---|---|
| | CD3⁺ CD8⁺ CD44⁺/CD3⁺ | CD4⁺ FoxP3⁺ |
| PBS | 1.583781 | 1.783809 |
| IL-2/NARA1 (105192) | 6.665295 | 8.944873 |
| IL-2/104348 | 2.579217 | 2.717633 |
| IL-2/106260 | 1.594227 | 3.040019 |
| IL-2/108923 | 20.0742 | 13.36359 |
| IL-2/108924 | 9.511421 | 11.36187 |
| IL-2/108925 | 14.08746 | 18.35283 |
| IL-2/108926 | 18.86737 | 13.0982 |
| IL-2/108929 | 8.386427 | 12.5274 |
| IL-2/108930 | 10.20839 | 11.8301 |

As can be seen in Table 32, Table 33, and Table 34, the antibodies 104348, 106260, 108923, 108924, 108925, 108926, 108929 and 108930 in complex with IL-2 can preferentially stimulate CD8⁺ T cells and NK cells in vivo.

Figure 16:
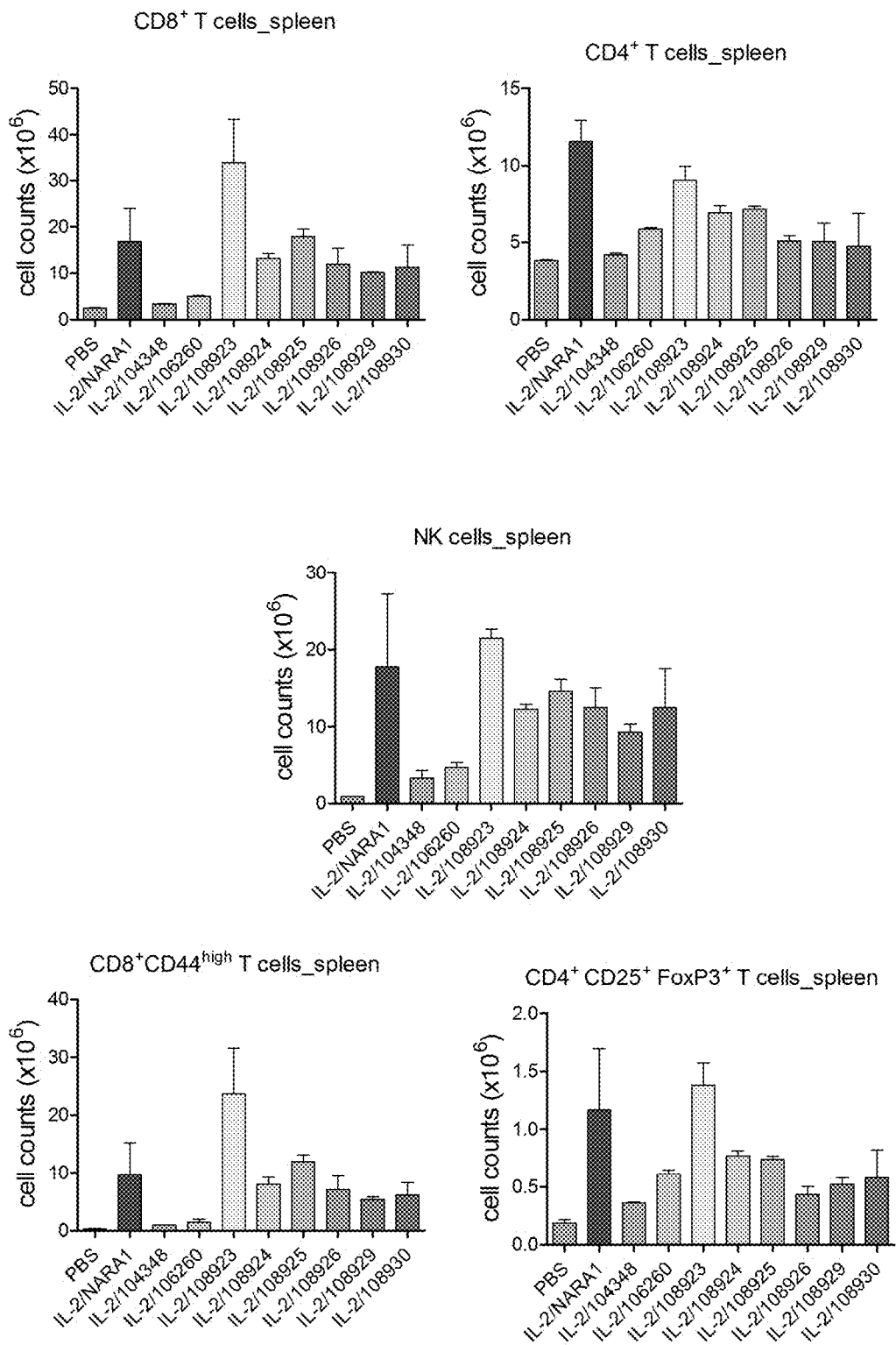
FIGS. 16 and 17 show the counts of immune cell subsets and CD8⁺CD44⁺ T cell-to-CD4⁺CD25$^{high}$Foxp3⁺ Treg cell ratios obtained from spleens of mice treated as in FIG. 6, according to an example.
Figure 17:
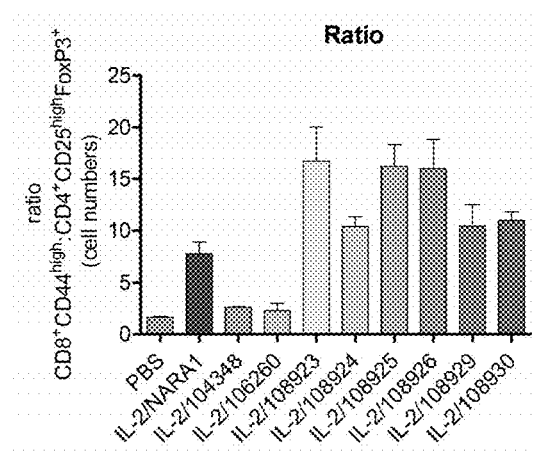
Figure 18:
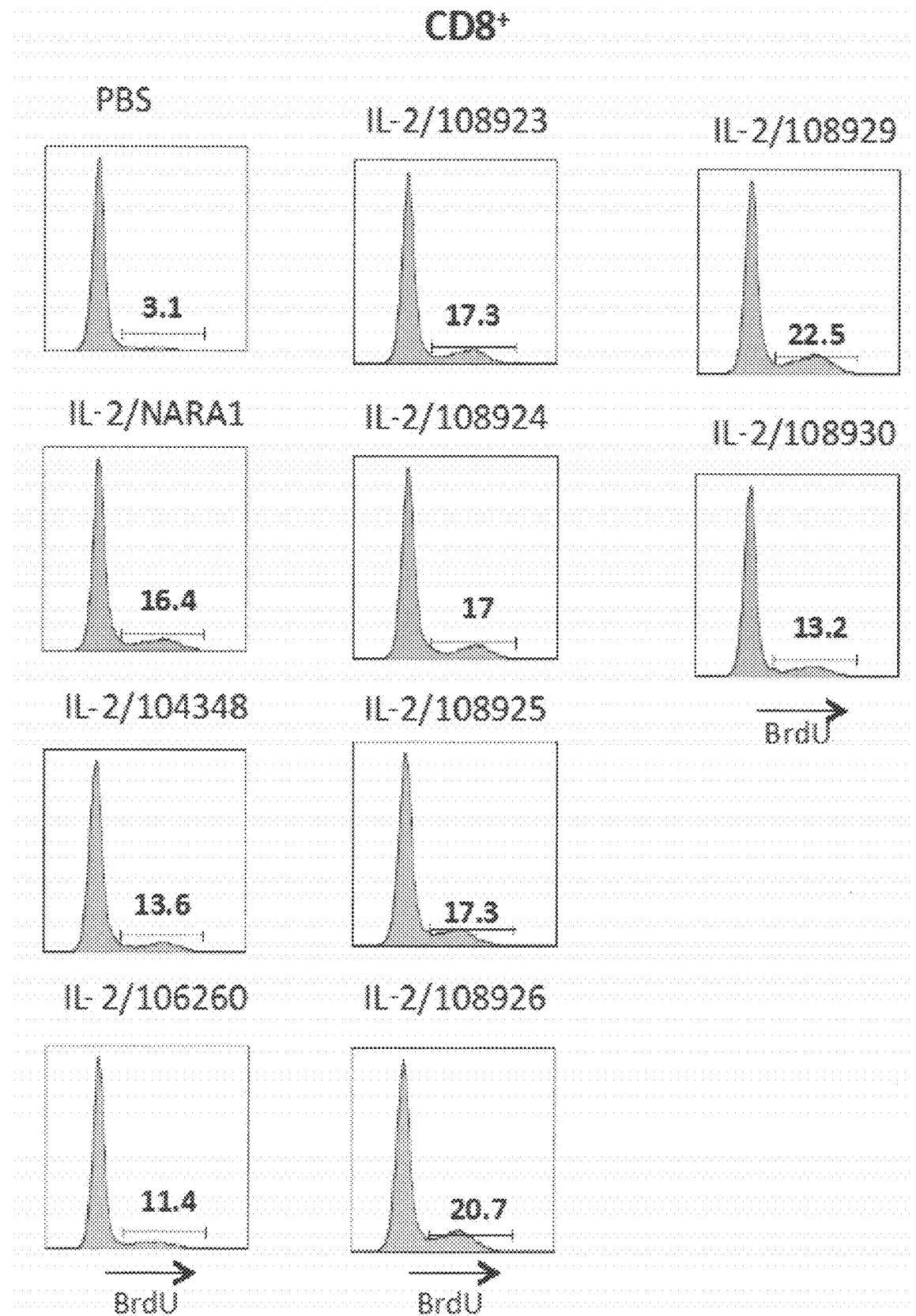
FIGS. 18 to 22 show representative BrdU profiles of CD8⁺, CD8⁺CD44⁺ CD122⁺ T cells, CD3⁻NK1.1⁺ DX5⁺ NK cells, CD4⁺ T cells and CD4⁺ CD25⁺ T cells, from spleens of mice treated as in FIG. 6, according to an example.
Figure 19:
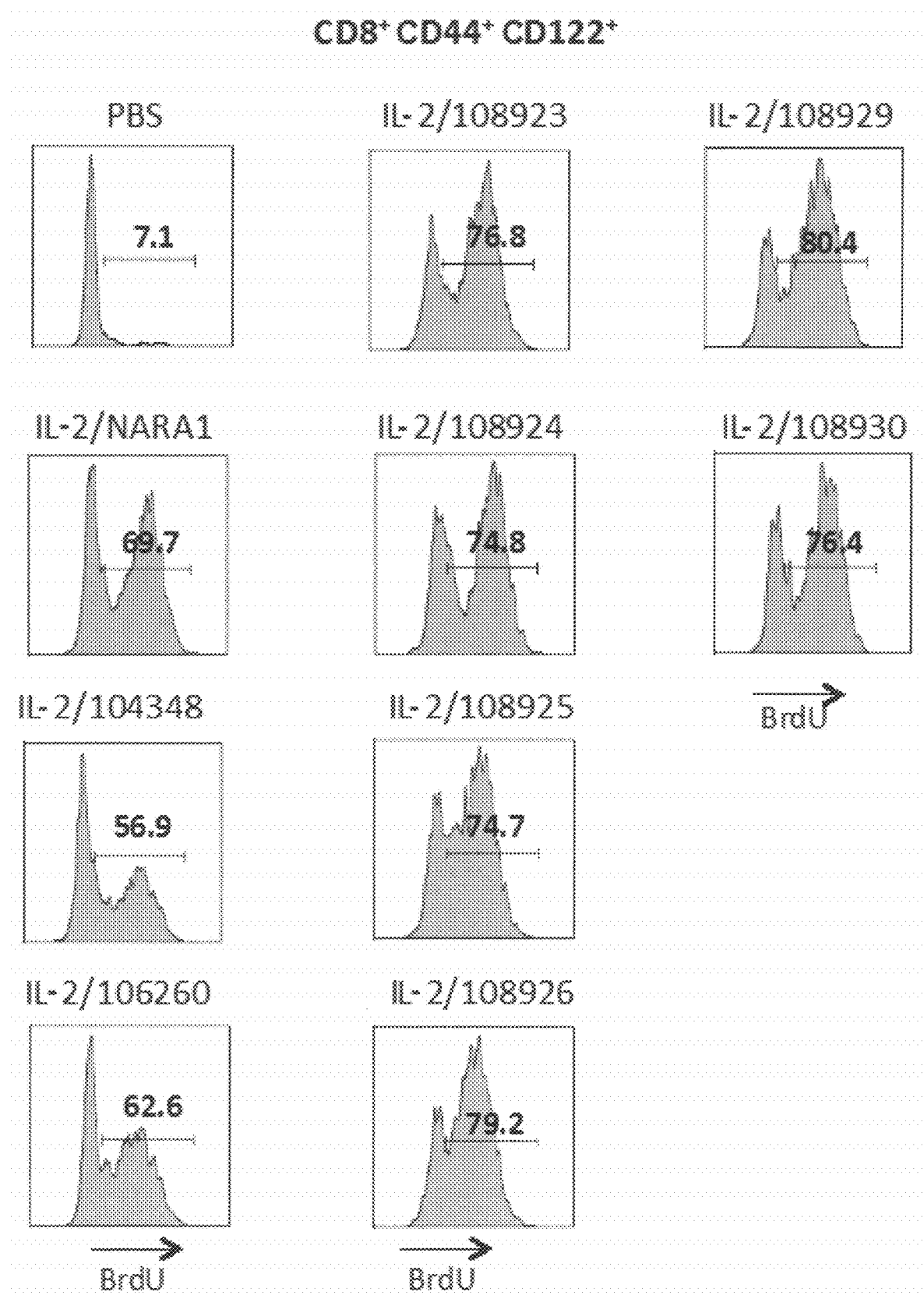
Figure 20:
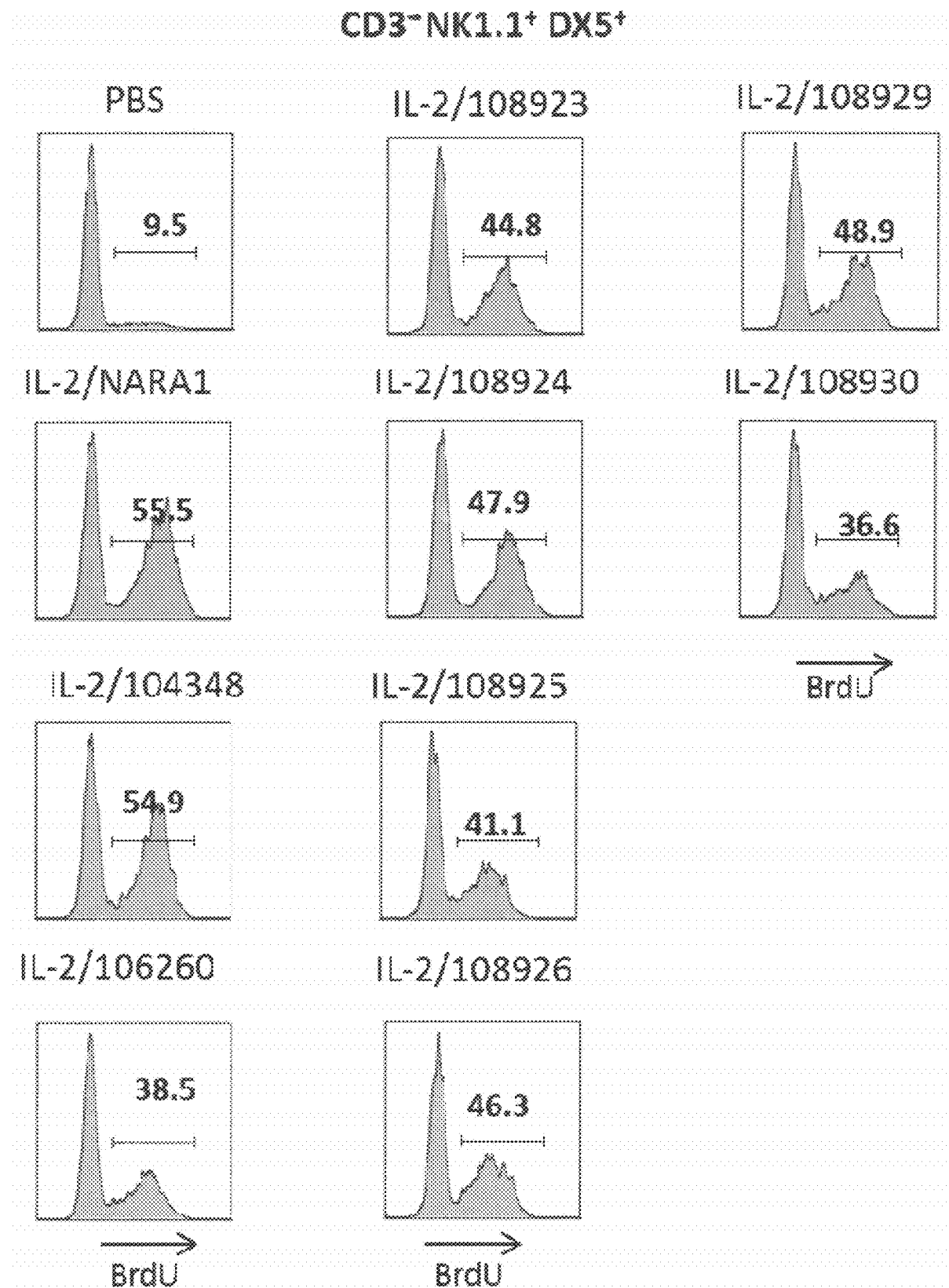
Figure 21:
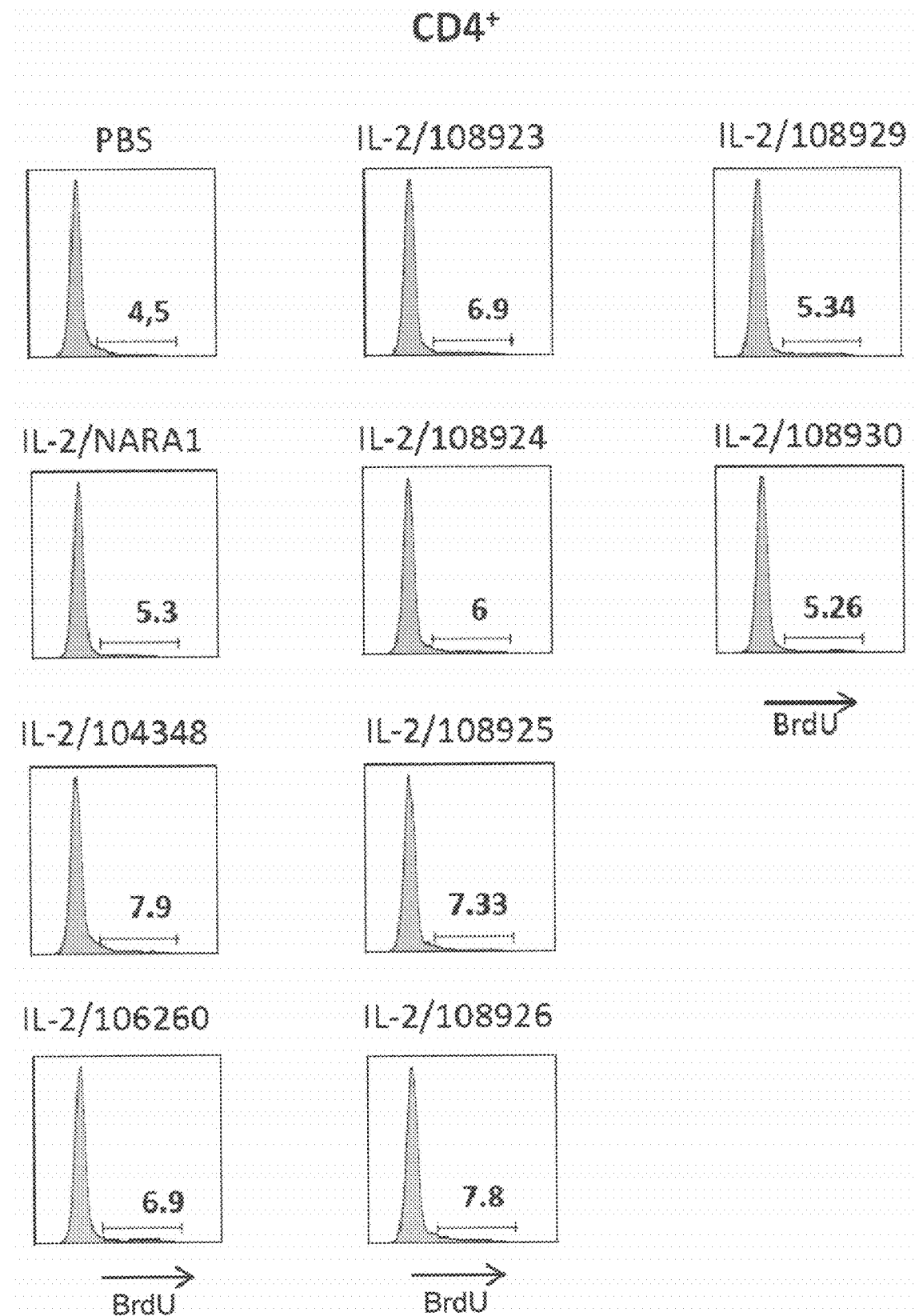
Figure 22:
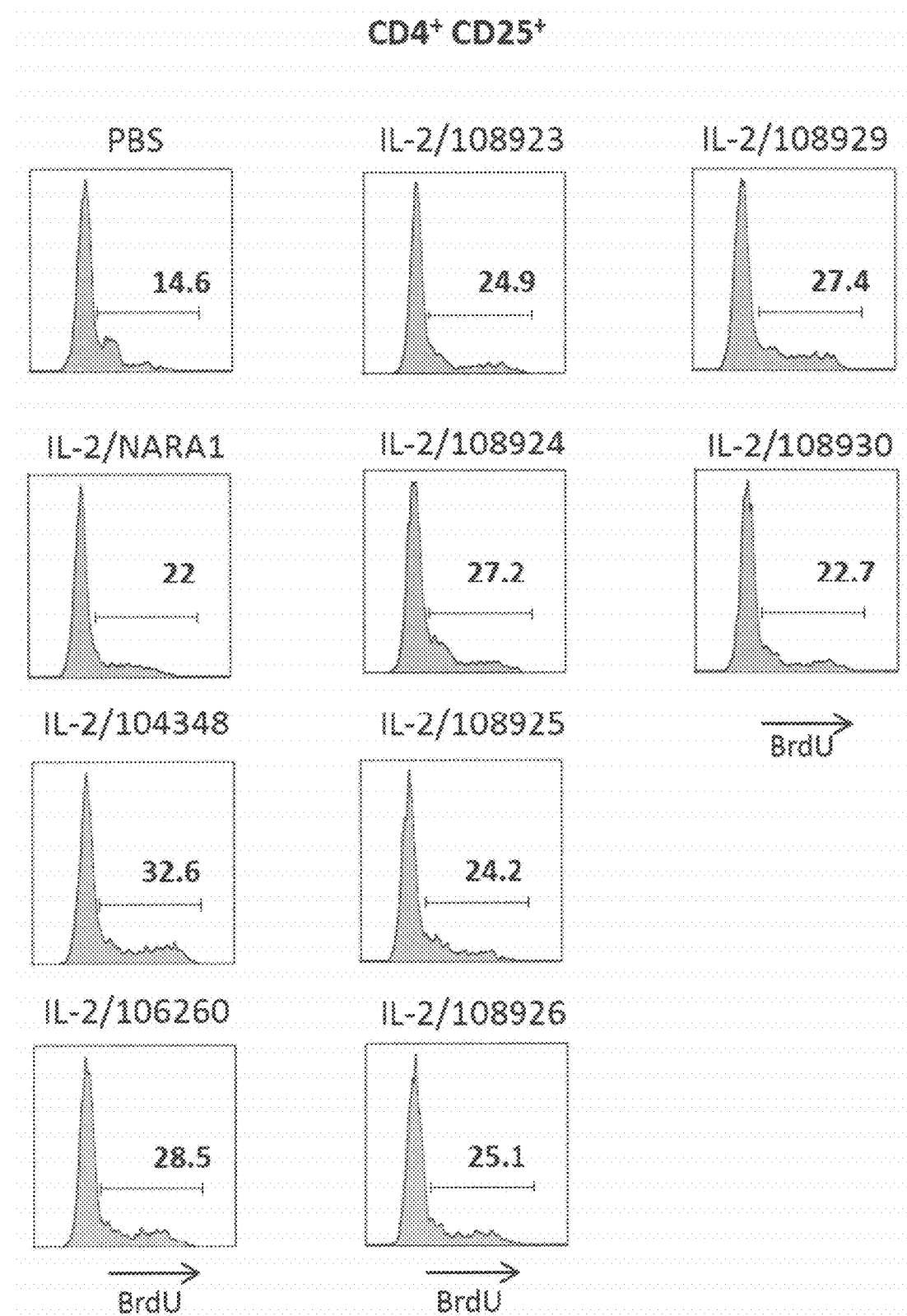

Also, FIGS. 12-15 show phenotypic characterization of endogenous CD8⁺, CD8⁺ CD44⁺ CD122⁺, CD4⁺ T cells, Treg cells and NK cells. FIGS. 16-17 show the number of immune cell subsets obtained in the spleen of mice; plotted values of Table 32, Table 33, and Table 34. FIGS. 18-22 show representative BrdU profiles of CD8⁺, CD8⁺ CD44⁺ CD122⁺ T cells, CD3⁻NK1.1⁺ DX5⁺NK cells, CD4⁺ and CD4⁺ CD25⁺ T cells, in the spleen of mice. As we can see the humanized antibodies 104348, 106260 and the affinity matured humanized antibodies 108923, 108924, 108925,

TABLE 32

Cell count data

| | Cell counts (×10⁶) | | | | | |
|---|---|---|---|---|---|---|
| | CD3⁺ CD8⁺ | | CD3⁺ CD4⁺ | | CD3⁻ NK1.1⁺ DX5⁺ | |
| PBS | 2.495371 | 2.543511 | 3.8753 | 3.765718 | 0.936491 | 0.865639 |
| IL-2/NARA1 (105192) | 9.711202 | 24.05544 | 10.23144 | 12.94353 | 8.302392 | 27.26912 |
| IL-2/104348 | 3.434657 | 3.326519 | 4.306137 | 4.117778 | 4.371078 | 2.262703 |
| IL-2/106260 | 4.819404 | 5.134374 | 5.958536 | 5.784579 | 4.108989 | 5.38501 |
| IL-2/108923 | 43.34794 | 24.56542 | 9.965975 | 8.123486 | 22.66742 | 20.29286 |
| IL-2/108924 | 12.17483 | 14.31066 | 6.465253 | 7.388885 | 11.60917 | 12.92698 |
| IL-2/108925 | 16.40202 | 19.57112 | 6.966743 | 7.345211 | 13.00835 | 16.15564 |
| IL-2/108926 | 15.40003 | 8.585168 | 5.453268 | 4.761522 | 15.08973 | 9.894915 |
| IL-2/108929 | 10.28953 | 10.05284 | 6.239835 | 3.892643 | 8.272205 | 10.35257 |
| IL-2/108930 | 16.0777 | 6.489082 | 6.878161 | 2.625737 | 17.55283 | 7.434181 |

TABLE 33

Cell count data

| | Cell counts (×10⁶) | | | |
|---|---|---|---|---|
| | CD3⁺ CD8⁺ CD44⁺ | | CD3⁺ CD4⁺ FoxP3⁺ | |
| PBS | 0.341866 | 0.278769 | 0.215854 | 0.1562773 |
| IL-2/NARA1 (105192) | 4.269044 | 15.16695 | 0.640488 | 1.695603 |
| IL-2/104348 | 0.950713 | 0.959035 | 0.368605 | 0.3528936 |
| IL-2/106260 | 0.918578 | 1.969546 | 0.57619 | 0.6478728 |
| IL-2/108923 | 31.60932 | 15.84961 | 1.574624 | 1.186029 |
| IL-2/108924 | 6.8873 | 9.234667 | 0.724108 | 0.8127773 |
| IL-2/108925 | 10.79581 | 13.11657 | 0.766342 | 0.7146891 |
| IL-2/108926 | 9.517218 | 4.714974 | 0.504427 | 0.359971 |
| IL-2/108929 | 4.882382 | 5.851761 | 0.582177 | 0.4671171 |
| IL-2/108930 | 8.355582 | 4.038156 | 0.818501 | 0.3413458 |

108926, 108929 and 108930 in complex with IL-2 enhance the proliferation levels of CD8⁺ T cells (especially of CD8⁺ CD44⁺ CD122⁺ T cells) and NK cells in vivo over CD4⁺ and CD4⁺ CD25⁺ T cells.

From these results we can conclude that the humanized antibodies 104348, 106260, and the affinity matured humanized antibodies 108923, 108924, 108925, 108926, 108929 and 108930 similar to the parental NARA1 antibody (105192), when mixed with hIL-2 (Proleukin), are able to preferentially stimulate CD8⁺ T cells and NK cells.

Example 14: Generation of Expression Plasmids of NARA1-Based Fusion Proteins

DNA sequences coding for human IL-2 (pORF-hIL-2 plasmid, Invivogen, porf-hIL-2) and the light chain of NARA1 were subcloned by cut and paste and ligated using standard cloning techniques (PCR amplification/assembly using phusion polymerase, Finnzymes, F-530S) adding within the primers the linkers aimed for (e.g 15, 20 or 25 amino acid linkers as shown in tables Table 35, Table 36, and Table 37). The resulting PCR products were inserted by cut and paste into expression vectors suitable for secretion in mammalian cells. The heavy chain of NARA1 and light chain of NARA1 fused to hIL-2 were cloned into individual expression vectors to allow co-transfection. Elements of the expression vector include a promoter (Cytomegalovirus (CMV) enhancer-promoter), a signal sequence to facilitate secretion, a polyadenylation signal and transcription terminator (Bovine Growth Hormone (BGH) gene), an element allowing episomal replication and replication in prokaryotes (e.g. SV40 origin and ColE1 or others known in the art) and elements to allow selection (ampicillin resistance gene and zeocin marker).

TABLE 35

| Light regions | |
|---|---|
| Light region | Sequence listing |
| IL-2-(G4S)$_3$- L (NARA1) | SEQ ID NO: 413 (DNA) |
| IL-2-(G4S)$_4$- L (NARA1) | SEQ ID NO: 414 (DNA) |
| IL-2-(G4S)$_5$- L (NARA1) | SEQ ID NO: 415 (DNA) |

Example 15: Expression and Purification of NARA1-Based Fusion Proteins

Chinese hamster Ovary (CHO) cells are one of the preferred host cell lines for transient expression of IgG proteins. Transfection is performed using PEI (Polyethylenimine, MW 25.000 linear, Polysciences, USA Cat. No. 23966) as transfection reagent. The PEI stock solution is prepared by carefully dissolving 1 g of PEI in 900 ml cell culture grade water at room temperature (RT). To facilitate dissolution of PEI, the solution is acidified by addition of HCl to pH 3-5, followed by neutralization with NaOH to a final pH of 7. Finally, the volume is adjusted to 1 L and the solution is filtered through a 0.22 µm filter, aliquoted and frozen at −80° C. until further use. CHO cells are cultivated using Power CHO-2D medium and ProCHO-4 medium (serum-free culture mediums for propagation and transfection respectively, 12-770Q and 12-029Q Lonza) with sodium hypoxanthine and thymidine (HT, 41065012, Invitrogen), L-Glutamine (17-605C, Lonza) and antibiotic-antimycotic (Ser. No. 15/240,062, ThermoFisher) as supplements. Cells prepared for transient transfections are cultivated in suspension culture on a shaker at 150 rpm. Cells in the seed cultures should be maintained in the exponential growth phase (cell densities between $1.5 \times 10^5$ and $3 \times 10^6$/mL) and display a viability of >98% for transfection. Cell densities outside of this range will result in either a lag phase after dilution or reduced transfection efficiency. For transfections an aliquot of cells is taken out of the seed cultures and adjusted to $2 \times 10^6$ cells/mL in 50% of the final volume with Power CHO-4 serum-free culture medium. The DNA solution (total DNA=125 ug for 100 ml scale, adjusted to 1:1 molar ratio of the heavy chain and the light chain(s) fused to IL-2) is prepared by diluting the DNA in 150 mM NaCL solution. Then PEI solution (0.5 ml for 100 ml scale) is added to the DNA solution. The mixture is vortexed and incubated for 10-12 min at room temperature. The transfection mix is then added to the cells and the cultivation of cells is continued for 3 to 4 hours. Finally, the remaining 50% of total production volume are achieved by addition of Power CHO-2D serum-free culture medium. The cell cultivation is continued for four to six days post transfection. The culture is harvested by centrifugation at 4700 rpm for 45 minutes at 4° C. (Heraeus®, Multifuge 3 S-R, Thermo Scientific, Rockford, Ill.). The cell supernatant recovered is sterile filtered through a stericup filter (0.22 µm) and stored at 4° C. with 2.5 mM ETDA and sodium azide (0.01%) until further processing.

Purification was performed using protein G agarose (20397, Thermo Scientific) at 4° C. Accordingly, three fusion proteins where the C terminus of IL-2 was fused to the N-terminus of the light chain of NARA1 with Glycin-Serin linkers of 15, 20 or 25 amino acids length were generated, as highlighted in Table 36. The heavy chain of NARA1 remains the same (SEQ ID NO: 115).

TABLE 36

| Light regions | |
|---|---|
| Light region | Sequence listing |
| IL-2-(G4S)$_3$- L (NARA1) | SEQ ID NO: 416 |
| IL-2-(G4S)$_4$- L (NARA1) | SEQ ID NO: 417 |
| IL-2-(G4S)$_5$- L (NARA1) | SEQ ID NO: 418 |

TABLE 37

| NARA1-based fusion protein | | | | |
|---|---|---|---|---|
| Fusion Protein | Light region | Light SEQ ID | Heavy region | Heavy SEQ ID |
| L15 | IL-2-(G4S)$_3$- L (NARA1) | SEQ ID NO: 416 (AA) | H1 | SEQ ID NO: 115 |
| L20 | IL-2-(G4S)$_4$- L (NARA1) | SEQ ID NO: 417 (AA) | H1 | SEQ ID NO: 115 |
| L25 | IL-2-(G4S)$_5$- L (NARA1) | SEQ ID NO: 418 (AA) | H1 | SEQ ID NO: 115 |

Example 16: Evaluation of the NARA1-Based Fusion Proteins In Vivo

Percentages and counts of CD8$^+$ T cells, CD4$^+$ T cells, and NK cells were determined in WT C57BL/6 mice receiving L15, L20, L25, or IL-2/NARA1 as described below. In parallel, the proliferation levels of CD8$^+$ T cells and NK cells were evaluated using bromodeoxyuridine (BrdU).

(1) Materials and Methods

The following antibodies and fusion proteins were used: NARA1. L15, L20 and L25. Recombinant human IL-2 (Teceleukin®) was used.

Mice received 3 consecutive injections of hIL-2 at 2 g (20'000 IU) with hIL-2/monoclonal antibody (NARA1, 10 µg, corresponding to a 2:1 molar ratio), L15, L20, L25 (the corresponding IL-2 amount in term of activity) or PBS. The day of the last injection BrdU was given in the drinking water at 0.8 mg/ml for 24 hours. The following day, mice were sacrificed and spleens and lymph nodes (LNs) were analyzed by flow cytometry. To do so, single cell suspensions of LNs and spleens were prepared according to standard protocols and 2*10$^6$ cells were stained for flow cytometry analysis using PBS with 2% fetal calf serum (FCS), 2 mM EDTA and fluorochrome-conjugated antibodies (see below).

Two different stains were performed: The first staining was done in order to identify and quantify CD4$^+$ CD25$^+$ forkhead box P3 (FoxP3)$^+$ T regulatory cells. To this end, single cell suspensions were stained using the FoxP3 staining buffer and following the supplier's recommendations (eBiosciences, 00-5523-00) and using fluorochrome-conjugated antibodies to the following markers: CD25, CD8a, CD4, CD3, FoxP3. A second staining was performed in order to identify and quantify cell proliferation of particular cell subsets whereby a fluorochrome-conjugated anti-BrdU antibody was used to stain cells that had proliferated. The BrdU stain was performed using the FITC BrdU kit and following the supplier's recommendations (BD Pharmingen, 51-2354 AK) and using fluorochrome-conjugated antibodies to the following markers: CD44, CD8a, CD4, NK1.1, CD3, CD122, Brdu.

Data was collected using a Becton Dickinson LSR Fortessa flow cytometer, well known to a person skilled in the art.

(2) Results

The results of the cell count data are shown in Table 38.

TABLE 38

| | Cell counts | | | | | |
|---|---|---|---|---|---|---|
| | CD8$^+$CD44$^+$ | | CD3$^-$NK1.1$^+$DX5$^+$ | | CD4$^+$CD25$^+$FoxP3$^+$ | |
| PBS | 2.988014 | 1.905477 | 2.636173 | 2.153964 | 1.704692 | 1.612001 |
| hIL-2/NARA1 | 11.58204 | 12.41452 | 4.885715 | 5.945634 | 3.763952 | 4.461254 |
| L15 | 21.08623 | 9.229327 | 6.761334 | 4.056121 | 8.416243 | 7.998698 |
| L20 | 12.9221 | 15.2443 | 7.870497 | 6.671924 | 8.024002 | 3.606802 |
| L25 | 12.36608 | 14.4394 | 6.9261 | 6.736377 | 7.07191 | 5.494133 |

As can be seen in the Table 38 the fusion proteins L15, L20 and L25 can stimulate CD8$^+$ T cells and NK cells in vivo.

Figure 23:
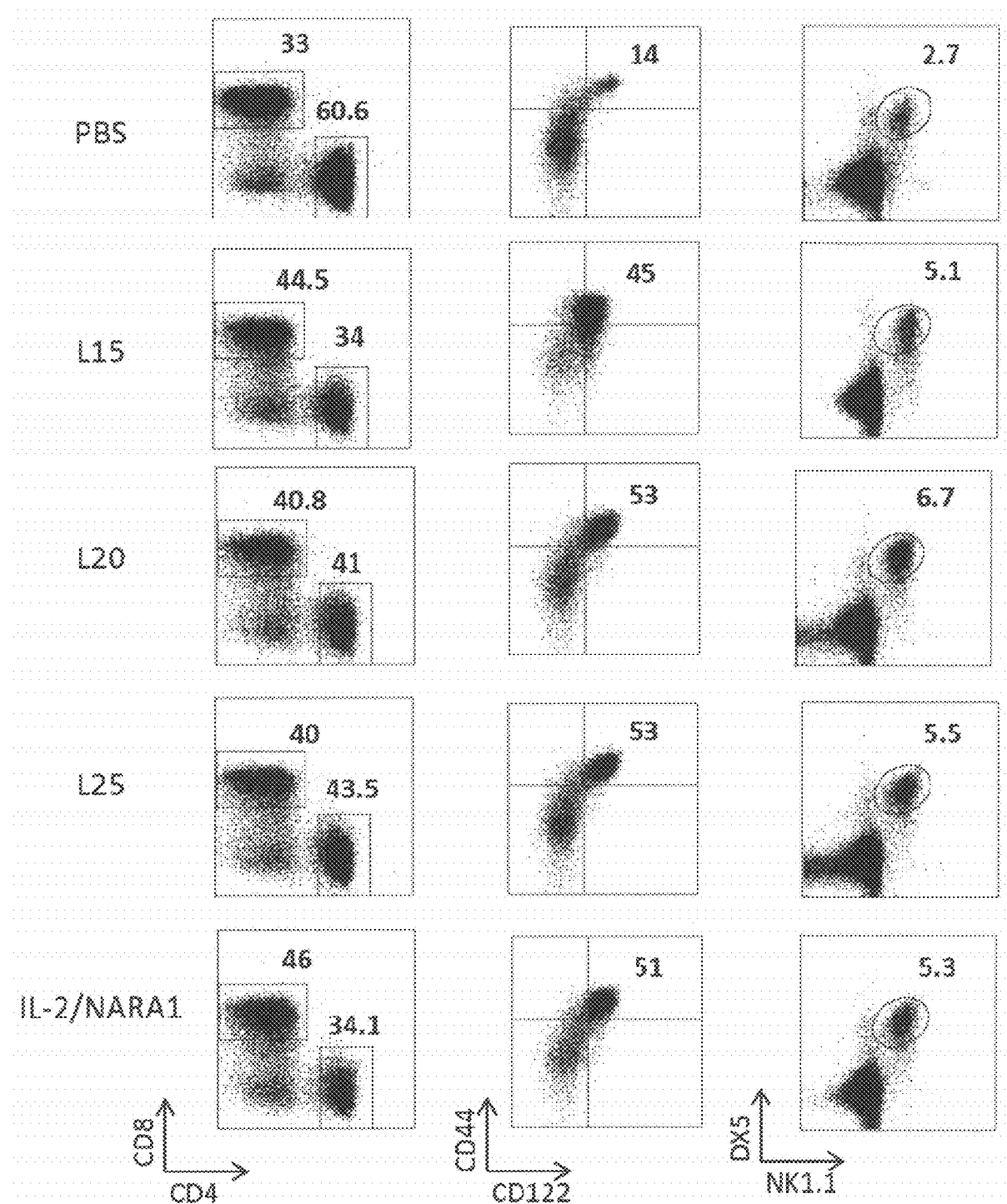
FIG. 23 shows phenotypic characterization of endogenous CD8⁺ T cells and NK cells from spleens of mice receiving PBS, fusion proteins L15, L20 or L25, or human IL-2/NARA1 complexes, according to an example.
Figure 24:
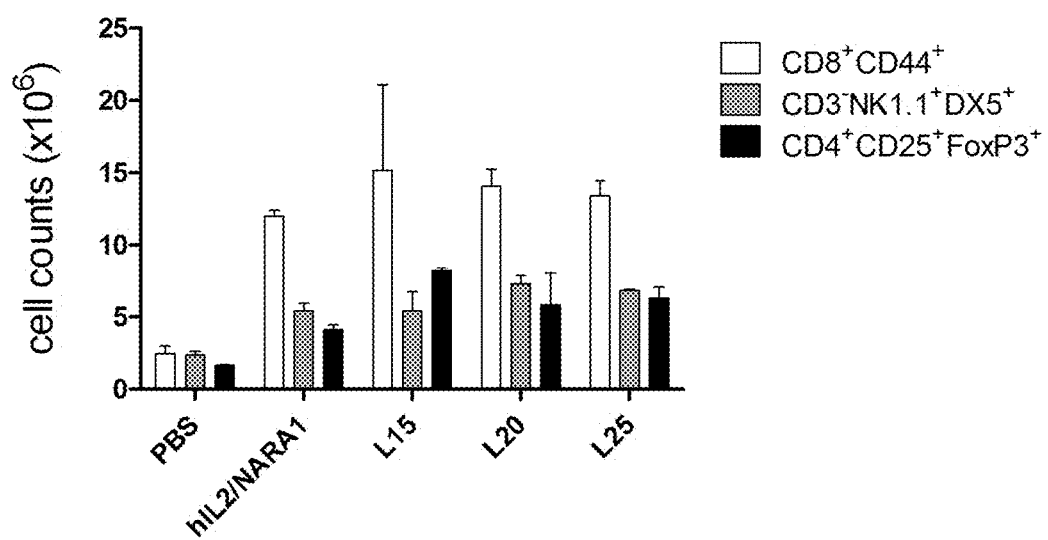
FIG. 24 shows the cell counts of the indicated immune cells obtained from spleens of mice treated as in FIG. 23, according to an example.
Figure 25:
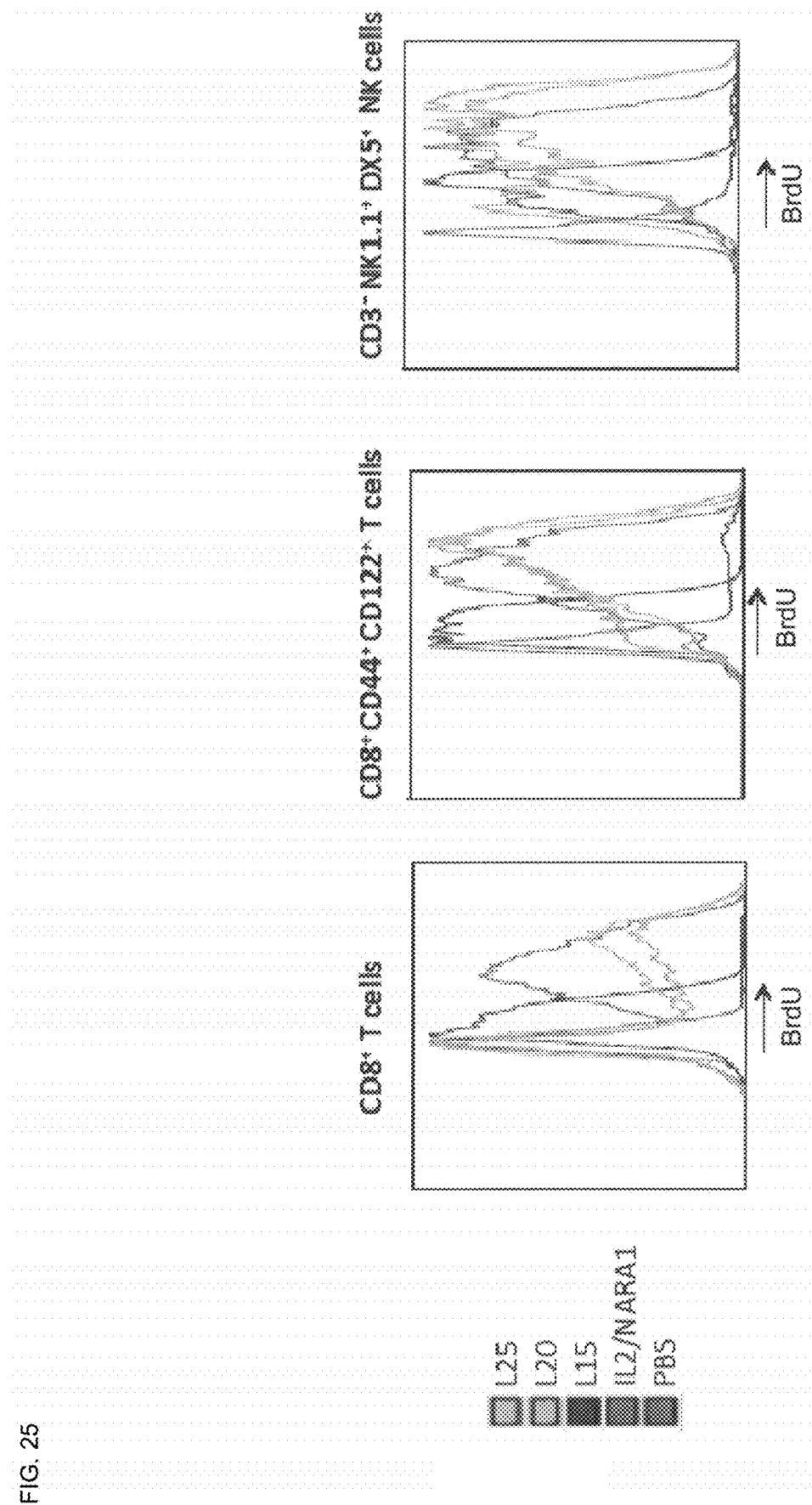
FIG. 25 shows representative BrdU profiles of CD8⁺ CD44⁺ CD122⁺ T cells and CD3⁻NK1.1⁺NK cells from spleens of mice treated as in FIG. 23, according to an example.

Also, FIG. 23 shows phenotypic characterization of endogenous CD8$^+$ T cells and NK cells. FIG. 24 shows the number of immune cells obtained in the spleen of mice, plotted values of Table 38. FIG. 25 shows representative BrdU profiles of CD8$^+$ CD44$^+$ CD122$^+$ T cells and CD3$^-$ NK1.1$^+$ NK cells in the spleen of mice. From these results we can conclude that the NARA1-based fusion proteins are able to preferentially stimulate CD8$^+$ T cells and NK cells, similar to the parental NARA1 antibody in combination with human IL-2.

Example 17: Evaluation of the NARA1-Based Fusion Proteins In Vitro

The activity of NARA1-based fusion proteins was compared to NARA1 and IL-2 alone in a cell proliferation assay using CTLL-2 murine cell lines responsive to human IL-2.

CTLL-2 cells were seeded into 96-well plates (10000 cells/well) and stimulated using, hIL-2, or hIL-2/NARA1 complex (2:1 molar ratio), L15, L20 or L25 (the corresponding IL-2 amount) and proliferation was assessed after 48 hours of incubation at 37° C. Proliferation was assessed by adding WST-1 (Sigma-Aldrich) for the least 4 hours to the cells, followed by reading at 450 nm on an iMark microplate reader.

The experiment was run in duplicates and Table 39 provides the EC50 values obtained.

TABLE 39

| CTTL-2 cell proliferation data (EC50) | | | | | |
|---|---|---|---|---|---|
| | L15 | L20 | L25 | hIL-2 | hIL-2/Nara1 |
| EC50 (ng/ml) | 2.7 | 1.6 | 2.6 | 0.8 | 0.7 |

As seen in Table 39 the NARA1-based fusion proteins have the ability to induce CTLL-2 cell proliferation in vitro but to a lower extent compared to hIL-2 and hIL-2/NARA1.

Figure 26:
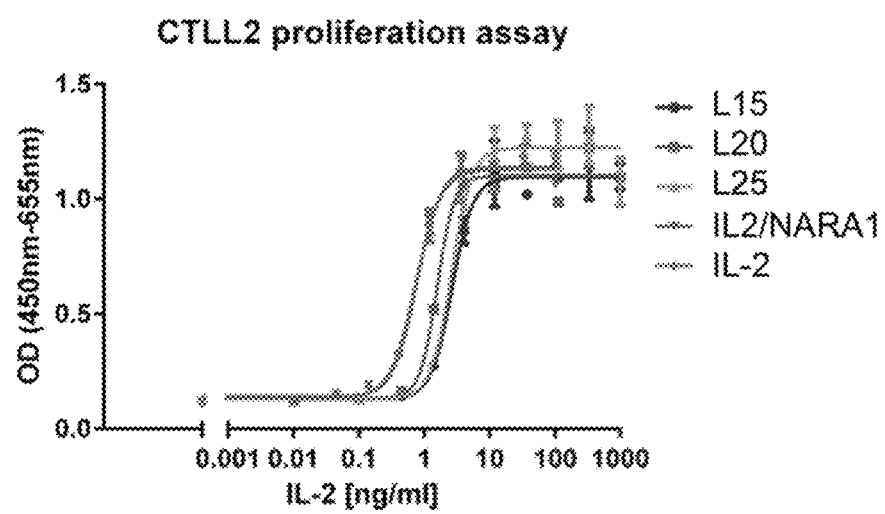
FIG. 26 shows CTLL-2 cell proliferation curves from in vitro experiments using CTLL-2 cells stimulated with titrated doses of the fusion proteins L15, L20 or L25, of human IL-2/NARA1 complexes, or of human IL-2, according to an example.

Also, FIG. 26 shows the proliferation curves obtained.

The activity of the NARA1-based fusion proteins was compared to NARA1 and IL-2 alone in a STAT5 phosphorylation (P-STAT5) assay using CTLL-2 murine cell lines responsive to human IL-2. CTLL-2 (200000 cells/well) were seeded in 96-well plates and stimulated using hIL-2 hIL-2/NARA1 complex (at 2:1 molar ratio), L15, L20 or L25 (the corresponding IL-2 amount). Phosphorylation of STAT5 was assessed after 15 minutes of stimulation and detected using intracellular staining with pSTAT5-specific mAbs (BD Biosciences).

The experiment was run in duplicates and Table 40 provides the EC50 values obtained.

TABLE 40

| P-STAT5 (EC50) | | | | | |
|---|---|---|---|---|---|
| | hIL-2 | hIL-2/NARA1 | L15 | L20 | L25 |
| EC50 (ng/ml) | 1.03 | 1.4 | 107.2 | ~426.6 | ~434.8 |

Figure 27:
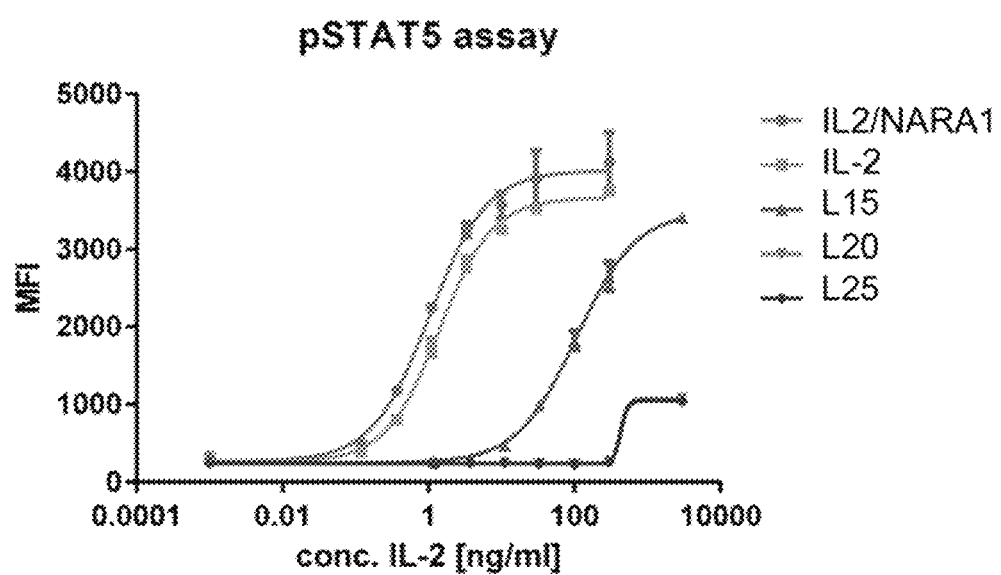
FIG. 27 shows STAT5 phosphorylation levels of CTLL-2 cells stimulated with titrated doses of human IL-2/NARA1 complexes, of human IL-2, or of the fusion proteins L15, L20 or L25, according to an example.

Also, FIG. 27 provides the phosphorylation levels obtained. As observed the in vitro effect obtained on cells expressing high CD25 levels such as CTLL-2 cells is lower when stimulating the cells with L15, L20 and L25 than with IL-2 or IL-2/NARA1. This difference is more prominent for a short time (such as 15 minutes stimulation for P-STAT5). Indeed, with the shortest linker: L15, IL-2 might dissociate easier to NARA1 allowing the stimulation of cells in a short time. On the other hand, for the fusions L20 and L25, IL-2 might remain bound longer to NARA1 preventing the stimulation of CTLL-2 cells.

Sequence Table

Useful amino acids and nucleotide sequences for practicing the invention are found in Table 41. Throughout the text of this application, should there be a discrepancy between the text of the specification (e.g., Table 41) and the sequence listing, the text of the specification shall prevail.

TABLE 41

| Sequence list | | | |
|---|---|---|---|
| >VH1 | | | |
| SEQ ID NO: 1 (Combined) | HCDR1 | | GYAFTNYLIE |
| SEQ ID NO: 2 (Combined) | HCDR2 | | VINPGSGGTNYNEKFKG |
| SEQ ID NO: 3 (Combined) | HCDR3 | | WRGDGYYAYFDV |
| SEQ ID NO: 4 (Kabat) | HCDR1 | | NYLIE |
| SEQ ID NO: 2 (Kabat) | HCDR2 | | VINPGSGGTNYNEKFKG |
| SEQ ID NO: 3 (Kabat) | HCDR3 | | WRGDGYYAYFDV |
| SEQ ID NO: 5 (Chothia) | HCDR1 | | GYAFTNY |
| SEQ ID NO: 6 (Chothia) | HCDR2 | | NPGSGG |
| SEQ ID NO: 3 (Chothia) | HCDR3 | | WRGDGYYAYFDV |
| SEQ ID NO: 7 | VH | | QVQLVQSGAEVKKPGSSVKVSCKASGYAFTNYLIEWVR QAPGQGLEWMGVINPGSGGTNYNEKFKGRVTITADKS TSTAYMELSSLRSEDTAVYYCARWRGDGYYAYFDVWG QGTTVTVSS |
| SEQ ID NO: 8 | DNA VH | | CAAGTGCAGCTGGTGCAGTCTGGCGCTGAAGTGAAG AAACCCGGCTCCTCCGTGAAAGTGTCCTGCAAGGCCT CCGGCTACGCCTTCACCAACTACCTGATCGAGTGGGTC CGACAGGCCCCAGGCCAGGGCCTGGAGTGGATGGGC GTGATCAACCCTGGCTCCGGCGGCACCAACTACAACG AGAAGTTCAAGGGCAGAGTGACCATCACCGCCGACAA GTCCACCTCCACCGCCTACATGGAACTGTCCTCCCTGC GGAGCGAGGACACCGCCGTGTACTACTGTGCCCGGTG GCGGGGAGATGGCTACTACGCCTACTTCGACGTGTGG GGCCAGGGCACCACCGTGACCGTGTCCTCT |
| >VH3 | | | |
| SEQ ID NO: 1 (Combined) | HCDR1 | | GYAFTNYLIE |
| SEQ ID NO: 2 (Combined) | HCDR2 | | VINPGSGGTNYNEKFKG |
| SEQ ID NO: 3 (Combined) | HCDR3 | | WRGDGYYAYFDV |
| SEQ ID NO: 4 (Kabat) | HCDR1 | | NYLIE |
| SEQ ID NO: 2 (Kabat) | HCDR2 | | VINPGSGGTNYNEKFKG |
| SEQ ID NO: 3 (Kabat) | HCDR3 | | WRGDGYYAYFDV |
| SEQ ID NO: 5 (Chothia) | HCDR1 | | GYAFTNY |
| SEQ ID NO: 6 (Chothia) | HCDR2 | | NPGSGG |
| SEQ ID NO: 3 (Chothia) | HCDR3 | | WRGDGYYAYFDV |
| SEQ ID NO: 9 | VH | | QVQLVESGGGVVQPGRSLRLSCAASGYAFTNYLIEWVR QAPGKGLEWVAVINPGSGGTNYNEKFKGRFTISADKSKS TAYLQMNSLRAEDTAVYYCARWRGDGYYAYFDVWGQ GTTVTVSS |
| SEQ ID NO: 10 | DNA VH | | CAGGTGCAGCTGGTGGAGAGCGGCGGCGGCGTGGTG CAGCCCGGCCGGAGCCTGCGGCTGAGCTGCGCCGCC AGCGGCTACGCCTTCACCAACTACCTGATCGAGTGGG TGCGGCAGGCCCCCGGCAAGGGCCTGGAGTGGGTGG CCGTGATCAACCCCGGCAGCGGCGGCACCAACTACAA CGAGAAGTTCAAGGGCCGGTTCACCATCAGCGCCGAC AAGAGCAAGAGCACCGCCTACCTGCAGATGAACAGCC TGCGGGCCGAGGACACCGCCGTGTACTACTGCGCCCG GTGGCGGGGCGACGGCTACTACGCCTACTTCGACGTG TGGGGCCAGGGCACCACCGTGACCGTGAGCAGC |
| >VH3s | | | |
| SEQ ID NO: 11 (Combined) | HCDR1 | | GYTFSSYLIE |
| SEQ ID NO: 12 (Combined) | HCDR2 | | VINPGSGGTNYADSVKG |
| SEQ ID NO: 3 (Combined) | HCDR3 | | WRGDGYYAYFDV |
| SEQ ID NO: 13 (Kabat) | HCDR1 | | SYLIE |
| SEQ ID NO: 12 (Kabat) | HCDR2 | | VINPGSGGTNYADSVKG |
| SEQ ID NO: 3 (Kabat) | HCDR3 | | WRGDGYYAYFDV |
| SEQ ID NO: 14 (Chothia) | HCDR1 | | GYTFSSY |
| SEQ ID NO: 6 (Chothia) | HCDR2 | | NPGSGG |
| SEQ ID NO: 3 (Chothia) | HCDR3 | | WRGDGYYAYFDV |
| SEQ ID NO: 15 | VH | | QVQLVESGGGVVQPGRSLRLSCAASGYTFSSYLIEWVRQ APGKGLEWVAVINPGSGGTNYADSVKGRFTISADKSKN TAYLQMNSLRAEDTAVYYCARWRGDGYYAYFDVWGQ GTTVTVSS |
| SEQ ID NO: 16 | DNA VH | | CAGGTGCAATTGGTGGAAAGCGGCGGAGGCGTGGTG CAGCCTGGAAGAAGCCTGAGACTGAGCTGTGCCGCCA GCGGCTACACCTTCAGCAGCTACCTGATCGAGTGGGT GCGCCAGGCCCCTGGCAAAGGACTGGAATGGGTGGC CGTGATCAACCCTGGCAGCGGCGGCACCAATTACGCC GATAGCGTGAAGGGCCGGTTCACCATCAGCGCCGACA AGAGCAAGAACACCGCCTACCTCCAGATGAACAGCCT GCGGGCCGAGGACACCGCCGTGTACTATTGTGCTCGG TGGCGGGGAGATGGCTACTACGCCTACTTCGACGTGT GGGGCCAGGGCACCACAGTGACCGTCAGCTCA |

TABLE 41-continued

Sequence list

>VH5

| SEQ ID NO: 1 (Combined) | HCDR1 | GYAFTNYLIE |
| SEQ ID NO: 2 (Combined) | HCDR2 | VINPGSGGTNYNEKFKG |
| SEQ ID NO: 3 (Combined) | HCDR3 | WRGDGYYAYFDV |
| SEQ ID NO: 4 (Kabat) | HCDR1 | NYLIE |
| SEQ ID NO: 2 (Kabat) | HCDR2 | VINPGSGGTNYNEKFKG |
| SEQ ID NO: 3 (Kabat) | HCDR3 | WRGDGYYAYFDV |
| SEQ ID NO: 5 (Chothia) | HCDR1 | GYAFTNY |
| SEQ ID NO: 6 (Chothia) | HCDR2 | NPGSGG |
| SEQ ID NO: 3 (Chothia) | HCDR3 | WRGDGYYAYFDV |
| SEQ ID NO: 17 | VH | EVQLVQSGAEVKKPGESLKISCKGSGYAFTNYLIEWVRQMPGKGLEWMGVINPGSGGTNYNEKFKGQVTISADKSISTAYLQWSSLKASDTAMYYCARWRGDGYYAYFDVWGQGTTVTVSS |
| SEQ ID NO: 18 | DNA VH | GAAGTGCAGCTGGTGCAGTCTGGCGCTGAAGTGAAGAAGCCCGGCGAGTCCCTGAAGATCTCCTGCAAGGGCTCCGGCTACGCCTTCACCAACTACCTGATCGAGTGGGTCCGACAGATGCCCGGCAAGGGCCTGGAGTGGATGGGCGTGATCAACCCCGGCTCCGGCGGCACCAACTACAACGAGAAGTTCAAGGGCCAAGTCACAATCTCCGCCGACAAGTCCATCTCCACCGCCTACCTGCAGTGGTCCTCCCTGAAGGCCTCCGACACCGCCATGTACTACTGCGCCAGATGGCGGGGAGATGGCTACTACGCCTACTTCGACGTGTGGGGCCAGGGCACCACCGTGACCGTGTCCTCT |

>VK1

| SEQ ID NO: 19 (Combined) | LCDR1 | KASQSVDYDGDSYMN |
| SEQ ID NO: 20 (Combined) | LCDR2 | AASNLES |
| SEQ ID NO: 21 (Combined) | LCDR3 | QQSNEDPYT |
| SEQ ID NO: 19 (Kabat) | LCDR1 | KASQSVDYDGDSYMN |
| SEQ ID NO: 20 (Kabat) | LCDR2 | AASNLES |
| SEQ ID NO: 21 (Kabat) | LCDR3 | QQSNEDPYT |
| SEQ ID NO: 22 (Chothia) | LCDR1 | SQSVDYDGDSY |
| SEQ ID NO: 23 (Chothia) | LCDR2 | AAS |
| SEQ ID NO: 24 (Chothia) | LCDR3 | SNEDPY |
| SEQ ID NO: 25 | VL | AIRLTQSPSSFSASTGDRVTITCKASQSVDYDGDSYMNWYQQKPGKAPKLLIYAASNLESGVPSRFSGSGSGTDFTLTISSLQSEDFATYYCQQSNEDPYTFGGGTKVEIK |
| SEQ ID NO: 26 | DNA VL | GCCATCAGACTGACCCAGAGCCCCTCCAGCTTCTCCGCCTCCACCGGCGACAGAGTGACCATCACATGCAAGGCCTCCCAGTCCGTGGACTACGACGGCGACTCCTACATGAACTGGTATCAGCAGAAGCCCGGCAAGGCCCCTAAGCTGCTGATCTACGCCGCCTCCAACCTGGAATCCGGCGTGCCCTCCCGGTTCTCCGGCTCTGGCTCTGGCACCGACTTCACCCTGACCATCTCCAGCCTGCAGTCCGAGGACTTCGCCACCTACTACTGCCAGCAGTCCAACGAGGACCCCTACACCTTCGGCGGAGGCACCAAAGTGGAAATCAAG |

>VK2

| SEQ ID NO: 19 (Combined) | LCDR1 | KASQSVDYDGDSYMN |
| SEQ ID NO: 20 (Combined) | LCDR2 | AASNLES |
| SEQ ID NO: 21 (Combined) | LCDR3 | QQSNEDPYT |
| SEQ ID NO: 19 (Kabat) | LCDR1 | KASQSVDYDGDSYMN |
| SEQ ID NO: 20 (Kabat) | LCDR2 | AASNLES |
| SEQ ID NO: 21 (Kabat) | LCDR3 | QQSNEDPYT |
| SEQ ID NO: 22 (Chothia) | LCDR1 | SQSVDYDGDSY |
| SEQ ID NO: 23 (Chothia) | LCDR2 | AAS |
| SEQ ID NO: 24 (Chothia) | LCDR3 | SNEDPY |
| SEQ ID NO: 27 | VL | DIVLTQSPLSLPVTLGQPASISCKASQSVDYDGDSYMNWYQQRPGQSPRLLIYAASNLESGVPDRFSGSGSGTDFTLKISRVEAEDVGVYYCQQSNEDPYTFGGGTKVEIK |
| SEQ ID NO: 28 | DNA VL | GACATCGTGCTGACACAGAGCCCTCTGTCCCTGCCCGTGACCCTGGGCCAGCCTGCCTCCATCTCCTGCAAGGCCTCCCAGTCCGTGGACTACGACGGCGACTCCTACATGAACTGGTATCAGCAGCGGCCTGGCCAGTCCCCTCGGCTGCTGATCTACGCCGCCTCCAACCTGGAATCCGGCGTGCCCGACAGATTCTCCGGCTCCGGCTCTGGCACCGACTTCACCCTGAAGATCTCCCGGGTGGAAGCCGAGGACGTGGGCGTGTACTACTGCCAGCAGTCCAACGAGGACCCCTACACCTTCGGCGGAGGCACCAAAGTGGAAATCAAG |

TABLE 41-continued

Sequence list

>VK3

| SEQ ID NO: 19 (Combined) | LCDR1 | KASQSVDYDGDSYMN |
| SEQ ID NO: 20 (Combined) | LCDR2 | AASNLES |
| SEQ ID NO: 21 (Combined) | LCDR3 | QQSNEDPYT |
| SEQ ID NO: 19 (Kabat) | LCDR1 | KASQSVDYDGDSYMN |
| SEQ ID NO: 20 (Kabat) | LCDR2 | AASNLES |
| SEQ ID NO: 21 (Kabat) | LCDR3 | QQSNEDPYT |
| SEQ ID NO: 22 (Chothia) | LCDR1 | SQSVDYDGDSY |
| SEQ ID NO: 23 (Chothia) | LCDR2 | AAS |
| SEQ ID NO: 24 (Chothia) | LCDR3 | SNEDPY |
| SEQ ID NO: 29 | VL | EIVLTQSPATLSVSPGERATLSCKASQSVDYDGDSYMNW YQQKPGQAPRLLIYAASNLESGIPARFSGSGSGTEFTLTIS SLQSEDAAVYYCQQSNEDPYTFGGGTKVEIK |
| SEQ ID NO: 30 | DNA VL | GAGATCGTGCTGACCCAGAGCCCCGCCACCCTGAGCG TGAGCCCCGGCGAGCGGGCCACCCTGAGCTGCAAGG CCAGCCAGAGCGTGGACTACGACGGCGACAGCTACAT GAACTGGTACCAGCAGAAGCCCGGCCAGGCCCCCCG GCTGCTGATCTACGCCGCCAGCAACCTGGAGAGCGGC ATCCCCGCCCGGTTCAGCGGCAGCGGCAGCGGCACCG AGTTCACCCTGACCATCAGCAGCCTGCAGAGCGAGGA CGCCGCCGTGTACTACTGCCAGCAGAGCAACGAGGAC CCCTACACCTTCGGCGGCGGCACCAAGGTGGAGATCA AG |

>VK3s

| SEQ ID NO: 31 (Combined) | LCDR1 | RASQSVSYDGDSYMN |
| SEQ ID NO: 32 (Combined) | LCDR2 | AASNLAS |
| SEQ ID NO: 21 (Combined) | LCDR3 | QQSNEDPYT |
| SEQ ID NO: 31 (Kabat) | LCDR1 | RASQSVSYDGDSYMN |
| SEQ ID NO: 32 (Kabat) | LCDR2 | AASNLAS |
| SEQ ID NO: 21 (Kabat) | LCDR3 | QQSNEDPYT |
| SEQ ID NO: 33 (Chothia) | LCDR1 | SQSVSYDGDSY |
| SEQ ID NO: 23 (Chothia) | LCDR2 | AAS |
| SEQ ID NO: 24 (Chothia) | LCDR3 | SNEDPY |
| SEQ ID NO: 34 | VL | EIVLTQSPATLSVSPGERATLSCRASQSVSYDGDSYMNW YQQKPGQAPRLLIYAASNLASGIPARFSGSGSGTEFTLTIS SLQSEDAAVYYCQQSNEDPYTFGGGTKVEIK |
| SEQ ID NO: 35 | DNA VL | GAAATCGTGCTGACCCAGAGCCCTGCCACCCTGAGTG TGTCTCCAGGCGAGAGAGCCACACTGAGCTGTAGAGC CAGCCAGAGCGTGTCCTACGACGGCGACAGCTACATG AACTGGTATCAGCAGAAGCCCGGCCAGGCCCCCAGAC TGCTGATCTACGCCGCTTCCAATCTGGCCAGCGGCATC CCCGCCAGATTTTCCGGCTCTGGCTCCGGCACCGAGTT CACCCTGACAATCAGCAGCCTCCAGAGCGAGGACGCC GCCGTGTACTACTGCCAGCAGAGCAACGAGGACCCCT ACACCTTTGGCGGAGGCACCAAGGTGGAAATCAAG |

>VH1_D98E

| SEQ ID NO: 1 (Combined) | HCDR1 | GYAFTNYLIE |
| SEQ ID NO: 2 (Combined) | HCDR2 | VINPGSGGTNYNEKFKG |
| SEQ ID NO: 36 (Combined) | HCDR3 | WRGEGYYAYFDV |
| SEQ ID NO: 4 (Kabat) | HCDR1 | NYLIE |
| SEQ ID NO: 2 (Kabat) | HCDR2 | VINPGSGGTNYNEKFKG |
| SEQ ID NO: 36 (Kabat) | HCDR3 | WRGEGYYAYFDV |
| SEQ ID NO: 5 (Chothia) | HCDR1 | GYAFTNY |
| SEQ ID NO: 6 (Chothia) | HCDR2 | NPGSGG |
| SEQ ID NO: 36 (Chothia) | HCDR3 | WRGEGYYAYFDV |
| SEQ ID NO: 37 | VH | QVQLVQSGAEVKKPGSSVKVSCKASGYAFTNYLIEWVR QAPGQGLEWMGVINPGSGGTNYNEKFKGRVTITADKS TSTAYMELSSLRSEDTAVYYCARWRGEGYYAYFDVWGQ GTTVTVSS |
| SEQ ID NO: 38 | DNA VH | CAAGTGCAGCTGGTGCAGTCTGGCGCTGAAGTGAAG AAACCCGGCTCCTCCGTGAAAGTGTCCTGCAAGGCCT CCGGCTACGCCTTCACCAACTACCTGATCGAGTGGGTC CGACAGGCCCCAGGCCAGGGCCTGGAGTGGATGGGC GTGATCAACCCTGGCTCCGGCGGCACCAACTACAACG AGAAGTTCAAGGGCAGAGTGACCATCACCGCCGACAA GTCCACCTCCACCGCCTACATGGAACTGTCCTCCCTGC GGAGCGAGGACACCGCCGTGTACTACTGCGCCAGAT GGCGGGGAGAGGGCTACTACGCCTACTTCGACGTGT GGGGCCAGGGCACCACCGTGACCGTGTCCTCT |

TABLE 41-continued

Sequence list

>VH1_G99A

| SEQ ID NO: 1 (Combined) | HCDR1 | GYAFTNYLIE |
| SEQ ID NO: 2 (Combined) | HCDR2 | VINPGSGGTNYNEKFKG |
| SEQ ID NO: 39 (Combined) | HCDR3 | WRGDAYYAYFDV |
| SEQ ID NO: 4 (Kabat) | HCDR1 | NYLIE |
| SEQ ID NO: 2 (Kabat) | HCDR2 | VINPGSGGTNYNEKFKG |
| SEQ ID NO: 39 (Kabat) | HCDR3 | WRGDAYYAYFDV |
| SEQ ID NO: 5 (Chothia) | HCDR1 | GYAFTNY |
| SEQ ID NO: 6 (Chothia) | HCDR2 | NPGSGG |
| SEQ ID NO: 39 (Chothia) | HCDR3 | WRGDAYYAYFDV |
| SEQ ID NO: 40 | VH | QVQLVQSGAEVKKPGSSVKVSCKASGYAFTNYLIEWVR QAPGQGLEWMGVINPGSGGTNYNEKFKGRVTITADKS TSTAYMELSSLRSEDTAVYYCARWRGDAYYAYFDVWGQ GTTVTVSS |
| SEQ ID NO: 41 | DNA VH | CAAGTGCAGCTGGTGCAGTCTGGCGCTGAAGTGAAG AAACCCGGCTCCTCCGTGAAAGTGTCCTGCAAGGCCT CCGGCTACGCCTTCACCAACTACCTGATCGAGTGGGTC CGACAGGCCCCAGGCCAGGGCCTGGAGTGGATGGGC GTGATCAACCCTGGCTCCGGCGGCACCAACTACAACG AGAAGTTCAAGGGCAGAGTGACCATCACCGCCGACAA GTCCACCTCCACCGCCTACATGGAACTGTCCTCCCTGC GGAGCGAGGACACCGCCGTGTACTACTGTGCCCGGTG GCGGGGAGATGCCTACTACGCCTACTTCGACGTGTGG GGCCAGGGCACCACCGTGACCGTGTCCTCT |

>VH1_D98Q

| SEQ ID NO: 1 (Combined) | HCDR1 | GYAFTNYLIE |
| SEQ ID NO: 2 (Combined) | HCDR2 | VINPGSGGTNYNEKFKG |
| SEQ ID NO: 42 (Combined) | HCDR3 | WRGQGYYAYFDV |
| SEQ ID NO: 4 (Kabat) | HCDR1 | NYLIE |
| SEQ ID NO: 2 (Kabat) | HCDR2 | VINPGSGGTNYNEKFKG |
| SEQ ID NO: 42 (Kabat) | HCDR3 | WRGQGYYAYFDV |
| SEQ ID NO: 5 (Chothia) | HCDR1 | GYAFTNY |
| SEQ ID NO: 6 (Chothia) | HCDR2 | NPGSGG |
| SEQ ID NO: 42 (Chothia) | HCDR3 | WRGQGYYAYFDV |
| SEQ ID NO: 43 | VH | QVQLVQSGAEVKKPGSSVKVSCKASGYAFTNYLIEWVR QAPGQGLEWMGVINPGSGGTNYNEKFKGRVTITADKS TSTAYMELSSLRSEDTAVYYCARWRGQGYYAYFDVWG QGTTVTVSS |
| SEQ ID NO: 44 | DNA VH | CAAGTGCAGCTGGTGCAGTCTGGCGCTGAAGTGAAG AAACCCGGCTCCTCCGTGAAAGTGTCCTGCAAGGCCT CCGGCTACGCCTTCACCAACTACCTGATCGAGTGGGTC CGACAGGCCCCAGGCCAGGGCCTGGAGTGGATGGGC GTGATCAACCCTGGCTCCGGCGGCACCAACTACAACG AGAAGTTCAAGGGCAGAGTGACCATCACCGCCGACAA GTCCACCTCCACCGCCTACATGGAACTGTCCTCCCTGC GGAGCGAGGACACCGCCGTGTACTACTGCGCCAGAT GGCGGGGACAGGGCTACTACGCCTACTTCGACGTGTG GGGCCAGGGCACCACCGTGACCGTGTCCTCT |

>VH1_D98S

| SEQ ID NO: 1 (Combined) | HCDR1 | GYAFTNYLIE |
| SEQ ID NO: 2 (Combined) | HCDR2 | VINPGSGGTNYNEKFKG |
| SEQ ID NO: 45 (Combined) | HCDR3 | WRGSGYYAYFDV |
| SEQ ID NO: 4 (Kabat) | HCDR1 | NYLIE |
| SEQ ID NO: 2 (Kabat) | HCDR2 | VINPGSGGTNYNEKFKG |
| SEQ ID NO: 45 (Kabat) | HCDR3 | WRGSGYYAYFDV |
| SEQ ID NO: 5 (Chothia) | HCDR1 | GYAFTNY |
| SEQ ID NO: 6 (Chothia) | HCDR2 | NPGSGG |
| SEQ ID NO: 45 (Chothia) | HCDR3 | WRGSGYYAYFDV |
| SEQ ID NO: 46 | VH | QVQLVQSGAEVKKPGSSVKVSCKASGYAFTNYLIEWVR QAPGQGLEWMGVINPGSGGTNYNEKFKGRVTITADKS TSTAYMELSSLRSEDTAVYYCARWRGSGYYAYFDVWGQ GTTVTVSS |
| SEQ ID NO: 47 | DNA VH | CAAGTGCAGCTGGTGCAGTCTGGCGCTGAAGTGAAG AAACCCGGCTCCTCCGTGAAAGTGTCCTGCAAGGCCT CCGGCTACGCCTTCACCAACTACCTGATCGAGTGGGTC CGACAGGCCCCAGGCCAGGGCCTGGAGTGGATGGGC GTGATCAACCCTGGCTCCGGCGGCACCAACTACAACG AGAAGTTCAAGGGCAGAGTGACCATCACCGCCGACAA GTCCACCTCCACCGCCTACATGGAACTGTCCTCCCTGC GGAGCGAGGACACCGCCGTGTACTACTGCGCCAGAT GGCGGGGATCTGGCTACTACGCCTACTTCGACGTGTG GGGCCAGGGCACCACCGTGACCGTGTCCTCT |

TABLE 41-continued

Sequence list

>VH3_D98E

| SEQ ID NO: 1 (Combined) | HCDR1 | GYAFTNYLIE |
| SEQ ID NO: 2 (Combined) | HCDR2 | VINPGSGGTNYNEKFKG |
| SEQ ID NO: 36 (Combined) | HCDR3 | WRGEGYYAYFDV |
| SEQ ID NO: 4 (Kabat) | HCDR1 | NYLIE |
| SEQ ID NO: 2 (Kabat) | HCDR2 | VINPGSGGTNYNEKFKG |
| SEQ ID NO: 36 (Kabat) | HCDR3 | WRGEGYYAYFDV |
| SEQ ID NO: 5 (Chothia) | HCDR1 | GYAFTNY |
| SEQ ID NO: 6 (Chothia) | HCDR2 | NPGSGG |
| SEQ ID NO: 36 (Chothia) | HCDR3 | WRGEGYYAYFDV |
| SEQ ID NO: 48 | VH | QVQLVESGGGVVQPGRSLRLSCAASGYAFTNYLIEWVR QAPGKGLEWVAVINPGSGGTNYNEKFKGRFTISADKSKS TAYLQMNSLRAEDTAVYYCARWRGEGYYAYFDVWGQ GTTVTVSS |
| SEQ ID NO: 419 | DNA VH | CAGGTGCAGCTGGTGGAGAGCGGCGGCGGCGTGGTG CAGCCCGGCCGGAGCCTGCGGCTGAGCTGCGCCGCC AGCGGCTACGCCTTCACCAACTACCTGATCGAGTGGG TGCGGCAGGCCCCCGGCAAGGGCCTGGAGTGGGTGG CCGTGATCAACCCCGGCAGCGGCGGCACCAACTACAA CGAGAAGTTCAAGGGCCGGTTCACCATCAGCGCCGAC AAGAGCAAGAGCACCGCCTACCTGCAGATGAACAGCC TGCGGGCCGAGGACACCGCCGTGTACTACTGCGCCCG GTGGCGGGGCGAGGGCTACTACGCCTACTTCGACGTG TGGGGCCAGGGCACCACCGTGACCGTGAGCAGC |

>VH3_G99A

| SEQ ID NO: 1 (Combined) | HCDR1 | GYAFTNYLIE |
| SEQ ID NO: 2 (Combined) | HCDR2 | VINPGSGGTNYNEKFKG |
| SEQ ID NO: 39 (Combined) | HCDR3 | WRGDAYYAYFDV |
| SEQ ID NO: 4 (Kabat) | HCDR1 | NYLIE |
| SEQ ID NO: 2 (Kabat) | HCDR2 | VINPGSGGTNYNEKFKG |
| SEQ ID NO: 39 (Kabat) | HCDR3 | WRGDAYYAYFDV |
| SEQ ID NO: 5 (Chothia) | HCDR1 | GYAFTNY |
| SEQ ID NO: 6 (Chothia) | HCDR2 | NPGSGG |
| SEQ ID NO: 39 (Chothia) | HCDR3 | WRGDAYYAYFDV |
| SEQ ID NO: 51 | VH | QVQLVESGGGVVQPGRSLRLSCAASGYAFTNYLIEWVR QAPGKGLEWVAVINPGSGGTNYNEKFKGRFTISADKSKS TAYLQMNSLRAEDTAVYYCARWRGDAYYAYFDVWGQ GTTVTVSS |
| SEQ ID NO: 52 | DNA VH | CAGGTGCAGCTGGTGGAGAGCGGCGGCGGCGTGGTG CAGCCCGGCCGGAGCCTGCGGCTGAGCTGCGCCGCC AGCGGCTACGCCTTCACCAACTACCTGATCGAGTGGG TGCGGCAGGCCCCCGGCAAGGGCCTGGAGTGGGTGG CCGTGATCAACCCCGGCAGCGGCGGCACCAACTACAA CGAGAAGTTCAAGGGCCGGTTCACCATCAGCGCCGAC AAGAGCAAGAGCACCGCCTACCTGCAGATGAACAGCC TGCGGGCCGAGGACACCGCCGTGTACTACTGCGCCCG GTGGCGGGGCGACGCCTACTACGCCTACTTCGACGTG TGGGGCCAGGGCACCACCGTGACCGTGAGCAGC |

>VH3_D98Q

| SEQ ID NO: 1 (Combined) | HCDR1 | GYAFTNYLIE |
| SEQ ID NO: 2 (Combined) | HCDR2 | VINPGSGGTNYNEKFKG |
| SEQ ID NO: 42 (Combined) | HCDR3 | WRGQGYYAYFDV |
| SEQ ID NO: 4 (Kabat) | HCDR1 | NYLIE |
| SEQ ID NO: 2 (Kabat) | HCDR2 | VINPGSGGTNYNEKFKG |
| SEQ ID NO: 42 (Kabat) | HCDR3 | WRGQGYYAYFDV |
| SEQ ID NO: 5 (Chothia) | HCDR1 | GYAFTNY |
| SEQ ID NO: 6 (Chothia) | HCDR2 | NPGSGG |
| SEQ ID NO: 42 (Chothia) | HCDR3 | WRGQGYYAYFDV |
| SEQ ID NO: 53 | VH | QVQLVESGGGVVQPGRSLRLSCAASGYAFTNYLIEWVR QAPGKGLEWVAVINPGSGGTNYNEKFKGRFTISADKSKS TAYLQMNSLRAEDTAVYYCARWRGQGYYAYFDVWGQ GTTVTVSS |
| SEQ ID NO: 54 | DNA VH | CAGGTGCAGCTGGTGGAGAGCGGCGGCGGCGTGGTG CAGCCCGGCCGGAGCCTGCGGCTGAGCTGCGCCGCC AGCGGCTACGCCTTCACCAACTACCTGATCGAGTGGG TGCGGCAGGCCCCCGGCAAGGGCCTGGAGTGGGTGG CCGTGATCAACCCCGGCAGCGGCGGCACCAACTACAA CGAGAAGTTCAAGGGCCGGTTCACCATCAGCGCCGAC AAGAGCAAGAGCACCGCCTACCTGCAGATGAACAGCC TGCGGGCCGAGGACACCGCCGTGTACTACTGCGCCCG GTGGCGGGGCCAGGGCTACTACGCCTACTTCGACGTG TGGGGCCAGGGCACCACCGTGACCGTGAGCAGC |

TABLE 41-continued

Sequence list

>VH3_D98S

| SEQ ID NO: 1 (Combined) | HCDR1 | GYAFTNYLIE |
| SEQ ID NO: 2 (Combined) | HCDR2 | VINPGSGGTNYNEKFKG |
| SEQ ID NO: 45 (Combined) | HCDR3 | WRGSGYYAYFDV |
| SEQ ID NO: 4 (Kabat) | HCDR1 | NYLIE |
| SEQ ID NO: 2 (Kabat) | HCDR2 | VINPGSGGTNYNEKFKG |
| SEQ ID NO: 45 (Kabat) | HCDR3 | WRGSGYYAYFDV |
| SEQ ID NO: 5 (Chothia) | HCDR1 | GYAFTNY |
| SEQ ID NO: 6 (Chothia) | HCDR2 | NPGSGG |
| SEQ ID NO: 45 (Chothia) | HCDR3 | WRGSGYYAYFDV |
| SEQ ID NO: 55 | VH | QVQLVESGGGVVQPGRSLRLSCAASGYAFTNYLIEWVR<br>QAPGKGLEWVAVINPGSGGTNYNEKFKGRFTISADKSKS<br>TAYLQMNSLRAEDTAVYYCARWRGSGYYAYFDVWGQ<br>GTTVTVSS |
| SEQ ID NO: 56 | DNA VH | CAGGTGCAGCTGGTGGAGAGCGGCGGCGGCGTGGTG<br>CAGCCCGGCCGGAGCCTGCGGCTGAGCTGCGCCGCC<br>AGCGGCTACGCCTTCACCAACTACCTGATCGAGTGGG<br>TGCGGCAGGCCCCCGGCAAGGGCCTGGAGTGGGTGG<br>CCGTGATCAACCCCGGCAGCGGCGGCACCAACTACAA<br>CGAGAAGTTCAAGGGCCGGTTCACCATCAGCGCCGAC<br>AAGAGCAAGAGCACCGCCTACCTGCAGATGAACAGCC<br>TGCGGGCCGAGGACACCGCCGTGTACTACTGCGCCCG<br>GTGGCGGGGCAGCGGCTACTACGCCTACTTCGACGTG<br>TGGGGCCAGGGCACCACCGTGACCGTGAGCAGC |

>VH3s_D98E

| SEQ ID NO: 11 (Combined) | HCDR1 | GYTFSSYLIE |
| SEQ ID NO: 12 (Combined) | HCDR2 | VINPGSGGTNYADSVKG |
| SEQ ID NO: 36 (Combined) | HCDR3 | WRGEGYYAYFDV |
| SEQ ID NO: 13 (Kabat) | HCDR1 | SYLIE |
| SEQ ID NO: 12 (Kabat) | HCDR2 | VINPGSGGTNYADSVKG |
| SEQ ID NO: 36 (Kabat) | HCDR3 | WRGEGYYAYFDV |
| SEQ ID NO: 14 (Chothia) | HCDR1 | GYTFSSY |
| SEQ ID NO: 6 (Chothia) | HCDR2 | NPGSGG |
| SEQ ID NO: 36 (Chothia) | HCDR3 | WRGEGYYAYFDV |
| SEQ ID NO: 57 | VH | QVQLVESGGGVVQPGRSLRLSCAASGYTFSSYLIEWVRQ<br>APGKGLEWVAVINPGSGGTNYADSVKGRFTISADKSKN<br>TAYLQMNSLRAEDTAVYYCARWRGEGYYAYFDVWGQ<br>GTTVTVSS |
| SEQ ID NO: 58 | DNA VH | CAGGTGCAATTGGTGGAAAGCGGCGGAGGCGTGGTG<br>CAGCCTGGAAGAAGCCTGAGACTGAGCTGTGCCGCCA<br>GCGGCTACACCTTCAGCAGCTACCTGATCGAGTGGGT<br>GCGCCAGGCCCCTGGCAAAGGACTGGAATGGGTGGC<br>CGTGATCAACCCTGGCAGCGGCGGCACCAATTACGCC<br>GATAGCGTGAAGGGCCGGTTCACCATCAGCGCCGACA<br>AGAGCAAGAACACCGCCTACCTCCAGATGAACAGCCT<br>GCGGGCCGAGGACACCGCCGTGTACTATTGTGCTCGG<br>TGGCGGGGAGAGGGCTACTACGCCTACTTCGACGTGT<br>GGGGCCAGGGCACCACAGTGACCGTCAGCTCA |

>VH3s_G99A

| SEQ ID NO: 11 (Combined) | HCDR1 | GYTFSSYLIE |
| SEQ ID NO: 12 (Combined) | HCDR2 | VINPGSGGTNYADSVKG |
| SEQ ID NO: 39 (Combined) | HCDR3 | WRGDAYYAYFDV |
| SEQ ID NO: 13 (Kabat) | HCDR1 | SYLIE |
| SEQ ID NO: 12 (Kabat) | HCDR2 | VINPGSGGTNYADSVKG |
| SEQ ID NO: 39 (Kabat) | HCDR3 | WRGDAYYAYFDV |
| SEQ ID NO: 14 (Chothia) | HCDR1 | GYTFSSY |
| SEQ ID NO: 6 (Chothia) | HCDR2 | NPGSGG |
| SEQ ID NO: 39 (Chothia) | HCDR3 | WRGDAYYAYFDV |
| SEQ ID NO: 59 | VH | QVQLVESGGGVVQPGRSLRLSCAASGYTFSSYLIEWVRQ<br>APGKGLEWVAVINPGSGGTNYADSVKGRFTISADKSKN<br>TAYLQMNSLRAEDTAVYYCARWRGDAYYAYFDVWGQ<br>GTTVTVSS |
| SEQ ID NO: 60 | DNA VH | CAGGTGCAATTGGTGGAAAGCGGCGGAGGCGTGGTG<br>CAGCCTGGAAGAAGCCTGAGACTGAGCTGTGCCGCCA<br>GCGGCTACACCTTCAGCAGCTACCTGATCGAGTGGGT<br>GCGCCAGGCCCCTGGCAAAGGACTGGAATGGGTGGC<br>CGTGATCAACCCTGGCAGCGGCGGCACCAATTACGCC<br>GATAGCGTGAAGGGCCGGTTCACCATCAGCGCCGACA<br>AGAGCAAGAACACCGCCTACCTCCAGATGAACAGCCT<br>GCGGGCCGAGGACACCGCCGTGTACTATTGTGCTCGG<br>TGGCGGGGAGATGCCTACTACGCCTACTTCGACGTGT<br>GGGGCCAGGGCACCACAGTGACCGTCAGCTCA |

TABLE 41-continued

Sequence list

>VH3s_D98Q

| SEQ ID NO: 11 (Combined) | HCDR1 | GYTFSSYLIE |
| SEQ ID NO: 12 (Combined) | HCDR2 | VINPGSGGTNYADSVKG |
| SEQ ID NO: 42 (Combined) | HCDR3 | WRGQGYYAYFDV |
| SEQ ID NO: 13 (Kabat) | HCDR1 | SYLIE |
| SEQ ID NO: 12 (Kabat) | HCDR2 | VINPGSGGTNYADSVKG |
| SEQ ID NO: 42 (Kabat) | HCDR3 | WRGQGYYAYFDV |
| SEQ ID NO: 14 (Chothia) | HCDR1 | GYTFSSY |
| SEQ ID NO: 6 (Chothia) | HCDR2 | NPGSGG |
| SEQ ID NO: 42 (Chothia) | HCDR3 | WRGQGYYAYFDV |
| SEQ ID NO: 61 | VH | QVQLVESGGGVVQPGRSLRLSCAASGYTFSSYLIEWVRQ APGKGLEWVAVINPGSGGTNYADSVKGRFTISADKSKN TAYLQMNSLRAEDTAVYYCARWRGQGYYAYFDVWGQ GTTVTVSS |
| SEQ ID NO: 62 | DNA VH | CAGGTGCAATTGGTGGAAAGCGGCGGAGGCGTGGTG CAGCCTGGAAGAAGCCTGAGACTGAGCTGTGCCGCCA GCGGCTACACCTTCAGCAGCTACCTGATCGAGTGGGT GCGCCAGGCCCCTGGCAAAGGACTGGAATGGGTGGC CGTGATCAACCCTGGCAGCGGCGGCACCAATTACGCC GATAGCGTGAAGGGCCGGTTCACCATCAGCGCCGACA AGAGCAAGAACACCGCCTACCTCCAGATGAACAGCCT GCGGGCCGAGGACACCGCCGTGTACTATTGTGCTCGG TGGCGGGGACAGGGCTACTACGCCTACTTCGACGTGT GGGGCCAGGGCACCACAGTGACCGTCAGCTCA |

>VH3s_D98S

| SEQ ID NO: 11 (Combined) | HCDR1 | GYTFSSYLIE |
| SEQ ID NO: 12 (Combined) | HCDR2 | VINPGSGGTNYADSVKG |
| SEQ ID NO: 45 (Combined) | HCDR3 | WRGSGYYAYFDV |
| SEQ ID NO: 13 (Kabat) | HCDR1 | SYLIE |
| SEQ ID NO: 12 (Kabat) | HCDR2 | VINPGSGGTNYADSVKG |
| SEQ ID NO: 45 (Kabat) | HCDR3 | WRGSGYYAYFDV |
| SEQ ID NO: 14 (Chothia) | HCDR1 | GYTFSSY |
| SEQ ID NO: 6 (Chothia) | HCDR2 | NPGSGG |
| SEQ ID NO: 45 (Chothia) | HCDR3 | WRGSGYYAYFDV |
| SEQ ID NO: 63 | VH | QVQLVESGGGVVQPGRSLRLSCAASGYTFSSYLIEWVRQ APGKGLEWVAVINPGSGGTNYADSVKGRFTISADKSKN TAYLQMNSLRAEDTAVYYCARWRGSGYYAYFDVWGQ GTTVTVSS |
| SEQ ID NO: 64 | DNA VH | CAGGTGCAATTGGTGGAAAGCGGCGGAGGCGTGGTG CAGCCTGGAAGAAGCCTGAGACTGAGCTGTGCCGCCA GCGGCTACACCTTCAGCAGCTACCTGATCGAGTGGGT GCGCCAGGCCCCTGGCAAAGGACTGGAATGGGTGGC CGTGATCAACCCTGGCAGCGGCGGCACCAATTACGCC GATAGCGTGAAGGGCCGGTTCACCATCAGCGCCGACA AGAGCAAGAACACCGCCTACCTCCAGATGAACAGCCT GCGGGCCGAGGACACCGCCGTGTACTATTGTGCTCGG TGGCGGGGAAGCGGCTACTACGCCTACTTCGACGTGT GGGGCCAGGGCACCACAGTGACCGTCAGCTCA |

>VH5_D98E

| SEQ ID NO: 1 (Combined) | HCDR1 | GYAFTNYLIE |
| SEQ ID NO: 2 (Combined) | HCDR2 | VINPGSGGTNYNEKFKG |
| SEQ ID NO: 36 (Combined) | HCDR3 | WRGEGYYAYFDV |
| SEQ ID NO: 4 (Kabat) | HCDR1 | NYLIE |
| SEQ ID NO: 2 (Kabat) | HCDR2 | VINPGSGGTNYNEKFKG |
| SEQ ID NO: 36 (Kabat) | HCDR3 | WRGEGYYAYFDV |
| SEQ ID NO: 5 (Chothia) | HCDR1 | GYAFTNY |
| SEQ ID NO: 6 (Chothia) | HCDR2 | NPGSGG |
| SEQ ID NO: 36 (Chothia) | HCDR3 | WRGEGYYAYFDV |
| SEQ ID NO: 49 | VH | EVQLVQSGAEVKKPGESLKISCKGSGYAFTNYLIEWVRQ MPGKGLEWMGVINPGSGGTNYNEKFKGQVTISADKSIS TAYLQWSSLKASDTAMYYCARWRGEGYYAYFDVWGQ GTTVTVSS |
| SEQ ID NO: 50 | DNA VH | GAAGTGCAGCTGGTGCAGTCTGGCGCTGAAGTGAAG AAGCCCGGCGAGTCCCTGAAGATCTCCTGCAAGGGCT CCGGCTACGCCTTCACCAACTACCTGATCGAGTGGGTC CGACAGATGCCCGGCAAGGGCCTGGAGTGGATGGGC GTGATCAACCCCGGCTCCGGCGGCACCAACTACAACG AGAAGTTCAAGGGCCAAGTCACAATCTCCGCCGACAA GTCCATCTCCACCGCCTACCTGCAGTGGTCCTCCCTGA AGGCCTCCGACACCGCCATGTACTACTGCGCCAGATG GCGGGGAGAGGGCTACTACGCCTACTTCGACGTGTG GGGCCAGGGCACCACCGTGACCGTGTCCTCT |

TABLE 41-continued

Sequence list

>VH5_G99A

| SEQ ID NO: 1 (Combined) | HCDR1 | GYAFTNYLIE |
| SEQ ID NO: 2 (Combined) | HCDR2 | VINPGSGGTNYNEKFKG |
| SEQ ID NO: 39 (Combined) | HCDR3 | WRGDAYYAYFDV |
| SEQ ID NO: 4 (Kabat) | HCDR1 | NYLIE |
| SEQ ID NO: 2 (Kabat) | HCDR2 | VINPGSGGTNYNEKFKG |
| SEQ ID NO: 39 (Kabat) | HCDR3 | WRGDAYYAYFDV |
| SEQ ID NO: 5 (Chothia) | HCDR1 | GYAFTNY |
| SEQ ID NO: 6 (Chothia) | HCDR2 | NPGSGG |
| SEQ ID NO: 39 (Chothia) | HCDR3 | WRGDAYYAYFDV |
| SEQ ID NO: 65 | VH | EVQLVQSGAEVKKPGESLKISCKGSGYAFTNYLIEWVRQ MPGKGLEWMGVINPGSGGTNYNEKFKGQVTISADKSIS TAYLQWSSLKASDTAMYYCARWRGDAYYAYFDVWGQ GTTVTVSS |
| SEQ ID NO: 66 | DNA VH | GAGGTGCAATTGGTGCAGAGCGGAGCCGAAGTGAAG AAGCCCGGCGAGAGCCTGAAGATCAGCTGCAAGGGC AGCGGCTACGCCTTCACCAACTACCTGATCGAGTGGG TGCGCCAGATGCCCGGCAAGGGCCTGGAATGGATGG GCGTGATCAATCCTGGCAGCGGCGGCACCAATTACAA CGAGAAGTTCAAGGGCCAAGTGACCATCAGCGCCGA CAAGAGCATCAGCACCGCCTACCTCCAGTGGTCCAGC CTGAAGGCCAGCGACACCGCCATGTACTACTGCGCCA GGTGGCGGGGAGATGCCTACTACGCCTACTTCGACGT GTGGGGCCAGGGCACCACAGTGACCGTCAGCTCA |

>VH5_D98Q

| SEQ ID NO: 1 (Combined) | HCDR1 | GYAFTNYLIE |
| SEQ ID NO: 2 (Combined) | HCDR2 | VINPGSGGTNYNEKFKG |
| SEQ ID NO: 42 (Combined) | HCDR3 | WRGQGYYAYFDV |
| SEQ ID NO: 4 (Kabat) | HCDR1 | NYLIE |
| SEQ ID NO: 2 (Kabat) | HCDR2 | VINPGSGGTNYNEKFKG |
| SEQ ID NO: 42 (Kabat) | HCDR3 | WRGQGYYAYFDV |
| SEQ ID NO: 5 (Chothia) | HCDR1 | GYAFTNY |
| SEQ ID NO: 6 (Chothia) | HCDR2 | NPGSGG |
| SEQ ID NO: 42 (Chothia) | HCDR3 | WRGQGYYAYFDV |
| SEQ ID NO: 67 | VH | EVQLVQSGAEVKKPGESLKISCKGSGYAFTNYLIEWVRQ MPGKGLEWMGVINPGSGGTNYNEKFKGQVTISADKSIS TAYLQWSSLKASDTAMYYCARWRGQGYYAYFDVWGQ GTTVTVSS |
| SEQ ID NO: 68 | DNA VH | GAGGTGCAATTGGTGCAGAGCGGAGCCGAAGTGAAG AAGCCCGGCGAGAGCCTGAAGATCAGCTGCAAGGGC AGCGGCTACGCCTTCACCAACTACCTGATCGAGTGGG TGCGCCAGATGCCCGGCAAGGGCCTGGAATGGATGG GCGTGATCAATCCTGGCAGCGGCGGCACCAATTACAA CGAGAAGTTCAAGGGCCAAGTGACCATCAGCGCCGA CAAGAGCATCAGCACCGCCTACCTCCAGTGGTCCAGC CTGAAGGCCAGCGACACCGCCATGTACTACTGCGCCA GGTGGCGGGGACAGGGCTACTACGCCTACTTCGACGT GTGGGGCCAGGGCACCACAGTGACCGTCAGCTCA |

>VH5_D98S

| SEQ ID NO: 1 (Combined) | HCDR1 | GYAFTNYLIE |
| SEQ ID NO: 2 (Combined) | HCDR2 | VINPGSGGTNYNEKFKG |
| SEQ ID NO: 45 (Combined) | HCDR3 | WRGSGYYAYFDV |
| SEQ ID NO: 4 (Kabat) | HCDR1 | NYLIE |
| SEQ ID NO: 2 (Kabat) | HCDR2 | VINPGSGGTNYNEKFKG |
| SEQ ID NO: 45 (Kabat) | HCDR3 | WRGSGYYAYFDV |
| SEQ ID NO: 5 (Chothia) | HCDR1 | GYAFTNY |
| SEQ ID NO: 6 (Chothia) | HCDR2 | NPGSGG |
| SEQ ID NO: 45 (Chothia) | HCDR3 | WRGSGYYAYFDV |
| SEQ ID NO: 46 | VH | EVQLVQSGAEVKKPGESLKISCKGSGYAFTNYLIEWVRQ MPGKGLEWMGVINPGSGGTNYNEKFKGQVTISADKSIS TAYLQWSSLKASDTAMYYCARWRGSGYYAYFDVWGQ GTTVTVSS |
| SEQ ID NO: 47 | DNA VH | GAGGTGCAATTGGTGCAGAGCGGAGCCGAAGTGAAG AAGCCCGGCGAGAGCCTGAAGATCAGCTGCAAGGGC AGCGGCTACGCCTTCACCAACTACCTGATCGAGTGGG TGCGCCAGATGCCCGGCAAGGGCCTGGAATGGATGG GCGTGATCAATCCTGGCAGCGGCGGCACCAATTACAA CGAGAAGTTCAAGGGCCAAGTGACCATCAGCGCCGA CAAGAGCATCAGCACCGCCTACCTCCAGTGGTCCAGC CTGAAGGCCAGCGACACCGCCATGTACTACTGCGCCA GGTGGCGGGGAAGCGGCTACTACGCCTACTTCGACGT GTGGGGCCAGGGCACCACAGTGACCGTCAGCTCA |

TABLE 41-continued

Sequence list

>VK1_D28Q

| SEQ ID NO: 69 (Combined) | LCDR1 | KASQSVDYQGDSYMN |
| SEQ ID NO: 20 (Combined) | LCDR2 | AASNLES |
| SEQ ID NO: 21 (Combined) | LCDR3 | QQSNEDPYT |
| SEQ ID NO: 69 (Kabat) | LCDR1 | KASQSVDYQGDSYMN |
| SEQ ID NO: 20 (Kabat) | LCDR2 | AASNLES |
| SEQ ID NO: 21 (Kabat) | LCDR3 | QQSNEDPYT |
| SEQ ID NO: (Chothia) | LCDR1 | SQSVDYQGDSY |
| SEQ ID NO: 23 (Chothia) | LCDR2 | AAS |
| SEQ ID NO: 24 (Chothia) | LCDR3 | SNEDPY |
| SEQ ID NO: 70 | VL | AIRLTQSPSSFSASTGDRVTITCKASQSVDYQGDSYMNW YQQKPGKAPKLLIYAASNLESGVPSRFSGSGSGTDFTLTIS SLQSEDFATYYCQQSNEDPYTFGGGTKVEIK |
| SEQ ID NO: 71 | DNA VL | GCCATCAGACTGACCCAGAGCCCCTCCAGCTTCTCCGC CTCCACCGGCGACAGAGTGACCATCACATGCAAGGCC TCCCAGTCCGTGGACTACCAGGGCGACTCCTACATGA ACTGGTATCAGCAGAAGCCCGGCAAGGCCCCTAAGCT GCTGATCTACGCCGCCTCCAACCTGGAATCCGGCGTG CCCTCCCGGTTCTCCGGCTCTGGCTCTGGCACCGACTT CACCCTGACCATCTCCAGCCTGCAGTCCGAGGACTTCG CCACCTACTACTGCCAGCAGTCCAACGAGGACCCCTAC ACCTTCGGCGGAGGCACCAAAGTGGAAATCAAG |

>VK1_G29A

| SEQ ID NO: 72 (Combined) | LCDR1 | KASQSVDYDADSYMN |
| SEQ ID NO: 20 (Combined) | LCDR2 | AASNLES |
| SEQ ID NO: 21 (Combined) | LCDR3 | QQSNEDPYT |
| SEQ ID NO: 72 (Kabat) | LCDR1 | KASQSVDYDADSYMN |
| SEQ ID NO: 20 (Kabat) | LCDR2 | AASNLES |
| SEQ ID NO: 21 (Kabat) | LCDR3 | QQSNEDPYT |
| SEQ ID NO: 78 (Chothia) | LCDR1 | SQSVDYDADSY |
| SEQ ID NO: 23 (Chothia) | LCDR2 | AAS |
| SEQ ID NO: 24 (Chothia) | LCDR3 | SNEDPY |
| SEQ ID NO: 73 | VL | AIRLTQSPSSFSASTGDRVTITCKASQSVDYDADSYMNW YQQKPGKAPKLLIYAASNLESGVPSRFSGSGSGTDFTLTIS SLQSEDFATYYCQQSNEDPYTFGGGTKVEIK |
| SEQ ID NO: 74 | DNA VL | GACATCGTGCTGACACAGAGCCCTGCCTCTCTGCCCGT GACCCTGGGCCAGCCTGCCTCCATCTCCTGCAAGGCCT CCCAGTCCGTGGACTACGACGCCGACTCCTACATGAA CTGGTATCAGCAGCGGCCTGGCCAGTCCCCTCGGCTG CTGATCTACGCCGCCTCCAACCTGGAATCCGGCGTGCC CGACAGATTCTCCGGCTCCGGCTCTGGCACCGACTTCA CCCTGAAGATCTCCCGGGTGGAAGCCGAGGACGTGG GCGTGTACTACTGCCAGCAGTCCAACGAGGACCCCTA CACCTTCGGCGGAGGCACCAAAGTGGAAATCAAG |

>VK2_D28Q

| SEQ ID NO: 69 (Combined) | LCDR1 | KASQSVDYQGDSYMN |
| SEQ ID NO: 20 (Combined) | LCDR2 | AASNLES |
| SEQ ID NO: 21 (Combined) | LCDR3 | QQSNEDPYT |
| SEQ ID NO: 69 (Kabat) | LCDR1 | KASQSVDYQGDSYMN |
| SEQ ID NO: 20 (Kabat) | LCDR2 | AASNLES |
| SEQ ID NO: 21 (Kabat) | LCDR3 | QQSNEDPYT |
| SEQ ID NO: 75 (Chothia) | LCDR1 | SQSVDYQGDSY |
| SEQ ID NO: 23 (Chothia) | LCDR2 | AAS |
| SEQ ID NO: 24 (Chothia) | LCDR3 | SNEDPY |
| SEQ ID NO: 79 | VL | DIVLTQSPLSLPVTLGQPASISCKASQSVDYQGDSYMNW YQQRPGQSPRLLIYAASNLESGVPDRFSGSGSGTDFTLKI SRVEAEDVGVYYCQQSNEDPYTFGGGTKVEIK |
| SEQ ID NO: 80 | DNA VL | GAGATCGTGCTGACCCAGAGCCCCGCCACCCTGAGCG TGAGCCCCGGCGAGCGGGCCACCCTGAGCTGCAAGG CCAGCCAGAGCGTGGACTACCAGGGCGACAGCTACAT GAACTGGTACCAGCAGAAGCCCGGCCAGGCCCCCCG GCTGCTGATCTACGCCGCCAGCAACCTGGAGAGCGGC ATCCCCGCCCGGTTCAGCGGCAGCGGCAGCGGCACCG AGTTCACCCTGACCATCAGCAGCCTGCAGAGCGAGGA CGCCGCCGTGTACTACTGCCAGCAGAGCAACGAGGAC CCCTACACCTTCGGCGGCGGCACCAAGGTGGAGATCA AG |

TABLE 41-continued

Sequence list

>VK2_G29A

| SEQ ID NO: 72 (Combined) | LCDR1 | KASQSVDYDADSYMN |
|---|---|---|
| SEQ ID NO: 20 (Combined) | LCDR2 | AASNLES |
| SEQ ID NO: 21 (Combined) | LCDR3 | QQSNEDPYT |
| SEQ ID NO: 72 (Kabat) | LCDR1 | KASQSVDYDADSYMN |
| SEQ ID NO: 20 (Kabat) | LCDR2 | AASNLES |
| SEQ ID NO: 21 (Kabat) | LCDR3 | QQSNEDPYT |
| SEQ ID NO: 78 (Chothia) | LCDR1 | SQSVDYDADSY |
| SEQ ID NO: 23 (Chothia) | LCDR2 | AAS |
| SEQ ID NO: 24 (Chothia) | LCDR3 | SNEDPY |
| SEQ ID NO: 81 | VL | DIVLTQSPLSLPVTLGQPASISCKASQSVDYDADSYMNW<br>YQQRPGQSPRLLIYAASNLESGVPDRFSGSGSGTDFTLKI<br>SRVEAEDVGVYYCQQSNEDPYTFGGGTKVEIK |
| SEQ ID NO: 82 | DNA VL | GAGATCGTGCTGACCCAGAGCCCCGCCACCCTGAGCG<br>TGAGCCCCGGCGAGCGGGCCACCCTGAGCTGCAAGG<br>CCAGCCAGAGCGTGGACTACGACGCCGACAGCTACAT<br>GAACTGGTACCAGCAGAAGCCCGGCCAGGCCCCCCG<br>GCTGCTGATCTACGCCGCCAGCAACCTGGAGAGCGGC<br>ATCCCCGCCCGGTTCAGCGGCAGCGGCAGCGGCACCG<br>AGTTCACCCTGACCATCAGCAGCCTGCAGAGCGAGGA<br>CGCCGCCGTGTACTACTGCCAGCAGAGCAACGAGGAC<br>CCCTACACCTTCGGCGGCGGCACCAAGGTGGAGATCA<br>AG |

>VK3_D28Q

| SEQ ID NO: 69 (Combined) | LCDR1 | KASQSVDYQGDSYMN |
|---|---|---|
| SEQ ID NO: 20 (Combined) | LCDR2 | AASNLES |
| SEQ ID NO: 21 (Combined) | LCDR3 | QQSNEDPYT |
| SEQ ID NO: 69 (Kabat) | LCDR1 | KASQSVDYQGDSYMN |
| SEQ ID NO: 20 (Kabat) | LCDR2 | AASNLES |
| SEQ ID NO: 21 (Kabat) | LCDR3 | QQSNEDPYT |
| SEQ ID NO: 75 (Chothia) | LCDR1 | SQSVDYQGDSY |
| SEQ ID NO: 23 (Chothia) | LCDR2 | AAS |
| SEQ ID NO: 24 (Chothia) | LCDR3 | SNEDPY |
| SEQ ID NO: 76 | VL | EIVLTQSPATLSVSPGERATLSCKASQSVDYQGDSYMNW<br>YQQKPGQAPRLLIYAASNLESGIPARFSGSGSGTEFTLTIS<br>SLQSEDAAVYYCQQSNEDPYTFGGGTKVEIK |
| SEQ ID NO: 77 | DNA VL | GAAATCGTGCTGACCCAGAGCCCTGCCACCCTGAGTG<br>TGTCTCCAGGCGAGAGAGCCACACTGAGCTGTAGAGC<br>CAGCCAGAGCGTGTCCTACCAGGGCGACAGCTACATG<br>AACTGGTATCAGCAGAAGCCCGGCCAGGCCCCCAGAC<br>TGCTGATCTACGCCGCCTTCCAATCTGGCCAGCGGCATC<br>CCCGCCAGATTTTCCGGCTCTGGCTCCGGCACCGAGTT<br>CACCCTGACAATCAGCAGCCTCCAGAGCGAGGACGCC<br>GCCGTGTACTACTGCCAGCAGAGCAACGAGGACCCCT<br>ACACCTTTGGCGGAGGCACCAAGGTGGAAATCAAG |

>VK3_G29A

| SEQ ID NO: 72 (Combined) | LCDR1 | KASQSVDYDADSYMN |
|---|---|---|
| SEQ ID NO: 20 (Combined) | LCDR2 | AASNLES |
| SEQ ID NO: 21 (Combined) | LCDR3 | QQSNEDPYT |
| SEQ ID NO: 72 (Kabat) | LCDR1 | KASQSVDYDADSYMN |
| SEQ ID NO: 20 (Kabat) | LCDR2 | AASNLES |
| SEQ ID NO: 21 (Kabat) | LCDR3 | QQSNEDPYT |
| SEQ ID NO: 78 (Chothia) | LCDR1 | SQSVDYDADSY |
| SEQ ID NO: 23 (Chothia) | LCDR2 | AAS |
| SEQ ID NO: 24 (Chothia) | LCDR3 | SNEDPY |
| SEQ ID NO: 84 | VL | EIVLTQSPATLSVSPGERATLSCKASQSVDYDADSYMNW<br>YQQKPGQAPRLLIYAASNLESGIPARFSGSGSGTEFTLTIS<br>SLQSEDAAVYYCQQSNEDPYTFGGGTKVEIK |
| SEQ ID NO: 85 | DNA VL | GAAATCGTGCTGACCCAGAGCCCTGCCACCCTGAGTG<br>TGTCTCCAGGCGAGAGAGCCACACTGAGCTGTAGAGC<br>CAGCCAGAGCGTGTCCTACGACGCCGACAGCTACATG<br>AACTGGTATCAGCAGAAGCCCGGCCAGGCCCCCAGAC<br>TGCTGATCTACGCCGCCTTCCAATCTGGCCAGCGGCATC<br>CCCGCCAGATTTTCCGGCTCTGGCTCCGGCACCGAGTT<br>CACCCTGACAATCAGCAGCCTCCAGAGCGAGGACGCC<br>GCCGTGTACTACTGCCAGCAGAGCAACGAGGACCCCT<br>ACACCTTTGGCGGAGGCACCAAGGTGGAAATCAAG |

TABLE 41-continued

Sequence list

>VK3s_D28Q

| SEQ ID NO: 86 (Combined) | LCDR1 | RASQSVSYQGDSYMN |
| SEQ ID NO: 32 (Combined) | LCDR2 | AASNLAS |
| SEQ ID NO: 21 (Combined) | LCDR3 | QQSNEDPYT |
| SEQ ID NO: 86 (Kabat) | LCDR1 | RASQSVSYQGDSYMN |
| SEQ ID NO: 32 (Kabat) | LCDR2 | AASNLAS |
| SEQ ID NO: 21 (Kabat) | LCDR3 | QQSNEDPYT |
| SEQ ID NO: 87 (Chothia) | LCDR1 | SQSVSYQGDSY |
| SEQ ID NO: 23 (Chothia) | LCDR2 | AAS |
| SEQ ID NO: 24 (Chothia) | LCDR3 | SNEDPY |
| SEQ ID NO: 88 | VL | EIVLTQSPATLSVSPGERATLSCRASQSVSYQGDSYMNW YQQKPGQAPRLLIYAASNLASGIPARFSGSGSGTEFTLTIS SLQSEDAAVYYCQQSNEDPYTFGGGTKVEIK |
| SEQ ID NO: 89 | DNA VL | GAAATCGTGCTGACCCAGAGCCCTGCCACCCTGAGTG TGTCTCCAGGCGAGAGAGCCACACTGAGCTGTAGAGC CAGCCAGAGCGTGTCCTACCAGGGCGACAGCTACATG AACTGGTATCAGCAGAAGCCCGGCCAGGCCCCCAGAC TGCTGATCTACGCCGCTTCCAATCTGGCCAGCGGCATC CCCGCCAGATTTTCCGGCTCTGGCTCCGGCACCGAGTT CACCCTGACAATCAGCAGCCTCCAGAGCGAGGACGCC GCCGTGTACTACTGCCAGCAGAGCAACGAGGACCCCT ACACCTTTGGCGGAGGCACCAAGGTGGAAATCAAG |

>VK3s_G29A

| SEQ ID NO: 90 (Combined) | LCDR1 | RASQSVSYDADSYMN |
| SEQ ID NO: 32 (Combined) | LCDR2 | AASNLAS |
| SEQ ID NO: 21 (Combined) | LCDR3 | QQSNEDPYT |
| SEQ ID NO: 90 (Kabat) | LCDR1 | RASQSVSYDADSYMN |
| SEQ ID NO: 32 (Kabat) | LCDR2 | AASNLAS |
| SEQ ID NO: 21 (Kabat) | LCDR3 | QQSNEDPYT |
| SEQ ID NO: 420 (Chothia) | LCDR1 | SQSVSYDADSY |
| SEQ ID NO: 23 (Chothia) | LCDR2 | AAS |
| SEQ ID NO: 24 (Chothia) | LCDR3 | SNEDPY |
| SEQ ID NO: 91 | VL | EIVLTQSPATLSVSPGERATLSCRASQSVSYDADSYMNW YQQKPGQAPRLLIYAASNLASGIPARFSGSGSGTEFTLTIS SLQSEDAAVYYCQQSNEDPYTFGGGTKVEIK |
| SEQ ID NO: 92 | DNA VL | GAAATCGTGCTGACCCAGAGCCCTGCCACCCTGAGTG TGTCTCCAGGCGAGAGAGCCACACTGAGCTGTAGAGC CAGCCAGAGCGTGTCCTACGACGCCGACAGCTACATG AACTGGTATCAGCAGAAGCCCGGCCAGGCCCCCAGAC TGCTGATCTACGCCGCTTCCAATCTGGCCAGCGGCATC CCCGCCAGATTTTCCGGCTCTGGCTCCGGCACCGAGTT CACCCTGACAATCAGCAGCCTCCAGAGCGAGGACGCC GCCGTGTACTACTGCCAGCAGAGCAACGAGGACCCCT ACACCTTTGGCGGAGGCACCAAGGTGGAAATCAAG |

>hIgG1

| SEQ ID NO: 93 | Constant HC | ASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKKVEPKSCDKTHTCPPCPAPELLG GPSVFLFPPKPKDTLMISRTPEVTCVVVDVSHEDPEVKFN WYVDGVEVHNAKTKPREEQYNSTYRVVSVLTVLHQDW LNGKEYKCKVSNKALPAPIEKTISKAKGQPREPQVYTLPP SREEMTKNQVSLTCLVKGFYPSDIAVEWESNGQPENNY KTTPPVLDSDGSFFLYSKLTVDKSRWQQGNVFSCSVMH EALHNHYTQKSLSLSPGK |
| SEQ ID NO: 94 | DNA Constant HC | GCGTCGACCAAGGGCCCCAGCGTGTTCCCCCTGGCCC CCAGCAGCAAGAGCACCAGCGGCGGCACAGCCGCCC TGGGCTGCCTGGTGAAGGACTACTTCCCCGAGCCCGT GACCGTGTCCTGGAACAGCGGAGCCCTGACCTCCGGC GTGCACACCTTCCCCGCCGTGCTGCAGAGCAGCGGCC TGTACAGCCTGTCCAGCGTGGTGACAGTGCCCAGCAG CAGCCTGGGCACCCAGACCTACATCTGCAACGTGAAC CACAAGCCCAGCAACACCAAGGTGGACAAGAGAGTG GAGCCCAAGAGCTGCGACAAGACCCACACCTGCCCCC CTGCCCAGCCCCAGAGCTGCTGGGCGGACCCTCCGT GTTCCTGTTCCCCCCAAGCCCAAGGACACCCTGATGA TCAGCAGGACCCCCGAGGTGACCTGCGTGGTGGTGG ACGTGAGCCACGAGGACCCCGAGGTGAAGTTCAACT GGTACGTGGACGGCGTGGAGGTGCACAACGCCAAGA CCAAGCCCAGAGAGGAGCAGTACAACAGCACCTACA GGGTGGTGTCCGTGCTGACCGTGCTGCACCAGGACTG GCTGAACGGCAAGGAATACAAGTGCAAGGTCTCCAAC AAGGCCCTGCCAGCCCCATCGAAAAGACCATCAGCA |

TABLE 41-continued

Sequence list

AGGCCAAGGGCCAGCCACGGGAGCCCCAGGTGTACA
CCCTGCCCCCCTCCCGGGAGGAGATGACCAAGAACCA
GGTGTCCCTGACCTGTCTGGTGAAGGGCTTCTACCCCA
GCGACATCGCCGTGGAGTGGGAGAGCAACGGCCAGC
CCGAGAACAACTACAAGACCACCCCCCCAGTGCTGGA
CAGCGACGGCAGCTTCTTCCTGTACAGCAAGCTGACC
GTGGACAAGTCCAGGTGGCAGCAGGGCAACGTGTTC
AGCTGCAGCGTGATGCACGAGGCCCTGCACAACCACT
ACACCCAGAAGAGCCTGAGCCTGTCCCCCGGCAAG

>hIgG2

| | | |
|---|---|---|
| SEQ ID NO: 95 | Constant HC | ASTKGPSVFPLAPCSRSTSESTAALGCLVKDYFPEPVTVS<br>WNSGALTSGVHTFPAVLQSSGLYSLSSVVTVPSSNFGTQ<br>TYTCNVDHKPSNTKVDKTVERKCCVECPPCPAPPVAGPS<br>VFLFPPKPKDTLMISRTPEVTCVVVDVSHEDPEVQFNWY<br>VDGVEVHNAKTKPREEQFNSTFRVVSVLTVVHQDWLN<br>GKEYKCKVSNKGLPAPIEKTISKTKGQPREPQVYTLPPSRE<br>EMTKNQVSLTCLVKGFYPSDIAVEWESNGQPENNYKTT<br>PPMLDSDGSFFLYSKLTVDKSRWQQGNVFSCSVMHEAL<br>HNHYTQKSLSLSPGK |
| SEQ ID NO: 96 | DNA Constant HC | GCCAGCACCAAGGGCCCCAGCGTGTTCCCCCTGGCCC<br>CCTGCAGCAGAAGCACCAGCGAGAGCACAGCCGCCCT<br>GGGCTGCCTGGTGAAGGACTACTTCCCCGAGCCAGTG<br>ACCGTGTCCTGGAACAGCGGAGCCCTGACCAGCGGC<br>GTGCACACCTTCCCCGCCGTGCTGCAGAGCAGCGGCC<br>TGTACAGCCTGTCCAGCGTGGTGACCGTGCCCAGCAG<br>CAACTTCGGCACCCAGACCTACACCTGCAACGTGGAC<br>CACAAGCCCAGCAACACCAAGGTGGACAAGACCGTG<br>GAGAGGAAGTGCTGCGTGGAGTGCCCCCCCTGCCCA<br>GCCCCCCAGTGGCCGGACCCTCCGTGTTCCTGTTCCC<br>CCCCAAGCCCAAGGACACCCTGATGATCAGCAGGACC<br>CCCGAGGTGACCTGCGTGGTGGTGGACGTGAGCCAC<br>GAGGACCCAGAGGTGCAGTTCAACTGGTACGTGGAC<br>GGCGTGGAGGTGCACAACGCCAAGACCAAGCCCAGA<br>GAGGAACAGTTTAACAGCACCTTCAGGGTGGTGTCCG<br>TGCTGACCGTGGTGCACCAGGACTGGCTGAACGGCAA<br>AGAGTACAAGTGCAAGGTCTCCAACAAGGGCCTGCCA<br>GCCCCCATCGAGAAAACCATCAGCAAGACCAAGGGCC<br>AGCCACGGGAGCCCCAGGTGTACACCCTGCCCCCCAG<br>CCGGGAGGAAATGACCAAGAACCAGGTGTCCCTGAC<br>CTGTCTGGTGAAGGGCTTCTACCCCAGCGACATCGCC<br>GTGGAGTGGGAGAGCAACGGCCAGCCCGAGAACAAC<br>TACAAGACCACCCCCCCCATGCTGGACAGCGACGGCA<br>GCTTCTTCCTGTACAGCAAGCTGACAGTGGACAAGAG<br>CAGGTGGCAGCAGGGCAACGTGTTCAGCTGCAGCGT<br>GATGCACGAGGCCCTGCACAACCACTACACCCAGAAG<br>AGCCTGAGCCTGTCCCCCGGCAAG |

>hIgG3

| | | |
|---|---|---|
| SEQ ID NO: 97 | Constant HC | ASTKGPSVFPLAPCSRSTSGGTAALGCLVKDYFPEPVTVS<br>WNSGALTSGVHTFPAVLQSSGLYSLSSVVTVPSSSLGTQ<br>TYTCNVNHKPSNTKVDKRVELKTPLGDTTHTCPRCPEPK<br>SCDTPPPCPRCPEPKSCDTPPPCPRCPEPKSCDTPPPCPR<br>CPAPELLGGPSVFLFPPKPKDTLMISRTPEVTCVVVDVSH<br>EDPEVQFKWYVDGVEVHNAKTKPREEQYNSTFRVVSVL<br>TVLHQDWLNGKEYKCKVSNKALPAPIEKTISKTKGQPRE<br>PQVYTLPPSREEMTKNQVSLTCLVKGFYPSDIAVEWESS<br>GQPENNYNTTPPMLDSDGSFFLYSKLTVDKSRWQQGNI<br>FSCSVMHEALHNRFTQKSLSLSPGK |
| SEQ ID NO: 98 | DNA Constant HC | GCCAGCACCAAGGGCCCCAGCGTGTTCCCCCTGGCCC<br>CCTGCAGCCGGAGCACCAGCGGCGGCACCGCCGCCCT<br>GGGCTGCCTGGTGAAGGACTACTTCCCCGAGCCCGTG<br>ACCGTGAGCTGGAACAGCGGCGCCCTGACCAGCGGC<br>GTGCACACCTTCCCCGCCGTGCTGCAGAGCAGCGGCC<br>TGTACAGCCTGAGCAGCGTGGTGACCGTGCCCAGCAG<br>CAGCCTGGGCACCCAGACCTACACCTGCAACGTGAAC<br>CACAAGCCCAGCAACACCAAGGTGGACAAGCGGGTG<br>GAGCTGAAGACCCCCCTGGGCGACACCACCCACACCT<br>GCCCCCGGTGCCCCGAGCCCAAGAGCTGCGACACCCC<br>CCCCCCTGCCCCGGTGCCCCGAGCCCAAGAGCTGC<br>GACACCCCCCCCCCTGCCCCGGTGCCCCGAGCCCAA<br>GAGCTGCGACACCCCCCCCCCCTGCCCCGGTGCCCC<br>GCCCCCGAGCTGCTGGGCGGCCCCAGCGTGTTCCTGT<br>TCCCCCCCAAGCCCAAGGACACCCTGATGATCAGCCG<br>GACCCCCGAGGTGACCTGCGTGGTGGTGGACGTGAG<br>CCACGAGGACCCCGAGGTGCAGTTCAAGTGGTACGTG TABLE 41-continued Sequence list

```
GACGGCGTGGAGGTGCACAACGCCAAGACCAAGCCC
CGGGAGGAGCAGTACAACAGCACCTTCCGGGTGGTG
AGCGTGCTGACCGTGCTGCACCAGGACTGGCTGAACG
GCAAGGAGTACAAGTGCAAGGTGAGCAACAAGGCCC
TGCCCGCCCCCATCGAGAAGACCATCAGCAAGACCAA
GGGCCAGCCCCGGGAGCCCCAGGTGTACACCCTGCCC
CCCAGCCGGGAGGAGATGACCAAGAACCAGGTGAGC
CTGACCTGCCTGGTGAAGGGCTTCTACCCCAGCGACA
TCGCCGTGGAGTGGGAGAGCAGCGGCCAGCCCGAGA
ACAACTACAACACCACCCCCCCCATGCTGGACAGCGA
CGGCAGCTTCTTCCTGTACAGCAAGCTGACCGTGGAC
AAGAGCCGGTGGCAGCAGGGCAACATCTTCAGCTGC
AGCGTGATGCACGAGGCCCTGCACAACCGGTTCACCC
AGAAGAGCCTGAGCCTGAGCCCCGGCAAG
```

>hIgG4

SEQ ID NO: 99     Constant HC

```
ASTKGPSVFPLAPCSRSTSESTAALGCLVKDYFPEPVTVS
WNSGALTSGVHTFPAVLQSSGLYSLSSVVTVPSSSLGTKT
YTCNVDHKPSNTKVDKRVESKYGPPCPSCPAPEFLGGPS
VFLFPPKPKDTLMISRTPEVTCVVVDVSQEDPEVQFNWY
VDGVEVHNAKTKPREEQFNSTYRVVSVLTVLHQDWLN
GKEYKCKVSNKGLPSSIEKTISKAKGQPREPQVYTLPPSQE
EMTKNQVSLTCLVKGFYPSDIAVEWESNGQPENNYKTT
PPVLDSDGSFFLYSRLTVDKSRWQEGNVFSCSVMHEAL
HNHYTQKSLSLSLGK
```

SEQ ID NO: 10     DNA Constant HC

```
GCCTCTACCAAGGGCCCCAGCGTGTTCCCCCTGGCCCC
CTGCAGCAGAAGCACCAGCGAGAGCACAGCCGCCCT
GGGCTGCCTGGTGAAGGACTACTTCCCCGAGCCAGTG
ACCGTGTCCTGGAACAGCGGAGCCCTGACCAGCGGC
GTGCACACCTTCCCCGCCGTGCTGCAGAGCAGCGGCC
TGTACAGCCTGTCCAGCGTGGTGACCGTGCCCAGCAG
CAGCCTGGGCACCAAGACCTACACCTGCAACGTGGAC
CACAAGCCCAGCAACACCAAGGTGGACAAGAGGGTG
GAGAGCAAGTACGGCCCACCCTGCCCCTCTTGCCCAG
CCCCCGAGTTCCTGGGCGGACCCTCCGTGTTCCTGTTC
CCCCCAAGCCCAAGGACACCCTGATGATCAGCAGGA
CCCCCGAGGTGACCTGCGTGGTGGTGGACGTGAGCC
AGGAAGATCCAGAGGTCCAGTTCAACTGGTACGTGGA
CGGCGTGGAGGTGCACAACGCCAAGACCAAGCCCAG
AGAGGAACAGTTTAACAGCACCTACAGGGTGGTGTCC
GTGCTGACCGTGCTGCACCAGGACTGGCTGAACGGCA
AAGAGTACAAGTGCAAGGTCTCCAACAAGGGCCTGCC
CAGCTCCATCGAGAAAACCATCAGCAAGGCCAAGGGC
CAGCCACGGGAGCCCCAGGTGTACACCCTGCCACCCT
CCCAGGAAGAGATGACCAAGAACCAGGTGTCCCTGAC
CTGTCTGGTGAAGGGCTTCTACCCCAGCGACATCGCC
GTGGAGTGGGAGAGCAACGGCCAGCCCGAGAACAAC
TACAAGACCACCCCCCCAGTGCTGGACAGCGACGGCA
GCTTCTTCCTGTACAGCAGGCTGACCGTGGACAAGTC
CAGGTGGCAGGAAGGCAACGTCTTTAGCTGCAGCGT
GATGCACGAGGCCCTGCACAACCACTACACCCAGAAG
AGCCTGAGCCTGTCCCTGGGCAAG
```

>hIgG1 LALA

SEQ ID NO: 101     Constant HC

```
ASTKGPSVFPLAPSSKSTSGGTAALGCLVKDYFPEPVTVS
WNSGALTSGVHTFPAVLQSSGLYSLSSVVTVPSSSLGTQ
TYICNVNHKPSNTKVDKKVEPKSCDKTHTCPPCPAPEAA
GGPSVFLFPPKPKDTLMISRTPEVTCVVVDVSHEDPEVKF
NWYVDGVEVHNAKTKPREEQYNSTYRVVSVLTVLHQD
WLNGKEYKCKVSNKALPAPIEKTISKAKGQPREPQVYTLP
PSREEMTKNQVSLTCLVKGFYPSDIAVEWESNGQPENN
YKTTPPVLDSDGSFFLYSKLTVDKSRWQQGNVFSCSVM
HEALHNHYTQKSLSLSPGK
```

SEQ ID NO: 102     DNA Constant HC

```
GCCTCCACCAAGGGTCCATCGGTCTTCCCCCTGGCACC
CTCCTCCAAGAGCACCTCTGGGGGCACAGCGGCCCTG
GGCTGCCTGGTCAAGGACTACTTCCCCGAACCGGTGA
CGGTGTCGTGGAACTCAGGCGCCCTGACCAGCGGCGT
GCACACCTTCCCGGCTGTCCTACAGTCCTCAGGACTCT
ACTCCCTCAGCAGCGTGGTGACCGTGCCCTCCAGCAG
CTTGGGCACCCAGACCTACATCTGCAACGTGAATCAC
AAGCCCAGCAACACCAAGGTGGACAAGAGAGTTGAG
CCCAAATCTTGTGACAAAACTCACACATGCCCACCGTG
CCCAGCACCTGAAGCAGCGGGGGGACCGTCAGTCTTC
CTCTTCCCCCCAAAACCCAAGGACACCCTCATGATCTC
CCGGACCCCTGAGGTCACATGCGTGGTGGTGGACGTG
AGCCACGAAGACCCTGAGGTCAAGTTCAACTGGTACG
```

TABLE 41-continued

Sequence list

TGGACGGCGTGGAGGTGCATAATGCCAAGACAAAGC
CGCGGGAGGAGCAGTACAACAGCACGTACCGGGTGG
TCAGCGTCCTCACCGTCCTGCACCAGGACTGGCTGAAT
GGCAAGGAGTACAAGTGCAAGGTCTCCAACAAAGCCC
TCCCAGCCCCCATCGAGAAAACCATCTCCAAAGCCAAA
GGGCAGCCCCGAGAACCACAGGTGTACACCCTGCCCC
CATCCCGGGAGGAGATGACCAAGAACCAGGTCAGCC
TGACCTGCCTGGTCAAAGGCTTCTATCCCAGCGACATC
GCCGTGGAGTGGGAGAGCAATGGGCAGCCGGAGAA
CAACTACAAGACCACGCCTCCCGTGCTGGACTCCGAC
GGCTCCTTCTTCCTCTACAGCAAGCTCACCGTGGACAA
GAGCAGGTGGCAGCAGGGGAACGTCTTCTCATGCTCC
GTGATGCATGAGGCTCTGCACAACCACTACACGCAGA
AGAGCCTCTCCCTGTCTCCGGGTAAA

>hIgG1 N297A

| SEQ ID NO: 103 | Constant HC | ASTKGPSVFPLAPSSKSTSGGTAALGCLVKDYFPEPVTVS<br>WNSGALTSGVHTFPAVLQSSGLYSLSSVVTVPSSSLGTQ<br>TYICNVNHKPSNTKVDKKVEPKSCDKTHTCPPCPAPELLG<br>GPSVFLFPPKPKDTLMISRTPEVTCVVVDVSHEDPEVKFN<br>WYVDGVEVHNAKTKPREEQYASTYRVVSVLTVLHQDW<br>LNGKEYKCKVSNKALPAPIEKTISKAKGQPREPQVYTLPP<br>SREEMTKNQVSLTCLVKGFYPSDIAVEWESNGQPENNY<br>KTTPPVLDSDGSFFLYSKLTVDKSRWQQGNVFSCSVMH<br>EALHNHYTQKSLSLSPGK |
|---|---|---|
| SEQ ID NO: 104 | DNA Constant HC | GCTAGCACCAAGGGCCCCTCCGTGTTCCCTCTGGCCCC<br>CTCCAGCAAGTCCACCTCTGGCGGCACCGCCGCTCTG<br>GGCTGCCTGGTGAAAGACTACTTCCCCGAGCCCGTGA<br>CCGTGTCCTGGAACTCTGGCGCCCTGACCTCCGGCGT<br>GCACACCTTTCCAGCCGTGCTGCAGTCCTCCGGCCTGT<br>ACTCCCTGTCCTCCGTGGTGACCGTGCCCTCTAGCTCT<br>CTGGGCACCCAGACCTACATCTGCAACGTGAACCACA<br>AGCCCTCCAACACCAAGGTGGACAAGCGGGTGGAAC<br>CCAAGTCCTGCGACAAGACCCACACCTGTCCCCCCTGC<br>CCTGCCCCTGAACTGCTGGGCGGACCTTCCGTGTTCCT<br>GTTCCCCCCAAAGCCCAAGGACACCCTGATGATCTCCC<br>GGACCCCCGAAGTGACCTGCGTGGTGGTGGACGTGTC<br>CCACGAGGACCCTGAAGTGAAGTTCAATTGGTACGTG<br>GACGGCGTGGAAGTGCACAACGCCAAGACCAAGCCC<br>AGAGAGGAACAGTACGCCTCCACCTACCGGGTGGTGT<br>CTGTGCTGACCGTGCTGCACCAGGACTGGCTGAACGG<br>CAAAGAGTACAAGTGCAAGGTCTCCAACAAGGCCCTG<br>CCTGCCCCCATCGAAAAGACCATCTCCAAGGCCAAGG<br>GCCAGCCCCGCGAGCCACAGGTGTACACACTGCCCCC<br>CAGCCGGGAAGAGATGACCAAGAACCAGGTGTCCCT<br>GACCTGTCTGGTCAAAGGCTTCTACCCCTCCGATATCG<br>CCGTGGAGTGGGAGTCCAACGGACAGCCCGAGAACA<br>ACTACAAGACCACCCCCCCTGTGCTGGACTCCGACGG<br>CTCATTCTTCCTGTACTCCAAGCTGACCGTGGACAAGT<br>CCCGGTGGCAGCAGGGCAACGTGTTCTCCTGCTCCGT<br>GATGCACGAGGCCCTGCACAACCACTACACCCAGAAG<br>TCCCTGTCCCTGAGCCCCGGCAAG |

>hIgG1 DAPA

| SEQ ID NO: 105 | Constant HC | ASTKGPSVFPLAPSSKSTSGGTAALGCLVKDYFPEPVTVS<br>WNSGALTSGVHTFPAVLQSSGLYSLSSVVTVPSSSLGTQ<br>TYICNVNHKPSNTKVDKKVEPKSCDKTHTCPPCPAPELLG<br>GPSVFLFPPKPKDTLMISRTPEVTCVVVAVSHEDPEVKFN<br>WYVDGVEVHNAKTKPREEQYNSTYRVVSVLTVLHQDW<br>LNGKEYKCKVSNKALAAPIEKTISKAKGQPREPQVYTLPP<br>SREEMTKNQVSLTCLVKGFYPSDIAVEWESNGQPENNY<br>KTTPPVLDSDGSFFLYSKLTVDKSRWQQGNVFSCSVMH<br>EALHNHYTQKSLSLSPGK |
|---|---|---|
| SEQ ID NO:106 | DNA Constant HC | GCTAGCACCAAGGGCCCCAGCGTGTTCCCCCTGGCCC<br>CCAGCAGCAAGAGCACCAGCGGCGGCACAGCCGCCC<br>TGGGCTGCCTGGTGAAGGACTACTTCCCCGAGCCCGT<br>GACCGTGTCCTGGAACAGCGGAGCCCTGACCTCCGGC<br>GTGCACACCTTCCCCGCCGTGCTGCAGAGCAGCGGCC<br>TGTACAGCCTGTCCAGCGTGGTGACAGTGCCCAGCAG<br>CAGCCTGGGCACCCAGACCTACATCTGCAACGTGAAC<br>CACAAGCCCAGCAACACCAAGGTGGACAAGAGAGTG<br>GAGCCCAAGAGCTGCGACAAGACCCACACCTGCCCCC<br>CCTGCCCAGCCCCAGAGCTGCTGGGCGGACCCTCCGT<br>GTTCCTGTTCCCCCCCAAGCCCAAGGACACCCTGATGA<br>TCAGCAGGACCCCCGAGGTGACCTGCGTGGTGGTGG<br>CCGTGAGCCACGAGGACCCAGAGGTGAAGTTCAACT |

TABLE 41-continued

Sequence list

```
GGTACGTGGACGGCGTGGAGGTGCACAACGCCAAGA
CCAAGCCCAGAGAGGAGCAGTACAACAGCACCTACA
GGGTGGTGTCCGTGCTGACCGTGCTGCACCAGGACTG
GCTGAACGGCAAGGAATACAAGTGCAAGGTCTCCAAC
AAGGCCCTGCCAGCCCCCATCGAAAAGACCATCAGCA
AGGCCAAGGGCCAGCCACGGGAGCCCCAGGTGTACA
CCCTGCCCCCCTCCCGGGAGGAGATGACCAAGAACCA
GGTGTCCCTGACCTGTCTGGTGAAGGGCTTCTACCCCA
GCGACATCGCCGTGGAGTGGGAGAGCAACGGCCAGC
CCGAGAACAACTACAAGACCACCCCCCCAGTGCTGGA
CAGCGACGGCAGCTTCTTCCTGTACAGCAAGCTGACC
GTGGACAAGTCCAGGTGGCAGCAGGGCAACGTGTTC
AGCTGCAGCGTGATGCACGAGGCCCTGCACAACCACT
ACACCCAGAAGAGCCTGAGCCTGTCCCCCGGCAAG
```

>hkappa

| SEQ ID NO: 107 | Constant LC | RTVAAPSVFIFPPSDEQLKSGTASVVCLLNNFYPREAKVQ<br>WKVDNALQSGNSQESVTEQDSKDSTYSLSSTLTLSKADY<br>EKHKVYACEVTHQGLSSPVTKSFNRGEC |
|---|---|---|
| SEQ ID NO: 108 | DNA Constant LC | CGTACGGTGGCCGCTCCCAGCGTGTTCATCTTCCCCCC<br>CAGCGACGAGCAGCTGAAGAGCGGCACCGCCAGCGT<br>GGTGTGCCTGCTGAACAACTTCTACCCCCGGGAGGCC<br>AAGGTGCAGTGGAAGGTGGACAACGCCCTGCAGAGC<br>GGCAACAGCCAGGAGAGCGTCACCGAGCAGGACAGC<br>AAGGACTCCACCTACAGCCTGAGCAGCACCCTGACCC<br>TGAGCAAGGCCGACTACGAGAAGCATAAGGTGTACG<br>CCTGCGAGGTGACCCACCAGGGCCTGTCCAGCCCCGT<br>GACCAAGAGCTTCAACAGGGGCGAGTGC |

>IL-2

| SEQ ID NO: 109 | Human IL-2 | MYRMQLLSCIALSLALVTNSAPTSSSTKKTQLQLEHLLLDL<br>QMILNGINNYKNPKLTRMLTFKFYMPKKATELKHLQCLE<br>EELKPLEEVLNLAQSKNFHLRPRDLISNINVIVLELKGSETT<br>FMCEYADETATIVEFLNRWITFCQSIISTLT |
|---|---|---|
| SEQ ID NO: 110 | Proleukin ® (aldesleukin) | MAPTSSSTKKTQLQLEHLLLDLQMILNGINNYKNPKLTR<br>MLTFKFYMPKKATELKHLQCLEEELKPLEEVLNLAQSKNF<br>HLRPRDLISNINVIVLELKGSETTFMCEYADETATIVEFLN<br>RWITFSQSIISTLT |

>NARA1

| SEQ ID NO: 4 (Kabat) | HCDR1 | NYLIE |
|---|---|---|
| SEQ ID NO: 2 (Kabat) | HCDR2 | VINPGSGGTNYNEKFKG |
| SEQ ID NO: 3 (Kabat) | HCDR3 | WRGDGYYAYFDV |
| SEQ ID NO: 19 (Kabat) | LCDR1 | KASQSVDYDGDSYMN |
| SEQ ID NO: 20 (Kabat) | LCDR2 | AASNLES |
| SEQ ID NO: 21 (Kabat) | LCDR3 | QQSNEDPYT |
| SEQ ID NO: 111 | VH | QVQLQQSGAELVRPGTSVKVSCKASGYAFTNYLIEWVK<br>QRPGQGLEWIGVINPGSGGTNYNEKFKGKATLTADKSS<br>STAYMQLSSLTSDDSAVYFCARWRGDGYYAYFDVWGA<br>GTTVTVSS |
| SEQ ID NO: 112 | DNA VH | CAGGTCCAGCTGCAGCAGTCTGGAGCTGAGCTGGTAA<br>GGCCTGGGACTTCAGTGAAGGTGTCCTGCAAGGCTTC<br>TGGATACGCCTTCACTAATTACTTGATAGAGTGGGTAA<br>AGCAGAGGCCTGGACAGGGCCTTGAGTGGATTGGAG<br>TGATTAATCCTGGAAGTGGTGGTACTAACTACAATGA<br>GAAGTTCAAGGGCAAGGCAACACTGACTGCAGACAA<br>ATCCTCCAGCACTGCCTACATGCAGCTCAGCAGCCTGA<br>CATCTGATGACTCTGCGGTCTATTTCTGTGCAAGATGG<br>AGGGGGGATGGTTACTACGCGTACTTCGATGTCTGGG<br>GCGCAGGGACCACGGTCACCGTCTCCTCA |
| SEQ ID NO: 113 | VL | DIVLTQSPASLAVSLGQRATISCKASQSVDYDGDSYMN<br>WYQQKPGQPPKLLIYAASNLESGIPARFSGSGSGTDFTL<br>NIHPVEEEDAATYYCQQSNEDPYTFGGGTKLEIK |
| SEQ ID NO: 114 | DNA VL | GACATTGTGCTGACCCAATCTCCAGCTTCTTTGGCTGT<br>GTCTCTAGGGCAGAGGGCCACCATCTCCTGCAAGGCC<br>AGCCAAAGTGTTGATTATGATGGTGATAGTTATATGA<br>ACTGGTACCAACAGAAACCAGGACAGCCACCCAAACT<br>CCTCATCTATGCTGCATCCAATCTAGAATCTGGGATCC<br>CAGCCAGGTTTAGTGGCAGTGGGTCTGGGACAGACTT<br>CACCCTCAACATCCATCCTGTGGAGGAGGAGGATGCT<br>GCAACCTATTACTGTCAGCAAAGTAATGAGGATCCGT<br>ACACGTTCGGAGGGGGGACCAAGCTGGAAATAAAA |
| SEQ ID NO: 115 | Heavy Chain | QVQLQQSGAELVRPGTSVKVSCKASGYAFTNYLIEWVK<br>QRPGQGLEWIGVINPGSGGTNYNEKFKGKATLTADKSS<br>STAYMQLSSLTSDDSAVYFCARWRGDGYYAYFDVWGA |

TABLE 41-continued

| | | Sequence list |
|---|---|---|
| | | GTTVTVSSAKTTAPSVYPLAPVCGDTTGSSVTLGCLVKGY FPEPVTLTWNSGSLSSGVHTFPAVLQSDLYTLSSSVTVTS STWPSQSITCNVAHPASSTKVDKKIEPRGPTIKPCPPCKC PAPNLLGGPSVFIFPPKIKDVLMISLSPIVTCVVVDVSEDD PDVQISWFVNNVEVHTAQTQTHREDYNSTLRVVSALPI QHQDWMSGKEFKCKVNNKDLPAPIERTISKPKGSVRAP QVYVLPPPEEEMTKKQVTLTCMVTDFMPEDIYVEWTN NGKTELNYKNTEPVLDSDGSYFMYSKLRVEKKNWVERN SYSCSVVHEGLHNHHTTKSFSRTPGK |
| SEQ ID NO: 116 | DNA Heavy Chain | CAGGTCCAGCTGCAGCAGTCTGGAGCTGAGCTGGTAA GGCCTGGGACTTCAGTGAAGGTGTCCTGCAAGGCTTC TGGATACGCCTTCACTAATTACTTGATAGAGTGGGTAA AGCAGAGGCCTGGACAGGGCCTTGAGTGGATTGGAG TGATTAATCCTGGAAGTGGTGGTACTAACTACAATGA GAAGTTCAAGGGCAAGGCAACACTGACTGCAGACAA ATCCTCCAGCACTGCCTACATGCAGCTCAGCAGCCTGA CATCTGATGACTCTGCGGTCTATTTCTGTGCAAGATGG AGGGGGGATGGTTACTACGCGTACTTCGATGTCTGGG GCGCAGGGACCACGGTCACCGTCTCCTCAGCCAAAAC AACAGCCCCATCGGTCTATCCACTGGCCCCTGTGTGTG GAGATACAACTGGCTCCTCGGTGACTCTAGGATGCCT GGTCAAGGGTTATTTCCCTGAGCCAGTGACCTTGACCT GGAACTCTGGATCCCTGTCCAGTGGTGTGCACACCTTC CCAGCTGTCCTGCAGTCTGACCTCTACACCCTCAGCAG CTCAGTGACTGTAACCTCGAGCACCTGGCCCAGCCAG TCCATCACCTGCAATGTGGCCCACCCGGCAAGCAGCA CCAAGGTGGACAAGAAAATTGAGCCCAGAGGGCCCA CAATCAAGCCCTGTCCTCCATGCAAATGCCCAGCACCT AACCTCTTGGGTGGACCATCCGTCTTCATCTTCCCTCCA AAGATCAAGGATGTACTCATGATCTCCCTGAGCCCCAT AGTCACATGTGTGGTGGTGGATGTGAGCGAGGATGA CCCAGATGTCCAGATCAGCTGGTTTGTGAACAACGTG GAAGTACACACAGCTCAGACACAAACCCATAGAGAGG ATTACAACAGTACTCTCCGGGTGGTCAGTGCCCTCCCC ATCCAGCACCAGGACTGGATGAGTGGCAAGGAGTTC AAATGCAAGGTCAACAACAAAGACCTCCCAGCGCCCA TCGAGAGAACCATCTCAAAACCCAAAGGGTCAGTAAG AGCTCCACAGGTATATGTCTTGCCTCCACCAGAAGAA GAGATGACTAAGAAACAGGTCACTCTGACCTGCATGG TCACAGACTTCATGCCTGAAGACATTTACGTGGAGTG GACCAACAACGGGAAAACAGAGCTAAACTACAAGAA CACTGAACCAGTCCTGGACTCTGATGGTTCTTACTTCA TGTACAGCAAGCTGAGAGTGGAAAAGAAGAACTGGG TGGAAAGAAATAGCTACTCCTGTTCAGTGGTCCACGA GGGTCTGCACAATCACCACACGACTAAGAGCTTCTCCC GGACTCCGGGTAAA |
| SEQ ID NO: 117 | Light Chain | DIVLTQSPASLAVSLGQRATISCKASQSVDYDGDSYMN WYQQKPGQPPKLLIYAASNLESGIPARFSGSGSGTDFTL NIHPVEEEDAATYYCQQSNEDPYTFGGGTKLEIKRADAA PTVSIFPPSSEQLTSGGASVVCFLNNFYPKDINVKWKIDG SERQNGVLNSWTDQDSKDSTYSMSSTLTLTKDEYERHN SYTCEATHKTSTSPIVKSFNRNEC |
| SEQ ID NO: 118 | DNA Light Chain | GACATTGTGCTGACCCAATCTCCAGCTTCTTTGGCTGT GTCTCTAGGGCAGAGGGCCACCATCTCCTGCAAGGCC AGCCAAAGTGTTGATTATGATGGTGATAGTTATATGA ACTGGTACCAACAGAAACAGGACAGCCACCCAAACT CCTCATCTATGCTGCATCCAATCTAGAATCTGGGATCC CAGCCAGGTTTAGTGGCAGTGGGTCTGGGACAGACTT CACCCTCAACATCCATCCTGTGGAGGAGGAGGATGCT GCAACCTATTACTGTCAGCAAAGTAATGAGGATCCGT ACACGTTCGGAGGGGGGACCAAGCTGGAAATAAAAC GGGCTGATGCTGCACCAACTGTATCCATCTTCCCACCA TCCAGTGAGCAGTTAACATCTGGAGGTGCCTCAGTCG TGTGCTTCTTGAACAACTTCTACCCCAAAGACATCAAT GTCAAGTGGAAGATTGATGGCAGTGAACGACAAAAT GGCGTCCTGAACAGTTGGACTGATCAGGACAGCAAA GACAGCACCTACAGCATGAGCAGCACCCTCACGTTGA CCAAGGACGAGTATGAACGACATAACAGCTATACCTG TGAGGCCACTCACAAGACATCAACTTCACCCATTGTCA AGAGCTTCAACAGGAATGAGTGT |
| SEQ ID NO: 119 | HCDR1 consensus HCDR1 variable amino acids | X1YLIE X1 = N or S |

TABLE 41-continued

Sequence list

| SEQ ID NO: 120 | HCDR2 consensus | VINPGSGGTNYX1X2X3X4KG |
|---|---|---|
| | HCDR2 variable amino acids | X1 = N or A; X2 = E or D; X3 = K or S; X4 = F or V |
| SEQ ID NO: 121 | HCDR3 consensus | WRGX1X2YYAYFDV |
| | HCDR3 variable amino acids | X1 = E, D, A, G, or T; X2 = G, A, T, or S |
| SEQ ID NO: 122 | LCDR1 consensus | X1ASQSVX2YX3X4DSYMN |
| | LCDR1 variable amino acids | X1 = R or K; X2 = S or D; X3 = D, Q, A, G or T; X4 = G, T or S |
| SEQ ID NO: 123 | LCDR2 consensus | AASNLX1S |
| | LCDR2 variable amino acids | X1 = E or A |

>104343

| SEQ ID NO: 124 = SEQ ID NO: 27 + SEQ ID NO: 107 | Light chain | DIVLTQSPLSLPVTLGQPASISCKASQSVDYDGDSYMNW YQQRPGQSPRLLIYAASNLESGVPDRFSGSGSGTDFTLKI SRVEAEDVGVYYCQQSNEDPYTFGGGTKVEIK RTVAAPSVFIFPPSDEQLKSGTASVVCLLNNFYPREAKVQ WKVDNALQSGNSQESVTEQDSKDSTYSLSSTLTLSKADY EKHKVYACEVTHQGLSSPVTKSFNRGEC |
|---|---|---|
| SEQ ID NO: 125 = SEQ ID NO: 28 + SEQ ID NO: 108 | DNA encoding light chain | GACATCGTGCTGACACAGAGCCCTCTGTCCCTGCCCGT GACCCTGGGCCAGCCTGCCTCCATCTCCTGCAAGGCCT CCCAGTCCGTGGACTACGACGGCGACTCCTACATGAA CTGGTATCAGCAGCGGCCTGGCCAGTCCCCTCGGCTG CTGATCTACGCCGCCTCCAACCTGGAATCCGGCGTGCC CGACAGATTCTCCGGCTCCGGCTCTGGCACCGACTTCA CCCTGAAGATCTCCCGGGTGGAAGCCGAGGACGTGG GCGTGTACTACTGCCAGCAGTCCAACGAGGACCCCTA CACCTTCGGCGGAGGCACCAAAGTGGAAATCAAGCGT ACGGTGGCCGCTCCCAGCGTGTTCATCTTCCCCCCCAG CGACGAGCAGCTGAAGAGCGGCACCGCCAGCGTGGT GTGCCTGCTGAACAACTTCTACCCCCGGGAGGCCAAG GTGCAGTGGAAGGTGGACAACGCCCTGCAGAGCGGC AACAGCCAGGAGAGCGTCACCGAGCAGGACAGCAAG GACTCCACCTACAGCCTGAGCAGCACCCTGACCCTGA GCAAGGCCGACTACGAGAAGCATAAGGTGTACGCCT GCGAGGTGACCCACCAGGGCCTGTCCAGCCCCGTGAC CAAGAGCTTCAACAGGGGCGAGTGC |
| SEQ ID NO: 126 = SEQ ID NO: 7 + SEQ ID NO: 103 | Heavy chain | QVQLVQSGAEVKKPGSSVKVSCKASGYAFTNYLIEWVR QAPGQGLEWMGVINPGSGGTNYNEKFKGRVTITADKS TSTAYMELSSLRSEDTAVYYCARWRGDGYYAYFDVWG QGTTVTVSSASTKGPSVFPLAPSSKSTSGGTAALGCLVKD YFPEPVTVSWNSGALTSGVHTFPAVLQSSGLYSLSSVVTV PSSSLGTQTYICNVNHKPSNTKVDKKVEPKSCDKTHTCPP CPAPELLGGPSVFLFPPKPKDTLMISRTPEVTCVVVDVSH EDPEVKFNWYVDGVEVHNAKTKPREEQYASTYRVVSVL TVLHQDWLNGKEYKCKVSNKALPAPIEKTISKAKGQPRE PQVYTLPPSREEMTKNQVSLTCLVKGFYPSDIAVEWESN GQPENNYKTTPPVLDSDGSFFLYSKLTVDKSRWQQGNV FSCSVMHEALHNHYTQKSLSLSPGK |
| SEQ ID NO: 127 = SEQ ID NO: 8 + SEQ ID NO: 104 | DNA encoding heavy chain | CAAGTGCAGCTGGTGCAGTCTGGCGCTGAAGTGAAG AAACCCGGCTCCTCCGTGAAAGTGTCCTGCAAGGCCT CCGGCTACGCCTTCACCAACTACCTGATCGAGTGGGTC CGACAGGCCCCAGGCCAGGGCCTGGAGTGGATGGGC GTGATCAACCCTGGCTCCGGCGGCACCAACTACAACG AGAAGTTCAAGGGCAGAGTGACCATCACCGCCGACAA GTCCACCTCCACCGCCTACATGGAACTGTCCTCCCTGC GGAGCGAGGACACCGCCGTGTACTACTGTGCCCGGTG GCGGGGAGATGGCTACTACGCCTACTTCGACGTGTGG GGCCAGGGCACCACCGTGACCGTGTCCTCTGCTAGCA CCAAGGGCCCCTCCGTGTTCCCTCTGGCCCCCTCCAGC AAGTCCACCTCTGGCGGCACCGCCGCTCTGGGCTGCC TGGTCAAGGACTACTTCCCCGAGCCCGTGACCGTGTC CTGGAACTCTGGCGCTCTGACCTCCGGCGTGCACACC TTTCCAGCCGTGCTGCAGTCCTCCGGCCTGTACTCCCT GTCCTCCGTGGTGACCGTGCCCTCTAGCTCTCTGGGCA CCCAGACCTACATCTGCAACGTGAACCACAAGCCCTCC AACACCAAGGTGGACAAGCGGGTGGAACCCAAGTCC TGCGACAAGACCCACACCTGTCCCCCCTGCCCTGCCCC |

TABLE 41-continued

Sequence list

TGAACTGCTGGGCGGACCTTCCGTGTTCCTGTTCCCCC
CAAAGCCCAAGGACACCCTGATGATCTCCCGGACCCC
CGAAGTGACCTGCGTGGTGGTGGACGTGTCCCACGA
GGACCCTGAAGTGAAGTTCAATTGGTACGTGGACGGC
GTGGAAGTGCACAACGCCAAGACCAAGCCCAGAGAG
GAACAGTACGCCTCCACCTACCGGGTGGTGTCTGTGC
TGACCGTGCTGCACCAGGACTGGCTGAACGGCAAAG
AGTACAAGTGCAAGGTCTCCAACAAGGCCCTGCCTGC
CCCCATCGAAAAGACCATCTCCAAGGCCAAGGGCCAG
CCCCGCGAGCCACAGGTGTACACACTGCCCCCCCAGCC
GGGAAGAGATGACCAAGAACCAGGTGTCCCTGACCT
GTCTGGTCAAAGGCTTCTACCCCTCCGATATCGCCGTG
GAGTGGGAGTCCAACGGACAGCCCGAGAACAACTAC
AAGACCACCCCCCCTGTGCTGGACTCCGACGGCTCATT
CTTCCTGTACTCCAAGCTGACCGTGGACAAGTCCCGGT
GGCAGCAGGGCAACGTGTTCTCCTGCTCCGTGATGCA
CGAGGCCCTGCACAACCACTACACCCAGAAGTCCCTG
TCCCTGAGCCCCGGCAAG

>104348

| SEQ ID NO: 128 =<br>SEQ ID NO: 25 + SEQ ID NO:<br>107 | Light chain | AIRLTQSPSSFSASTGDRVTITCKASQSVDYDGDSYMNW<br>YQQKPGKAPKLLIYAASNLESGVPSRFSGSGSGTDFTLTIS<br>SLQSEDFATYYCQQSNEDPYTFGGGTKVEIKRTVAAPSV<br>FIFPPSDEQLKSGTASVVCLLNNFYPREAKVQWKVDNAL<br>QSGNSQESVTEQDSKDSTYSLSSTLTLSKADYEKHKVYAC<br>EVTHQGLSSPVTKSFNRGEC |
| SEQ ID NO: 129 =<br>SEQ ID NO: 26 + SEQ ID NO:<br>108 | DNA encoding<br>light chain | GCCATCAGACTGACCCAGAGCCCCTCCAGCTTCTCCGC<br>CTCCACCGGCGACAGAGTGACCATCACATGCAAGGCC<br>TCCCAGTCCGTGGACTACGACGGCGACTCCTACATGA<br>ACTGGTATCAGCAGAAGCCCGGCAAGGCCCCTAAGCT<br>GCTGATCTACGCCGCCTCCAACCTGGAATCCGGCGTG<br>CCCTCCCGGTTCTCCGGCTCTGGCTCTGGCACCGACTT<br>CACCCTGACCATCTCCAGCCTGCAGTCCGAGGACTTCG<br>CCACCTACTACTGCCAGCAGTCCAACGAGGACCCCTAC<br>ACCTTCGGCGGAGGCACCAAAGTGGAAATCAAGCGT<br>ACGGTGGCCGCTCCCAGCGTGTTCATCTTCCCCCCCAG<br>CGACGAGCAGCTGAAGAGCGGCACCGCCAGCGTGGT<br>GTGCCTGCTGAACAACTTCTACCCCCGGGAGGCCAAG<br>GTGCAGTGGAAGGTGGACAACGCCCTGCAGAGCGGC<br>AACAGCCAGGAGAGCGTCACCGAGCAGGACAGCAAG<br>GACTCCACCTACAGCCTGAGCAGCACCCTGACCCTGA<br>GCAAGGCCGACTACGAGAAGCATAAGGTGTACGCCT<br>GCGAGGTGACCCACCAGGGCCTGTCCAGCCCCGTGAC<br>CAAGAGCTTCAACAGGGGCGAGTGC |
| SEQ ID NO: 130 =<br>SEQ ID NO: 17 + SEQ ID NO:<br>103 | Heavy chain | EVQLVQSGAEVKKPGESLKISCKGSGYAFTNYLIEWVRQ<br>MPGKGLEWMGVINPGSGGTNYNEKFKGQVTISADKSIS<br>TAYLQWSSLKASDTAMYYCARWRGDGYYAYFDVWGQ<br>GTTVTVSSASTKGPSVFPLAPSSKSTSGGTAALGCLVKDY<br>FPEPVTVSWNSGALTSGVHTFPAVLQSSGLYSLSSVVTV<br>PSSSLGTQTYICNVNHKPSNTKVDKKVEPKSCDKTHTCPP<br>CPAPELLGGPSVFLFPPKPKDTLMISRTPEVTCVVVDVSH<br>EDPEVKFNWYVDGVEVHNAKTKPREEQYASTYRVVSVL<br>TVLHQDWLNGKEYKCKVSNKALPAPIEKTISKAKGQPRE<br>PQVYTLPPSREEMTKNQVSLTCLVKGFYPSDIAVEWESN<br>GQPENNYKTTPPVLDSDGSFFLYSKLTVDKSRWQQGNV<br>FSCSVMHEALHNHYTQKSLSLSPGK |
| SEQ ID NO: 131 =<br>SEQ ID NO: 18 + SEQ ID NO:<br>104 | DNA encoding<br>heavy chain | GAAGTGCAGCTGGTGCAGTCTGGCGCTGAAGTGAAG<br>AAGCCCGGCGAGTCCCTGAAGATCTCCTGCAAGGGCT<br>CCGGCTACGCCTTCACCAACTACCTGATCGAGTGGGTC<br>CGACAGATGCCCGGCAAGGGCCTGGAGTGGATGGGC<br>GTGATCAACCCCGGCTCCGGCGGCACCAACTACAACG<br>AGAAGTTCAAGGGCCAAGTCACAATCTCCGCCGACAA<br>GTCCATCTCCACCGCCTACCTGCAGTGGTCCTCCCTGA<br>AGGCCTCCGACACCGCCATGTACTACTGCGCCAGATG<br>GCGGGGAGATGGCTACTACGCCTACTTCGACGTGTGG<br>GGCCAGGGCACCACCGTGACCGTGTCCTCTGCTAGCA<br>CCAAGGGCCCCTCCGTGTTCCCTCTGGCCCCCTCCAGC<br>AAGTCCACCTCTGGCGGCACCGCCGCTCTGGGCTGCC<br>TGGTGAAAGACTACTTCCCCGAGCCCGTGACCGTGTC<br>CTGGAACTCTGGCGCCCTGACCTCCGGCGTGCACACC<br>TTTCCAGCCGTGCTGCAGTCCTCCGGCCTGTACTCCCT<br>GTCCTCCGTGGTGACCGTGCCCTCTAGCTCTCTGGGCA<br>CCCAGACCTACATCTGCAACGTGAACCACAAGCCCTCC<br>AACACCAAGGTGGACAAGGGGTGGAACCCAAGTCC<br>TGCGACAAGACCCACACCTGTCCCCCCTGCCCTGCCCC<br>TGAACTGCTGGGCGGACCTTCCGTGTTCCTGTTCCCCC<br>CAAAGCCCAAGGACACCCTGATGATCTCCCGGACCCC |

TABLE 41-continued

Sequence list

|  |  |  | CGAAGTGACCTGCGTGGTGGTGGACGTGTCCCACGA |
|---|---|---|---|
|  |  |  | GGACCCTGAAGTGAAGTTCAATTGGTACGTGGACGGC |
|  |  |  | GTGGAAGTGCACAACGCCAAGACCAAGCCCAGAGAG |
|  |  |  | GAACAGTACGCCTCCACCTACCGGGTGGTGTCTGTGC |
|  |  |  | TGACCGTGCTGCACCAGGACTGGCTGAACGGCAAAG |
|  |  |  | AGTACAAGTGCAAGGTCTCCAACAAGGCCCTGCCTGC |
|  |  |  | CCCCATCGAAAAGACCATCTCCAAGGCCAAGGGCCAG |
|  |  |  | CCCCGCGAGCCACAGGTGTACACACTGCCCCCCAGCC |
|  |  |  | GGGAAGAGATGACCAAGAACCAGGTGTCCCTGACCT |
|  |  |  | GTCTGGTCAAAGGCTTCTACCCCTCCGATATCGCCGTG |
|  |  |  | GAGTGGGAGTCCAACGGACAGCCCGAGAACAACTAC |
|  |  |  | AAGACCACCCCCCCTGTGCTGGACTCCGACGGCTCATT |
|  |  |  | CTTCCTGTACTCCAAGCTGACCGTGGACAAGTCCCGGT |
|  |  |  | GGCAGCAGGGCAACGTGTTCTCCTGCTCCGTGATGCA |
|  |  |  | CGAGGCCCTGCACAACCACTACACCCAGAAGTCCCTG |
|  |  |  | TCCCTGAGCCCCGGCAAG |
| SEQ ID NO: 132 |  | Epitope section | GINNYKNPKLTRMLTFKFYMPKKATELKHLQCLEEELKPL EEVLNLAQSKNF |

>VH-F100dY/N58Y/T30S

| SEQ ID NO: 133 | (Combined) | HCDR1 | GYAFSNYLIE |
|---|---|---|---|
| SEQ ID NO: 134 | (Combined) | HCDR2 | VINPGSGGTYYNEKFKG |
| SEQ ID NO: 135 | (Combined) | HCDR3 | WRGEGYYAYYDV |
| SEQ ID NO: 136 | (Kabat) | HCDR1 | NYLIE |
| SEQ ID NO: 137 | (Kabat) | HCDR2 | VINPGSGGTYYNEKFKG |
| SEQ ID NO: 138 | (Kabat) | HCDR3 | WRGEGYYAYYDV |
| SEQ ID NO: 139 | (Chothia) | HCDR1 | GYAFSNY |
| SEQ ID NO: 140 | (Chothia) | HCDR2 | NPGSGG |
| SEQ ID NO: 141 | (Chothia) | HCDR3 | WRGEGYYAYYDV |
| SEQ ID NO: 142 | (IMGT) | HCDR1 | GYAFSNYL |
| SEQ ID NO: 143 | (IMGT) | HCDR2 | INPGSGGT |
| SEQ ID NO: 144 | (IMGT) | HCDR3 | ARWRGEGYYAYYDV |
| SEQ ID NO: 145 |  | VH | EVQLVQSGAEVKKPGESLKISCKGSGYAFSNYLIEWVRQ MPGKGLEWMGVINPGSGGTYYNEKFKGQVTISADKSIS TAYLQWSSLKASDTAMYYCARWRGEGYYAYYDVWGQ GTTVTVSS |
| SEQ ID NO: 146 |  | DNA VH | GAGGTGCAATTGGTGCAGAGCGGAGCCGAAGTGAAG AAGCCCGGCGAGAGCCTGAAGATCAGCTGCAAGGGC AGCGGCTACGCCTTCAGCAACTACCTGATCGAGTGGG TGCGCCAGATGCCCGGCAAGGGCCTGGAATGGATGG GCGTGATCAATCCTGGCAGCGGCGGCACCTACTACAA CGAGAAGTTCAAGGGCCAAGTGACCATCAGCGCCGA CAAGAGCATCAGCACCGCCTACCTCCAGTGGTCCAGC CTGAAGGCCAGCGACACCGCCATGTACTACTGCGCCA GGTGGCGGGGAGAGGGCTACTACGCCTACTACGACG TGTGGGGCCAGGGCACCACAGTGACCGTCAGCTCA |
| SEQ ID NO: 147 |  | Heavy Chain | EVQLVQSGAEVKKPGESLKISCKGSGYAFSNYLIEWVRQ MPGKGLEWMGVINPGSGGTYYNEKFKGQVTISADKSIS TAYLQWSSLKASDTAMYYCARWRGEGYYAYYDVWGQ GTTVTVSSASTKGPSVFPLAPSSKSTSGGTAALGCLVKDY FPEPVTVSWNSGALTSGVHTFPAVLQSSGLYSLSSVVTV PSSSLGTQTYICNVNHKPSNTKVDKRVEPKSCDKTHTCP PCPAPELLGGPSVFLFPPKPKDTLMISRTPEVTCVVVDVS HEDPEVKFNWYVDGVEVHNAKTKPREEQYASTYRVVSV LTVLHQDWLNGKEYKCKVSNKALPAPIEKTISKAKGQPR EPQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPGK |
| SEQ ID NO: 148 |  | DNA Heavy Chain | GAGGTGCAATTGGTGCAGAGCGGAGCCGAAGTGAAG AAGCCCGGCGAGAGCCTGAAGATCAGCTGCAAGGGC AGCGGCTACGCCTTCAGCAACTACCTGATCGAGTGGG TGCGCCAGATGCCCGGCAAGGGCCTGGAATGGATGG GCGTGATCAATCCTGGCAGCGGCGGCACCTACTACAA CGAGAAGTTCAAGGGCCAAGTGACCATCAGCGCCGA CAAGAGCATCAGCACCGCCTACCTCCAGTGGTCCAGC CTGAAGGCCAGCGACACCGCCATGTACTACTGCGCCA GGTGGCGGGGAGAGGGCTACTACGCCTACTACGACG TGTGGGGCCAGGGCACCACAGTGACCGTCAGCTCAGC TAGCACCAAGGGCCCCAGCGTGTTCCCCCTGGCCCCC AGCAGCAAGAGCACCAGCGGCGGCACAGCCGCCCTG GGCTGCCTGGTGAAGGACTACTTCCCCGAGCCCGTGA CCGTGTCCTGGAACAGCGGAGCCCTGACCTCCGGCGT GCACACCTTCCCCGCCGTGCTGCAGAGCAGCGGCCTG TACAGCCTGTCCAGCGTGGTGACAGTGCCCAGCAGCA GCCTGGGCACCCAGACCTACATCTGCAACGTGAACCA CAAGCCCAGCAACACCAAGGTGGACAAGAGAGTGGA GCCCAAGAGCTGCGACAAGACCCACACCTGCCCCCCC

TABLE 41-continued

Sequence list

```
TGCCCAGCCCCAGAGCTGCTGGGCGGACCCTCCGTGT
TCCTGTTCCCCCCCAAGCCCAAGGACACCCTGATGATC
AGCAGGACCCCCGAGGTGACCTGCGTGGTGGTGGAC
GTGAGCCACGAGGACCCAGAGGTGAAGTTCAACTGG
TACGTGGACGGCGTGGAGGTGCACAACGCCAAGACC
AAGCCCAGAGAGGAGCAGTACGCCAGCACCTACAGG
GTGGTGTCCGTGCTGACCGTGCTGCACCAGGACTGGC
TGAACGGCAAGGAATACAAGTGCAAGGTCTCCAACAA
GGCCCTGCCAGCCCCCATCGAAAAGACCATCAGCAAG
GCCAAGGGCCAGCCACGGGAGCCCCAGGTGTACACC
CTGCCCCCCTCCCGGGAGGAGATGACCAAGAACCAGG
TGTCCCTGACCTGTCTGGTGAAGGGCTTCTACCCCAGC
GACATCGCCGTGGAGTGGGAGAGCAACGGCCAGCCC
GAGAACAACTACAAGACCACCCCCCCAGTGCTGGACA
GCGACGGCAGCTTCTTCCTGTACAGCAAGCTGACCGT
GGACAAGTCCAGGTGGCAGCAGGGCAACGTGTTCAG
CTGCAGCGTGATGCACGAGGCCCTGCACAACCACTAC
ACCCAGAAGAGCCTGAGCCTGTCCCCCGGCAAG
```

>VH-F100dY/N58Y

| SEQ ID NO: 149 | (Combined) | HCDR1 | GYAFTNYLIE |
|---|---|---|---|
| SEQ ID NO: 150 | (Combined) | HCDR2 | VINPGSGGTYYNEKFKG |
| SEQ ID NO: 151 | (Combined) | HCDR3 | WRGEGYYAYYDV |
| SEQ ID NO: 152 | (Kabat) | HCDR1 | NYLIE |
| SEQ ID NO: 153 | (Kabat) | HCDR2 | VINPGSGGTYYNEKFKG |
| SEQ ID NO: 154 | (Kabat) | HCDR3 | WRGEGYYAYYDV |
| SEQ ID NO: 155 | (Chothia) | HCDR1 | GYAFTNY |
| SEQ ID NO: 156 | (Chothia) | HCDR2 | NPGSGG |
| SEQ ID NO: 157 | (Chothia) | HCDR3 | WRGEGYYAYYDV |
| SEQ ID NO: 158 | (IMGT) | HCDR1 | GYAFTNYL |
| SEQ ID NO: 159 | (IMGT) | HCDR2 | INPGSGGT |
| SEQ ID NO: 160 | (IMGT) | HCDR3 | ARWRGEGYYAYYDV |
| SEQ ID NO: 161 | | VH | EVQLVQSGAEVKKPGESLKISCKGSGYAFTNYLIEWVRQ MPGKGLEWMGVINPGSGGTYYNEKFKGQVTISADKSIS TAYLQWSSLKASDTAMYYCARWRGEGYYAYYDVWGQ GTTVTVSS |
| SEQ ID NO: 162 | | DNA VH | GAGGTGCAATTGGTGCAGAGCGGAGCCGAAGTGAAG AAGCCCGGCGAGAGCCTGAAGATCAGCTGCAAGGGC AGCGGCTACGCCTTCACCAACTACCTGATCGAGTGGG TGCGCCAGATGCCCGGCAAGGGCCTGGAATGGATGG GCGTGATCAATCCTGGCAGCGGCGGCACCTACTACAA CGAGAAGTTCAAGGGCCAAGTGACCATCAGCGCCGA CAAGAGCATCAGCACCGCCTACCTCCAGTGGTCCAGC CTGAAGGCCAGCGACACCGCCATGTACTACTGCGCCA GGTGGCGGGGAGAGGGCTACTACGCCTACTACGACG TGTGGGGCCAGGGCACCACAGTGACCGTCAGCTCA |
| SEQ ID NO: 163 | | Heavy Chain | EVQLVQSGAEVKKPGESLKISCKGSGYAFTNYLIEWVRQ MPGKGLEWMGVINPGSGGTYYNEKFKGQVTISADKSIS TAYLQWSSLKASDTAMYYCARWRGEGYYAYYDVWGQ GTTVTVSSASTKGPSVFPLAPSSKSTSGGTAALGCLVKDY FPEPVTVSWNSGALTSGVHTFPAVLQSSGLYSLSSVVTV PSSSLGTQTYICNVNHKPSNTKVDKRVEPKSCDKTHTCP PCPAPELLGGPSVFLFPPKPKDTLMISRTPEVTCVVVDVS HEDPEVKFNWYVDGVEVHNAKTKPREEQYASTYRVVSV LTVLHQDWLNGKEYKCKVSNKALPAPIEKTISKAKGQPR EPQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPGK |
| SEQ ID NO: 164 | | DNA Heavy Chain | GAGGTGCAATTGGTGCAGAGCGGAGCCGAAGTGAAG AAGCCCGGCGAGAGCCTGAAGATCAGCTGCAAGGGC AGCGGCTACGCCTTCACCAACTACCTGATCGAGTGGG TGCGCCAGATGCCCGGCAAGGGCCTGGAATGGATGG GCGTGATCAATCCTGGCAGCGGCGGCACCTACTACAA CGAGAAGTTCAAGGGCCAAGTGACCATCAGCGCCGA CAAGAGCATCAGCACCGCCTACCTCCAGTGGTCCAGC CTGAAGGCCAGCGACACCGCCATGTACTACTGCGCCA GGTGGCGGGGAGAGGGCTACTACGCCTACTACGACG TGTGGGGCCAGGGCACCACAGTGACCGTCAGCTCAGC TAGCACCAAGGGCCCCAGCGTGTTCCCCCTGGCCCCC AGCAGCAAGAGCACCAGCGGCGGCACAGCCGCCCTG GGCTGCCTGGTGAAGGACTACTTCCCCGAGCCCGTGA CCGTGTCCTGGAACAGCGGAGCCCTGACCTCCGGCGT GCACACCTTCCCCGCCGTGCTGCAGAGCAGCGGCCTG TACAGCCTGTCCAGCGTGGTGACAGTGCCCAGCAGCA GCCTGGGCACCCAGACCTACATCTGCAACGTGAACCA CAAGCCCAGCAACACCAAGGTGGACAAGAGAGTGGA GCCCAAGAGCTGCGACAAGACCCACACCTGCCCCCCC |

TABLE 41-continued

Sequence list

TGCCCAGCCCCAGAGCTGCTGGGCGGACCCTCCGTGT
TCCTGTTCCCCCCCAAGCCCAAGGACACCCTGATGATC
AGCAGGACCCCCGAGGTGACCTGCGTGGTGGTGGAC
GTGAGCCACGAGGACCCAGAGGTGAAGTTCAACTGG
TACGTGGACGGCGTGGAGGTGCACAACGCCAAGACC
AAGCCCAGAGAGGAGCAGTACGCCAGCACCTACAGG
GTGGTGTCCGTGCTGACCGTGCTGCACCAGGACTGGC
TGAACGGCAAGGAATACAAGTGCAAGGTCTCCAACAA
GGCCCTGCCAGCCCCCATCGAAAAGACCATCAGCAAG
GCCAAGGGCCAGCCACGGGAGCCCCAGGTGTACACC
CTGCCCCCCTCCCGGGAGGAGATGACCAAGAACCAGG
TGTCCCTGACCTGTCTGGTGAAGGGCTTCTACCCCAGC
GACATCGCCGTGGAGTGGGAGAGCAACGGCCAGCCC
GAGAACAACTACAAGACCACCCCCCCAGTGCTGGACA
GCGACGGCAGCTTCTTCCTGTACAGCAAGCTGACCGT
GGACAAGTCCAGGTGGCAGCAGGGCAACGTGTTCAG
CTGCAGCGTGATGCACGAGGCCCTGCACAACCACTAC
ACCCAGAAGAGCCTGAGCCTGTCCCCCGGCAAG

>VH-F100dY/T30S

| SEQ ID NO: 165 | (Combined) | HCDR1 | GYAFSNYLIE |
| SEQ ID NO: 166 | (Combined) | HCDR2 | VINPGSGGTNYNEKFKG |
| SEQ ID NO: 167 | (Combined) | HCDR3 | WRGEGYYAYYDV |
| SEQ ID NO: 168 | (Kabat) | HCDR1 | NYLIE |
| SEQ ID NO: 169 | (Kabat) | HCDR2 | VINPGSGGTNYNEKFKG |
| SEQ ID NO: 170 | (Kabat) | HCDR3 | WRGEGYYAYYDV |
| SEQ ID NO: 171 | (Chothia) | HCDR1 | GYAFSNY |
| SEQ ID NO: 172 | (Chothia) | HCDR2 | NPGSGG |
| SEQ ID NO: 173 | (Chothia) | HCDR3 | WRGEGYYAYYDV |
| SEQ ID NO: 174 | (IMGT) | HCDR1 | GYAFSNYL |
| SEQ ID NO: 175 | (IMGT) | HCDR2 | INPGSGGT |
| SEQ ID NO: 176 | (IMGT) | HCDR3 | ARWRGEGYYAYYDV |
| SEQ ID NO: 177 | | VH | EVQLVQSGAEVKKPGESLKISCKGSGYAFSNYLIEWVRQ<br>MPGKGLEWMGVINPGSGGTNYNEKFKGQVTISADKSIS<br>TAYLQWSSLKASDTAMYYCARWRGEGYYAYYDVWGQ<br>GTTVTVSS |
| SEQ ID NO: 178 | | DNA VH | GAGGTGCAATTGGTGCAGAGCGGAGCCGAAGTGAAG<br>AAGCCCGGCGAGAGCCTGAAGATCAGCTGCAAGGGC<br>AGCGGCTACGCCTTCAGCAACTACCTGATCGAGTGGG<br>TGCGCCAGATGCCCGGCAAGGGCCTGGAATGGATGG<br>GCGTGATCAATCCTGGCAGCGGCGGCACCAATTACAA<br>CGAGAAGTTCAAGGGCCAAGTGACCATCAGCGCCGA<br>CAAGAGCATCAGCACCGCCTACCTCCAGTGGTCCAGC<br>CTGAAGGCCAGCGACACCGCCATGTACTACTGCGCCA<br>GGTGGCGGGGAGAGGGCTACTACGCCTACTACGACG<br>TGTGGGGCCAGGGCACCACAGTGACCGTCAGCTCA |
| SEQ ID NO: 179 | | Heavy Chain | EVQLVQSGAEVKKPGESLKISCKGSGYAFSNYLIEWVRQ<br>MPGKGLEWMGVINPGSGGTNYNEKFKGQVTISADKSIS<br>TAYLQWSSLKASDTAMYYCARWRGEGYYAYYDVWGQ<br>GTTVTVSSASTKGPSVFPLAPSSKSTSGGTAALGCLVKDY<br>FPEPVTVSWNSGALTSGVHTFPAVLQSSGLYSLSSVVTV<br>PSSSLGTQTYICNVNHKPSNTKVDKRVEPKSCDKTHTCP<br>PCPAPELLGGPSVFLFPPKPKDTLMISRTPEVTCVVVDVS<br>HEDPEVKFNWYVDGVEVHNAKTKPREEQYASTYRVVSV<br>LTVLHQDWLNGKEYKCKVSNKALPAPIEKTISKAKGQPR<br>EPQVYTLPPSREEMTKNQVSLTCLVKGFYPSDIAVEWES<br>NGQPENNYKTTPPVLDSDGSFFLYSKLTVDKSRWQQGN<br>VFSCSVMHEALHNHYTQKSLSLSPGK |
| SEQ ID NO: 180 | | DNA Heavy Chain | GAGGTGCAATTGGTGCAGAGCGGAGCCGAAGTGAAG<br>AAGCCCGGCGAGAGCCTGAAGATCAGCTGCAAGGGC<br>AGCGGCTACGCCTTCAGCAACTACCTGATCGAGTGGG<br>TGCGCCAGATGCCCGGCAAGGGCCTGGAATGGATGG<br>GCGTGATCAATCCTGGCAGCGGCGGCACCAATTACAA<br>CGAGAAGTTCAAGGGCCAAGTGACCATCAGCGCCGA<br>CAAGAGCATCAGCACCGCCTACCTCCAGTGGTCCAGC<br>CTGAAGGCCAGCGACACCGCCATGTACTACTGCGCCA<br>GGTGGCGGGGAGAGGGCTACTACGCCTACTACGACG<br>TGTGGGGCCAGGGCACCACAGTGACCGTCAGCTCAGC<br>TAGCACCAAGGGCCCCAGCGTGTTCCCCCTGGCCCCC<br>AGCAGCAAGAGCACCAGCGGCGGCACAGCCGCCCTG<br>GGCTGCCTGGTGAAGGACTACTTCCCCGAGCCCGTGA<br>CCGTGTCCTGGAACAGCGGAGCCCTGACCTCCGGCGT<br>GCACACCTTCCCCGCCGTGCTGCAGAGCAGCGGCCTG<br>TACAGCCTGTCCAGCGTGGTGACAGTGCCCAGCAGCA<br>GCCTGGGCACCCAGACCTACATCTGCAACGTGAACCA<br>CAAGCCCAGCAACACCAAGGTGGACAAGAGAGTGGA<br>GCCCAAGAGCTGCGACAAGACCCACACCTGCCCCCCC |

TABLE 41-continued

Sequence list

TGCCCAGCCCCAGAGCTGCTGGGCGGACCCTCCGTGT
TCCTGTTCCCCCCCAAGCCCAAGGACACCCTGATGATC
AGCAGGACCCCCGAGGTGACCTGCGTGGTGGTGGAC
GTGAGCCACGAGGACCCAGAGGTGAAGTTCAACTGG
TACGTGGACGGCGTGGAGGTGCACAACGCCAAGACC
AAGCCCAGAGAGGAGCAGTACGCCAGCACCTACAGG
GTGGTGTCCGTGCTGACCGTGCTGCACCAGGACTGGC
TGAACGGCAAGGAATACAAGTGCAAGGTCTCCAACAA
GGCCCTGCCAGCCCCCATCGAAAAGACCATCAGCAAG
GCCAAGGGCCAGCCACGGGAGCCCCAGGTGTACACC
CTGCCCCCCTCCCGGGAGGAGATGACCAAGAACCAGG
TGTCCCTGACCTGTCTGGTGAAGGGCTTCTACCCCAGC
GACATCGCCGTGGAGTGGGAGAGCAACGGCCAGCCC
GAGAACAACTACAAGACCACCCCCCCAGTGCTGGACA
GCGACGGCAGCTTCTTCCTGTACAGCAAGCTGACCGT
GGACAAGTCCAGGTGGCAGCAGGGCAACGTGTTCAG
CTGCAGCGTGATGCACGAGGCCCTGCACAACCACTAC
ACCCAGAAGAGCCTGAGCCTGTCCCCCGGCAAG

>VH-F100dY

| SEQ ID NO: 181 | (Combined) | HCDR1 | GYAFTNYLIE |
| SEQ ID NO: 182 | (Combined) | HCDR2 | VINPGSGGTNYNEKFKG |
| SEQ ID NO: 183 | (Combined) | HCDR3 | WRGEGYYAYYDV |
| SEQ ID NO: 184 | (Kabat) | HCDR1 | NYLIE |
| SEQ ID NO: 185 | (Kabat) | HCDR2 | VINPGSGGTNYNEKFKG |
| SEQ ID NO: 186 | (Kabat) | HCDR3 | WRGEGYYAYYDV |
| SEQ ID NO: 187 | (Chothia) | HCDR1 | GYAFTNY |
| SEQ ID NO: 188 | (Chothia) | HCDR2 | NPGSGG |
| SEQ ID NO: 189 | (Chothia) | HCDR3 | WRGEGYYAYYDV |
| SEQ ID NO: 190 | (IMGT) | HCDR1 | GYAFTNYL |
| SEQ ID NO: 191 | (IMGT) | HCDR2 | INPGSGGT |
| SEQ ID NO: 192 | (IMGT) | HCDR3 | ARWRGEGYYAYYDV |
| SEQ ID NO: 193 | | VH | EVQLVQSGAEVKKPGESLKISCKGSGYAFTNYLIEWVRQ<br>MPGKGLEWMGVINPGSGGTNYNEKFKGQVTISADKSIS<br>TAYLQWSSLKASDTAMYYCARWRGEGYYAYYDVWGQ<br>GTTVTVSS |
| SEQ ID NO: 194 | | DNA VH | GAGGTGCAATTGGTGCAGAGCGGAGCCGAAGTGAAG<br>AAGCCCGGCGAGAGCCTGAAGATCAGCTGCAAGGGC<br>AGCGGCTACGCCTTCACCAACTACCTGATCGAGTGGG<br>TGCGCCAGATGCCCGGCAAGGGCCTGGAATGGATGG<br>GCGTGATCAATCCTGGCAGCGGCGGCACCAATTACAA<br>CGAGAAGTTCAAGGGCCAAGTGACCATCAGCGCCGA<br>CAAGAGCATCAGCACCGCCTACCTCCAGTGGTCCAGC<br>CTGAAGGCCAGCGACACCGCCATGTACTACTGCGCCA<br>GGTGGCGGGGAGAGGGCTACTACGCCTACTACGACG<br>TGTGGGGCCAGGGCACCACAGTGACCGTCAGCTCA |
| SEQ ID NO: 195 | | Heavy Chain | EVQLVQSGAEVKKPGESLKISCKGSGYAFTNYLIEWVRQ<br>MPGKGLEWMGVINPGSGGTNYNEKFKGQVTISADKSIS<br>TAYLQWSSLKASDTAMYYCARWRGEGYYAYYDVWGQ<br>GTTVTVSSASTKGPSVFPLAPSSKSTSGGTAALGCLVKDY<br>FPEPVTVSWNSGALTSGVHTFPAVLQSSGLYSLSSVVTV<br>PSSSLGTQTYICNVNHKPSNTKVDKRVEPKSCDKTHTCP<br>PCPAPELLGGPSVFLFPPKPKDTLMISRTPEVTCVVVDVS<br>HEDPEVKFNWYVDGVEVHNAKTKPREEQYASTYRVVSV<br>LTVLHQDWLNGKEYKCKVSNKALPAPIEKTISKAKGQPR<br>EPQVYTLPPSREEMTKNQVSLTCLVKGFYPSDIAVEWES<br>NGQPENNYKTTPPVLDSDGSFFLYSKLTVDKSRWQQGN<br>VFSCSVMHEALHNHYTQKSLSLSPGK |
| SEQ ID NO: 196 | | DNA Heavy Chain | GAGGTGCAATTGGTGCAGAGCGGAGCCGAAGTGAAG<br>AAGCCCGGCGAGAGCCTGAAGATCAGCTGCAAGGGC<br>AGCGGCTACGCCTTCACCAACTACCTGATCGAGTGGG<br>TGCGCCAGATGCCCGGCAAGGGCCTGGAATGGATGG<br>GCGTGATCAATCCTGGCAGCGGCGGCACCAATTACAA<br>CGAGAAGTTCAAGGGCCAAGTGACCATCAGCGCCGA<br>CAAGAGCATCAGCACCGCCTACCTCCAGTGGTCCAGC<br>CTGAAGGCCAGCGACACCGCCATGTACTACTGCGCCA<br>GGTGGCGGGGAGAGGGCTACTACGCCTACTACGACG<br>TGTGGGGCCAGGGCACCACAGTGACCGTCAGCTCAGC<br>TAGCACCAAGGGCCCCAGCGTGTTCCCCCTGGCCCCC<br>AGCAGCAAGAGCACCAGCGGCGGCACAGCCGCCCTG<br>GGCTGCCTGGTGAAGGACTACTTCCCCGAGCCCGTGA<br>CCGTGTCCTGGAACAGCGGAGCCCTGACCTCCGGCGT<br>GCACACCTTCCCCGCCGTGCTGCAGAGCAGCGGCCTG<br>TACAGCCTGTCCAGCGTGGTGACAGTGCCCAGCAGCA<br>GCCTGGGCACCCAGACCTACATCTGCAACGTGAACCA<br>CAAGCCCAGCAACACCAAGGTGGACAAGAGAGTGGA<br>GCCCAAGAGCTGCGACAAGACCCACACCTGCCCCCCC |

TABLE 41-continued

Sequence list

TGCCCAGCCCCAGAGCTGCTGGGCGGACCCTCCGTGT
TCCTGTTCCCCCCCAAGCCCAAGGACACCCTGATGATC
AGCAGGACCCCCGAGGTGACCTGCGTGGTGGTGGAC
GTGAGCCACGAGGACCCAGAGGTGAAGTTCAACTGG
TACGTGGACGGCGTGGAGGTGCACAACGCCAAGACC
AAGCCCAGAGAGGAGCAGTACGCCAGCACCTACAGG
GTGGTGTCCGTGCTGACCGTGCTGCACCAGGACTGGC
TGAACGGCAAGGAATACAAGTGCAAGGTCTCCAACAA
GGCCCTGCCAGCCCCATCGAAAAGACCATCAGCAAG
GCCAAGGGCCAGCCACGGGAGCCCCAGGTGTACACC
CTGCCCCCCTCCCGGGAGGAGATGACCAAGAACCAGG
TGTCCCTGACCTGTCTGGTGAAGGGCTTCTACCCCAGC
GACATCGCCGTGGAGTGGGAGAGCAACGGCCAGCCC
GAGAACAACTACAAGACCACCCCCCCAGTGCTGGACA
GCGACGGCAGCTTCTTCCTGTACAGCAAGCTGACCGT
GGACAAGTCCAGGTGGCAGCAGGGCAACGTGTTCAG
CTGCAGCGTGATGCACGAGGCCCTGCACAACCACTAC
ACCCAGAAGAGCCTGAGCCTGTCCCCCGGCAAG

>VH-N58Y/T30S

| SEQ ID NO: 197 | (Combined) | HCDR1 | GYAFSNYLIE |
|---|---|---|---|
| SEQ ID NO: 198 | (Combined) | HCDR2 | VINPGSGGTYYNEKFKG |
| SEQ ID NO: 199 | (Combined) | HCDR3 | WRGEGYYAYFDV |
| SEQ ID NO: 200 | (Kabat) | HCDR1 | NYLIE |
| SEQ ID NO: 201 | (Kabat) | HCDR2 | VINPGSGGTYYNEKFKG |
| SEQ ID NO: 202 | (Kabat) | HCDR3 | WRGEGYYAYFDV |
| SEQ ID NO: 203 | (Chothia) | HCDR1 | GYAFSNY |
| SEQ ID NO: 204 | (Chothia) | HCDR2 | NPGSGG |
| SEQ ID NO: 205 | (Chothia) | HCDR3 | WRGEGYYAYFDV |
| SEQ ID NO: 206 | (IMGT) | HCDR1 | GYAFSNYL |
| SEQ ID NO: 207 | (IMGT) | HCDR2 | INPGSGGT |
| SEQ ID NO: 208 | (IMGT) | HCDR3 | ARWRGEGYYAYFDV |
| SEQ ID NO: 209 | | VH | EVQLVQSGAEVKKPGESLKISCKGSGYAFSNYLIEWVRQ MPGKGLEWMGVINPGSGGTYYNEKFKGQVTISADKSIS TAYLQWSSLKASDTAMYYCARWRGEGYYAYFDVWGQ GTTVTVSS |
| SEQ ID NO: 210 | | DNA VH | GAGGTGCAATTGGTGCAGAGCGGAGCCGAAGTGAAG AAGCCCGGCGAGAGCCTGAAGATCAGCTGCAAGGGC AGCGGCTACGCCTTCAGCAACTACCTGATCGAGTGGG TGCGCCAGATGCCCGGCAAGGGCCTGGAATGGATGG GCGTGATCAATCCTGGCAGCGGCGGCACCTACTACAA CGAGAAGTTCAAGGGCCAAGTGACCATCAGCGCCGA CAAGAGCATCAGCACCGCCTACCTCCAGTGGTCCAGC CTGAAGGCCAGCGACACCGCCATGTACTACTGCGCCA GGTGGCGGGGAGAGGGCTACTACGCCTACTTCGACG TGTGGGGCCAGGGCACCACAGTGACCGTCAGCTCA |
| SEQ ID NO: 211 | | Heavy Chain | EVQLVQSGAEVKKPGESLKISCKGSGYAFSNYLIEWVRQ MPGKGLEWMGVINPGSGGTYYNEKFKGQVTISADKSIS TAYLQWSSLKASDTAMYYCARWRGEGYYAYFDVWGQ GTTVTVSSASTKGPSVFPLAPSSKSTSGGTAALGCLVKDY FPEPVTVSWNSGALTSGVHTFPAVLQSSGLYSLSSVVTV PSSSLGTQTYICNVNHKPSNTKVDKRVEPKSCDKTHTCP PCPAPELLGGPSVFLFPPKPKDTLMISRTPEVTCVVVDVS HEDPEVKFNWYVDGVEVHNAKTKPREEQYASTYRVVSV LTVLHQDWLNGKEYKCKVSNKALPAPIEKTISKAKGQPR EPQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPGK |
| SEQ ID NO: 212 | | DNA Heavy Chain | GAGGTGCAATTGGTGCAGAGCGGAGCCGAAGTGAAG AAGCCCGGCGAGAGCCTGAAGATCAGCTGCAAGGGC AGCGGCTACGCCTTCAGCAACTACCTGATCGAGTGGG TGCGCCAGATGCCCGGCAAGGGCCTGGAATGGATGG GCGTGATCAATCCTGGCAGCGGCGGCACCTACTACAA CGAGAAGTTCAAGGGCCAAGTGACCATCAGCGCCGA CAAGAGCATCAGCACCGCCTACCTCCAGTGGTCCAGC CTGAAGGCCAGCGACACCGCCATGTACTACTGCGCCA GGTGGCGGGGAGAGGGCTACTACGCCTACTTCGACG TGTGGGGCCAGGGCACCACAGTGACCGTCAGCTCAGC TAGCACCAAGGGCCCCAGCGTGTTCCCCCTGGCCCCC AGCAGCAAGAGCACCAGCGGCGGCACAGCCGCCCTG GGCTGCCTGGTGAAGGACTACTTCCCCGAGCCCGTGA CCGTGTCCTGGAACAGCGGAGCCCTGACCTCCGGCGT GCACACCTTCCCCGCCGTGCTGCAGAGCAGCGGCCTG TACAGCCTGTCCAGCGTGGTGACAGTGCCCAGCAGCA GCCTGGGCACCCAGACCTACATCTGCAACGTGAACCA CAAGCCCAGCAACACCAAGGTGGACAAGAGAGTGGA GCCCAAGAGCTGCGACAAGACCCACACCTGCCCCCCC |

TABLE 41-continued

Sequence list

```
                            TGCCCAGCCCCAGAGCTGCTGGGCGGACCCTCCGTGT
                            TCCTGTTCCCCCCCAAGCCCAAGGACACCCTGATGATC
                            AGCAGGACCCCCGAGGTGACCTGCGTGGTGGTGGAC
                            GTGAGCCACGAGGACCCAGAGGTGAAGTTCAACTGG
                            TACGTGGACGGCGTGGAGGTGCACAACGCCAAGACC
                            AAGCCCAGAGAGGAGCAGTACGCCAGCACCTACAGG
                            GTGGTGTCCGTGCTGACCGTGCTGCACCAGGACTGGC
                            TGAACGGCAAGGAATACAAGTGCAAGGTCTCCAACAA
                            GGCCCTGCCAGCCCCCATCGAAAAGACCATCAGCAAG
                            GCCAAGGGCCAGCCACGGGAGCCCCAGGTGTACACC
                            CTGCCCCCCTCCCGGGAGGAGATGACCAAGAACCAGG
                            TGTCCCTGACCTGTCTGGTGAAGGGCTTCTACCCCAGC
                            GACATCGCCGTGGAGTGGGAGAGCAACGGCCAGCCC
                            GAGAACAACTACAAGACCACCCCCCCAGTGCTGGACA
                            GCGACGGCAGCTTCTTCCTGTACAGCAAGCTGACCGT
                            GGACAAGTCCAGGTGGCAGCAGGGCAACGTGTTCAG
                            CTGCAGCGTGATGCACGAGGCCCTGCACAACCACTAC
                            ACCCAGAAGAGCCTGAGCCTGTCCCCCGGCAAG
```

>VH-N58Y

| | | |
|---|---|---|
| SEQ ID NO: 213 (Combined) | HCDR1 | GYAFTNYLIE |
| SEQ ID NO: 214 (Combined) | HCDR2 | VINPGSGGTYYNEKFKG |
| SEQ ID NO: 215 (Combined) | HCDR3 | WRGEGYYAYFDV |
| SEQ ID NO: 216 (Kabat) | HCDR1 | NYLIE |
| SEQ ID NO: 217 (Kabat) | HCDR2 | VINPGSGGTYYNEKFKG |
| SEQ ID NO: 218 (Kabat) | HCDR3 | WRGEGYYAYFDV |
| SEQ ID NO: 219 (Chothia) | HCDR1 | GYAFTNY |
| SEQ ID NO: 220 (Chothia) | HCDR2 | NPGSGG |
| SEQ ID NO: 221 (Chothia) | HCDR3 | WRGEGYYAYFDV |
| SEQ ID NO: 222 (IMGT) | HCDR1 | GYAFTNYL |
| SEQ ID NO: 223 (IMGT) | HCDR2 | INPGSGGT |
| SEQ ID NO: 224 (IMGT) | HCDR3 | ARWRGEGYYAYFDV |
| SEQ ID NO: 225 | VH | EVQLVQSGAEVKKPGESLKISCKGSGYAFTNYLIEWVRQ MPGKGLEWMGVINPGSGGTYYNEKFKGQVTISADKSIS TAYLQWSSLKASDTAMYYCARWRGEGYYAYFDVWGQ GTTVTVSS |
| SEQ ID NO: 226 | DNA VH | GAGGTGCAATTGGTGCAGAGCGGAGCCGAAGTGAAG AAGCCCGGCGAGAGCCTGAAGATCAGCTGCAAGGGC AGCGGCTACGCCTTCACCAACTACCTGATCGAGTGGG TGCGCCAGATGCCCGGCAAGGGCCTGGAATGGATGG GCGTGATCAATCCTGGCAGCGGCGGCACCTACTACAA CGAGAAGTTCAAGGGCCAAGTGACCATCAGCGCCGA CAAGAGCATCAGCACCGCCTACCTCCAGTGGTCCAGC CTGAAGGCCAGCGACACCGCCATGTACTACTGCGCCA GGTGGCGGGGAGAGGGCTACTACGCCTACTTCGACG TGTGGGGCCAGGGCACCACAGTGACCGTCAGCTCA |
| SEQ ID NO: 227 | Heavy Chain | EVQLVQSGAEVKKPGESLKISCKGSGYAFTNYLIEWVRQ MPGKGLEWMGVINPGSGGTYYNEKFKGQVTISADKSIS TAYLQWSSLKASDTAMYYCARWRGEGYYAYFDVWGQ GTTVTVSSASTKGPSVFPLAPSSKSTSGGTAALGCLVKDY FPEPVTVSWNSGALTSGVHTFPAVLQSSGLYSLSSVVTV PSSSLGTQTYICNVNHKPSNTKVDKRVEPKSCDKTHTCP PCPAPELLGGPSVFLFPPKPKDTLMISRTPEVTCVVVDVS HEDPEVKFNWYVDGVEVHNAKTKPREEQYASTYRVVSV LTVLHQDWLNGKEYKCKVSNKALPAPIEKTISKAKGQPR EPQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPGK |
| SEQ ID NO: 228 | DNA Heavy Chain | GAGGTGCAATTGGTGCAGAGCGGAGCCGAAGTGAAG AAGCCCGGCGAGAGCCTGAAGATCAGCTGCAAGGGC AGCGGCTACGCCTTCACCAACTACCTGATCGAGTGGG TGCGCCAGATGCCCGGCAAGGGCCTGGAATGGATGG GCGTGATCAATCCTGGCAGCGGCGGCACCTACTACAA CGAGAAGTTCAAGGGCCAAGTGACCATCAGCGCCGA CAAGAGCATCAGCACCGCCTACCTCCAGTGGTCCAGC CTGAAGGCCAGCGACACCGCCATGTACTACTGCGCCA GGTGGCGGGGAGAGGGCTACTACGCCTACTTCGACG TGTGGGGCCAGGGCACCACAGTGACCGTCAGCTCAGC TAGCACCAAGGGCCCCAGCGTGTTCCCCCTGGCCCCC AGCAGCAAGAGCACCAGCGGCGGCACAGCCGCCCTG GGCTGCCTGGTGAAGGACTACTTCCCCGAGCCCGTGA CCGTGTCCTGGAACAGCGGAGCCCTGACCTCCGGCGT GCACACCTTCCCCGCCGTGCTGCAGAGCAGCGGCCTG TACAGCCTGTCCAGCGTGGTGACAGTGCCCAGCAGCA GCCTGGGCACCCAGACCTACATCTGCAACGTGAACCA CAAGCCCAGCAACACCAAGGTGGACAAGAGAGTGGA GCCCAAGAGCTGCGACAAGACCCACACCTGCCCCCCC |

TABLE 41-continued

Sequence list

TGCCCAGCCCCAGAGCTGCTGGGCGGACCCTCCGTGT
TCCTGTTCCCCCCCAAGCCCAAGGACACCCTGATGATC
AGCAGGACCCCCGAGGTGACCTGCGTGGTGGTGGAC
GTGAGCCACGAGGACCCAGAGGTGAAGTTCAACTGG
TACGTGGACGGCGTGGAGGTGCACAACGCCAAGACC
AAGCCCAGAGAGGAGCAGTACGCCAGCACCTACAGG
GTGGTGTCCGTGCTGACCGTGCTGCACCAGGACTGGC
TGAACGGCAAGGAATACAAGTGCAAGGTCTCCAACAA
GGCCCTGCCAGCCCCCATCGAAAAGACCATCAGCAAG
GCCAAGGGCCAGCCACGGGAGCCCCAGGTGTACACC
CTGCCCCCCTCCCGGGAGGAGATGACCAAGAACCAGG
TGTCCCTGACCTGTCTGGTGAAGGGCTTCTACCCCAGC
GACATCGCCGTGGAGTGGGAGAGCAACGGCCAGCCC
GAGAACAACTACAAGACCACCCCCCCAGTGCTGGACA
GCGACGGCAGCTTCTTCCTGTACAGCAAGCTGACCGT
GGACAAGTCCAGGTGGCAGCAGGGCAACGTGTTCAG
CTGCAGCGTGATGCACGAGGCCCTGCACAACCACTAC
ACCCAGAAGAGCCTGAGCCTGTCCCCCGGCAAG

>104348_VH5D98E_VK1D28
Q heavy

| | | |
|---|---|---|
| SEQ ID NO: 229 | Heavy Chain | EVQLVQSGAEVKKPGESLKISCKGSGYAFTNYLIEWVRQ<br>MPGKGLEWMGVINPSGGTNYNEKFKGQVTISADKSIS<br>TAYLQWSSLKASDTAMYYCARWRGEGYYAYFDVWGQ<br>GTTVTVSSASTKGPSVFPLAPSSKSTSGGTAALGCLVKDY<br>FPEPVTVSWNSGALTSGVHTFPAVLQSSGLYSLSSVVTV<br>PSSSLGTQTYICNVNHKPSNTKVDKRVEPKSCDKTHTCP<br>PCPAPELLGGPSVFLFPPKPKDTLMISRTPEVTCVVVDVS<br>HEDPEVKFNWYVDGVEVHNAKTKPREEQYASTYRVVSV<br>LTVLHQDWLNGKEYKCKVSNKALPAPIEKTISKAKGQPR<br>EPQVYTLPPSREEMTKNQVSLTCLVKGFYPSDIAVEWES<br>NGQPENNYKTTPPVLDSDGSFFLYSKLTVDKSRWQQGN<br>VFSCSVMHEALHNHYTQKSLSLSPGK |
| SEQ ID NO: 230 | DNA Heavy Chain | GAGGTGCAATTGGTGCAGAGCGGAGCCGAAGTGAAG<br>AAGCCCGGCGAGAGCCTGAAGATCAGCTGCAAGGGC<br>AGCGGCTACGCCTTCACCAACTACCTGATCGAGTGGG<br>TGCGCCAGATGCCCGGCAAGGGCCTGGAATGGATGG<br>GCGTGATCAATCCTGGCAGCGGCGGCACCAATTACAA<br>CGAGAAGTTCAAGGGCCAAGTGACCATCAGCGCCGA<br>CAAGAGCATCAGCACCGCCTACCTCCAGTGGTCCAGC<br>CTGAAGGCCAGCGACACCGCCATGTACTACTGCGCCA<br>GGTGGCGGGGAGAGGGCTACTACGCCTACTTCGACG<br>TGTGGGGCCAGGGCACCACAGTGACCGTCAGCTCAGC<br>TAGCACCAAGGGCCCCAGCGTGTTCCCCCTGGCCCCC<br>AGCAGCAAGAGCACCAGCGGCGGCACAGCCGCCCTG<br>GGCTGCCTGGTGAAGGACTACTTCCCCGAGCCCGTGA<br>CCGTGTCCTGGAACAGCGGAGCCCTGACCTCCGGCGT<br>GCACACCTTCCCCGCCGTGCTGCAGAGCAGCGGCCTG<br>TACAGCCTGTCCAGCGTGGTGACAGTGCCCAGCAGCA<br>GCCTGGGCACCCAGACCTACATCTGCAACGTGAACCA<br>CAAGCCCAGCAACACCAAGGTGGACAAGAGAGTGGA<br>GCCCAAGAGCTGCGACAAGACCCACACCTGCCCCCCC<br>TGCCCAGCCCCAGAGCTGCTGGGCGGACCCTCCGTGT<br>TCCTGTTCCCCCCCAAGCCCAAGGACACCCTGATGATC<br>AGCAGGACCCCCGAGGTGACCTGCGTGGTGGTGGAC<br>GTGAGCCACGAGGACCCAGAGGTGAAGTTCAACTGG<br>TACGTGGACGGCGTGGAGGTGCACAACGCCAAGACC<br>AAGCCCAGAGAGGAGCAGTACGCCAGCACCTACAGG<br>GTGGTGTCCGTGCTGACCGTGCTGCACCAGGACTGGC<br>TGAACGGCAAGGAATACAAGTGCAAGGTCTCCAACAA<br>GGCCCTGCCAGCCCCCATCGAAAAGACCATCAGCAAG<br>GCCAAGGGCCAGCCACGGGAGCCCCAGGTGTACACC<br>CTGCCCCCCTCCCGGGAGGAGATGACCAAGAACCAGG<br>TGTCCCTGACCTGTCTGGTGAAGGGCTTCTACCCCAGC<br>GACATCGCCGTGGAGTGGGAGAGCAACGGCCAGCCC<br>GAGAACAACTACAAGACCACCCCCCCAGTGCTGGACA<br>GCGACGGCAGCTTCTTCCTGTACAGCAAGCTGACCGT<br>GGACAAGTCCAGGTGGCAGCAGGGCAACGTGTTCAG<br>CTGCAGCGTGATGCACGAGGCCCTGCACAACCACTAC<br>ACCCAGAAGAGCCTGAGCCTGTCCCCCGGCAAG |

TABLE 41-continued

Sequence list

>VK-A50S

| | | | |
|---|---|---|---|
| SEQ ID NO: 231 | (Combined) | LCDR1 | KASQSVDYQGDSYMN |
| SEQ ID NO: 232 | (Combined) | LCDR2 | SASNLES |
| SEQ ID NO: 233 | (Combined) | LCDR3 | QQSNEDPYT |
| SEQ ID NO: 234 | (Kabat) | LCDR1 | KASQSVDYQGDSYMN |
| SEQ ID NO: 235 | (Kabat) | LCDR2 | SASNLES |
| SEQ ID NO: 236 | (Kabat) | LCDR3 | QQSNEDPYT |
| SEQ ID NO: 237 | (Chothia) | LCDR1 | SQSVDYQGDSY |
| SEQ ID NO: 238 | (Chothia) | LCDR2 | SAS |
| SEQ ID NO: 239 | (Chothia) | LCDR3 | SNEDPY |
| SEQ ID NO: 240 | (IMGT) | LCDR1 | QSVDYQGDSY |
| SEQ ID NO: 241 | (IMGT) | LCDR2 | SAS |
| SEQ ID NO: 242 | (IMGT) | LCDR3 | QQSNEDPYT |
| SEQ ID NO: 243 | | VL | AIRLTQSPSSFSASTGDRVTITCKASQSVDYQGDSYMNW YQQKPGKAPKLLIYSASNLESGVPSRFSGSGSGTDFTLTIS SLQSEDFATYYCQQSNEDPYTFGGGTKVEIK |
| SEQ ID NO: 244 | | DNA VL | GCCATCAGACTGACCCAGAGCCCCAGCAGCTTTAGCG CCAGCACCGGCGACAGAGTGACCATCACATGCAAGGC CAGCCAGAGCGTGGACTACCAGGGCGACAGCTACAT GAACTGGTATCAGCAGAAGCCCGGCAAGGCCCCCAA GCTGCTGATCTACTCCGCCAGCAATCTGGAAAGCGGC GTGCCCAGCAGATTCAGCGGCTCTGGCAGCGGCACCG ACTTCACCCTGACAATCAGCAGCCTCCAGTCCGAGGA CTTCGCCACCTACTACTGCCAGCAGAGCAACGAGGAC CCCTACACCTTTGGCGGAGGCACCAAGGTGGAAATCA AG |
| SEQ ID NO: 245 | | Light Chain | AIRLTQSPSSFSASTGDRVTITCKASQSVDYQGDSYMNW YQQKPGKAPKLLIYSASNLESGVPSRFSGSGSGTDFTLTIS SLQSEDFATYYCQQSNEDPYTFGGGTKVEIKRTVAAPSV FIFPPSDEQLKSGTASVVCLLNNFYPREAKVQWKVDNAL QSGNSQESVTEQDSKDSTYSLSSTLTLSKADYEKHKVYAC EVTHQGLSSPVTKSFNRGEC |
| SEQ ID NO: 246 | | DNA Light Chain | GCCATCAGACTGACCCAGAGCCCCAGCAGCTTTAGCG CCAGCACCGGCGACAGAGTGACCATCACATGCAAGGC CAGCCAGAGCGTGGACTACCAGGGCGACAGCTACAT GAACTGGTATCAGCAGAAGCCCGGCAAGGCCCCCAA GCTGCTGATCTACTCCGCCAGCAATCTGGAAAGCGGC GTGCCCAGCAGATTCAGCGGCTCTGGCAGCGGCACCG ACTTCACCCTGACAATCAGCAGCCTCCAGTCCGAGGA CTTCGCCACCTACTACTGCCAGCAGAGCAACGAGGAC CCCTACACCTTTGGCGGAGGCACCAAGGTGGAAATCA AGCGTACGGTGGCCGCTCCCAGCGTGTTCATCTTCCCC CCCAGCGACGAGCAGCTGAAGAGCGGCACCGCCAGC GTGGTGTGCCTGCTGAACAACTTCTACCCCCGGGAGG CCAAGGTGCAGTGGAAGGTGGACAACGCCCTGCAGA GCGGCAACAGCCAGGAGAGCGTCACCGAGCAGGACA GCAAGGACTCCACCTACAGCCTGAGCAGCACCCTGAC CCTGAGCAAGGCCGACTACGAGAAGCATAAGGTGTA CGCCTGCGAGGTGACCCACCAGGGCCTGTCCAGCCCC GTGACCAAGAGCTTCAACAGGGGCGAGTGC |

>VK-A50T

| | | | |
|---|---|---|---|
| SEQ ID NO: 247 | (Combined) | LCDR1 | KASQSVDYQGDSYMN |
| SEQ ID NO: 248 | (Combined) | LCDR2 | TASNLES |
| SEQ ID NO: 249 | (Combined) | LCDR3 | QQSNEDPYT |
| SEQ ID NO: 250 | (Kabat) | LCDR1 | KASQSVDYQGDSYMN |
| SEQ ID NO: 251 | (Kabat) | LCDR2 | TASNLES |
| SEQ ID NO: 252 | (Kabat) | LCDR3 | QQSNEDPYT |
| SEQ ID NO: 253 | (Chothia) | LCDR1 | SQSVDYQGDSY |
| SEQ ID NO: 254 | (Chothia) | LCDR2 | TAS |
| SEQ ID NO: 255 | (Chothia) | LCDR3 | SNEDPY |
| SEQ ID NO: 256 | (IMGT) | LCDR1 | QSVDYQGDSY |
| SEQ ID NO: 257 | (IMGT) | LCDR2 | TAS |
| SEQ ID NO: 258 | (IMGT) | LCDR3 | QQSNEDPYT |
| SEQ ID NO: 259 | | VL | AIRLTQSPSSFSASTGDRVTITCKASQSVDYQGDSYMNW YQQKPGKAPKLLIYTASNLESGVPSRFSGSGSGTDFTLTIS SLQSEDFATYYCQQSNEDPYTFGGGTKVEIK |

TABLE 41-continued

Sequence list

| SEQ ID NO: 260 | DNA VL | GCCATCAGACTGACCCAGAGCCCCAGCAGCTTTAGCG<br>CCAGCACCGGCGACAGAGTGACCATCACATGCAAGGC<br>CAGCCAGAGCGTGGACTACCAGGGCGACAGCTACAT<br>GAACTGGTATCAGCAGAAGCCCGGCAAGGCCCCCAA<br>GCTGCTGATCTACACCGCCAGCAATCTGGAAAGCGGC<br>GTGCCCAGCAGATTCAGCGGCTCTGGCAGCGGCACCG<br>ACTTCACCCTGACAATCAGCAGCCTCCAGTCCGAGGA<br>CTTCGCCACCTACTACTGCCAGCAGAGCAACGAGGAC<br>CCCTACACCTTTGGCGGAGGCACCAAGGTGGAAATCA<br>AG |
| --- | --- | --- |
| SEQ ID NO: 261 | Light Chain | AIRLTQSPSSFSASTGDRVTITCKASQSVDYQGDSYMNW<br>YQQKPGKAPKLLIYTASNLESGVPSRFSGSGSGTDFTLTIS<br>SLQSEDFATYYCQQSNEDPYTFGGGTKVEIKRTVAAPSV<br>FIFPPSDEQLKSGTASVVCLLNNFYPREAKVQWKVDNAL<br>QSGNSQESVTEQDSKDSTYSLSSTLTLSKADYEKHKVYAC<br>EVTHQGLSSPVTKSFNRGEC |
| SEQ ID NO: 262 | DNA Light Chain | GCCATCAGACTGACCCAGAGCCCCAGCAGCTTTAGCG<br>CCAGCACCGGCGACAGAGTGACCATCACATGCAAGGC<br>CAGCCAGAGCGTGGACTACCAGGGCGACAGCTACAT<br>GAACTGGTATCAGCAGAAGCCCGGCAAGGCCCCCAA<br>GCTGCTGATCTACACCGCCAGCAATCTGGAAAGCGGC<br>GTGCCCAGCAGATTCAGCGGCTCTGGCAGCGGCACCG<br>ACTTCACCCTGACAATCAGCAGCCTCCAGTCCGAGGA<br>CTTCGCCACCTACTACTGCCAGCAGAGCAACGAGGAC<br>CCCTACACCTTTGGCGGAGGCACCAAGGTGGAAATCA<br>AGCGTACGGTGGCCGCTCCCAGCGTGTTCATCTTCCCC<br>CCCAGCGACGAGCAGCTGAAGAGCGGCACCGCCAGC<br>GTGGTGTGCCTGCTGAACAACTTCTACCCCCGGGAGG<br>CCAAGGTGCAGTGGAAGGTGGACAACGCCCTGCAGA<br>GCGGCAACAGCCAGGAGAGCGTCACCGAGCAGGACA<br>GCAAGGACTCCACCTACAGCCTGAGCAGCACCCTGAC<br>CCTGAGCAAGGCCGACTACGAGAAGCATAAGGTGTA<br>CGCCTGCGAGGTGACCCACCAGGGCCTGTCCAGCCCC<br>GTGACCAAGAGCTTCAACAGGGGCGAGTGC |
| >VK-M33L/A50S | | |
| SEQ ID NO: 263 (Combined) | LCDR1 | KASQSVDYQGDSYLN |
| SEQ ID NO: 264 (Combined) | LCDR2 | SASNLES |
| SEQ ID NO: 265 (Combined) | LCDR3 | QQSNEDPYT |
| SEQ ID NO: 266 (Kabat) | LCDR1 | KASQSVDYQGDSYLN |
| SEQ ID NO: 267 (Kabat) | LCDR2 | SASNLES |
| SEQ ID NO: 268 (Kabat) | LCDR3 | QQSNEDPYT |
| SEQ ID NO: 269 (Chothia) | LCDR1 | SQSVDYQGDSY |
| SEQ ID NO: 270 (Chothia) | LCDR2 | SAS |
| SEQ ID NO: 271 (Chothia) | LCDR3 | SNEDPY |
| SEQ ID NO: 272 (IMGT) | LCDR1 | QSVDYQGDSY |
| SEQ ID NO: 273 (IMGT) | LCDR2 | SAS |
| SEQ ID NO: 274 (IMGT) | LCDR3 | QQSNEDPYT |
| SEQ ID NO: 275 | VL | AIRLTQSPSSFSASTGDRVTITCKASQSVDYQGDSYLNWY<br>QQKPGKAPKLLIYSASNLESGVPSRFSGSGSGTDFTLTISS<br>LQSEDFATYYCQQSNEDPYTFGGGTKVEIK |
| SEQ ID NO: 276 | DNA VL | GCCATCAGACTGACCCAGAGCCCCAGCAGCTTTAGCG<br>CCAGCACCGGCGACAGAGTGACCATCACATGCAAGGC<br>CAGCCAGAGCGTGGACTACCAGGGCGACAGCTACCT<br>GAACTGGTATCAGCAGAAGCCCGGCAAGGCCCCCAA<br>GCTGCTGATCTACTCCGCCAGCAATCTGGAAAGCGGC<br>GTGCCCAGCAGATTCAGCGGCTCTGGCAGCGGCACCG<br>ACTTCACCCTGACAATCAGCAGCCTCCAGTCCGAGGA<br>CTTCGCCACCTACTACTGCCAGCAGAGCAACGAGGAC<br>CCCTACACCTTTGGCGGAGGCACCAAGGTGGAAATCA<br>AG |
| SEQ ID NO: 277 | Light Chain | AIRLTQSPSSFSASTGDRVTITCKASQSVDYQGDSYLNWY<br>QQKPGKAPKLLIYSASNLESGVPSRFSGSGSGTDFTLTISS<br>LQSEDFATYYCQQSNEDPYTFGGGTKVEIKRTVAAPSVFI<br>FPPSDEQLKSGTASVVCLLNNFYPREAKVQWKVDNALQ<br>SGNSQESVTEQDSKDSTYSLSSTLTLSKADYEKHKVYACE<br>VTHQGLSSPVTKSFNRGEC |
| SEQ ID NO: 278 | DNA Light Chain | GCCATCAGACTGACCCAGAGCCCCAGCAGCTTTAGCG<br>CCAGCACCGGCGACAGAGTGACCATCACATGCAAGGC<br>CAGCCAGAGCGTGGACTACCAGGGCGACAGCTACCT<br>GAACTGGTATCAGCAGAAGCCCGGCAAGGCCCCCAA<br>GCTGCTGATCTACTCCGCCAGCAATCTGGAAAGCGGC<br>GTGCCCAGCAGATTCAGCGGCTCTGGCAGCGGCACCG<br>ACTTCACCCTGACAATCAGCAGCCTCCAGTCCGAGGA<br>CTTCGCCACCTACTACTGCCAGCAGAGCAACGAGGAC<br>CCCTACACCTTTGGCGGAGGCACCAAGGTGGAAATCA<br>AGCGTACGGTGGCCGCTCCCAGCGTGTTCATCTTCCCC |

TABLE 41-continued

Sequence list

```
CCCAGCGACGAGCAGCTGAAGAGCGGCACCGCCAGC
GTGGTGTGCCTGCTGAACAACTTCTACCCCCGGGAGG
CCAAGGTGCAGTGGAAGGTGGACAACGCCCTGCAGA
GCGGCAACAGCCAGGAGAGCGTCACCGAGCAGGACA
GCAAGGACTCCACCTACAGCCTGAGCAGCACCCTGAC
CCTGAGCAAGGCCGACTACGAGAAGCATAAGGTGTA
CGCCTGCGAGGTGACCCACCAGGGCCTGTCCAGCCCC
GTGACCAAGAGCTTCAACAGGGGCGAGTGC
```

>VK-M33L

| SEQ ID NO: 279 (Combined) | LCDR1 | KASQSVDYQGDSYLN |
|---|---|---|
| SEQ ID NO: 280 (Combined) | LCDR2 | AASNLES |
| SEQ ID NO: 281 (Combined) | LCDR3 | QQSNEDPYT |
| SEQ ID NO: 282 (Kabat) | LCDR1 | KASQSVDYQGDSYLN |
| SEQ ID NO: 283 (Kabat) | LCDR2 | AASNLES |
| SEQ ID NO: 284 (Kabat) | LCDR3 | QQSNEDPYT |
| SEQ ID NO: 285 (Chothia) | LCDR1 | SQSVDYQGDSY |
| SEQ ID NO: 386 (Chothia) | LCDR2 | AAS |
| SEQ ID NO: 387 (Chothia) | LCDR3 | SNEDPY |
| SEQ ID NO: 388 (IMGT) | LCDR1 | QSVDYQGDSY |
| SEQ ID NO: 389 (IMGT) | LCDR2 | AAS |
| SEQ ID NO: 390 (IMGT) | LCDR3 | QQSNEDPYT |
| SEQ ID NO: 391 | VL | AIRLTQSPSSFSASTGDRVTITCKASQSVDYQGDSYLNWY QQKPGKAPKLLIYAASNLESGVPSRFSGSGSGTDFTLTISS LQSEDFATYYCQQSNEDPYTFGGGTKVEIK |
| SEQ ID NO: 392 | DNA VL | GCCATCAGACTGACCCAGAGCCCCAGCAGCTTTAGCG CCAGCACCGGCGACAGAGTGACCATCACATGCAAGGC CAGCCAGAGCGTGGACTACCAGGGCGACAGCTACCT GAACTGGTATCAGCAGAAGCCCGGCAAGGCCCCCAA GCTGCTGATCTACGCCGCCAGCAATCTGGAAAGCGGC GTGCCCAGCAGATTCAGCGGCTCTGGCAGCGGCACCG ACTTCACCCTGACAATCAGCAGCCTCCAGTCCGAGGA CTTCGCCACCTACTACTGCCAGCAGAGCAACGAGGAC CCCTACACCTTTGGCGGAGGCACCAAGGTGGAAATCA AG |
| SEQ ID NO: 393 | Light Chain | AIRLTQSPSSFSASTGDRVTITCKASQSVDYQGDSYLNWY QQKPGKAPKLLIYAASNLESGVPSRFSGSGSGTDFTLTISS LQSEDFATYYCQQSNEDPYTFGGGTKVEIKRTVAAPSVFI FPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC |
| SEQ ID NO: 394 | DNA Light Chain | GCCATCAGACTGACCCAGAGCCCCAGCAGCTTTAGCG CCAGCACCGGCGACAGAGTGACCATCACATGCAAGGC CAGCCAGAGCGTGGACTACCAGGGCGACAGCTACCT GAACTGGTATCAGCAGAAGCCCGGCAAGGCCCCCAA GCTGCTGATCTACGCCGCCAGCAATCTGGAAAGCGGC GTGCCCAGCAGATTCAGCGGCTCTGGCAGCGGCACCG ACTTCACCCTGACAATCAGCAGCCTCCAGTCCGAGGA CTTCGCCACCTACTACTGCCAGCAGAGCAACGAGGAC CCCTACACCTTTGGCGGAGGCACCAAGGTGGAAATCA AGCGTACGGTGGCCGCTCCCAGCGTGTTCATCTTCCCC CCCAGCGACGAGCAGCTGAAGAGCGGCACCGCCAGC GTGGTGTGCCTGCTGAACAACTTCTACCCCCGGGAGG CCAAGGTGCAGTGGAAGGTGGACAACGCCCTGCAGA GCGGCAACAGCCAGGAGAGCGTCACCGAGCAGGACA GCAAGGACTCCACCTACAGCCTGAGCAGCACCCTGAC CCTGAGCAAGGCCGACTACGAGAAGCATAAGGTGTA CGCCTGCGAGGTGACCCACCAGGGCCTGTCCAGCCCC GTGACCAAGAGCTTCAACAGGGGCGAGTGC |

>104348_VH5D98E_VK1D28Q light

| SEQ ID NO: 395 = SEQ ID NO: 70 + SEQ ID NO: 107 | Light Chain | AIRLTQSPSSFSASTGDRVTITCKASQSVDYQGDSYMNW YQQKPGKAPKLLIYAASNLESGVPSRFSGSGSGTDFTLTIS SLQSEDFATYYCQQSNEDPYTFGGGTKVEIKRTVAAPSV FIFPPSDEQLKSGTASVVCLLNNFYPREAKVQWKVDNAL QSGNSQESVTEQDSKDSTYSLSSTLTLSKADYEKHKVYAC EVTHQGLSSPVTKSFNRGEC |
| SEQ ID NO: 396 | DNA Light Chain | GCCATCAGACTGACCCAGAGCCCCAGCAGCTTTAGCG CCAGCACCGGCGACAGAGTGACCATCACATGCAAGGC CAGCCAGAGCGTGGACTACCAGGGCGACAGCTACAT GAACTGGTATCAGCAGAAGCCCGGCAAGGCCCCCAA GCTGCTGATCTACGCCGCCAGCAATCTGGAAAGCGGC GTGCCCAGCAGATTCAGCGGCTCTGGCAGCGGCACCG ACTTCACCCTGACAATCAGCAGCCTCCAGTCCGAGGA CTTCGCCACCTACTACTGCCAGCAGAGCAACGAGGAC |

TABLE 41-continued

Sequence list

CCCTACACCTTTGGCGGAGGCACCAAGGTGGAAATCA
AGCGTACGGTGGCCGCTCCCAGCGTGTTCATCTTCCCC
CCCAGCGACGAGCAGCTGAAGAGCGGCACCGCCAGC
GTGGTGTGCCTGCTGAACAACTTCTACCCCCGGGAGG
CCAAGGTGCAGTGGAAGGTGGACAACGCCCTGCAGA
GCGGCAACAGCCAGGAGAGCGTCACCGAGCAGGACA
GCAAGGACTCCACCTACAGCCTGAGCAGCACCCTGAC
CCTGAGCAAGGCCGACTACGAGAAGCATAAGGTGTA
CGCCTGCGAGGTGACCCACCAGGGCCTGTCCAGCCCC
GTGACCAAGAGCTTCAACAGGGGCGAGTGC

>Linkers

| SEQ ID NO: 397 | (G4S)3 | GGGGSGGGGSGGGGS |
| SEQ ID NO: 398 | (G4S)4 | GGGGSGGGGSGGGGSGGGGS |
| SEQ ID NO: 399 | (G4S)5 | GGGGSGGGGSGGGGSGGGGSGGGGS |
| SEQ ID NO: 400 | (G4S)6 | GGGGSGGGGSGGGGSGGGGSGGGGSGGGGS |
| SEQ ID NO: 401 | (G4S)7 | GGGGSGGGGSGGGGSGGGGSGGGGSGGGGSGGGGS |
| SEQ ID NO: 402 | (G4S)8 | GGGGSGGGGSGGGGSGGGGSGGGGSGGGGSGGGGS<br>GGGGS |
| SEQ ID NO: 403 | (G4S)9 | GGGGSGGGGSGGGGSGGGGSGGGGSGGGGSGGGGS<br>GGGGSGGGGS |
| SEQ ID NO: 404 | (G3S)4 | GGGSGGGSGGGSGGGS |
| SEQ ID NO: 405 | (G3S)5 | GGGSGGGSGGGSGGGSGGGS |
| SEQ ID NO: 406 | (G3S)6 | GGGSGGGSGGGSGGGSGGGSGGGS |
| SEQ ID NO: 407 | (G3S)7 | GGGSGGGSGGGSGGGSGGGSGGGSGGGS |
| SEQ ID NO: 408 | (G3S)8 | GGGSGGGSGGGSGGGSGGGSGGGSGGGSGGGS |
| SEQ ID NO: 409 | (G3S)9 | GGGSGGGSGGGSGGGSGGGSGGGSGGGSGGGSGGG<br>S |
| SEQ ID NO: 410 | (G3S)10 | GGGSGGGSGGGSGGGSGGGSGGGSGGGSGGGSGGG<br>SGGGS |
| SEQ ID NO: 411 | (G3S)11 | GGGSGGGSGGGSGGGSGGGSGGGSGGGSGGGSGGG<br>SGGGSGGGS |
| SEQ ID NO: 412 | G4 | GGGG |

>Fusions

| SEQ ID NO: 413 (DNA without signal peptide) | IL-2-(G4S)3-L (NARA1) | ATGTACAGGATGCAACTCCTGTCTTGCATTGCACTAAG<br>TCTTGCACTTGTCACAAACAGTGCACCTACTTCAAGTT<br>CTACAAAGAAAACACAGCTACAACTGGAGCATTTACTT<br>CTGGATTTACAGATGATTTTGAATGAATTAATAATTA<br>CAAGAATCCCAAACTCACCAGGATGCTCACATTTAAGT<br>TTTACATGCCCAAGAAGGCCACAGAACTGAAACATCT<br>TCAGTGTCTAGAAGAAGAACTCAAACCTCTGGAGGAA<br>GTGCTAAATTTAGCTCAAAGCAAAAACTTTCACTTAAG<br>ACCCAGGGACTTAATCAGCAATATCAACGTAATAGTTC<br>TGGAACTAAAGGGATCTGAAACAACATTCATGTGTGA<br>ATATGCTGATGAGACAGCAACCATTGTAGAATTTCTG<br>AACAGATGGATTACCTTTTGTCAAAGCATCATCTCAAC<br>ACTGACTGGCGGGGGAGGTTCTGGCGGTGGGGGATC<br>GGGCGGTGGAGGGAGCGACATTGTGCTGACCCAATC<br>TCCAGCTTCTTTGGCTGTGTCTCTAGGGCAGAGGGCC<br>ACCATCTCCTGCAAGGCCAGCCAAAGTGTTGATTATG<br>ATGGTGATAGTTATATGAACTGGTACCAACAGAAACC<br>AGGACAGCCACCCAAACTCCTCATCTATGCTGCATCCA<br>ATCTAGAATCTGGGATCCCAGCCAGGTTTAGTGGCAG<br>TGGGTCTGGGACAGACTTCACCCTCAACATCCATCCTG<br>TGGAGGAGGAGGATGCTGCAACCTATTACTGTCAGCA<br>AAGTAATGAGGATCCGTACACGTTCGGAGGGGGGAC<br>CAAGCTGGAAATAAAACGGGCTGATGCTGCACCAACT<br>GTATCCATCTTCCCACCATCCAGTGAGCAGTTAACATC<br>TGGAGGTGCCTCAGTCGTGTGCTTCTTGAACAACTTCT<br>ACCCCAAAGACATCAATGTCAAGTGGAAGATTGATGG<br>CAGTGAACGACAAAATGGCGTCCTGAACAGTTGGACT<br>GATCAGGACAGCAAAGACAGCACCTACAGCATGAGC<br>AGCACCCTCACGTTGACCAAGGACGAGTATGAA |
| SEQ ID NO: 414 (DNA without signal peptide) | IL-2-(G4S)4-L (NARA1) | ATGTACAGGATGCAACTCCTGTCTTGCATTGCACTAAG<br>TCTTGCACTTGTCACAAACAGTGCACCTACTTCAAGTT<br>CTACAAAGAAAACACAGCTACAACTGGAGCATTTACTT<br>CTGGATTTACAGATGATTTTGAATGAATTAATAATTA<br>CAAGAATCCCAAACTCACCAGGATGCTCACATTTAAGT<br>TTTACATGCCCAAGAAGGCCACAGAACTGAAACATCT<br>TCAGTGTCTAGAAGAAGAACTCAAACCTCTGGAGGAA<br>GTGCTAAATTTAGCTCAAAGCAAAAACTTTCACTTAAG<br>ACCCAGGGACTTAATCAGCAATATCAACGTAATAGTTC<br>TGGAACTAAAGGGATCTGAAACAACATTCATGTGTGA<br>ATATGCTGATGAGACAGCAACCATTGTAGAATTTCTG<br>AACAGATGGATTACCTTTTGTCAAAGCATCATCTCAAC |

TABLE 41-continued

| | Sequence list | |
|---|---|---|
| | | ACTGACTGGCGGTGGGGGATCAGGGGGCGGAGGTTC<br>TGGAGGTGGCGGGTCGGGGGGAGGTGGGAGCGACA<br>TTGTGCTGACCCAATCTCCAGCTTCTTTGGCTGTGTCTC<br>TAGGGCAGAGGGCCACCATCTCCTGCAAGGCCAGCCA<br>AAGTGTTGATTATGATGGTGATAGTTATATGAACTGG<br>TACCAACAGAAACCAGGACAGCCACCCAAACTCCTCA<br>TCTATGCTGCATCCAATCTAGAATCTGGGATCCCAGCC<br>AGGTTTAGTGGCAGTGGGTCTGGGACAGACTTCACCC<br>TCAACATCCATCCTGTGGAGGAGGAGGATGCTGCAAC<br>CTATTACTGTCAGCAAAGTAATGAGGATCCGTACACG<br>TTCGGAGGGGGGACCAAGCTGGAAATAAAACGGGCT<br>GATGCTGCACCAACTGTATCCATCTTCCCACCATCCAG<br>TGAGCAGTTAACATCTGGAGGTGCCTCAGTCGTGTGC<br>TTCTTGAACAACTTCTACCCCAAAGACATCAATGTCAA<br>GTGGAAGATTGATGGCAGTGAACGACAAAATGGCGT<br>CCTGAACAGTTGGACTGATCAGGACAGCAAAGACAGC<br>ACCTACAGCATGAGCAGCACCCTCACGTTGACCAAGG<br>ACGAGTATGAACGACATAACAGCTATACCTGTGAGGC<br>CACTCACAAGACATCAACTTCACCCATTGTCAAGAGCT<br>TCAACAGGAATGAGTGT |
| SEQ ID NO: 415 (DNA<br>without signal peptide) | IL-2-(G4S)$_5$-<br>L (NARA1) | ATGTACAGGATGCAACTCCTGTCTTGCATTGCACTAAG<br>TCTTGCACTTGTCACAAACAGTGCACCTACTTCAAGTT<br>CTACAAAGAAAACACAGCTACAACTGGAGCATTTACTT<br>CTGGATTTACAGATGATTTTGAATGGAATTAATAATTA<br>CAAGAATCCCAAACTCACCAGGATGCTCACATTTAAGT<br>TTTACATGCCCAAGAAGGCCACAGAACTGAAACATCT<br>TCAGTGTCTAGAAGAAGAACTCAAACCTCTGGAGGAA<br>GTGCTAAATTTAGCTCAAAGCAAAAACTTTCACTTAAG<br>ACCCAGGGACTTAATCAGCAATATCAACGTAATAGTTC<br>TGGAACTAAAGGGATCTGAAACAACATTCATGTGTGA<br>ATATGCTGATGAGACAGCAACCATTGTAGAATTTCTG<br>AACAGATGGATTACCTTTTGTCAAAGCATCATCTCAAC<br>ACTGACTGGCGGTGGGGGATCAGGGGGCGGAGGTTC<br>TGGAGGTGGCGGGTCGGGGGGAGGTGGGAGCGGTG<br>GCGGGGGATCAGACATTGTGCTGACCCAATCTCCAGC<br>TTCTTTGGCTGTGTCTCTAGGGCAGAGGGCCACCATCT<br>CCTGCAAGGCCAGCCAAAGTGTTGATTATGATGGTGA<br>TAGTTATATGAACTGGTACCAACAGAAACCAGGACAG<br>CCACCCAAACTCCTCATCTATGCTGCATCCAATCTAGA<br>ATCTGGGATCCCAGCCAGGTTTAGTGGCAGTGGGTCT<br>GGGACAGACTTCACCCTCAACATCCATCCTGTGGAGG<br>AGGAGGATGCTGCAACCTATTACTGTCAGCAAAGTAA<br>TGAGGATCCGTACACGTTCGGAGGGGGGACCAAGCT<br>GGAAATAAAACGGGCTGATGCTGCACCAACTGTATCC<br>ATCTTCCCACCATCCAGTGAGCAGTTAACATCTGGAGG<br>TGCCTCAGTCGTGTGCTTCTTGAACAACTTCTACCCCA<br>AAGACATCAATGTCAAGTGGAAGATTGATGGCAGTGA<br>ACGACAAAATGGCGTCCTGAACAGTTGGACTGATCAG<br>GACAGCAAAGACAGCACCTACAGCATGAGCAGCACCC<br>TCACGTTGACCAAGGACGAGTATGAACGACATAACAG<br>CTATACCTGTGAGGCCACTCACAAGACATCAACTTCAC<br>CCATTGTCAAGAGCTTCAACAGGAATGAGTGT |
| SEQ ID NO: 416 | IL-2-(G4S)$_3$-<br>L (NARA1) | A P T S S S T K K T Q L Q L E H L L L D L Q M I L N G I<br>N N Y K N P K L T R M L T F K F Y M P K K A T E L K H<br>L Q C L E E E L K P L E E V L N L A Q S K N F H L R P R<br>D L I S N I N V I V L E L K G S E T T F M C E Y A D E T A<br>T I V E F L N R W I T F C Q S I I S T L T G G G G S G G<br>G G S G G G G S D I V L T Q S P A S L A V S L G Q R A<br>T I S C K A S Q S V D Y D G D S Y M N W Y Q Q K P G<br>Q P P K L L I Y A A S N L E S G I P A R F S G S G S G T<br>D F T L N I H P V E E E D A A T Y Y C Q Q S N E D P Y T<br>F G G G T K L E I K R A D A A P T V S I F P P S S E Q L T<br>S G G A S V V C F L N N F Y P K D I N V K W K I D G S<br>E R Q N G V L N S W T D Q D S K D S T Y S M S S T L T<br>L T K D E Y E R H N S Y T C E A T H K T S T S P I V K S F<br>N R N E C |
| SEQ ID NO: 417 | IL-2-(G4S)$_4$-<br>L (NARA1) | A P T S S S T K K T Q L Q L E H L L L D L Q M I L N G I<br>N N Y K N P K L T R M L T F K F Y M P K K A T E L K H<br>L Q C L E E E L K P L E E V L N L A Q S K N F H L R P R<br>D L I S N I N V I V L E L K G S E T T F M C E Y A D E T A<br>T I V E F L N R W I T F C Q S I I S T L T G G G G S G G<br>G G S G G G G S G G G G S D I V L T Q S P A S L A V S<br>L G Q R A T I S C K A S Q S V D Y D G D S Y M N W Y<br>Q Q K P G Q P P K L L I Y A A S N L E S G I P A R F S G<br>S G S G T D F T L N I H P V E E E D A A T Y Y C Q Q S N<br>E D P Y T F G G G T K L E I K R A D A A P T V S I F P P S |

TABLE 41-continued

Sequence list

| SEQ ID NO: 418 | IL-2-(G4S)₅-L (NARA1) | S E Q L T S G G A S V V C F L N N F Y P K D I N V K W K I D G S E R Q N G V L N S W T D Q D S K D S T Y S M S S T L T L T K D E Y E R H N S Y T C E A T H K T S T S P I V K S F N R N E C A P T S S S T K K T Q L Q L E H L L L D L Q M I L N G I N N Y K N P K L T R M L T F K F Y M P K K A T E L K H L Q C L E E E L K P L E E V L N L A Q S K N F H L R P R D L I S N I N V I V L E L K G S E T T F M C E Y A D E T A T I V E F L N R W I T F C Q S I I S T L T G G G G S G G G G S G G G G S G G G G S G G G G S D I V L T Q S P A S L A V S L G Q R A T I S C K A S Q S V D Y D G D S Y M N W Y Q Q K P G Q P P K L L I Y A A S N L E S G I P A R F S G S G S G T D F T L N I H P V E E E D A A T Y Y C Q Q S N E D P Y T F G G G T K L E I K R A D A A P T V S I F P P S S E Q L T S G G A S V V C F L N N F Y P K D I N V K W K I D G S E R Q N G V L N S W T D Q D S K D S T Y S M S S T L T L T K D E Y E R H N S Y T C E A T H K T S T S P I V K S F N R N E C |

---

The invention claimed is:

1. An antibody/IL-2 fusion protein comprising: an antibody comprising a light chain (LC), a heavy chain (HC), and a human interleukin-2 protein (hIL-2) polypeptide inserted, directly or through a linker, within at least one of its six complementarity determining regions (CDRs), wherein the amino acid sequence of the original CDRs, comprise HC-CDRs of SEQ ID NOs: 119, 120, and 121, respectively, and LC-CDRs of SEQ ID NOs: 122, 123, and 21, respectively; and wherein said antibody/IL-2 fusion protein has hIL-2 activity.

2. The antibody/IL-2 fusion protein of claim 1, wherein:
(a) said VL domain comprises: (1) a LCDR1 selected from the group consisting of SEQ ID NO: 19, SEQ ID NO: 31, SEQ ID NO: 69, SEQ ID NO: 72, SEQ ID NO: 86 and SEQ ID NO: 90; (2) LCDR2 selected from the group consisting of SEQ ID NO: 20 and SEQ ID NO: 32; and (3) a LCDR3 selected from SEQ ID NO: 21 and
(b) said VH domain comprises: (a) a HCDR1 selected from the group consisting of SEQ ID NO: 1, SEQ ID NO: 4 and SEQ ID NO: 13; (b) a HCDR2 selected from the group consisting of SEQ ID NO: 2 and SEQ ID NO: 12; and
(c) a HCDR3 selected from the group consisting of SEQ ID NO: 3, SEQ ID NO: 36, SEQ ID NO: 39, SEQ ID NO: 42, and SEQ ID NO: 45.

3. The antibody/IL-2 fusion protein of claim 1, wherein said antibody/IL-2 fusion protein comprises:
(a) the LCDR1, LCDR2, and LCDR3 are SEQ ID NOs: 19, 20, and 21, respectively and the HCDR1, HCDR2, and HCDR3 are SEQ ID NOs: 4, 2, and 3, respectively; or
(b) the LCDR1, LCDR2, and LCDR3 are SEQ ID NOs: 31, 32, and 21, respectively and the HCDR1, HCDR2, and HCDR3 are SEQ ID NOs: 4, 2 and 3, respectively; or
(c) the LCDR1, LCDR2, and LCDR3 are SEQ ID NOs: 19, 20, and 21 and the HCDR1, HCDR2 and HCDR3 are SEQ ID NOs: 13, 12 and 3; or
(d) the LCDR1, LCDR2, and LCDR3 are SEQ ID NOs: 31, 32, and 21 and the HCDR1, HCDR2, and HCDR3 are SEQ ID NOs: 13, 12, and 3; or
(e) the LCDR1, LCDR2, and LCDR3 are SEQ ID NOs: 69, 20, and 21 and the HCDR1, HCDR2, and HCDR3 are SEQ ID NOs: 4, 2, and 3, respectively; or
(f) the LCDR1, LCDR2, and LCDR3 are SEQ ID NOs: 31, 32, and 21, respectively and the HCDR1, HCDR2, and HCDR3 are SEQ ID NOs: 4, 2, and 36, respectively; or
(g) the LCDR1, LCDR2, and LCDR3 are SEQ ID NOs: 69, 20, and 21, respectively and the HCDR1, HCDR2, and HCDR3 are SEQ ID NOs: 13, 12, and 3, respectively; or
(h) the LCDR1, LCDR2, and LCDR3 are SEQ ID NOs: 19, 20, and 21, respectively, and the HCDR1, HCDR2, and HCDR3 are SEQ ID NOs: 4, 2, and 36, respectively; or
(i) the LCDR1, LCDR2, and LCDR3 are SEQ ID NO: 69, 20, and 21, respectively, and the HCDR1, flail HCDR2, and HCDR3 are SEQ ID NOs: 4, 2, and 36, respectively; or
(j) the LCDR1, LCDR2, and LCDR3 are SEQ ID NO SEQ ID NOs: 19, 20, 21, respectively, and the HCDR1, HCDR2, and HCDR3 are SEQ ID NO SEQ ID NOs: 1, 2, and 36, respectively; or
(k) the LCDR1, LCDR2, and LCDR3 are SEQ ID NOs: 69, 20, 21, respectively, and the HCDR1, HCDR2, and HCDR3 are SEQ ID NOs: 4, 2, and 36, respectively; or
(l) LC-CDR1, LC-CDR2, and LC-CDR3 of SEQ ID NOs: 31, 32, 21, respectively, and HC-CDR1, HC-CDR2, and HC-CDR3 of SEQ ID NOs: 1, 2, and 36, respectively; or
(m) LC-CDR1, LC-CDR2, and LC-CDR3 of SEQ ID NOs: 19, 20, 21, respectively, and HC-CDR1, HC-CDR2, and HC-CDR3 of SEQ ID NOs: 4, 2, and 39, respectively; or
(n) LC-CDR1, LC-CDR2, and LC-CDR3 of SEQ ID NOs: 31, 32, 21, respectively, and HC-CDR1, HC-CDR2, and HC-CDR3 of SEQ ID NOs: 4, 2, and 39, respectively; or
(o) LC-CDR1, LC-CDR2, and LC-CDR3 of SEQ ID NOs: 69, 20, 21, respectively, and HC-CDR1, HC-CDR2, and HC-CDR3 of SEQ ID NOs: 4, 2, and 39, respectively.

4. The antibody/IL-2 fusion protein of claim 1, comprising a LC and a HC, wherein the hIL-2 polypeptide is inserted within at least one original CDR of an original LC or an original HC, wherein (1) said original LC comprises a VL polypeptide having at least 95% amino acid sequence identity to SEQ ID NO: 25, SEQ ID NO: 27, SEQ ID NO: 34, SEQ ID NO: 70, or SEQ ID NO: 79; or wherein (2) said original HC comprises a VH polypeptide having at least 95% amino acid sequence identity to SEQ ID NO: 7, SEQ ID NO: 15, SEQ ID NO: 17, SEQ ID NO: 37, or SEQ ID NO: 49;
wherein an original LC or original HC is a LC or HC without hIL-2 insertions, respectively.

5. The antibody/IL-2 fusion protein of claim 4, wherein said original LC and original HC comprise, respectively, an amino acid sequence selected from:
a) SEQ ID NO: 25 and SEQ ID NO: 7; and
b) SEQ ID NO: 27 and SEQ ID NO: 7; and
c) SEQ ID NO: 34 and SEQ ID NO: 7; and
d) SEQ ID NO: 25 and SEQ ID NO: 15; and
e) SEQ ID NO: 27 and SEQ ID NO: 15; and
f) SEQ ID NO: 34 and SEQ ID NO: 15; and
g) SEQ ID NO: 25 and SEQ ID NO: 17; and
h) SEQ ID NO: 27 and SEQ ID NO: 17; and
i) SEQ ID NO: 34 and SEQ ID NO: 17; and
j) SEQ ID NO: 70 and SEQ ID NO: 7; and
k) SEQ ID NO: 25 and SEQ ID NO: 37; and
l) SEQ ID NO: 70 and SEQ ID NO: 37; and
m) SEQ ID NO: 79 and SEQ ID NO: 7; and
n) SEQ ID NO: 27 and SEQ ID NO: 37; and o) SEQ ID NO: 79 and SEQ ID NO: 37; and
p) SEQ ID NO: 70 and SEQ ID NO: 17; and
q) SEQ ID NO: 25 and SEQ ID NO: 49; and
r) SEQ ID NO: 70 and SEQ ID NO: 49; and
s) SEQ ID NO: 79 and SEQ ID NO: 17; and
t) SEQ ID NO: 27 and SEQ ID NO: 49; and
u) SEQ ID NO: 79 and SEQ ID NO: 49; and
v) SEQ ID NO: 34 and SEQ ID NO: 37; and
w) SEQ ID NO: 70 and SEQ ID NO: 15; and
x) SEQ ID NO: 79 and SEQ ID NO: 15; and
y) SEQ ID NO: 34 and SEQ ID NO: 49.

6. The antibody/IL-2 fusion protein of claim 1, comprising a LC and a HC, wherein the hIL-2 polypeptide is inserted within at least one original CDR of an original LC or original HC, wherein (1) said original LC comprises a polypeptide having at least 95% sequence identity to SEQ ID NO: 124 or SEQ ID NO: 128; and (2) said original HC comprises a polypeptide having at least 95% sequence identity to SEQ ID NO: 126 or SEQ ID NO: 130.

7. The antibody/IL-2 fusion protein of claim 6, wherein said antibody/IL-2 fusion protein comprises at least one hIL-2 polypeptide inserted within an original CDR of an original LC or original HC, respectively, of
a. SEQ ID NO: 124 and SEQ ID NO: 126; or
b. SEQ ID NO: 128 and SEQ ID NO: 130.

8. The antibody/IL-2 fusion protein of claim 1, wherein the antibody/IL-2 fusion protein comprises at least one linker sequence between the hIL-2 polypeptide and the original CDR, wherein said linker is 1 to 10 glycine(s).

9. The antibody/IL-2 fusion protein according to claim 8, wherein the linker sequence is GGG and/or SEQ ID NO: 412.

10. The antibody/IL-2 fusion protein according to claim 1, wherein the hIL-2 polypeptide is inserted within the original CDR of SEQ ID NO: 122.

11. The antibody/IL-2 fusion protein of claim 10, wherein the hIL-2 polypeptide is inserted between the amino acids at position 8 and at position 11 within the original CDR of SEQ ID NO: 122.

12. The antibody/IL-2 fusion protein of claim 11, wherein the hIL-2 polypeptide comprises a hIL-2 wherein the amino acid sequence order has been rearranged as circularly permuted, and comprises amino acid residues 97 to 153 linked to amino acid residues 22 to 96 of SEQ ID NO: 109, in that order.

13. The antibody/IL-2 fusion protein of claim 11, wherein the hIL-2 polypeptide comprises SEQ ID NO: 109 or SEQ ID NO:110.

14. The antibody/IL-2 fusion protein according to claim 10, wherein the hIL-2 polypeptide is inserted within the original CDRs of SEQ ID NO: 19, SEQ ID NO: 31, SEQ ID NO: 69, SEQ ID NO: 72, SEQ ID NO: 86, or SEQ ID NO: 90.

15. The antibody/IL-2 fusion protein of claim 8, wherein the hIL-2 polypeptide is inserted between amino acids tyrosine at position 8 and aspartic acid at position 11 of the original CDR of SEQ ID NO: 122.

16. The antibody/IL-2 fusion protein of claim 1, wherein the hIL2 polypeptide is circularly permuted and comprises amino acid residues 97 to 153 fused to amino acid residues 22 to 96 of SEQ ID NO: 109, or the corresponding residues of SEQ ID NO: 110, in that order.

17. The antibody/IL-2 fusion protein of claim 1, wherein the hIL-2 polypeptide comprises SEQ ID NO:109.

18. The antibody/IL-2 fusion protein of claim 1, hIL-2 polypeptide comprises or consists of amino acid residues 97 to 153 linked to amino acid residues 22 to 96 of SEQ ID NO: 109, in that order, directly or through a linker.

19. The antibody/IL-2 fusion protein of claim 15, wherein the hIL-2 polypeptide comprises SEQ ID NO:109.

20. The antibody/M-2 fusion protein of claim 14, wherein the hIL-2 polypeptide comprises or consists of amino acid residues 97 to 153 linked to amino acid residues 22 to 96 of SEQ ID NO: 109, in that order, directly or through a linker.

21. A pharmaceutical composition comprising the antibody/IL-2 fusion protein of claim 1.

* * * * *